United States Patent [19]

Svendsen et al.

[11] Patent Number: 5,985,818
[45] Date of Patent: Nov. 16, 1999

[54] LACCASE MUTANTS

[75] Inventors: Allan Svendsen, Birkerod, Denmark; Feng Xu, Woodland, Calif.

[73] Assignee: Novo Nordisk A/S, Bagsvaerd, Denmark

[21] Appl. No.: 09/032,315

[22] Filed: Feb. 27, 1998

[30] Foreign Application Priority Data

Feb. 28, 1997 [DK] Denmark .................. 0222/97

[51] Int. Cl.[6] .............. C11D 3/48; C11D 7/42; C12N 9/02
[52] U.S. Cl. ............. 510/392; 435/189
[58] Field of Search .............. 435/189; 510/392

[56] References Cited

U.S. PATENT DOCUMENTS 5,480,801  1/1996  Wahleithner et al. .......... 435/254.3

FOREIGN PATENT DOCUMENTS

WO 92/01046  1/1992  WIPO .
WO 95/33836  12/1995  WIPO .
WO 96/00290  1/1996  WIPO .
WO 96/06930  3/1996  WIPO .
WO 96/23874  8/1996  WIPO .
WO 97/09431  3/1997  WIPO .

OTHER PUBLICATIONS

Kojima et al., Cloning, Sequence Analysis, and Expression of Ligninolytic Phenoloxidase Genes of the White–rot Basidiomycete Coriolus hirsutus, J. Bio. Chem., vol. 265, No. 25, Sep. 5, 1990, pp. 15224–15230.
Xu et al., BBA, vol. 1292, pp. 303–311 (1996).
Messerschmidt et al., Chemical Abstracts, vol. 111, No. 3, p. 297 (Jul. 17, 1989).
Hanna et al., Biochem J., vol. 253, pp. 561–568 (1988).

*Primary Examiner*—Robert A. Wax
*Attorney, Agent, or Firm*—Steve T. Zelson, Esq.; Reza Green, Esq.

[57] ABSTRACT

The present invention relates to a method of designing laccase mutants with increased oxidation potential and/or changed pH optimum and/or altered mediator pathway and/or altered $O_2$/$OH^-$-pathway, which method is based on the three-dimensional structure of laccases.

7 Claims, No Drawings

LACCASE MUTANTS

CROSS-REFERENCE TO RELATED APPLICATIONS

This application claims priority of Danish application 0222/97 filed Feb. 28, 1997, the contents of which are fully incorporated herein by reference.

FIELD OF THE INVENTION

The present invention relates to a method of designing laccase mutants with increased oxidation potential and/or changed pH optimum and/or altered mediator pathway and/or altered $O_2/OH^-$-pathway, which method is based on the hitherto unknown three-dimensional structure of laccases.

BACKGROUND OF THE INVENTION

Laccase is a polyphenol oxidase (EC 1.10.3.2) which catalyses the oxidation of a variety of inorganic and aromatic compounds, particularly phenols, with the concomitant reduction of molecular oxygen to water.

Laccase belongs to a family of blue copper-containing oxidases which includes ascorbate oxidase and the mammalian plasma protein ceruloplasmin. All these enzymes are multi-copper-containing proteins.

Because laccases are able to catalyze the oxidation of a variety of inorganic and aromatic compounds, laccases have been suggested in many potential industrial applications such as lignin modification, paper strengthening, dye transfer inhibition in detergents, phenol polymerization, hair colouring, and waste water treatment.

No three-dimensional structural information has been available for a laccase before.

We have now elucidated the three-dimensional structure of a *Coprinus cinereus* laccase. By having this three-dimensional structure we are able to create laccase variants with altered properties: increased oxidation potential and/or changed pH optimum and/or altered mediator pathway and/or altered $O_2/OH^-$-pathway.

BRIEF DISCLOSURE OF THE INVENTION

The three-dimensional structure of a laccase has now been elucidated. On the basis of an analysis of said structure it is possible to identify structural parts or specific amino acid residues which from structural or functional considerations appear to be important for increased oxidation potential and/or changed pH optimum and/or altered mediator pathway and/or altered $O_2/OH^-$-pathway of a laccase.

Furthermore, when comparing the three-dimensional structure of the Coprinus laccase structure with known amino acid sequences of various laccases, it has been found that some similarities exist between the sequences. The present invention is based on these findings.

Accordingly, in a first aspect the invention relates to a method of constructing a variant of a parent Coprinus laccase, which variant has laccase activity and increased oxidation potential and/or changed pH optimum and/or altered mediator pathway and/or altered $O_2/OH^-$-pathway as compared to said parent laccase, which method comprises i) analysing the three-dimensional structure of the parent Coprinus laccase to identify at least one amino acid residue or at least one structural part of the Coprinus laccase structure, which amino acid residue or structural part is believed to be of relevance for altering the oxidation potential and/or altering the pH optimum and/or altering the mediator pathway and/or altering the $O_2/OH^-$-pathway of the parent Coprinus laccase (as evaluated on the basis of structural or functional considerations), ii) constructing a Coprinus laccase variant, which as compared to the parent Coprinus laccase, has been modified in the amino acid residue or structural part identified in i) so as to alter the oxidation potential and/or alter the pH optimum and/or alter the mediator pathway and/or alter the $O_2/OH^-$-pathway, and, optionally, iii) testing the resulting Coprinus laccase variant with respect to oxidation potential and/or pH optimum and/or mediator pathway and/or $O_2/OH^-$-pathway.

In a second aspect the present invention relates to a method of constructing a variant of a parent Coprinus-like laccase, which variant has laccase activity and increased oxidation potential and/or changed pH optimum and/or altered mediator pathway and/or altered $O_2/OH^-$-pathway as compared to said parent laccase, which method comprises i) comparing the three-dimensional amino acid structure of the Coprinus laccase with an amino acid sequence of a Coprinus-like laccase, ii) identifying a part of the Coprinus-like laccase amino acid sequence which is different from the Coprinus laccase amino acid sequence and which from structural or functional considerations is contemplated to be responsible for differences in the stability of the Coprinus and Coprinus-like laccase, iii) modifying the part of the Coprinus-like laccase identified in ii) whereby a Coprinus-like laccase variant is obtained, which has an increased oxidation potential and/or changed pH optimum and/or altered mediator pathway and/or altered $O_2/OH^-$-pathway as compared to the parent Coprinus-like laccase, and optionally, iv) testing the resulting Coprinus-like laccase variant with respect to oxidation potential and/or pH optimum and/or mediator pathway and/or $O_2/OH^-$-pathway.

In still further aspects the invention relates to variants of a Coprinus laccase and of Coprinus-like laccases, DNA encoding such variants and methods of preparing the variants. Finally, the invention relates to the use of the variants for various industrial purposes.

DETAILED DISCLOSURE OF THE INVENTION

The Coprinus-like Laccases

A number of laccases produced by different fungi are homologous on the amino acid level. For instance, when using the 35 homology percent obtained from UWGCG program using the GAP program with the default parameters (penalties: gap weight=3.0, length weight=0.1; WISCONSIN PACKAGE Version 8.1-UNIX, August 1995, Genetics Computer Group, 575 Science Drive, Madison, Wis., USA 53711) the following homology was found:

*Coprinus cinereus* laccase comprising the amino acid sequence shown in SEQ ID No. 1: 100%;

*Polyporus pinsitus* (I) laccase comprising the amino acid sequence shown in SEQ ID No. 2: 74.4%;

*Polyporus pinsitus* (II) laccase comprising the amino acid sequence shown in SEQ ID No. 3: 73.8%;

*Phlebia radiata* laccase comprising the amino acid sequence shown in SEQ ID No. 4: 69.9%;

*Rhizoctonia solani* (I) laccase comprising the amino acid sequence shown in SEQ ID No. 5: 64.8%;

*Rhizoctonia solani* (II) laccase comprising the amino acid sequence shown in SEQ ID No. 6: 63.0%;

*Rhizoctonia solani* (III) laccase comprising the amino acid sequence shown in SEQ ID No. 7: 61.0%;

*Rhizoctonia solani* (IV) laccase comprising the amino acid sequence shown in SEQ ID No. 8: 59.7%;

*Scytalidium thermophilum* laccase comprising the amino acid sequence shown in SEQ ID No. 9: 57.4%;

*Myceliophthora thermophila* laccase comprising the amino acid sequence shown in SEQ ID No. 10: 56.5%.

Because of the homology found between the above mentioned laccases, they are considered to belong to the same class of laccases, namely the class of "Coprinus-like laccases".

Accordingly, in the present context, the term "Coprinus-like laccase" is intended to indicate a laccase which, on the amino acid level, displays a homology of at least 50% and less than 100% to the *Coprinus cinereus* laccase SEQ ID NO 1, or at least 55% and less than 100% to the *Coprinus cinereus* laccase SEQ ID NO 1, or at least 60% and less than 100% to the *Coprinus cinereus* laccase SEQ ID NO 1, or at least 65% and less than 100% to the *Coprinus cinereus* laccase SEQ ID NO 1, or at least 70% and less than 100% to the *Coprinus cinereus* laccase SEQ ID NO 1, or at least 75% and less than 100% to the *Coprinus cinereus* laccase SEQ ID NO 1, or at least 80% and less than 100% to the *Coprinus cinereus* laccase SEQ ID NO 1, or at least 85% and less than 100% to the *Coprinus cinereus* laccase SEQ ID NO 1, or at least 90% and less than 100% to the *Coprinus cinereus* laccase SEQ ID NO 1, or at least 95% and less than 100% to the *Coprinus cinereus* laccase SEQ ID NO 1.

In the present context, "derived from" is intended not only to indicate a laccase produced or producible by a strain of the organism in question, but also a laccase encoded by a DNA sequence isolated from such strain and produced in a host organism containing said DNA sequence. Finally, the term is intended to indicate a laccase which is encoded by a DNA sequence of synthetic and/or cDNA origin and which has the identifying characteristics of the laccase in question.

The Three-dimensional Coprinus Laccase Structure

The Coprinus laccase which was used to elucidate the three-dimensional structure forming the basis for the present invention consists of the 539 amino acids derived from *Coprinus cinereus* laccase IFO 8371 as disclosed in sequence ID No. 1.

The obtained three-dimensional structure is believed to be representative for the structure of any Coprinus-like laccase.

The structure of the laccase was solved in accordance with the principle for X-ray crystallographic methods given in "X-Ray Structure Determination", Stout, G. K. and Jensen, L. H., John Wiley & Sons, inc. N.Y., 1989. The structural coordinates for the solved crystal structure of the laccase at 2.2 Å resolution using the isomorphous replacement method are given in a standard PDB format (Brookhaven Protein Data Base) in Appendix 1. It is to be understood that Appendix 1 forms part of the present application.

In Appendix 1 the amino acid residues of the enzyme are identified by three-letter amino acid code (capitalized letters).

The laccase structure is made up of three plastocyanin-like domains. These three domains all have a similar beta-barrel fold.

3 copper atoms were observed in the three-dimensional structure:

The so-called type 1 copper ion is coordinated by two histidines and one cysteine.

The so-called type 2 copper of the trinuclear centre is missing in the structure disclosed in the present application.

The so-called type 3 copper consists of two type 3 copper atoms (pair of copper atoms) bound to a total of 6 histidine ligands.

When comparing the amino acid sequence of the crystallized three-dimensional structure with *Coprinus cinereus* amino acid sequence ID No. 1 the following four differences are observed:

18 amino acids are missing from the N-terminal of the crystallized protein;

17 amino acids are missing from the C-terminal of the crystallized protein;

Q19 in sequence ID No. 1 is an A1 in the crystallized protein; and

Q243 in sequence ID No. 1 is an E225 in the crystallized protein.

Generality of Structure

Because of the homology between the Coprinus laccase and the various Coprinus-like laccases, the solved structure defined by the coordinates of Appendix 1 is believed to be representative for the structure of all Coprinus-like laccases. A model structure of Coprinus-like laccases may be built on the basis of the coordinates given in Appendix 1 adapted to the laccase in question by use of an alignment between the respective amino acid sequences.

The above identified structurally characteristic parts of the Coprinus laccase structure may be identified in other Coprinus-like laccases on the basis of a model (or solved) structure of the relevant Coprinus-like laccase or simply on the basis of an alignment between the amino acid sequence of the Coprinus-like laccase in question with that of the Coprinus laccase used herein for identifying the amino acid residues of the respective structural elements.

Furthermore, in connection with Coprinus laccase variants of the invention, which are defined by modification of specific amino acid residues of the parent Coprinus laccase, it will be understood that variants of Coprinus-like laccases modified in an equivalent position (as determined from the best possible amino acid sequence alignment between the respective sequences) are intended to be covered as well.

Methods of the Invention for Design of Novel Laccase Variants

The analysis or comparison performed in step i) of the methods of the invention may be performed by use of any suitable computer program capable of analyzing and/or comparing amino acid sequences.

The structural part which is identified in step i) of the methods of the invention may be composed of one amino acid residue. However, normally the structural part comprises more than one amino acid residue, typically constituting one of the above mentioned parts of the Coprinus structure such as one of the copper centers.

Modifications

The modification of an amino acid residue or structural part is typically accomplished by suitable modifications of a DNA sequence encoding the parent enzyme in question. The term "modified" as used in the methods according to the invention is intended to have the following meaning: When used in relation to an amino acid residue the term is intended to mean replacement of the amino acid residue in question with another amino acid residue. When used in relation to a structural part, the term is intended to mean: replacement of one or more amino acid residues of said structural part with other amino acid residues, or addition of one or more amino acid residues to said part, or deletion of one or more amino acid residues of said structural part.

The construction of the variant of interest is accomplished by cultivating a microorganism comprising a DNA sequence encoding the variant under conditions which are conducive for producing the variant, and optionally subsequently recovering the variant from the resulting culture broth. This is described in detail further below.

Variants with Altered Oxidation Potential

The redox potentials of various wild type laccases have been found to be the following (measured at pH 5.3):

|  | E°, V vs NHE |
|---|---|
| *Coprinus cinereus* (SEQ ID No. 1): | 0.55 |
| *Polyporus pinsitus* (SEQ ID No. 2): | 0.79 |
| *Myceliophthora thermophila* (SEQ ID No. 10): | 0.48 |
| *Rhizoctonia solani* (SEQ ID No. 7): | 0.75 |
| *Scytalidium thermophilum* (SEQ ID No. 9): | 0.53 |

It is contemplated that it is possible to increase the oxidation potential of a parent Coprinus laccase or a parent Coprinus-like laccase, wherein said variant is the result of a mutation, i.e. one or more amino acid residues have been deleted from, replaced or added to the parent laccase. Preferred positions for mutations are the following:
*Coprinus cinereus* laccase (SEQ ID No. 1):
G411A,V,P,L,I,F,Y,W;
G412A,V,P,L,I,F,Y,W;
V409P,L,I,F,Y,W;
T257A,V,P,L,I,F,Y,W;
F358Y,W,I;
T359A,V,P,L,I,F,Y,W;
L480I,F,Y,W;
L351I,F,Y,W;
E473A,V,P,L,I,F,Y,W;
D98A,V,P,L,I,F,Y,W;
G131A,V,P,L,I,F,Y,W;
D443A,V,P,L,I,F,Y,W;
R260 A,V,P,L,I,F,Y,W; in particular
G411A,V;
G412A,V,L,I;
V409L,I;
T257V;
F358W;
T359V,F;
L480I,F;
L351I,F;
E473L,I,F;
D98L,I,F;
G131V,L,I;
D443I,F;
R260I;
D443I+R260I;
D443F+R260I.
*Polyporus pinsitus* (SEQ ID No. 2):
A390V,P,L,I,F,Y,W;
G392A,V,P,L,I,F,Y,W;
E460D; in particular
A390V,L,I;
G392A,V.
*Myceliophthora thermophila* laccase (SEQ ID No. 10):
G511A,V,P,L,I,F,Y,W;
T428A,V,P,L,I,F,Y,W;
S510A,V,P,L,I,F,Y,W;
D106A,V,P,L,I,F,Y,W;
N109A,V,P,L,I,F,Y,W,Q;
L500I,F,Y,W;
A108V,P,L,I,F,Y,W;
G514A,V,P,L,I,F,Y,W; in particular
G511A,V,L,I,F;
T428V;
S510V;
D106L;
N109I,F,Q;
L500F;
A108V,I;
G514A,V,L,I,F.
Preferred variants include any combination of the above mentioned mutations.

Variants with Altered pH Optimum

The desired pH optimum of a laccase depends on which application is of interest, e.g., if the laccase is to be used for denim bleaching the preferred pH optimum will be around pH 5–8, whereas if the laccase is to be used for washing purposes the preferred pH optimum will be around pH 8–10.

It is contemplated that it is possible to alter the pH optimum of a parent Coprinus laccase or a parent Coprinus-like laccase by creating a mutation in an amino acid within 10 Å from the active His in the Cu1 site.

Preferred positions for mutations are the following:
*Coprinus cinereus* laccase (SEQ ID No. 1):
180–181;
222–224;
257;
281–284;
352–353;
357–358;
409–416;
470–490.
*Polyporus pinsitus* (SEQ ID No. 2):
E460L,I,F,M,S;
F463L,M.
*Myceliophthora thermophila* (SEQ ID No. 10):
192–193;
234–236;
269;
293–294;
364–365;
372–373;
426–433;
503–513.
Preferred substitutions are the following: E, D, L, I, F, Y, W.

Variants with Altered Mediator Efficiency

Laccases are often used in combination with so called mediators or enhancers, e.g., in combination with phenothiazine or phenothiazine related compounds (see WO 95/01426) or in combination with acetosyringone or acetosyringone related compounds (see WO 96/10079).

It is contemplated that it is possible to alter the mediator efficiency (in order to make the mediator more efficient), of a parent Coprinus laccase or a parent Coprinus-like laccase by creating a mutation in an amino acid in one or more of the following positions:
*Coprinus cinereus* laccase (SEQ ID No. 1):
179–182;
223;
281–282;
353–358;

410–412;
472;
474–475;
477–478.
Preferred substitutions are the following: W, F, M, Y, R, K, S, T, N, Q; in particular the following substitutions:
F358W;
N478Q.
*Myceliophthora thermophila* laccase (SEQ ID No. 10):
185–194;
235;
293–294;
365–373;
427–429;
505;
507–508;
510–511.
Preferred substitutions are in particular one or more of the following mutations:
N189G,A,S,T;
S190G,A;
F371* (deletion);
F371G,A.
*Polyporus pinsitus* (SEQ ID No. 2):
G392A;
A461T,S;
N260Q,Y;
G165K,R.

Altered $O_2$/$OH^-$-pathway

It is contemplated that it is possible to lower the possibility of $OH^-$ entering the trinuclear Cu site by producing one or more of the following mutations:
*Myceliophthora thermophila* (SEQ ID No. 10):
A506E;
N109D;
H93E;
H95E;
M433E;
M480E.
*Polyporus pinsitus* (SEQ ID No. 2):
F81D,E;
L112D,E;
A80D,E.

Methods of Preparing Laccase Variants

Several methods for introducing mutations into genes are known in the art. After a brief discussion of the cloning of laccase-encoding DNA sequences, methods for generating mutations at specific sites within the laccase-encoding sequence will be discussed.

Cloning a DNA Sequence Encoding a Laccase

The DNA sequence encoding a parent laccase may be isolated from any cell or microorganism producing the laccase in question, using various methods well known in the art. First, a genomic DNA and/or cDNA library should be constructed using chromosomal DNA or messenger RNA from the organism that produces the laccase to be studied. Then, if the amino acid sequence of the laccase is known, homologous, labelled oligonucleotide probes may be synthesized and used to identify laccase-encoding clones from a genomic library prepared from the organism in question. Alternatively, a labelled oligonucleotide probe containing sequences homologous to a known laccase gene could be used as a probe to identify laccase-encoding clones, using hybridization and washing conditions of lower stringency.

A method for identifying laccase-encoding clones involves inserting cDNA into an expression vector, such as a plasmid, transforming laccase-negative fungi with the resulting cDNA library, and then plating the transformed fungi onto agar containing a substrate for laccase, thereby allowing clones expressing the laccase to be identified.

Alternatively, the DNA sequence encoding the enzyme may be prepared synthetically by established standard methods, e.g. the phosphoroamidite method. In the phosphoroamidite method, oligonucleotides are synthesized, e.g. in an automatic DNA synthesizer, purified, annealed, ligated and cloned in appropriate vectors.

Finally, the DNA sequence may be of mixed genomic and synthetic origin, mixed synthetic and cDNA origin or mixed genomic and cDNA origin, prepared by ligating fragments of synthetic, genomic or cDNA origin (as appropriate, the fragments corresponding to various parts of the entire DNA sequence), in accordance with standard techniques. The DNA sequence may also be prepared by polymerase chain reaction (PCR) using specific primers.

Site-directed Mutagenesis

Once a laccase-encoding DNA sequence has been isolated, and desirable sites for mutation identified, mutations may be introduced using synthetic oligonucleotides. These oligonucleotides contain nucleotide sequences flanking the desired mutation sites; mutant nucleotides are inserted during oligonucleotide synthesis. In a specific method, a single-stranded gap of DNA, bridging the laccase-encoding sequence, is created in a vector carrying the laccase gene. Then the synthetic nucleotide, bearing the desired mutation, is annealed to a homologous portion of the single-stranded DNA. The remaining gap is then filled in with T7 DNA polymerase and the construct is ligated using T4 ligase. A specific example of this method is described in Morinaga et al. (1984). U.S. Pat. No. 4,760,025 discloses the introduction of oligonucleotides encoding multiple mutations by performing minor alterations of the cassette. However, an even greater variety of mutations can be introduced at any one time by the Morinaga method, because a multitude of oligonucleotides, of various lengths, can be introduced.

Another method of introducing mutations into laccase-encoding DNA sequences is described in Nelson and Long (1989). It involves the 3-step generation of a PCR fragment containing the desired mutation introduced by using a chemically synthesized DNA strand as one of the primers in the PCR reactions. From the PCR-generated fragment, a DNA fragment carrying the mutation may be isolated by cleavage with restriction endonucleases and reinserted into an expression plasmid.

Random Mutagenesis

The random mutagenesis of a DNA sequence encoding a parent laccase may conveniently be performed by use of any method known in the art.

For instance, the random mutagenesis may be performed by use of a suitable physical or chemical mutagenizing agent, by use of a suitable oligonucleotide, or by subjecting the DNA sequence to PCR generated mutagenesis. Furthermore, the random mutagenesis may be performed by use of any combination of these mutagenizing agents.

The mutagenizing agent may, e.g., be one which induces transitions, transversions, inversions, scrambling, deletions, and/or insertions.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the DNA sequence encoding the parent enzyme to be mutagenized in the presence of the mutagenizing agent of choice under suitable conditions for the mutagenesis to take place, and selecting for mutated DNA having the desired properties.

When the mutagenesis is performed by the use of an oligonucleotide, the oligonucleotide may be doped or spiked with the three non-parent nucleotides during the synthesis of the oligonucleotide at the positions which are to be changed. The doping or spiking may be done so that codons for unwanted amino acids are avoided. The doped or spiked oligonucleotide can be incorporated into the DNA encoding the laccase enzyme by any published technique, using e.g. PCR, LCR or any DNA polymerase and ligase.

When PCR-generated mutagenesis is used, either a chemically treated or non-treated gene encoding a parent laccase enzyme is subjected to PCR under conditions that increase the misincorporation of nucleotides (Deshler 1992; Leung et al., Technique, Vol.1, 1989, pp. 11–15).

A mutator strain of *E. coli* (Fowler et al., Molec. Gen. Genet., 133, 1974, pp. 179–191), *S. cereviseae* or any other microbial organism may be used for the random mutagenesis of the DNA encoding the laccase enzyme by e.g. transforming a plasmid containing the parent enzyme into the mutator strain, growing the mutator strain with the plasmid and isolating the mutated plasmid from the mutator strain. The mutated plasmid may subsequently be transformed into the expression organism.

The DNA sequence to be mutagenized may conveniently be present in a genomic or cDNA library prepared from an organism expressing the parent laccase enzyme. Alternatively, the DNA sequence may be present on a suitable vector such as a plasmid or a bacteriophage, which as such may be incubated with or otherwise exposed to the mutagenizing agent. The DNA to be mutagenized may also be present in a host cell either by being integrated in the genome of said cell or by being present on a vector harboured in the cell. Finally, the DNA to be mutagenized may be in isolated form. It will be understood that the DNA sequence to be subjected to random mutagenesis is preferably a cDNA or a genomic cDNA sequence.

In some cases it may be convenient to amplify the mutated DNA sequence prior to the expression step or the screening step being performed. Such amplification may be performed in accordance with methods known in the art, the presently preferred method being PCR-generated amplification using oligonucleotide primers prepared on the basis of the DNA or amino acid sequence of the parent enzyme.

Subsequent to the incubation with or exposure to the mutagenizing agent, the mutated DNA is expressed by culturing a suitable host cell carrying the DNA sequence under conditions allowing expression to take place. The host cell used for this purpose may be one which has been transformed with the mutated DNA sequence, optionally present on a vector, or one which was carried the DNA sequence encoding the parent enzyme during the mutagenesis treatment. Examples of suitable host cells are fungal hosts such as *Aspergillus niger* or *Aspergillus oryzae*.

The mutated DNA sequence may further comprise a DNA sequence encoding functions permitting expression of the mutated DNA sequence.

Localized Random Mutagenesis

The random mutagenesis may advantageously be localized to a part of the parent laccase in question. This may, e.g., be advantageous when certain regions of the enzyme have been identified to be of particular importance for a given property of the enzyme, and when modified are expected to result in a variant having improved properties. Such regions may normally be identified when the tertiary structure of the parent enzyme has been elucidated and related to the function of the enzyme.

The localized random mutagenesis is conveniently performed by use of PCR-generated mutagenesis techniques as described above or any other suitable technique known in the art.

Alternatively, the DNA sequence encoding the part of the DNA sequence to be modified may be isolated, e.g. by being inserted into a suitable vector, and said part may subsequently be subjected to mutagenesis by use of any of the mutagenesis methods discussed above.

With respect to the screening step in the above-mentioned method of the invention, this may conveniently be performed by use of aa filter assay based on the following principle:

A microorganism capable of expressing the mutated laccase enzyme of interest is incubated on a suitable medium and under suitable conditions for the enzyme to be secreted, the medium being provided with a double filter comprising a first protein binding filter and on top of that a second filter exhibiting a low protein binding capability. The microorganism is located on the second filter. Subsequent to the incubation, the first filter comprising enzymes secreted from the microorganisms is separated from the second filter comprising the microorganisms. The first filter is subjected to screening for the desired enzymatic activity and the corresponding microbial colonies present on the second filter are identified.

The filter used for binding the enzymatic activity may be any protein binding filter e.g. nylon or nitrocellulose. The top filter carrying the colonies of the expression organism may be any filter that has no or low affinity for binding proteins e.g. cellulose acetate or Durapore™. The filter may be pretreated with any of the conditions to be used for screening or may be treated during the detection of enzymatic activity.

The enzymatic activity may be detected by a dye, fluorescence, precipitation, pH indicator, IR-absorbance or any other known technique for detection of enzymatic activity.

The detecting compound may be immobilized by any immobilizing agent, e.g., agarose, agar, gelatin, polyacrylamide, starch, filter paper, cloth; or any combination of immobilizing agents.

Laccase Activity

In the context of this invention, the laccase activity was measured using 10-(2-hydroxyethyl)-phenoxazine (HEPO) as substrate for the various laccases. HEPO was synthesized using the same procedure as described for 10-(2-hydroxyethyl)-phenothiazine, (G. Cauquil in Bulletin de la Society Chemique de France, 1960, p. 1049). In the presence of oxygen laccases (E. C. 1.10.3.2) oxidize HEPO to a HEPO radical that can be monitored photometrically at 528 nm.

The *Coprinus cinereus* laccase and the *Polyporus pinsitus* laccase were measured using 0.4 mM HEPO in 50 mM MES-NaOH, pH 5.5. The absorbance at 528 nm was followed for 200 s and the rate calculated from the linear part of the progress curve.

The *Myceliophthora thermophila* laccase was measured using 0.4 mM HEPO in 25 mM Tris-HCl, pH 7.5, 0.05% Tween-20 at 30° C. The absorbance at 528 nm was followed for 200 s and the rate calculated from the linear part of the progress curve.

Expression of Laccase Variants

According to the invention, a DNA sequence encoding the variant produced by methods described above, or by any alternative methods known in the art, can be expressed, in enzyme form, using an expression vector which typically includes control sequences encoding a promoter, operator, ribosome binding site, translation initiation signal, and, optionally, a repressor gene or various activator genes.

The recombinant expression vector carrying the DNA sequence encoding a laccase variant of the invention may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid, a bacteriophage or an extrachromosomal element, minichromosome or an artificial chromosome. Alternatively, the vector may be one which, when introduced into a host cell, is integrated into the host cell genome and replicated together with the chromosome(s) into which it has been integrated.

In the vector, the DNA sequence should be operably connected to a suitable promoter sequence. The promoter may be any DNA sequence which shows transcriptional activity in the host cell of choice and may be derived from genes encoding proteins either homologous or heterologous to the host cell. Examples of suitable promoters for directing the transcription of the DNA sequence encoding a laccase variant of the invention, especially in a fungal host, are those derived from the gene encoding *A. oryzae* TAKA amylase, *Rhizomucor miehei* aspartic proteinase, *A. niger* neutral α-amylase, *A. niger* acid stable α-amylase, *A. niger* glucoamylase, *Rhizomucor miehei* lipase, *A. oryzae* alkaline protease, *A. oryzae* triose phosphate isomerase or *A. nidulans* acetamidase.

The expression vector of the invention may also comprise a suitable transcription terminator and, in eukaryotes, polyadenylation sequences operably connected to the DNA sequence encoding the laccase variant of the invention. Termination and polyadenylation sequences may suitably be derived from the same sources as the promoter.

The vector may further comprise a DNA sequence enabling the vector to replicate in the host cell in question. Examples of such sequences are the origins of replication of plasmids pUC19, pACYC177, pUB110, pE194, pAMB1 and pIJ702.

The vector may also comprise a selectable marker, e.g. a gene, the product of which complements a defect in the host cell, such as one which confers antibiotic resistance such as ampicillin, kanamycin, chloramphenicol or tetracyclin resistance. Furthermore, the vector may comprise Aspergillus selection markers such as amdS, argB, niaD and sC, a marker giving rise to hygromycin resistance, or the selection may be accomplished by co-transformation, e.g. as described in WO 91/17243.

The procedures used to ligate the DNA construct of the invention encoding a laccase variant, the promoter, terminator and other elements, respectively, and to insert them into suitable vectors containing the information necessary for replication, are well known to persons skilled in the art (cf., for instance, Sambrook et al. (1989)).

The cell of the invention, either comprising a DNA construct or an expression vector of the invention as defined above, is advantageously used as a host cell in the recombinant production of a laccase variant of the invention. The cell may be transformed with the DNA construct of the invention encoding the variant, conveniently by integrating the DNA construct (in one or more copies) in the host chromosome. This integration is generally considered to be an advantage as the DNA sequence is more likely to be stably maintained in the cell. Integration of the DNA constructs into the host chromosome may be performed according to conventional methods, e.g. by homologous or heterologous recombination. Alternatively, the cell may be transformed with an expression vector as described above in connection with the different types of host cells.

The cell of the invention may be a cell of a higher organism such as a mammal or an insect, but is preferably a microbial cell, e.g. a fungal cell.

The filamentous fungus may advantageously belong to a species of Aspergillus, e.g. *Aspergillus oryzae* or *Aspergillus niger*. Fungal cells may be transformed by a process involving protoplast formation and transformation of the protoplasts followed by regeneration of the cell wall in a manner known per se. A suitable procedure for transformation of Aspergillus host cells is described in EP 238 023.

In a yet further aspect, the present invention relates to a method of producing a laccase variant of the invention, which method comprises cultivating a host cell as described above under conditions conducive to the production of the variant and recovering the variant from the cells and/or culture medium.

The medium used to cultivate the cells may be any conventional medium suitable for growing the host cell in question and obtaining expression of the laccase variant of the invention. Suitable media are available from commercial suppliers or may be prepared according to published recipes (e.g. as described in catalogues of the American Type Culture Collection)

The laccase variant secreted from the host cells may conveniently be recovered from the culture medium by well-known procedures, including separating the cells from the medium by centrifugation or filtration, and precipitating proteinaceous components of the medium by means of a salt such as ammonium sulphate, followed by the use of chromatographic procedures such as ion exchange chromatography, affinity chromatography, or the like.

Industrial Applications

The laccase variants of this invention possesses valuable properties allowing for various industrial applications, in particular lignin modification, paper strengthening, dye transfer inhibition in detergents, phenol polymerization, hair dyeing, textile dyeing, bleaching of textiles (in particular bleaching of denim as described in WO 96/12845 and WO 96/12846) and waste water treatment.

A detergent additive comprising a laccase variant of the present invention may be in the form of a non-dusting granulate, a stabilized liquid or a protected enzyme. This detergent additive may further comprise one or more other enzymes, such as a protease, a lipase, an amylase and/or a cellulase. A detergent composition comprising a laccase variant of the present invention may further comprise a surfactant. This detergent composition may additionally comprise one or more other enzymes, such as a protease, a lipase, an amylase and/or a cellulase.

APPENDIX 1

```
SEQRES       1   A   504  GLN ILE VAL ASN SER VAL ASP THR MET THR LEU THR ASN
SEQRES       2   A   504  ALA ASN VAL SER PRO ASP GLY PHE THR ARG ALA GLY ILE
SEQRES       3   A   504  LEU VAL ASN GLY VAL HIS GLY PRO LEU ILE ARG GLY GLY
SEQRES       4   A   504  LYS ASN ASP ASN PHE GLU LEU ASN VAL VAL ASN ASP LEU
SEQRES       5   A   504  ASP ASN PRO THR MET LEU ARG PRO THR SER ILE HIS TRP
SEQRES       6   A   504  HIS GLY LEU PHE GLN ARG GLY THR ASN TRP ALA ASN GLY
SEQRES       7   A   504  ALA ASP GLY VAL ASN GLN CYS PRO ILE SER PRO GLY HIS
SEQRES       8   A   504  ALA PHE LEU TYR LYS PHE THR PRO ALA GLY HIS ALA GLY
SEQRES       9   A   504  THR PHE TRP TYR HIS SER HIS PHE GLY THR GLN TYR CYS
SEQRES      10   A   504  ASP GLY LEU ARG GLY PRO MET VAL ILE TYR ASP ASP ASN
SEQRES      11   A   504  ASP PRO HIS ALA ALA LEU TYR ASP GLU ASP ASP GLU ASN
SEQRES      12   A   504  THR ILE ILE THR LEU ALA ASP TRP TYR HIS ILE PRO ALA
SEQRES      13   A   504  PRO SER ILE GLN GLY ALA ALA GLN PRO ASP ALA THR LEU
SEQRES      14   A   504  ILE ASN GLY LYS GLY ARG TYR VAL GLY GLY PRO ALA ALA
SEQRES      15   A   504  GLU LEU SER ILE VAL ASN VAL GLU GLN ASP LYS LYS TYR
SEQRES      16   A   504  ARG MET ARG LEU ILE SER LEU SER CYS ASP PRO ASN TRP
SEQRES      17   A   504  GLN PHE SER ILE ASP GLY HIS GLU LEU THR ILE ILE GLU
SEQRES      18   A   504  VAL ASP GLY ASN LEU THR GLU PRO HIS THR VAL ASP ARG
SEQRES      19   A   504  LEU GLN ILE PHE THR GLY GLN ARG TYR SER PHE VAL LEU
SEQRES      20   A   504  ASP ALA ASN GLN PRO VAL ASP ASN TYR TRP ILE ARG ALA
SEQRES      21   A   504  GLN PRO ASN LYS GLY ARG ASN GLY LEU ALA GLY THR PHE
SEQRES      22   A   504  ALA ASN GLY VAL ASN SER ALA ILE LEU ARG TYR ALA GLY
SEQRES      23   A   504  ALA ALA ASN ALA ASP PRO THR THR SER ALA ASN PRO ASN
SEQRES      24   A   504  PRO ALA GLN LEU ASN GLU ALA ASP LEU HIS ALA LEU ILE
SEQRES      25   A   504  ASP PRO ALA ALA PRO GLY ILE PRO THR PRO GLY ALA ALA
SEQRES      26   A   504  ASN VAL ASN LEU ARG PHE GLN LEU GLY PHE SER GLY GLY
SEQRES      27   A   504  ARG PHE THR ILE ASN GLY THR ALA TYR GLU SER PRO SER
SEQRES      28   A   504  VAL PRO THR LEU LEU GLN ILE MET SER GLY ALA GLN SER
SEQRES      29   A   504  ALA ASN ASP LEU LEU PRO ALA GLY SER VAL TYR GLU LEU
SEQRES      30   A   504  PRO ARG ASN GLN VAL VAL GLU LEU VAL VAL PRO ALA GLY
SEQRES      31   A   504  VAL LEU GLY GLY PRO HIS PRO PHE HIS LEU HIS GLY HIS
SEQRES      32   A   504  ALA PHE SER VAL VAL ARG SER ALA GLY SER SER THR TYR
SEQRES      33   A   504  ASN PHE VAL ASN PRO VAL LYS ARG ASP VAL VAL SER LEU
SEQRES      34   A   504  GLY VAL THR GLY ASP GLU VAL THR ILE ARG PHE VAL THR
SEQRES      35   A   504  ASP ASN PRO GLY PRO TRP PHE PHE HIS CYS HIS ILE GLU
SEQRES      36   A   504  PHE HIS LEU MET ASN GLY LEU ALA ILE VAL PHE ALA GLU
SEQRES      37   A   504  ASP MET ALA ASN THR VAL ASP ALA ASN ASN PRO PRO VAL
SEQRES      38   A   504  GLU TRP ALA GLN LEU CYS GLU ILE TYR ASP ASP LEU PRO
SEQRES      39   A   504  PRO GLU ALA THR SER ILE GLN THR VAL VAL
SSBOND     1    CYS  85   CYS  487
SSBOND     2    CYS 117   CYS  204
CRYST    45.390 85.720 143.070  90.00  90.00  90.00 P212121
SCALE1      0.02203  0.00000  0.00000    0.00000
SCALE2      0.00000  0.01167  0.00000    0.00000
SCALE3      0.00000  0.00000  0.00699    0.00000
ATOM       1  N    ALA  A    1   0   18.748 34.495  5.326 1.00 36.36
ATOM       2  CA   ALA  A    1   0   19.554 35.757  5.185 1.00 35.87
ATOM       3  C    ALA  A    1   0   19.785 36.380  6.558 1.00 34.53
ATOM       4  O    ALA  A    1   0   19.248 35.884  7.577 1.00 35.40
ATOM       5  CB   ALA  A    1   0   19.050 36.675  4.107 1.00 36.65
ATOM       6  N    ILE  A    2   0   20.844 37.201  6.659 1.00 31.00
ATOM       7  CA   ILE  A    2   0   21.310 37.654  7.963 1.00 27.71
ATOM       8  C    ILE  A    2   0   21.368 39.165  8.117 1.00 25.19
ATOM       9  O    ILE  A    2   0   21.789 39.861  7.192 1.00 23.77
ATOM      10  CB   ILE  A    2   0   22.744 37.107  8.206 1.00 28.28
ATOM      11  CG1  ILE  A    2   0   22.790 35.590  8.022 1.00 28.54
ATOM      12  CG2  ILE  A    2   0   23.285 37.557  9.554 1.00 27.91
ATOM      13  CD1  ILE  A    2   0   23.334 34.738  9.130 1.00 29.32
ATOM      14  N    VAL  A    3   0   20.986 39.659  9.283 1.00 22.31
ATOM      15  CA   VAL  A    3   0   21.093 41.092  9.540 1.00 22.78
ATOM      16  C    VAL  A    3   0   22.246 41.297 10.524 1.00 22.62
ATOM      17  O    VAL  A    3   0   22.460 40.556 11.467 1.00 21.74
ATOM      18  CB   VAL  A    3   0   19.801 41.849  9.799 1.00 23.54
ATOM      19  CG1  VAL  A    3   0   18.537 40.985  9.684 1.00 21.30
ATOM      20  CG2  VAL  A    3   0   19.760 42.709 11.055 1.00 21.32
ATOM      21  N    ASN  A    4   0   23.122 42.261 10.209 1.00 23.39
ATOM      22  CA   ASN  A    4   0   24.303 42.520 11.021 1.00 23.45
ATOM      23  C    ASN  A    4   0   24.002 43.517 12.126 1.00 24.44
ATOM      24  O    ASN  A    4   0   22.928 44.122 12.160 1.00 23.05
ATOM      25  CB   ASN  A    4   0   25.477 42.965 10.149 1.00 24.77
ATOM      26  CG   ASN  A    4   0   25.726 41.991  9.021 1.00 26.62
ATOM      27  OD1  ASN  A    4   0   25.668 42.388  7.849 1.00 30.29
ATOM      28  ND2  ASN  A    4   0   25.923 40.719  9.324 1.00 27.59
ATOM      29  N    SER  A    5   0   24.960 43.707 13.040 1.00 24.28
ATOM      30  CA   SER  A    5   0   24.702 44.636 14.143 1.00 25.77
ATOM      31  C    SER  A    5   0   24.595 46.090 13.701 1.00 24.41
ATOM      32  O    SER  A    5   0   23.973 46.862 14.452 1.00 23.55
ATOM      33  CB   SER  A    5   0   25.741 44.405 15.240 1.00 26.18
ATOM      34  OG   SER  A    5   0   26.976 44.750 14.641 1.00 27.89
```

APPENDIX 1-continued

| | | | | | | | | | | |
|---|---|---|---|---|---|---|---|---|---|---|
| ATOM | 35 | N | VAL | A | 6 | 0 | 25.104 | 46.517 | 12.539 | 1.00 | 24.01 |
| ATOM | 36 | CA | VAL | A | 6 | 0 | 24.770 | 47.863 | 12.096 | 1.00 | 25.06 |
| ATOM | 37 | C | VAL | A | 6 | 0 | 24.131 | 47.617 | 10.731 | 1.00 | 25.57 |
| ATOM | 38 | O | VAL | A | 6 | 0 | 24.778 | 47.030 | 9.874 | 1.00 | 28.07 |
| ATOM | 39 | CB | VAL | A | 6 | 0 | 25.722 | 49.032 | 12.155 | 1.00 | 26.65 |
| ATOM | 40 | CG1 | VAL | A | 6 | 0 | 26.937 | 48.759 | 13.025 | 1.00 | 26.73 |
| ATOM | 41 | CG2 | VAL | A | 6 | 0 | 26.098 | 49.614 | 10.801 | 1.00 | 25.50 |
| ATOM | 42 | N | ASP | A | 7 | 0 | 22.848 | 47.952 | 10.605 | 1.00 | 23.82 |
| ATOM | 43 | CA | ASP | A | 7 | 0 | 22.173 | 47.543 | 9.369 | 1.00 | 24.07 |
| ATOM | 44 | C | ASP | A | 7 | 0 | 20.794 | 48.170 | 9.276 | 1.00 | 23.66 |
| ATOM | 45 | O | ASP | A | 7 | 0 | 20.342 | 48.845 | 10.204 | 1.00 | 23.47 |
| ATOM | 46 | CB | ASP | A | 7 | 0 | 21.996 | 46.012 | 9.444 | 1.00 | 23.43 |
| ATOM | 47 | CG | ASP | A | 7 | 0 | 22.017 | 45.317 | 8.111 | 1.00 | 23.78 |
| ATOM | 48 | OD1 | ASP | A | 7 | 0 | 21.805 | 45.937 | 7.055 | 1.00 | 23.74 |
| ATOM | 49 | OD2 | ASP | A | 7 | 0 | 22.255 | 44.089 | 8.099 | 1.00 | 24.62 |
| ATOM | 50 | N | THR | A | 8 | 0 | 20.155 | 47.881 | 8.158 | 1.00 | 23.88 |
| ATOM | 51 | CA | THR | A | 8 | 0 | 18.799 | 48.359 | 7.928 | 1.00 | 24.45 |
| ATOM | 52 | C | THR | A | 8 | 0 | 17.813 | 47.189 | 7.950 | 1.00 | 22.49 |
| ATOM | 53 | O | THR | A | 8 | 0 | 18.143 | 46.142 | 7.377 | 1.00 | 22.56 |
| ATOM | 54 | CB | THR | A | 8 | 0 | 18.694 | 49.108 | 6.579 | 1.00 | 25.75 |
| ATOM | 55 | OG1 | THR | A | 8 | 0 | 19.573 | 50.242 | 6.719 | 1.00 | 28.53 |
| ATOM | 56 | CG2 | THR | A | 8 | 0 | 17.295 | 49.656 | 6.339 | 1.00 | 25.55 |
| ATOM | 57 | N | MET | A | 9 | 0 | 16.677 | 47.364 | 8.602 | 1.00 | 19.10 |
| ATOM | 58 | CA | MET | A | 9 | 0 | 15.650 | 46.311 | 8.616 | 1.00 | 20.47 |
| ATOM | 59 | C | MET | A | 9 | 0 | 14.392 | 46.863 | 7.925 | 1.00 | 21.97 |
| ATOM | 60 | O | MET | A | 9 | 0 | 13.638 | 47.638 | 8.544 | 1.00 | 19.49 |
| ATOM | 61 | CB | MET | A | 9 | 0 | 15.308 | 45.871 | 10.022 | 1.00 | 20.49 |
| ATOM | 62 | CG | MET | A | 9 | 0 | 16.351 | 44.982 | 10.682 | 1.00 | 22.11 |
| ATOM | 63 | SD | MET | A | 9 | 0 | 16.192 | 44.917 | 12.482 | 1.00 | 24.71 |
| ATOM | 64 | CE | MET | A | 9 | 0 | 14.640 | 44.024 | 12.635 | 1.00 | 22.61 |
| ATOM | 65 | N | THR | A | 10 | 0 | 14.246 | 46.516 | 6.641 | 1.00 | 21.81 |
| ATOM | 66 | CA | THR | A | 10 | 0 | 13.073 | 47.064 | 5.926 | 1.00 | 23.43 |
| ATOM | 67 | C | THR | A | 10 | 0 | 11.912 | 46.081 | 6.046 | 1.00 | 22.90 |
| ATOM | 68 | O | THR | A | 10 | 0 | 12.056 | 44.890 | 5.719 | 1.00 | 23.55 |
| ATOM | 69 | CB | THR | A | 10 | 0 | 13.390 | 47.384 | 4.459 | 1.00 | 24.69 |
| ATOM | 70 | OG1 | THR | A | 10 | 0 | 14.533 | 48.261 | 4.456 | 1.00 | 26.08 |
| ATOM | 71 | CG2 | THR | A | 10 | 0 | 12.216 | 48.028 | 3.742 | 1.00 | 23.95 |
| ATOM | 72 | N | LEU | A | 11 | 0 | 10.820 | 46.600 | 6.583 | 1.00 | 21.13 |
| ATOM | 73 | CA | LEU | A | 11 | 0 | 9.615 | 45.836 | 6.846 | 1.00 | 21.10 |
| ATOM | 74 | C | LEU | A | 11 | 0 | 8.607 | 45.957 | 5.709 | 1.00 | 24.58 |
| ATOM | 75 | O | LEU | A | 11 | 0 | 8.124 | 47.056 | 5.358 | 1.00 | 23.89 |
| ATOM | 76 | CB | LEU | A | 11 | 0 | 9.045 | 46.411 | 8.129 | 1.00 | 21.29 |
| ATOM | 77 | CG | LEU | A | 11 | 0 | 9.474 | 45.955 | 9.508 | 1.00 | 22.26 |
| ATOM | 78 | CD1 | LEU | A | 11 | 0 | 10.952 | 45.742 | 9.692 | 1.00 | 22.42 |
| ATOM | 79 | CD2 | LEU | A | 11 | 0 | 8.978 | 46.931 | 10.583 | 1.00 | 22.75 |
| ATOM | 80 | N | THR | A | 12 | 0 | 8.272 | 44.836 | 5.057 | 1.00 | 24.01 |
| ATOM | 81 | CA | THR | A | 12 | 0 | 7.302 | 44.851 | 3.980 | 1.00 | 24.33 |
| ATOM | 82 | C | THR | A | 12 | 0 | 6.322 | 43.677 | 4.123 | 1.00 | 25.34 |
| ATOM | 83 | O | THR | A | 12 | 0 | 6.480 | 42.740 | 4.913 | 1.00 | 25.62 |
| ATOM | 84 | CB | THR | A | 12 | 0 | 7.882 | 44.776 | 2.560 | 1.00 | 25.12 |
| ATOM | 85 | OG1 | THR | A | 12 | 0 | 8.575 | 43.548 | 2.377 | 1.00 | 24.05 |
| ATOM | 86 | CG2 | THR | A | 12 | 0 | 8.847 | 45.905 | 2.217 | 1.00 | 25.26 |
| ATOM | 87 | N | ASN | A | 13 | 0 | 5.261 | 43.760 | 3.335 | 1.00 | 24.09 |
| ATOM | 88 | CA | ASN | A | 13 | 0 | 4.232 | 42.722 | 3.299 | 1.00 | 22.87 |
| ATOM | 89 | C | ASN | A | 13 | 0 | 4.422 | 41.954 | 1.989 | 1.00 | 22.13 |
| ATOM | 90 | O | ASN | A | 13 | 0 | 4.809 | 42.600 | 1.023 | 1.00 | 22.32 |
| ATOM | 91 | CB | ASN | A | 13 | 0 | 2.852 | 43.355 | 3.311 | 1.00 | 21.58 |
| ATOM | 92 | CG | ASN | A | 13 | 0 | 2.526 | 44.060 | 4.607 | 1.00 | 22.50 |
| ATOM | 93 | OD1 | ASN | A | 13 | 0 | 2.187 | 45.245 | 4.648 | 1.00 | 22.20 |
| ATOM | 94 | ND2 | ASN | A | 13 | 0 | 2.615 | 43.306 | 5.705 | 1.00 | 21.81 |
| ATOM | 95 | N | ALA | A | 14 | 0 | 4.218 | 40.655 | 1.985 | 1.00 | 21.00 |
| ATOM | 96 | CA | ALA | A | 14 | 0 | 4.270 | 39.869 | 0.762 | 1.00 | 21.93 |
| ATOM | 97 | C | ALA | A | 14 | 0 | 3.571 | 38.533 | 1.078 | 1.00 | 20.77 |
| ATOM | 98 | O | ALA | A | 14 | 0 | 3.292 | 38.309 | 2.259 | 1.00 | 20.45 |
| ATOM | 99 | CB | ALA | A | 14 | 0 | 5.676 | 39.618 | 0.248 | 1.00 | 23.72 |
| ATOM | 100 | N | ASN | A | 15 | 0 | 3.366 | 37.695 | 0.072 | 1.00 | 18.88 |
| ATOM | 101 | CA | ASN | A | 15 | 0 | 2.748 | 36.412 | 0.337 | 1.00 | 19.67 |
| ATOM | 102 | C | ASN | A | 15 | 0 | 3.798 | 35.457 | 0.873 | 1.00 | 19.19 |
| ATOM | 103 | O | ASN | A | 15 | 0 | 4.891 | 35.474 | 0.338 | 1.00 | 19.57 |
| ATOM | 104 | CB | ASN | A | 15 | 0 | 2.114 | 35.721 | -0.875 | 1.00 | 21.13 |
| ATOM | 105 | CG | ASN | A | 15 | 0 | 0.839 | 36.457 | -1.284 | 1.00 | 21.15 |
| ATOM | 106 | OD1 | ASN | A | 15 | 0 | 0.343 | 37.207 | -0.472 | 1.00 | 20.87 |
| ATOM | 107 | ND2 | ASN | A | 15 | 0 | 0.379 | 36.284 | -2.501 | 1.00 | 20.00 |
| ATOM | 108 | N | VAL | A | 16 | 0 | 3.358 | 34.614 | 1.772 | 1.00 | 19.11 |
| ATOM | 109 | CA | VAL | A | 16 | 0 | 4.322 | 33.628 | 2.342 | 1.00 | 18.90 |
| ATOM | 110 | C | VAL | A | 16 | 0 | 3.626 | 32.293 | 2.345 | 1.00 | 19.25 |
| ATOM | 111 | O | VAL | A | 16 | 0 | 2.386 | 32.281 | 2.406 | 1.00 | 15.71 |
| ATOM | 112 | CB | VAL | A | 16 | 0 | 4.612 | 34.317 | 3.691 | 1.00 | 19.95 |
| ATOM | 113 | CG1 | VAL | A | 16 | 0 | 3.990 | 33.749 | 4.937 | 1.00 | 18.58 |

APPENDIX 1-continued

| | | | | | | | | | | |
|---|---|---|---|---|---|---|---|---|---|---|
| ATOM | 114 | CG2 | VAL | A | 16 | 0 | 6.091 | 34.603 | 3.814 | 1.00 | 21.38 |
| ATOM | 115 | N | SER | A | 17 | 0 | 4.312 | 31.157 | 2.303 | 1.00 | 18.57 |
| ATOM | 116 | CA | SER | A | 17 | 0 | 3.678 | 29.869 | 2.410 | 1.00 | 20.90 |
| ATOM | 117 | C | SER | A | 17 | 0 | 4.608 | 28.866 | 3.065 | 1.00 | 21.12 |
| ATOM | 118 | O | SER | A | 17 | 0 | 5.106 | 27.939 | 2.448 | 1.00 | 21.24 |
| ATOM | 119 | CB | SER | A | 17 | 0 | 3.186 | 29.285 | 1.080 | 1.00 | 23.95 |
| ATOM | 120 | OG | SER | A | 17 | 0 | 4.204 | 29.399 | 0.125 | 1.00 | 26.79 |
| ATOM | 121 | N | PRO | A | 18 | 0 | 4.834 | 29.051 | 4.358 | 1.00 | 20.78 |
| ATOM | 122 | CA | PRO | A | 18 | 0 | 5.703 | 28.216 | 5.141 | 1.00 | 20.02 |
| ATOM | 123 | C | PRO | A | 18 | 0 | 5.197 | 26.793 | 5.376 | 1.00 | 19.74 |
| ATOM | 124 | O | PRO | A | 18 | 0 | 5.978 | 25.920 | 5.753 | 1.00 | 17.97 |
| ATOM | 125 | CB | PRO | A | 18 | 0 | 5.889 | 28.954 | 6.481 | 1.00 | 19.27 |
| ATOM | 126 | CG | PRO | A | 18 | 0 | 4.701 | 29.832 | 6.536 | 1.00 | 21.41 |
| ATOM | 127 | CD | PRO | A | 18 | 0 | 4.249 | 30.153 | 5.128 | 1.00 | 20.70 |
| ATOM | 128 | N | ASP | A | 19 | 0 | 3.899 | 26.534 | 5.241 | 1.00 | 18.82 |
| ATOM | 129 | CA | ASP | A | 19 | 0 | 3.323 | 25.227 | 5.475 | 1.00 | 16.87 |
| ATOM | 130 | C | ASP | A | 19 | 0 | 2.548 | 24.823 | 4.237 | 1.00 | 17.28 |
| ATOM | 131 | O | ASP | A | 19 | 0 | 1.713 | 23.929 | 4.337 | 1.00 | 17.84 |
| ATOM | 132 | CB | ASP | A | 19 | 0 | 2.419 | 25.207 | 6.701 | 1.00 | 16.54 |
| ATOM | 133 | CG | ASP | A | 19 | 0 | 1.192 | 26.120 | 6.596 | 1.00 | 16.67 |
| ATOM | 134 | OD1 | ASP | A | 19 | 0 | 1.032 | 26.935 | 5.654 | 1.00 | 14.17 |
| ATOM | 135 | OD2 | ASP | A | 19 | 0 | 0.360 | 26.045 | 7.529 | 1.00 | 14.56 |
| ATOM | 136 | N | GLY | A | 20 | 0 | 2.782 | 25.469 | 3.100 | 1.00 | 17.87 |
| ATOM | 137 | CA | GLY | A | 20 | 0 | 2.079 | 25.091 | 1.890 | 1.00 | 19.40 |
| ATOM | 138 | C | GLY | A | 20 | 0 | 0.732 | 25.789 | 1.699 | 1.00 | 22.52 |
| ATOM | 139 | O | GLY | A | 20 | 0 | 0.158 | 25.619 | 0.628 | 1.00 | 22.87 |
| ATOM | 140 | N | PHE | A | 21 | 0 | 0.240 | 26.587 | 2.631 | 1.00 | 21.35 |
| ATOM | 141 | CA | PHE | A | 21 | 0 | -0.913 | 27.443 | 2.534 | 1.00 | 20.39 |
| ATOM | 142 | C | PHE | A | 21 | 0 | -0.348 | 28.855 | 2.322 | 1.00 | 21.23 |
| ATOM | 143 | O | PHE | A | 21 | 0 | 0.475 | 29.316 | 3.122 | 1.00 | 21.26 |
| ATOM | 144 | CB | PHE | A | 21 | 0 | -1.742 | 27.472 | 3.814 | 1.00 | 20.80 |
| ATOM | 145 | CG | PHE | A | 21 | 0 | -3.059 | 28.180 | 3.695 | 1.00 | 21.91 |
| ATOM | 146 | CD1 | PHE | A | 21 | 0 | -3.171 | 29.527 | 3.963 | 1.00 | 22.49 |
| ATOM | 147 | CD2 | PHE | A | 21 | 0 | -4.207 | 27.470 | 3.327 | 1.00 | 22.51 |
| ATOM | 148 | CE1 | PHE | A | 21 | 0 | -4.370 | 30.207 | 3.845 | 1.00 | 22.27 |
| ATOM | 149 | CE2 | PHE | A | 21 | 0 | -5.419 | 28.128 | 3.203 | 1.00 | 22.79 |
| ATOM | 150 | CZ | PHE | A | 21 | 0 | -5.498 | 29.497 | 3.474 | 1.00 | 23.34 |
| ATOM | 151 | N | THR | A | 22 | 0 | -0.638 | 29.514 | 1.225 | 1.00 | 20.20 |
| ATOM | 152 | CA | THR | A | 22 | 0 | -0.143 | 30.850 | 0.977 | 1.00 | 21.36 |
| ATOM | 153 | C | THR | A | 22 | 0 | -1.083 | 31.939 | 1.488 | 1.00 | 21.79 |
| ATOM | 154 | O | THR | A | 22 | 0 | -2.271 | 31.952 | 1.162 | 1.00 | 21.19 |
| ATOM | 155 | CB | THR | A | 22 | 0 | 0.045 | 31.012 | -0.553 | 1.00 | 21.46 |
| ATOM | 156 | OG1 | THR | A | 22 | 0 | 0.838 | 29.881 | -0.934 | 1.00 | 20.09 |
| ATOM | 157 | CG2 | THR | A | 22 | 0 | 0.693 | 32.353 | -0.891 | 1.00 | 20.94 |
| ATOM | 158 | N | ARG | A | 23 | 0 | -0.562 | 32.871 | 2.257 | 1.00 | 20.80 |
| ATOM | 159 | CA | ARG | A | 23 | 0 | -1.230 | 34.008 | 2.844 | 1.00 | 20.78 |
| ATOM | 160 | C | ARG | A | 23 | 0 | -0.257 | 35.189 | 2.960 | 1.00 | 21.15 |
| ATOM | 161 | O | ARG | A | 23 | 0 | 0.954 | 35.018 | 2.740 | 1.00 | 20.42 |
| ATOM | 162 | CB | ARG | A | 23 | 0 | -1.874 | 33.685 | 4.172 | 1.00 | 20.47 |
| ATOM | 163 | CG | ARG | A | 23 | 0 | -0.964 | 33.152 | 5.295 | 1.00 | 21.52 |
| ATOM | 164 | CD | ARG | A | 23 | 0 | -0.552 | 34.357 | 6.113 | 1.00 | 22.75 |
| ATOM | 165 | NE | ARG | A | 23 | 0 | -0.905 | 34.419 | 7.477 | 1.00 | 21.60 |
| ATOM | 166 | CZ | ARG | A | 23 | 0 | -0.870 | 35.283 | 8.464 | 1.00 | 19.89 |
| ATOM | 167 | NH1 | ARG | A | 23 | 0 | -0.526 | 36.565 | 8.453 | 1.00 | 20.19 |
| ATOM | 168 | NH2 | ARG | A | 23 | 0 | -1.249 | 34.744 | 9.610 | 1.00 | 18.64 |
| ATOM | 169 | N | ALA | A | 24 | 0 | -0.784 | 36.389 | 3.199 | 1.00 | 20.05 |
| ATOM | 170 | CA | ALA | A | 24 | 0 | 0.140 | 37.541 | 3.243 | 1.00 | 22.03 |
| ATOM | 171 | C | ALA | A | 24 | 0 | 0.786 | 37.561 | 4.635 | 1.00 | 21.09 |
| ATOM | 172 | O | ALA | A | 24 | 0 | 0.200 | 37.124 | 5.637 | 1.00 | 21.16 |
| ATOM | 173 | CB | ALA | A | 24 | 0 | -0.578 | 38.836 | 2.902 | 1.00 | 22.98 |
| ATOM | 174 | N | GLY | A | 25 | 0 | 2.042 | 37.984 | 4.683 | 1.00 | 20.28 |
| ATOM | 175 | CA | GLY | A | 25 | 0 | 2.786 | 37.993 | 5.950 | 1.00 | 20.29 |
| ATOM | 176 | C | GLY | A | 25 | 0 | 3.649 | 39.254 | 5.979 | 1.00 | 21.38 |
| ATOM | 177 | O | GLY | A | 25 | 0 | 3.465 | 40.229 | 5.238 | 1.00 | 21.06 |
| ATOM | 178 | N | ILE | A | 26 | 0 | 4.604 | 39.221 | 6.897 | 1.00 | 20.33 |
| ATOM | 179 | CA | ILE | A | 26 | 0 | 5.475 | 40.365 | 7.145 | 1.00 | 20.64 |
| ATOM | 180 | C | ILE | A | 26 | 0 | 6.903 | 39.886 | 6.932 | 1.00 | 20.00 |
| ATOM | 181 | O | ILE | A | 26 | 0 | 7.247 | 38.851 | 7.485 | 1.00 | 21.34 |
| ATOM | 182 | CB | ILE | A | 26 | 0 | 5.278 | 40.933 | 8.564 | 1.00 | 20.38 |
| ATOM | 183 | CG1 | ILE | A | 26 | 0 | 3.883 | 41.536 | 8.667 | 1.00 | 20.72 |
| ATOM | 184 | CG2 | ILE | A | 26 | 0 | 6.333 | 42.007 | 8.821 | 1.00 | 22.34 |
| ATOM | 185 | CD1 | ILE | A | 26 | 0 | 3.310 | 41.822 | 10.024 | 1.00 | 20.76 |
| ATOM | 186 | N | LEU | A | 27 | 0 | 7.644 | 40.551 | 6.079 | 1.00 | 19.10 |
| ATOM | 187 | CA | LEU | A | 27 | 0 | 9.005 | 40.168 | 5.739 | 1.00 | 19.67 |
| ATOM | 188 | C | LEU | A | 27 | 0 | 9.964 | 41.226 | 6.280 | 1.00 | 19.85 |
| ATOM | 189 | O | LEU | A | 27 | 0 | 9.591 | 42.407 | 6.356 | 1.00 | 19.19 |
| ATOM | 190 | CB | LEU | A | 27 | 0 | 9.138 | 40.172 | 4.219 | 1.00 | 20.26 |
| ATOM | 191 | CG | LEU | A | 27 | 0 | 9.046 | 38.883 | 3.415 | 1.00 | 22.65 |
| ATOM | 192 | CD1 | LEU | A | 27 | 0 | 8.127 | 37.835 | 3.989 | 1.00 | 21.10 |

APPENDIX 1-continued

| ATOM | 193 | CD2 | LEU | A | 27 | 0 | 8.738 | 39.198 | 1.963 | 1.00 | 22.01 |
|---|---|---|---|---|---|---|---|---|---|---|---|
| ATOM | 194 | N | VAL | A | 28 | 0 | 11.162 | 40.804 | 6.630 | 1.00 | 18.03 |
| ATOM | 195 | CA | VAL | A | 28 | 0 | 12.199 | 41.723 | 7.088 | 1.00 | 17.24 |
| ATOM | 196 | C | VAL | A | 28 | 0 | 13.289 | 41.573 | 6.040 | 1.00 | 18.99 |
| ATOM | 197 | O | VAL | A | 28 | 0 | 13.791 | 40.453 | 5.863 | 1.00 | 20.36 |
| ATOM | 198 | CB | VAL | A | 28 | 0 | 12.762 | 41.415 | 8.491 | 1.00 | 16.50 |
| ATOM | 199 | CG1 | VAL | A | 28 | 0 | 13.899 | 42.361 | 8.845 | 1.00 | 15.41 |
| ATOM | 200 | CG2 | VAL | A | 28 | 0 | 11.681 | 41.517 | 9.558 | 1.00 | 15.42 |
| ATOM | 201 | N | ASN | A | 29 | 0 | 13.575 | 42.601 | 5.256 | 1.00 | 20.78 |
| ATOM | 202 | CA | ASN | A | 29 | 0 | 14.567 | 42.579 | 4.198 | 1.00 | 20.46 |
| ATOM | 203 | C | ASN | A | 29 | 0 | 14.316 | 41.435 | 3.226 | 1.00 | 23.05 |
| ATOM | 204 | O | ASN | A | 29 | 0 | 15.247 | 40.675 | 2.880 | 1.00 | 23.62 |
| ATOM | 205 | CB | ASN | A | 29 | 0 | 15.982 | 42.446 | 4.764 | 1.00 | 21.06 |
| ATOM | 206 | CG | ASN | A | 29 | 0 | 16.475 | 43.654 | 5.522 | 1.00 | 22.44 |
| ATOM | 207 | OD1 | ASN | A | 29 | 0 | 15.870 | 44.722 | 5.434 | 1.00 | 23.47 |
| ATOM | 208 | ND2 | ASN | A | 29 | 0 | 17.560 | 43.507 | 6.288 | 1.00 | 22.23 |
| ATOM | 209 | N | GLY | A | 30 | 0 | 13.053 | 41.215 | 2.878 | 1.00 | 23.18 |
| ATOM | 210 | CA | GLY | A | 30 | 0 | 12.662 | 40.181 | 1.922 | 1.00 | 23.36 |
| ATOM | 211 | C | GLY | A | 30 | 0 | 12.723 | 38.757 | 2.436 | 1.00 | 23.85 |
| ATOM | 212 | O | GLY | A | 30 | 0 | 12.707 | 37.814 | 1.633 | 1.00 | 25.17 |
| ATOM | 213 | N | VAL | A | 31 | 0 | 12.832 | 38.585 | 3.755 | 1.00 | 21.85 |
| ATOM | 214 | CA | VAL | A | 31 | 0 | 12.999 | 37.276 | 4.352 | 1.00 | 20.55 |
| ATOM | 215 | C | VAL | A | 31 | 0 | 12.031 | 37.190 | 5.548 | 1.00 | 19.91 |
| ATOM | 216 | O | VAL | A | 31 | 0 | 11.796 | 38.172 | 6.269 | 1.00 | 17.50 |
| ATOM | 217 | CB | VAL | A | 31 | 0 | 14.436 | 37.020 | 4.856 | 1.00 | 21.36 |
| ATOM | 218 | CG1 | VAL | A | 31 | 0 | 14.556 | 35.709 | 5.626 | 1.00 | 20.79 |
| ATOM | 219 | CG2 | VAL | A | 31 | 0 | 15.495 | 37.005 | 3.757 | 1.00 | 21.84 |
| ATOM | 220 | N | HIS | A | 32 | 0 | 11.489 | 35.984 | 5.698 | 1.00 | 17.05 |
| ATOM | 221 | CA | HIS | A | 32 | 0 | 10.592 | 35.729 | 6.797 | 1.00 | 18.61 |
| ATOM | 222 | C | HIS | A | 32 | 0 | 11.417 | 35.499 | 8.050 | 1.00 | 17.67 |
| ATOM | 223 | O | HIS | A | 32 | 0 | 11.873 | 34.385 | 8.216 | 1.00 | 18.72 |
| ATOM | 224 | CB | HIS | A | 32 | 0 | 9.676 | 34.543 | 6.493 | 1.00 | 21.00 |
| ATOM | 225 | CG | HIS | A | 32 | 0 | 8.639 | 34.208 | 7.517 | 1.00 | 23.80 |
| ATOM | 226 | ND1 | HIS | A | 32 | 0 | 7.744 | 33.174 | 7.332 | 1.00 | 25.14 |
| ATOM | 227 | CD2 | HIS | A | 32 | 0 | 8.331 | 34.720 | 8.735 | 1.00 | 25.32 |
| ATOM | 228 | CE1 | HIS | A | 32 | 0 | 6.942 | 33.061 | 8.385 | 1.00 | 25.36 |
| ATOM | 229 | NE2 | HIS | A | 32 | 0 | 7.271 | 33.986 | 9.260 | 1.00 | 26.23 |
| ATOM | 230 | N | GLY | A | 33 | 0 | 11.522 | 36.446 | 8.960 | 1.00 | 16.23 |
| ATOM | 231 | CA | GLY | A | 33 | 0 | 12.276 | 36.252 | 10.198 | 1.00 | 16.97 |
| ATOM | 232 | C | GLY | A | 33 | 0 | 13.740 | 35.869 | 10.083 | 1.00 | 15.54 |
| ATOM | 233 | O | GLY | A | 33 | 0 | 14.228 | 34.885 | 10.609 | 1.00 | 15.13 |
| ATOM | 234 | N | PRO | A | 34 | 0 | 14.555 | 36.734 | 9.475 | 1.00 | 15.75 |
| ATOM | 235 | CA | PRO | A | 34 | 0 | 16.012 | 36.561 | 9.359 | 1.00 | 14.70 |
| ATOM | 236 | C | PRO | A | 34 | 0 | 16.734 | 36.660 | 10.701 | 1.00 | 14.02 |
| ATOM | 237 | O | PRO | A | 34 | 0 | 16.241 | 37.252 | 11.673 | 1.00 | 10.44 |
| ATOM | 238 | CB | PRO | A | 34 | 0 | 16.491 | 37.699 | 8.435 | 1.00 | 14.40 |
| ATOM | 239 | CG | PRO | A | 34 | 0 | 15.441 | 38.742 | 8.783 | 1.00 | 15.11 |
| ATOM | 240 | CD | PRO | A | 34 | 0 | 14.113 | 38.005 | 8.905 | 1.00 | 13.69 |
| ATOM | 241 | N | LEU | A | 35 | 0 | 17.925 | 36.049 | 10.767 | 1.00 | 13.60 |
| ATOM | 242 | CA | LEU | A | 35 | 0 | 18.748 | 36.022 | 11.963 | 1.00 | 14.35 |
| ATOM | 243 | C | LEU | A | 35 | 0 | 19.462 | 37.359 | 12.161 | 1.00 | 16.25 |
| ATOM | 244 | O | LEU | A | 35 | 0 | 20.015 | 37.902 | 11.210 | 1.00 | 14.10 |
| ATOM | 245 | CB | LEU | A | 35 | 0 | 19.834 | 34.916 | 11.862 | 1.00 | 15.33 |
| ATOM | 246 | CG | LEU | A | 35 | 0 | 20.958 | 34.943 | 12.911 | 1.00 | 17.74 |
| ATOM | 247 | CD1 | LEU | A | 35 | 0 | 20.486 | 34.698 | 14.348 | 1.00 | 16.30 |
| ATOM | 248 | CD2 | LEU | A | 35 | 0 | 22.052 | 33.934 | 12.575 | 1.00 | 16.60 |
| ATOM | 249 | N | ILE | A | 36 | 0 | 19.471 | 37.855 | 13.384 | 1.00 | 16.71 |
| ATOM | 250 | CA | ILE | A | 36 | 0 | 20.265 | 39.027 | 13.738 | 1.00 | 16.66 |
| ATOM | 251 | C | ILE | A | 36 | 0 | 21.403 | 38.487 | 14.620 | 1.00 | 17.92 |
| ATOM | 252 | O | ILE | A | 36 | 0 | 21.183 | 37.732 | 15.573 | 1.00 | 17.20 |
| ATOM | 253 | CB | ILE | A | 36 | 0 | 19.560 | 40.129 | 14.533 | 1.00 | 16.60 |
| ATOM | 254 | CG1 | ILE | A | 36 | 0 | 18.389 | 40.771 | 13.771 | 1.00 | 16.09 |
| ATOM | 255 | CG2 | ILE | A | 36 | 0 | 20.565 | 41.226 | 14.917 | 1.00 | 17.67 |
| ATOM | 256 | CD1 | ILE | A | 36 | 0 | 17.590 | 41.754 | 14.629 | 1.00 | 15.88 |
| ATOM | 257 | N | ARG | A | 37 | 0 | 22.647 | 38.829 | 14.288 | 1.00 | 18.72 |
| ATOM | 258 | CA | ARG | A | 37 | 0 | 23.754 | 38.315 | 15.091 | 1.00 | 19.94 |
| ATOM | 259 | C | ARG | A | 37 | 0 | 24.839 | 39.369 | 15.280 | 1.00 | 20.08 |
| ATOM | 260 | O | ARG | A | 37 | 0 | 24.979 | 40.249 | 14.450 | 1.00 | 20.52 |
| ATOM | 261 | CB | ARG | A | 37 | 0 | 24.395 | 37.077 | 14.465 | 1.00 | 21.72 |
| ATOM | 262 | CG | ARG | A | 37 | 0 | 25.102 | 37.393 | 13.171 | 1.00 | 24.46 |
| ATOM | 263 | CD | ARG | A | 37 | 0 | 26.113 | 36.339 | 12.762 | 1.00 | 26.90 |
| ATOM | 264 | NE | ARG | A | 37 | 0 | 26.584 | 36.571 | 11.381 | 1.00 | 29.30 |
| ATOM | 265 | CZ | ARG | A | 37 | 0 | 26.838 | 35.571 | 10.528 | 1.00 | 31.29 |
| ATOM | 266 | NH1 | ARG | A | 37 | 0 | 26.711 | 34.283 | 10.851 | 1.00 | 31.37 |
| ATOM | 267 | NH2 | ARG | A | 37 | 0 | 27.252 | 35.827 | 9.291 | 1.00 | 31.66 |
| ATOM | 268 | N | GLY | A | 38 | 0 | 25.587 | 39.223 | 16.361 | 1.00 | 20.22 |
| ATOM | 269 | CA | GLY | A | 38 | 0 | 26.716 | 40.121 | 16.611 | 1.00 | 18.98 |
| ATOM | 270 | C | GLY | A | 38 | 0 | 27.533 | 39.545 | 17.765 | 1.00 | 18.08 |
| ATOM | 271 | O | GLY | A | 38 | 0 | 27.259 | 38.421 | 18.225 | 1.00 | 15.92 |

APPENDIX 1-continued

| ATOM | 272 | N | GLY | A | 39 | 0 | 28.436 | 40.412 | 18.238 | 1.00 | 17.65 |
|------|-----|-----|-----|---|----|----|--------|--------|--------|------|-------|
| ATOM | 273 | CA | GLY | A | 39 | 0 | 29.322 | 40.026 | 19.351 | 1.00 | 16.23 |
| ATOM | 274 | C | GLY | A | 39 | 0 | 28.861 | 40.774 | 20.592 | 1.00 | 17.21 |
| ATOM | 275 | O | GLY | A | 39 | 0 | 28.157 | 41.784 | 20.489 | 1.00 | 17.27 |
| ATOM | 276 | N | LYS | A | 40 | 0 | 29.276 | 40.328 | 21.764 | 1.00 | 16.58 |
| ATOM | 277 | CA | LYS | A | 40 | 0 | 28.839 | 40.805 | 23.057 | 1.00 | 18.03 |
| ATOM | 278 | C | LYS | A | 40 | 0 | 29.185 | 42.267 | 23.348 | 1.00 | 20.44 |
| ATOM | 279 | O | LYS | A | 40 | 0 | 28.562 | 42.878 | 24.221 | 1.00 | 19.42 |
| ATOM | 280 | CB | LYS | A | 40 | 0 | 29.394 | 39.933 | 24.185 | 1.00 | 16.74 |
| ATOM | 281 | CG | LYS | A | 40 | 0 | 30.892 | 39.997 | 24.370 | 1.00 | 17.98 |
| ATOM | 282 | CD | LYS | A | 40 | 0 | 31.333 | 39.170 | 25.569 | 1.00 | 20.66 |
| ATOM | 283 | CE | LYS | A | 40 | 0 | 32.809 | 38.768 | 25.493 | 1.00 | 21.70 |
| ATOM | 284 | NZ | LYS | A | 40 | 0 | 33.227 | 38.111 | 26.757 | 1.00 | 23.11 |
| ATOM | 285 | N | ASN | A | 41 | 0 | 30.181 | 42.780 | 22.645 | 1.00 | 21.43 |
| ATOM | 286 | CA | ASN | A | 41 | 0 | 30.536 | 44.171 | 22.840 | 1.00 | 25.14 |
| ATOM | 287 | C | ASN | A | 41 | 0 | 30.092 | 44.976 | 21.644 | 1.00 | 24.05 |
| ATOM | 288 | O | ASN | A | 41 | 0 | 30.409 | 46.161 | 21.655 | 1.00 | 25.66 |
| ATOM | 289 | CB | ASN | A | 41 | 0 | 32.052 | 44.326 | 23.111 | 1.00 | 27.02 |
| ATOM | 290 | CG | ASN | A | 41 | 0 | 32.434 | 43.606 | 24.404 | 1.00 | 29.76 |
| ATOM | 291 | OD1 | ASN | A | 41 | 0 | 33.398 | 42.832 | 24.431 | 1.00 | 31.54 |
| ATOM | 292 | ND2 | ASN | A | 41 | 0 | 31.663 | 43.825 | 25.473 | 1.00 | 30.13 |
| ATOM | 293 | N | ASP | A | 42 | 0 | 29.424 | 44.447 | 20.631 | 1.00 | 23.80 |
| ATOM | 294 | CA | ASP | A | 42 | 0 | 29.073 | 45.325 | 19.506 | 1.00 | 24.12 |
| ATOM | 295 | C | ASP | A | 42 | 0 | 28.169 | 46.484 | 19.891 | 1.00 | 24.24 |
| ATOM | 296 | O | ASP | A | 42 | 0 | 27.420 | 46.428 | 20.872 | 1.00 | 22.42 |
| ATOM | 297 | CB | ASP | A | 42 | 0 | 28.388 | 44.528 | 18.392 | 1.00 | 26.65 |
| ATOM | 298 | CG | ASP | A | 42 | 0 | 29.404 | 43.599 | 17.773 | 1.00 | 28.94 |
| ATOM | 299 | OD1 | ASP | A | 42 | 0 | 30.603 | 43.754 | 18.056 | 1.00 | 31.45 |
| ATOM | 300 | OD2 | ASP | A | 42 | 0 | 29.026 | 42.708 | 17.009 | 1.00 | 31.69 |
| ATOM | 301 | N | ASN | A | 43 | 0 | 28.258 | 47.547 | 19.090 | 1.00 | 24.72 |
| ATOM | 302 | CA | ASN | A | 43 | 0 | 27.316 | 48.660 | 19.255 | 1.00 | 26.50 |
| ATOM | 303 | C | ASN | A | 43 | 0 | 26.293 | 48.430 | 18.128 | 1.00 | 26.23 |
| ATOM | 304 | O | ASN | A | 43 | 0 | 26.723 | 48.420 | 16.979 | 1.00 | 25.02 |
| ATOM | 305 | CB | ASN | A | 43 | 0 | 27.934 | 50.047 | 19.128 | 1.00 | 28.45 |
| ATOM | 306 | CG | ASN | A | 43 | 0 | 28.858 | 50.244 | 20.323 | 1.00 | 31.09 |
| ATOM | 307 | OD1 | ASN | A | 43 | 0 | 30.041 | 50.502 | 20.106 | 1.00 | 33.11 |
| ATOM | 308 | ND2 | ASN | A | 43 | 0 | 28.364 | 50.055 | 21.531 | 1.00 | 31.18 |
| ATOM | 309 | N | PHE | A | 44 | 0 | 25.039 | 48.155 | 18.468 | 1.00 | 24.63 |
| ATOM | 310 | CA | PHE | A | 44 | 0 | 24.083 | 47.897 | 17.393 | 1.00 | 23.28 |
| ATOM | 311 | C | PHE | A | 44 | 0 | 23.450 | 49.191 | 16.916 | 1.00 | 22.36 |
| ATOM | 312 | O | PHE | A | 44 | 0 | 23.024 | 50.008 | 17.735 | 1.00 | 21.07 |
| ATOM | 313 | CB | PHE | A | 44 | 0 | 22.959 | 46.965 | 17.853 | 1.00 | 22.04 |
| ATOM | 314 | CG | PHE | A | 44 | 0 | 23.376 | 45.525 | 17.955 | 1.00 | 22.96 |
| ATOM | 315 | CD1 | PHE | A | 44 | 0 | 22.779 | 44.562 | 17.153 | 1.00 | 23.91 |
| ATOM | 316 | CD2 | PHE | A | 44 | 0 | 24.330 | 45.120 | 18.869 | 1.00 | 22.03 |
| ATOM | 317 | CE1 | PHE | A | 44 | 0 | 23.131 | 43.230 | 17.253 | 1.00 | 24.42 |
| ATOM | 318 | CE2 | PHE | A | 44 | 0 | 24.689 | 43.797 | 18.974 | 1.00 | 23.25 |
| ATOM | 319 | CZ | PHE | A | 44 | 0 | 24.095 | 42.837 | 18.168 | 1.00 | 24.02 |
| ATOM | 320 | N | GLU | A | 45 | 0 | 23.350 | 49.343 | 15.604 | 1.00 | 22.78 |
| ATOM | 321 | CA | GLU | A | 45 | 0 | 22.611 | 50.482 | 15.054 | 1.00 | 24.47 |
| ATOM | 322 | C | GLU | A | 45 | 0 | 21.619 | 49.884 | 14.055 | 1.00 | 23.79 |
| ATOM | 323 | O | GLU | A | 45 | 0 | 22.017 | 49.587 | 12.924 | 1.00 | 24.40 |
| ATOM | 324 | CB | GLU | A | 45 | 0 | 23.543 | 51.473 | 14.368 | 1.00 | 27.07 |
| ATOM | 325 | CG | GLU | A | 45 | 0 | 24.474 | 52.130 | 15.374 | 1.00 | 31.60 |
| ATOM | 326 | CD | GLU | A | 45 | 0 | 25.380 | 53.179 | 14.772 | 1.00 | 33.90 |
| ATOM | 327 | OE1 | GLU | A | 45 | 0 | 25.354 | 53.438 | 13.559 | 1.00 | 35.62 |
| ATOM | 328 | OE2 | GLU | A | 45 | 0 | 26.155 | 53.748 | 15.565 | 1.00 | 36.42 |
| ATOM | 329 | N | LEU | A | 46 | 0 | 20.369 | 49.684 | 14.465 | 1.00 | 22.18 |
| ATOM | 330 | CA | LEU | A | 46 | 0 | 19.419 | 49.044 | 13.556 | 1.00 | 21.22 |
| ATOM | 331 | C | LEU | A | 46 | 0 | 18.348 | 50.001 | 13.077 | 1.00 | 21.27 |
| ATOM | 332 | O | LEU | A | 46 | 0 | 17.464 | 50.429 | 13.812 | 1.00 | 21.60 |
| ATOM | 333 | CB | LEU | A | 46 | 0 | 18.837 | 47.811 | 14.262 | 1.00 | 20.72 |
| ATOM | 334 | CG | LEU | A | 46 | 0 | 19.827 | 46.658 | 14.403 | 1.00 | 21.28 |
| ATOM | 335 | CD1 | LEU | A | 46 | 0 | 19.334 | 45.621 | 15.397 | 1.00 | 20.83 |
| ATOM | 336 | CD2 | LEU | A | 46 | 0 | 20.148 | 46.034 | 13.052 | 1.00 | 18.33 |
| ATOM | 337 | N | ASN | A | 47 | 0 | 18.438 | 50.403 | 11.823 | 1.00 | 21.09 |
| ATOM | 338 | CA | ASN | A | 47 | 0 | 17.498 | 51.344 | 11.252 | 1.00 | 22.37 |
| ATOM | 339 | C | ASN | A | 47 | 0 | 16.273 | 50.558 | 10.803 | 1.00 | 22.18 |
| ATOM | 340 | O | ASN | A | 47 | 0 | 16.390 | 49.810 | 9.847 | 1.00 | 23.41 |
| ATOM | 341 | CB | ASN | A | 47 | 0 | 18.131 | 52.104 | 10.066 | 1.00 | 24.01 |
| ATOM | 342 | CG | ASN | A | 47 | 0 | 17.226 | 53.243 | 9.615 | 1.00 | 25.54 |
| ATOM | 343 | OD1 | ASN | A | 47 | 0 | 16.443 | 53.772 | 10.413 | 1.00 | 26.53 |
| ATOM | 344 | ND2 | ASN | A | 47 | 0 | 17.332 | 53.612 | 8.346 | 1.00 | 26.01 |
| ATOM | 345 | N | VAL | A | 48 | 0 | 15.147 | 50.692 | 11.475 | 1.00 | 22.04 |
| ATOM | 346 | CA | VAL | A | 48 | 0 | 13.918 | 49.995 | 11.140 | 1.00 | 21.99 |
| ATOM | 347 | C | VAL | A | 48 | 0 | 13.026 | 50.879 | 10.269 | 1.00 | 21.82 |
| ATOM | 348 | O | VAL | A | 48 | 0 | 12.532 | 51.910 | 10.699 | 1.00 | 20.61 |
| ATOM | 349 | CB | VAL | A | 48 | 0 | 13.176 | 49.579 | 12.430 | 1.00 | 22.64 |
| ATOM | 350 | CG1 | VAL | A | 48 | 0 | 11.819 | 48.931 | 12.148 | 1.00 | 21.99 |

APPENDIX 1-continued

| ATOM | 351 | CG2 | VAL | A | 48 | 0 | 14.098 | 48.631 | 13.216 | 1.00 | 21.68 |
|---|---|---|---|---|---|---|---|---|---|---|---|
| ATOM | 352 | N | VAL | A | 49 | 0 | 12.931 | 50.512 | 9.009 | 1.00 | 21.79 |
| ATOM | 353 | CA | VAL | A | 49 | 0 | 12.164 | 51.167 | 7.966 | 1.00 | 21.34 |
| ATOM | 354 | C | VAL | A | 49 | 0 | 10.816 | 50.460 | 7.795 | 1.00 | 21.12 |
| ATOM | 355 | O | VAL | A | 49 | 0 | 10.703 | 49.308 | 7.365 | 1.00 | 19.76 |
| ATOM | 356 | CB | VAL | A | 49 | 0 | 12.983 | 51.189 | 6.665 | 1.00 | 22.02 |
| ATOM | 357 | CG1 | VAL | A | 49 | 0 | 12.267 | 51.913 | 5.519 | 1.00 | 21.70 |
| ATOM | 358 | CG2 | VAL | A | 49 | 0 | 14.312 | 51.933 | 6.906 | 1.00 | 21.47 |
| ATOM | 359 | N | ASN | A | 50 | 0 | 9.767 | 51.112 | 8.257 | 1.00 | 20.26 |
| ATOM | 360 | CA | ASN | A | 50 | 0 | 8.424 | 50.611 | 8.215 | 1.00 | 22.70 |
| ATOM | 361 | C | ASN | A | 50 | 0 | 7.751 | 50.899 | 6.869 | 1.00 | 25.99 |
| ATOM | 362 | O | ASN | A | 50 | 0 | 7.043 | 51.925 | 6.735 | 1.00 | 27.06 |
| ATOM | 363 | CB | ASN | A | 50 | 0 | 7.549 | 51.230 | 9.318 | 1.00 | 21.92 |
| ATOM | 364 | CG | ASN | A | 50 | 0 | 6.198 | 50.569 | 9.471 | 1.00 | 22.44 |
| ATOM | 365 | OD1 | ASN | A | 50 | 0 | 5.818 | 49.801 | 8.572 | 1.00 | 24.19 |
| ATOM | 366 | ND2 | ASN | A | 50 | 0 | 5.435 | 50.833 | 10.526 | 1.00 | 20.19 |
| ATOM | 367 | N | ASP | A | 51 | 0 | 7.915 | 49.959 | 5.926 | 1.00 | 26.42 |
| ATOM | 368 | CA | ASP | A | 51 | 0 | 7.208 | 50.071 | 4.641 | 1.00 | 26.35 |
| ATOM | 369 | C | ASP | A | 51 | 0 | 5.951 | 49.200 | 4.600 | 1.00 | 24.86 |
| ATOM | 370 | O | ASP | A | 51 | 0 | 5.542 | 48.810 | 3.511 | 1.00 | 25.19 |
| ATOM | 371 | CB | ASP | A | 51 | 0 | 8.126 | 49.698 | 3.481 | 1.00 | 26.75 |
| ATOM | 372 | CG | ASP | A | 51 | 0 | 9.152 | 50.761 | 3.158 | 1.00 | 29.77 |
| ATOM | 373 | OD1 | ASP | A | 51 | 0 | 8.944 | 51.904 | 3.617 | 1.00 | 31.03 |
| ATOM | 374 | OD2 | ASP | A | 51 | 0 | 10.166 | 50.509 | 2.465 | 1.00 | 30.42 |
| ATOM | 375 | N | LEU | A | 52 | 0 | 5.332 | 48.801 | 5.700 | 1.00 | 25.05 |
| ATOM | 376 | CA | LEU | A | 52 | 0 | 4.172 | 47.911 | 5.640 | 1.00 | 25.44 |
| ATOM | 377 | C | LEU | A | 52 | 0 | 2.934 | 48.624 | 5.094 | 1.00 | 26.65 |
| ATOM | 378 | O | LEU | A | 52 | 0 | 2.553 | 49.696 | 5.586 | 1.00 | 24.56 |
| ATOM | 379 | CB | LEU | A | 52 | 0 | 3.837 | 47.374 | 7.029 | 1.00 | 24.19 |
| ATOM | 380 | CG | LEU | A | 52 | 0 | 4.896 | 46.503 | 7.699 | 1.00 | 24.60 |
| ATOM | 381 | CD1 | LEU | A | 52 | 0 | 4.611 | 46.424 | 9.196 | 1.00 | 24.05 |
| ATOM | 382 | CD2 | LEU | A | 52 | 0 | 4.891 | 45.119 | 7.061 | 1.00 | 23.49 |
| ATOM | 383 | N | ASP | A | 53 | 0 | 2.242 | 47.980 | 4.169 | 1.00 | 28.79 |
| ATOM | 384 | CA | ASP | A | 53 | 0 | 1.049 | 48.602 | 3.581 | 1.00 | 29.91 |
| ATOM | 385 | C | ASP | A | 53 | 0 | −0.135 | 47.658 | 3.492 | 1.00 | 29.90 |
| ATOM | 386 | O | ASP | A | 53 | 0 | −1.152 | 48.082 | 2.951 | 1.00 | 30.40 |
| ATOM | 387 | CB | ASP | A | 53 | 0 | 1.367 | 49.190 | 2.197 | 1.00 | 29.26 |
| ATOM | 388 | CG | ASP | A | 53 | 0 | 1.838 | 48.140 | 1.218 | 1.00 | 31.28 |
| ATOM | 389 | OD1 | ASP | A | 53 | 0 | 1.865 | 46.926 | 1.540 | 1.00 | 31.64 |
| ATOM | 390 | OD2 | ASP | A | 53 | 0 | 2.233 | 48.474 | 0.074 | 1.00 | 32.42 |
| ATOM | 391 | N | ASN | A | 54 | 0 | −0.060 | 46.437 | 4.014 | 1.00 | 29.44 |
| ATOM | 392 | CA | ASN | A | 54 | 0 | −1.237 | 45.554 | 3.983 | 1.00 | 26.89 |
| ATOM | 393 | C | ASN | A | 54 | 0 | −2.089 | 45.832 | 5.192 | 1.00 | 27.37 |
| ATOM | 394 | O | ASN | A | 54 | 0 | −1.772 | 45.528 | 6.350 | 1.00 | 27.99 |
| ATOM | 395 | CB | ASN | A | 54 | 0 | −0.831 | 44.095 | 3.913 | 1.00 | 25.11 |
| ATOM | 396 | CG | ASN | A | 54 | 0 | −1.978 | 43.141 | 3.690 | 1.00 | 24.20 |
| ATOM | 397 | OD1 | ASN | A | 54 | 0 | −1.874 | 42.344 | 2.746 | 1.00 | 25.13 |
| ATOM | 398 | ND2 | ASN | A | 54 | 0 | −3.030 | 43.182 | 4.481 | 1.00 | 23.26 |
| ATOM | 399 | N | PRO | A | 55 | 0 | −3.337 | 46.256 | 4.961 | 1.00 | 28.44 |
| ATOM | 400 | CA | PRO | A | 55 | 0 | −4.286 | 46.589 | 6.014 | 1.00 | 26.57 |
| ATOM | 401 | C | PRO | A | 55 | 0 | −4.909 | 45.414 | 6.723 | 1.00 | 27.10 |
| ATOM | 402 | O | PRO | A | 55 | 0 | −5.671 | 45.624 | 7.687 | 1.00 | 26.05 |
| ATOM | 403 | CB | PRO | A | 55 | 0 | −5.368 | 47.465 | 5.334 | 1.00 | 28.18 |
| ATOM | 404 | CG | PRO | A | 55 | 0 | −5.249 | 47.049 | 3.899 | 1.00 | 27.50 |
| ATOM | 405 | CD | PRO | A | 55 | 0 | −3.844 | 46.564 | 3.625 | 1.00 | 27.56 |
| ATOM | 406 | N | THR | A | 56 | 0 | −4.603 | 44.160 | 6.345 | 1.00 | 25.55 |
| ATOM | 407 | CA | THR | A | 56 | 0 | −5.214 | 43.024 | 7.065 | 1.00 | 25.52 |
| ATOM | 408 | C | THR | A | 56 | 0 | −4.446 | 42.647 | 8.326 | 1.00 | 24.87 |
| ATOM | 409 | O | THR | A | 56 | 0 | −4.766 | 41.764 | 9.115 | 1.00 | 23.97 |
| ATOM | 410 | CB | THR | A | 56 | 0 | −5.393 | 41.807 | 6.154 | 1.00 | 25.10 |
| ATOM | 411 | OG1 | THR | A | 56 | 0 | −4.100 | 41.345 | 5.763 | 1.00 | 24.26 |
| ATOM | 412 | CG2 | THR | A | 56 | 0 | −6.178 | 42.123 | 4.861 | 1.00 | 25.63 |
| ATOM | 413 | N | MET | A | 57 | 0 | −3.317 | 43.311 | 8.558 | 1.00 | 26.01 |
| ATOM | 414 | CA | MET | A | 57 | 0 | −2.553 | 43.099 | 9.801 | 1.00 | 26.57 |
| ATOM | 415 | C | MET | A | 57 | 0 | −2.026 | 44.475 | 10.201 | 1.00 | 25.88 |
| ATOM | 416 | O | MET | A | 57 | 0 | −2.026 | 45.416 | 9.397 | 1.00 | 25.18 |
| ATOM | 417 | CB | MET | A | 57 | 0 | −1.561 | 41.939 | 9.698 | 1.00 | 25.42 |
| ATOM | 418 | CG | MET | A | 57 | 0 | −0.639 | 41.868 | 8.554 | 1.00 | 24.37 |
| ATOM | 419 | SD | MET | A | 57 | 0 | −0.034 | 40.288 | 7.916 | 1.00 | 22.34 |
| ATOM | 420 | CE | MET | A | 57 | 0 | −0.275 | 40.640 | 6.167 | 1.00 | 19.23 |
| ATOM | 421 | N | LEU | A | 58 | 0 | −1.694 | 44.601 | 11.476 | 1.00 | 25.98 |
| ATOM | 422 | CA | LEU | A | 58 | 0 | −1.180 | 45.850 | 12.036 | 1.00 | 25.57 |
| ATOM | 423 | C | LEU | A | 58 | 0 | −0.053 | 46.425 | 11.195 | 1.00 | 24.52 |
| ATOM | 424 | O | LEU | A | 58 | 0 | 0.824 | 45.739 | 10.638 | 1.00 | 23.63 |
| ATOM | 425 | CB | LEU | A | 58 | 0 | −0.757 | 45.535 | 13.463 | 1.00 | 26.67 |
| ATOM | 426 | CG | LEU | A | 58 | 0 | −1.628 | 45.817 | 14.657 | 1.00 | 28.97 |
| ATOM | 427 | CD1 | LEU | A | 58 | 0 | −3.107 | 45.995 | 14.312 | 1.00 | 30.99 |
| ATOM | 428 | CD2 | LEU | A | 58 | 0 | −1.488 | 44.756 | 15.736 | 1.00 | 28.36 |
| ATOM | 429 | N | ARG | A | 59 | 0 | −0.078 | 47.741 | 11.030 | 1.00 | 24.96 |

APPENDIX 1-continued

| | | | | | | | | | | | |
|---|---|---|---|---|---|---|---|---|---|---|---|
| ATOM | 430 | CA | ARG | A | 59 | 0 | 0.918 | 48.434 | 10.231 | 1.00 | 26.92 |
| ATOM | 431 | C | ARG | A | 59 | 0 | 1.932 | 49.229 | 11.014 | 1.00 | 26.31 |
| ATOM | 432 | O | ARG | A | 59 | 0 | 3.120 | 49.198 | 10.699 | 1.00 | 28.82 |
| ATOM | 433 | CB | ARG | A | 59 | 0 | 0.260 | 49.277 | 9.132 | 1.00 | 28.35 |
| ATOM | 434 | CG | ARG | A | 59 | 0 | -0.252 | 48.385 | 7.986 | 1.00 | 29.50 |
| ATOM | 435 | CD | ARG | A | 59 | 0 | -0.986 | 49.274 | 6.996 | 1.00 | 30.33 |
| ATOM | 436 | NE | ARG | A | 59 | 0 | -2.333 | 49.604 | 7.459 | 1.00 | 32.26 |
| ATOM | 437 | CZ | ARG | A | 59 | 0 | -3.121 | 50.525 | 6.883 | 1.00 | 33.24 |
| ATOM | 438 | NH1 | ARG | A | 59 | 0 | -2.679 | 51.233 | 5.845 | 1.00 | 32.27 |
| ATOM | 439 | NH2 | ARG | A | 59 | 0 | -4.340 | 50.712 | 7.389 | 1.00 | 32.65 |
| ATOM | 440 | N | PRO | A | 60 | 0 | 1.542 | 49.961 | 12.020 | 1.00 | 26.30 |
| ATOM | 441 | CA | PRO | A | 60 | 0 | 2.460 | 50.669 | 12.916 | 1.00 | 26.19 |
| ATOM | 442 | C | PRO | A | 60 | 0 | 3.312 | 49.591 | 13.595 | 1.00 | 25.29 |
| ATOM | 443 | O | PRO | A | 60 | 0 | 2.879 | 48.432 | 13.668 | 1.00 | 24.63 |
| ATOM | 444 | CB | PRO | A | 60 | 0 | 1.623 | 51.464 | 13.925 | 1.00 | 25.93 |
| ATOM | 445 | CG | PRO | A | 60 | 0 | 0.235 | 51.357 | 13.325 | 1.00 | 26.19 |
| ATOM | 446 | CD | PRO | A | 60 | 0 | 0.165 | 50.073 | 12.508 | 1.00 | 26.23 |
| ATOM | 447 | N | THR | A | 61 | 0 | 4.544 | 49.932 | 13.976 | 1.00 | 24.60 |
| ATOM | 448 | CA | THR | A | 61 | 0 | 5.365 | 48.871 | 14.587 | 1.00 | 23.49 |
| ATOM | 449 | C | THR | A | 61 | 0 | 6.204 | 49.400 | 15.743 | 1.00 | 22.83 |
| ATOM | 450 | O | THR | A | 61 | 0 | 6.390 | 50.601 | 15.921 | 1.00 | 20.77 |
| ATOM | 451 | CB | THR | A | 61 | 0 | 6.245 | 48.170 | 13.535 | 1.00 | 22.69 |
| ATOM | 452 | OG1 | THR | A | 61 | 0 | 6.668 | 46.918 | 14.096 | 1.00 | 23.55 |
| ATOM | 453 | CG2 | THR | A | 61 | 0 | 7.444 | 48.976 | 13.119 | 1.00 | 20.92 |
| ATOM | 454 | N | SER | A | 62 | 0 | 6.702 | 48.449 | 16.507 | 1.00 | 22.38 |
| ATOM | 455 | CA | SER | A | 62 | 0 | 7.599 | 48.672 | 17.633 | 1.00 | 22.47 |
| ATOM | 456 | C | SER | A | 62 | 0 | 8.381 | 47.380 | 17.893 | 1.00 | 22.12 |
| ATOM | 457 | O | SER | A | 62 | 0 | 7.763 | 46.331 | 18.124 | 1.00 | 20.53 |
| ATOM | 458 | CB | SER | A | 62 | 0 | 6.784 | 49.033 | 18.882 | 1.00 | 22.02 |
| ATOM | 459 | OG | SER | A | 62 | 0 | 7.666 | 49.570 | 19.832 | 1.00 | 21.19 |
| ATOM | 460 | N | ILE | A | 63 | 0 | 9.716 | 47.451 | 17.806 | 1.00 | 21.17 |
| ATOM | 461 | CA | ILE | A | 63 | 0 | 10.513 | 46.240 | 17.960 | 1.00 | 18.32 |
| ATOM | 462 | C | ILE | A | 63 | 0 | 11.095 | 46.034 | 19.354 | 1.00 | 18.28 |
| ATOM | 463 | O | ILE | A | 63 | 0 | 11.832 | 46.909 | 19.826 | 1.00 | 19.63 |
| ATOM | 464 | CB | ILE | A | 63 | 0 | 11.642 | 46.234 | 16.924 | 1.00 | 16.68 |
| ATOM | 465 | CG1 | ILE | A | 63 | 0 | 11.166 | 46.509 | 15.508 | 1.00 | 18.51 |
| ATOM | 466 | CG2 | ILE | A | 63 | 0 | 12.319 | 44.848 | 16.906 | 1.00 | 16.78 |
| ATOM | 467 | CD1 | ILE | A | 63 | 0 | 10.055 | 45.625 | 14.994 | 1.00 | 18.25 |
| ATOM | 468 | N | HIS | A | 64 | 0 | 10.880 | 44.890 | 19.985 | 1.00 | 15.18 |
| ATOM | 469 | CA | HIS | A | 64 | 0 | 11.478 | 44.539 | 21.261 | 1.00 | 15.51 |
| ATOM | 470 | C | HIS | A | 64 | 0 | 12.648 | 43.559 | 21.029 | 1.00 | 16.73 |
| ATOM | 471 | O | HIS | A | 64 | 0 | 12.491 | 42.591 | 20.279 | 1.00 | 16.85 |
| ATOM | 472 | CB | HIS | A | 64 | 0 | 10.512 | 43.912 | 22.239 | 1.00 | 14.37 |
| ATOM | 473 | CG | HIS | A | 64 | 0 | 11.033 | 43.420 | 23.546 | 1.00 | 14.47 |
| ATOM | 474 | ND1 | HIS | A | 64 | 0 | 11.763 | 44.191 | 24.410 | 1.00 | 12.89 |
| ATOM | 475 | CD2 | HIS | A | 64 | 0 | 10.883 | 42.223 | 24.193 | 1.00 | 14.85 |
| ATOM | 476 | CE1 | HIS | A | 64 | 0 | 12.067 | 43.518 | 25.498 | 1.00 | 11.53 |
| ATOM | 477 | NE2 | HIS | A | 64 | 0 | 11.547 | 42.325 | 25.423 | 1.00 | 13.63 |
| ATOM | 478 | N | TRP | A | 65 | 0 | 13.761 | 43.781 | 21.723 | 1.00 | 14.37 |
| ATOM | 479 | CA | TRP | A | 65 | 0 | 14.966 | 42.926 | 21.577 | 1.00 | 13.92 |
| ATOM | 480 | C | TRP | A | 65 | 0 | 14.987 | 42.084 | 22.840 | 1.00 | 13.50 |
| ATOM | 481 | O | TRP | A | 65 | 0 | 15.482 | 42.538 | 23.901 | 1.00 | 12.84 |
| ATOM | 482 | CB | TRP | A | 65 | 0 | 16.189 | 43.825 | 21.371 | 1.00 | 13.50 |
| ATOM | 483 | CG | TRP | A | 65 | 0 | 15.890 | 45.020 | 20.492 | 1.00 | 13.19 |
| ATOM | 484 | CD1 | TRP | A | 65 | 0 | 15.453 | 46.247 | 20.913 | 1.00 | 12.42 |
| ATOM | 485 | CD2 | TRP | A | 65 | 0 | 15.908 | 45.087 | 19.068 | 1.00 | 13.61 |
| ATOM | 486 | NE1 | TRP | A | 65 | 0 | 15.234 | 47.067 | 19.862 | 1.00 | 11.49 |
| ATOM | 487 | CE2 | TRP | A | 65 | 0 | 15.511 | 46.390 | 18.710 | 1.00 | 13.77 |
| ATOM | 488 | CE3 | TRP | A | 65 | 0 | 16.251 | 44.174 | 18.061 | 1.00 | 14.35 |
| ATOM | 489 | CZ2 | TRP | A | 65 | 0 | 15.439 | 46.815 | 17.378 | 1.00 | 14.99 |
| ATOM | 490 | CZ3 | TRP | A | 65 | 0 | 16.169 | 44.572 | 16.735 | 1.00 | 13.99 |
| ATOM | 491 | CH2 | TRP | A | 65 | 0 | 15.756 | 45.869 | 16.411 | 1.00 | 15.82 |
| ATOM | 492 | N | HIS | A | 66 | 0 | 14.295 | 40.941 | 22.747 | 1.00 | 10.39 |
| ATOM | 493 | CA | HIS | A | 66 | 0 | 13.939 | 40.200 | 23.966 | 1.00 | 12.00 |
| ATOM | 494 | C | HIS | A | 66 | 0 | 15.158 | 39.653 | 24.698 | 1.00 | 11.34 |
| ATOM | 495 | O | HIS | A | 66 | 0 | 15.889 | 38.859 | 24.130 | 1.00 | 11.51 |
| ATOM | 496 | CB | HIS | A | 66 | 0 | 12.923 | 39.069 | 23.629 | 1.00 | 10.76 |
| ATOM | 497 | CG | HIS | A | 66 | 0 | 12.418 | 38.308 | 24.808 | 1.00 | 11.26 |
| ATOM | 498 | ND1 | HIS | A | 66 | 0 | 11.106 | 38.085 | 25.092 | 1.00 | 13.10 |
| ATOM | 499 | CD2 | HIS | A | 66 | 0 | 13.050 | 37.676 | 25.824 | 1.00 | 13.49 |
| ATOM | 500 | CE1 | HIS | A | 66 | 0 | 10.919 | 37.407 | 26.191 | 1.00 | 12.50 |
| ATOM | 501 | NE2 | HIS | A | 66 | 0 | 12.116 | 37.146 | 26.683 | 1.00 | 13.71 |
| ATOM | 502 | N | GLY | A | 67 | 0 | 15.345 | 39.971 | 25.948 | 1.00 | 12.84 |
| ATOM | 503 | CA | GLY | A | 67 | 0 | 16.492 | 39.469 | 26.719 | 1.00 | 13.36 |
| ATOM | 504 | C | GLY | A | 67 | 0 | 17.596 | 40.500 | 26.914 | 1.00 | 13.11 |
| ATOM | 505 | O | GLY | A | 67 | 0 | 18.435 | 40.289 | 27.788 | 1.00 | 13.36 |
| ATOM | 506 | N | LEU | A | 68 | 0 | 17.641 | 41.558 | 26.131 | 1.00 | 12.89 |
| ATOM | 507 | CA | LEU | A | 68 | 0 | 18.659 | 42.598 | 26.300 | 1.00 | 15.22 |
| ATOM | 508 | C | LEU | A | 68 | 0 | 18.235 | 43.501 | 27.448 | 1.00 | 16.14 |

APPENDIX 1-continued

| ATOM | 509 | O | LEU | A | 68 | 0 | 17.029 | 43.842 | 27.505 | 1.00 | 16.50 |
|---|---|---|---|---|---|---|---|---|---|---|---|
| ATOM | 510 | CB | LEU | A | 68 | 0 | 18.929 | 43.320 | 24.988 | 1.00 | 15.98 |
| ATOM | 511 | CG | LEU | A | 68 | 0 | 20.002 | 42.638 | 24.114 | 1.00 | 19.57 |
| ATOM | 512 | CD1 | LEU | A | 68 | 0 | 19.719 | 41.185 | 23.809 | 1.00 | 20.39 |
| ATOM | 513 | CD2 | LEU | A | 68 | 0 | 20.188 | 43.316 | 22.758 | 1.00 | 19.59 |
| ATOM | 514 | N | PHE | A | 69 | 0 | 19.125 | 43.848 | 28.386 | 1.00 | 13.24 |
| ATOM | 515 | CA | PHE | A | 69 | 0 | 18.700 | 44.657 | 29.526 | 1.00 | 13.85 |
| ATOM | 516 | C | PHE | A | 69 | 0 | 18.499 | 46.128 | 29.205 | 1.00 | 14.34 |
| ATOM | 517 | O | PHE | A | 69 | 0 | 17.806 | 46.879 | 29.895 | 1.00 | 15.02 |
| ATOM | 518 | CB | PHE | A | 69 | 0 | 19.770 | 44.579 | 30.637 | 1.00 | 16.02 |
| ATOM | 519 | CG | PHE | A | 69 | 0 | 20.112 | 43.187 | 31.072 | 1.00 | 16.45 |
| ATOM | 520 | CD1 | PHE | A | 69 | 0 | 19.172 | 42.162 | 31.026 | 1.00 | 16.68 |
| ATOM | 521 | CD2 | PHE | A | 69 | 0 | 21.381 | 42.927 | 31.578 | 1.00 | 16.78 |
| ATOM | 522 | CE1 | PHE | A | 69 | 0 | 19.504 | 40.883 | 31.448 | 1.00 | 18.86 |
| ATOM | 523 | CE2 | PHE | A | 69 | 0 | 21.717 | 41.652 | 32.001 | 1.00 | 17.34 |
| ATOM | 524 | CZ | PHE | A | 69 | 0 | 20.782 | 40.628 | 31.932 | 1.00 | 18.09 |
| ATOM | 525 | N | GLN | A | 70 | 0 | 19.081 | 46.611 | 28.130 | 1.00 | 12.22 |
| ATOM | 526 | CA | GLN | A | 70 | 0 | 18.919 | 47.990 | 27.708 | 1.00 | 15.20 |
| ATOM | 527 | C | GLN | A | 70 | 0 | 19.242 | 49.004 | 28.789 | 1.00 | 16.76 |
| ATOM | 528 | O | GLN | A | 70 | 0 | 18.555 | 50.016 | 28.919 | 1.00 | 16.08 |
| ATOM | 529 | CB | GLN | A | 70 | 0 | 17.488 | 48.115 | 27.232 | 1.00 | 15.52 |
| ATOM | 530 | CG | GLN | A | 70 | 0 | 17.168 | 47.303 | 26.003 | 1.00 | 17.37 |
| ATOM | 531 | CD | GLN | A | 70 | 0 | 17.781 | 47.744 | 24.709 | 1.00 | 17.70 |
| ATOM | 532 | OE1 | GLN | A | 70 | 0 | 17.557 | 47.090 | 23.676 | 1.00 | 21.63 |
| ATOM | 533 | NE2 | GLN | A | 70 | 0 | 18.549 | 48.805 | 24.620 | 1.00 | 16.79 |
| ATOM | 534 | N | ARG | A | 71 | 0 | 20.338 | 48.804 | 29.518 | 1.00 | 16.49 |
| ATOM | 535 | CA | ARG | A | 71 | 0 | 20.765 | 49.712 | 30.588 | 1.00 | 18.41 |
| ATOM | 536 | C | ARG | A | 71 | 0 | 21.239 | 51.011 | 29.970 | 1.00 | 16.23 |
| ATOM | 537 | O | ARG | A | 71 | 0 | 22.059 | 50.998 | 29.027 | 1.00 | 14.48 |
| ATOM | 538 | CB | ARG | A | 71 | 0 | 21.827 | 48.942 | 31.382 | 1.00 | 22.65 |
| ATOM | 539 | CG | ARG | A | 71 | 0 | 22.273 | 49.589 | 32.671 | 1.00 | 29.50 |
| ATOM | 540 | CD | ARG | A | 71 | 0 | 23.286 | 48.756 | 33.457 | 1.00 | 32.92 |
| ATOM | 541 | NE | ARG | A | 71 | 0 | 22.712 | 47.550 | 34.035 | 1.00 | 38.11 |
| ATOM | 542 | CZ | ARG | A | 71 | 0 | 22.551 | 46.358 | 33.452 | 1.00 | 40.14 |
| ATOM | 543 | NH1 | ARG | A | 71 | 0 | 22.939 | 46.138 | 32.190 | 1.00 | 41.23 |
| ATOM | 544 | NH2 | ARG | A | 71 | 0 | 22.022 | 45.333 | 34.130 | 1.00 | 40.89 |
| ATOM | 545 | N | GLY | A | 72 | 0 | 20.613 | 52.145 | 30.311 | 1.00 | 14.82 |
| ATOM | 546 | CA | GLY | A | 72 | 0 | 20.981 | 53.414 | 29.676 | 1.00 | 14.51 |
| ATOM | 547 | C | GLY | A | 72 | 0 | 20.268 | 53.606 | 28.338 | 1.00 | 15.55 |
| ATOM | 548 | O | GLY | A | 72 | 0 | 20.401 | 54.706 | 27.777 | 1.00 | 16.32 |
| ATOM | 549 | N | THR | A | 73 | 0 | 19.503 | 52.651 | 27.804 | 1.00 | 12.12 |
| ATOM | 550 | CA | THR | A | 73 | 0 | 18.857 | 52.781 | 26.516 | 1.00 | 12.50 |
| ATOM | 551 | C | THR | A | 73 | 0 | 17.418 | 52.252 | 26.621 | 1.00 | 13.98 |
| ATOM | 552 | O | THR | A | 73 | 0 | 16.890 | 51.534 | 25.776 | 1.00 | 13.81 |
| ATOM | 553 | CB | THR | A | 73 | 0 | 19.577 | 52.086 | 25.346 | 1.00 | 12.21 |
| ATOM | 554 | OG1 | THR | A | 73 | 0 | 19.854 | 50.711 | 25.666 | 1.00 | 12.83 |
| ATOM | 555 | CG2 | THR | A | 73 | 0 | 20.944 | 52.711 | 25.000 | 1.00 | 9.81 |
| ATOM | 556 | N | ASN | A | 74 | 0 | 16.744 | 52.617 | 27.708 | 1.00 | 12.97 |
| ATOM | 557 | CA | ASN | A | 74 | 0 | 15.354 | 52.273 | 27.951 | 1.00 | 14.93 |
| ATOM | 558 | C | ASN | A | 74 | 0 | 14.469 | 52.718 | 26.784 | 1.00 | 15.92 |
| ATOM | 559 | O | ASN | A | 74 | 0 | 13.501 | 52.030 | 26.455 | 1.00 | 16.56 |
| ATOM | 560 | CB | ASN | A | 74 | 0 | 14.851 | 52.821 | 29.271 | 1.00 | 13.06 |
| ATOM | 561 | CG | ASN | A | 74 | 0 | 13.385 | 52.519 | 29.556 | 1.00 | 15.47 |
| ATOM | 562 | OD1 | ASN | A | 74 | 0 | 12.557 | 53.250 | 29.021 | 1.00 | 13.99 |
| ATOM | 563 | ND2 | ASN | A | 74 | 0 | 13.063 | 51.500 | 30.367 | 1.00 | 13.91 |
| ATOM | 564 | N | TRP | A | 75 | 0 | 14.806 | 53.765 | 26.041 | 1.00 | 16.16 |
| ATOM | 565 | CA | TRP | A | 75 | 0 | 14.036 | 54.262 | 24.917 | 1.00 | 16.49 |
| ATOM | 566 | C | TRP | A | 75 | 0 | 14.050 | 53.345 | 23.701 | 1.00 | 17.29 |
| ATOM | 567 | O | TRP | A | 75 | 0 | 13.235 | 53.529 | 22.776 | 1.00 | 16.34 |
| ATOM | 568 | CB | TRP | A | 75 | 0 | 14.516 | 55.657 | 24.509 | 1.00 | 15.90 |
| ATOM | 569 | CG | TRP | A | 75 | 0 | 15.990 | 55.705 | 24.207 | 1.00 | 16.04 |
| ATOM | 570 | CD1 | TRP | A | 75 | 0 | 17.011 | 55.972 | 25.072 | 1.00 | 14.90 |
| ATOM | 571 | CD2 | TRP | A | 75 | 0 | 16.584 | 55.475 | 22.916 | 1.00 | 15.94 |
| ATOM | 572 | NE1 | TRP | A | 75 | 0 | 18.210 | 55.917 | 24.384 | 1.00 | 15.89 |
| ATOM | 573 | CE2 | TRP | A | 75 | 0 | 17.977 | 55.624 | 23.076 | 1.00 | 15.80 |
| ATOM | 574 | CE3 | TRP | A | 75 | 0 | 16.060 | 55.171 | 21.656 | 1.00 | 14.88 |
| ATOM | 575 | CZ2 | TRP | A | 75 | 0 | 18.867 | 55.459 | 22.016 | 1.00 | 17.60 |
| ATOM | 576 | CZ3 | TRP | A | 75 | 0 | 16.928 | 55.025 | 20.603 | 1.00 | 16.64 |
| ATOM | 577 | CH2 | TRP | A | 75 | 0 | 18.321 | 55.153 | 20.785 | 1.00 | 18.16 |
| ATOM | 578 | N | ALA | A | 76 | 0 | 14.962 | 52.372 | 23.675 | 1.00 | 15.12 |
| ATOM | 579 | CA | ALA | A | 76 | 0 | 15.075 | 51.430 | 22.578 | 1.00 | 14.61 |
| ATOM | 580 | C | ALA | A | 76 | 0 | 14.569 | 50.047 | 22.971 | 1.00 | 13.98 |
| ATOM | 581 | O | ALA | A | 76 | 0 | 14.617 | 49.132 | 22.159 | 1.00 | 14.20 |
| ATOM | 582 | CB | ALA | A | 76 | 0 | 16.554 | 51.354 | 22.157 | 1.00 | 13.68 |
| ATOM | 583 | N | ASP | A | 77 | 0 | 13.941 | 49.885 | 24.121 | 1.00 | 14.47 |
| ATOM | 584 | CA | ASP | A | 77 | 0 | 13.409 | 48.605 | 24.586 | 1.00 | 14.23 |
| ATOM | 585 | C | ASP | A | 77 | 0 | 12.198 | 48.167 | 23.762 | 1.00 | 15.04 |
| ATOM | 586 | O | ASP | A | 77 | 0 | 11.982 | 46.946 | 23.638 | 1.00 | 13.78 |
| ATOM | 587 | CB | ASP | A | 77 | 0 | 13.112 | 48.567 | 26.072 | 1.00 | 13.41 |

APPENDIX 1-continued

| ATOM | 588 | CG | ASP | A | 77 | 0 | 12.945 | 47.155 | 26.612 | 1.00 | 14.93 |
|------|-----|-----|-----|---|----|----|--------|--------|--------|------|-------|
| ATOM | 589 | OD1 | ASP | A | 77 | 0 | 11.943 | 46.986 | 27.345 | 1.00 | 15.07 |
| ATOM | 590 | OD2 | ASP | A | 77 | 0 | 13.744 | 46.217 | 26.334 | 1.00 | 13.73 |
| ATOM | 591 | N | GLY | A | 78 | 0 | 11.458 | 49.095 | 23.160 | 1.00 | 13.63 |
| ATOM | 592 | CA | GLY | A | 78 | 0 | 10.442 | 48.686 | 22.210 | 1.00 | 14.96 |
| ATOM | 593 | C | GLY | A | 78 | 0 | 9.040 | 48.309 | 22.631 | 1.00 | 16.75 |
| ATOM | 594 | O | GLY | A | 78 | 0 | 8.276 | 47.865 | 21.755 | 1.00 | 16.49 |
| ATOM | 595 | N | ALA | A | 79 | 0 | 8.631 | 48.436 | 23.886 | 1.00 | 15.34 |
| ATOM | 596 | CA | ALA | A | 79 | 0 | 7.252 | 48.176 | 24.270 | 1.00 | 14.70 |
| ATOM | 597 | C | ALA | A | 79 | 0 | 6.490 | 49.495 | 24.084 | 1.00 | 17.51 |
| ATOM | 598 | O | ALA | A | 79 | 0 | 6.690 | 50.486 | 24.807 | 1.00 | 17.05 |
| ATOM | 599 | CB | ALA | A | 79 | 0 | 7.145 | 47.701 | 25.708 | 1.00 | 14.78 |
| ATOM | 600 | N | ASP | A | 80 | 0 | 5.641 | 49.536 | 23.053 | 1.00 | 18.56 |
| ATOM | 601 | CA | ASP | A | 80 | 0 | 4.859 | 50.741 | 22.798 | 1.00 | 19.52 |
| ATOM | 602 | C | ASP | A | 80 | 0 | 3.959 | 50.963 | 24.010 | 1.00 | 17.61 |
| ATOM | 603 | O | ASP | A | 80 | 0 | 3.530 | 49.999 | 24.664 | 1.00 | 16.72 |
| ATOM | 604 | CB | ASP | A | 80 | 0 | 4.044 | 50.714 | 21.510 | 1.00 | 24.02 |
| ATOM | 605 | CG | ASP | A | 80 | 0 | 3.003 | 49.607 | 21.549 | 1.00 | 28.13 |
| ATOM | 606 | OD1 | ASP | A | 80 | 0 | 3.410 | 48.417 | 21.541 | 1.00 | 30.66 |
| ATOM | 607 | OD2 | ASP | A | 80 | 0 | 1.803 | 49.959 | 21.603 | 1.00 | 30.61 |
| ATOM | 608 | N | GLY | A | 81 | 0 | 3.776 | 52.242 | 24.337 | 1.00 | 15.85 |
| ATOM | 609 | CA | GLY | A | 81 | 0 | 2.991 | 52.566 | 25.532 | 1.00 | 16.27 |
| ATOM | 610 | C | GLY | A | 81 | 0 | 3.846 | 52.615 | 26.784 | 1.00 | 18.72 |
| ATOM | 611 | O | GLY | A | 81 | 0 | 3.405 | 52.983 | 27.890 | 1.00 | 20.61 |
| ATOM | 612 | N | VAL | A | 82 | 0 | 5.108 | 52.173 | 26.725 | 1.00 | 19.11 |
| ATOM | 613 | CA | VAL | A | 82 | 0 | 5.978 | 52.119 | 27.890 | 1.00 | 19.14 |
| ATOM | 614 | C | VAL | A | 82 | 0 | 7.288 | 52.851 | 27.590 | 1.00 | 18.41 |
| ATOM | 615 | O | VAL | A | 82 | 0 | 7.594 | 53.839 | 28.242 | 1.00 | 16.79 |
| ATOM | 616 | CB | VAL | A | 82 | 0 | 6.266 | 50.697 | 28.390 | 1.00 | 19.82 |
| ATOM | 617 | CG1 | VAL | A | 82 | 0 | 7.059 | 50.741 | 29.710 | 1.00 | 21.37 |
| ATOM | 618 | CG2 | VAL | A | 82 | 0 | 4.995 | 49.894 | 28.640 | 1.00 | 19.27 |
| ATOM | 619 | N | ASN | A | 83 | 0 | 7.982 | 52.408 | 26.551 | 1.00 | 17.90 |
| ATOM | 620 | CA | ASN | A | 83 | 0 | 9.271 | 52.926 | 26.147 | 1.00 | 16.94 |
| ATOM | 621 | C | ASN | A | 83 | 0 | 9.226 | 53.778 | 24.886 | 1.00 | 18.32 |
| ATOM | 622 | O | ASN | A | 83 | 0 | 10.175 | 54.551 | 24.634 | 1.00 | 20.58 |
| ATOM | 623 | CB | ASN | A | 83 | 0 | 10.249 | 51.747 | 25.937 | 1.00 | 15.23 |
| ATOM | 624 | CG | ASN | A | 83 | 0 | 10.112 | 50.745 | 27.063 | 1.00 | 16.00 |
| ATOM | 625 | OD1 | ASN | A | 83 | 0 | 9.493 | 49.676 | 26.879 | 1.00 | 14.98 |
| ATOM | 626 | ND2 | ASN | A | 83 | 0 | 10.583 | 51.131 | 28.249 | 1.00 | 13.17 |
| ATOM | 627 | N | GLN | A | 84 | 0 | 8.183 | 53.668 | 24.066 | 1.00 | 16.40 |
| ATOM | 628 | CA | GLN | A | 84 | 0 | 8.080 | 54.464 | 22.867 | 1.00 | 16.34 |
| ATOM | 629 | C | GLN | A | 84 | 0 | 6.658 | 54.465 | 22.309 | 1.00 | 17.95 |
| ATOM | 630 | O | GLN | A | 84 | 0 | 5.816 | 53.679 | 22.728 | 1.00 | 17.69 |
| ATOM | 631 | CB | GLN | A | 84 | 0 | 8.995 | 53.953 | 21.754 | 1.00 | 17.98 |
| ATOM | 632 | CG | GLN | A | 84 | 0 | 8.456 | 52.654 | 21.127 | 1.00 | 16.63 |
| ATOM | 633 | CD | GLN | A | 84 | 0 | 9.272 | 52.225 | 19.938 | 1.00 | 18.17 |
| ATOM | 634 | OE1 | GLN | A | 84 | 0 | 8.994 | 52.601 | 18.792 | 1.00 | 20.91 |
| ATOM | 635 | NE2 | GLN | A | 84 | 0 | 10.279 | 51.385 | 20.096 | 1.00 | 18.70 |
| ATOM | 636 | N | CYS | A | 85 | 0 | 6.419 | 55.350 | 21.365 | 1.00 | 18.60 |
| ATOM | 637 | CA | CYS | A | 85 | 0 | 5.140 | 55.344 | 20.622 | 1.00 | 20.25 |
| ATOM | 638 | C | CYS | A | 85 | 0 | 5.512 | 54.555 | 19.375 | 1.00 | 19.55 |
| ATOM | 639 | O | CYS | A | 85 | 0 | 6.690 | 54.546 | 18.995 | 1.00 | 18.92 |
| ATOM | 640 | CB | CYS | A | 85 | 0 | 4.772 | 56.786 | 20.228 | 1.00 | 22.20 |
| ATOM | 641 | SG | CYS | A | 85 | 0 | 3.899 | 57.783 | 21.481 | 1.00 | 24.65 |
| ATOM | 642 | N | PRO | A | 86 | 0 | 4.589 | 53.951 | 18.674 | 1.00 | 21.19 |
| ATOM | 643 | CA | PRO | A | 86 | 0 | 4.869 | 53.152 | 17.498 | 1.00 | 20.78 |
| ATOM | 644 | C | PRO | A | 86 | 0 | 5.560 | 53.930 | 16.394 | 1.00 | 21.46 |
| ATOM | 645 | O | PRO | A | 86 | 0 | 5.453 | 55.137 | 16.298 | 1.00 | 23.08 |
| ATOM | 646 | CB | PRO | A | 86 | 0 | 3.530 | 52.555 | 17.028 | 1.00 | 19.94 |
| ATOM | 647 | CG | PRO | A | 86 | 0 | 2.667 | 52.720 | 18.252 | 1.00 | 19.59 |
| ATOM | 648 | CD | PRO | A | 86 | 0 | 3.174 | 53.872 | 19.062 | 1.00 | 20.46 |
| ATOM | 649 | N | ILE | A | 87 | 0 | 6.318 | 53.259 | 15.550 | 1.00 | 20.95 |
| ATOM | 650 | CA | ILE | A | 87 | 0 | 6.907 | 53.773 | 14.337 | 1.00 | 22.43 |
| ATOM | 651 | C | ILE | A | 87 | 0 | 5.768 | 53.641 | 13.292 | 1.00 | 22.80 |
| ATOM | 652 | O | ILE | A | 87 | 0 | 5.148 | 52.562 | 13.228 | 1.00 | 21.61 |
| ATOM | 653 | CB | ILE | A | 87 | 0 | 8..105 | 52.954 | 13.844 | 1.00 | 21.99 |
| ATOM | 654 | CG1 | ILE | A | 87 | 0 | 9.130 | 52.696 | 14.944 | 1.00 | 24.18 |
| ATOM | 655 | CG2 | ILE | A | 87 | 0 | 8.773 | 53.656 | 12.674 | 1.00 | 22.91 |
| ATOM | 656 | CD1 | ILE | A | 87 | 0 | 10.256 | 51.776 | 14.514 | 1.00 | 23.87 |
| ATOM | 657 | N | SER | A | 88 | 0 | 5.464 | 54.702 | 12.570 | 1.00 | 22.64 |
| ATOM | 658 | CA | SER | A | 88 | 0 | 4.338 | 54.709 | 11.647 | 1.00 | 22.85 |
| ATOM | 659 | C | SER | A | 88 | 0 | 4.751 | 54.268 | 10.249 | 1.00 | 23.35 |
| ATOM | 660 | O | SER | A | 88 | 0 | 5.870 | 54.489 | 9.764 | 1.00 | 23.30 |
| ATOM | 661 | CB | SER | A | 88 | 0 | 3.767 | 56.137 | 11.518 | 1.00 | 24.00 |
| ATOM | 662 | OG | SER | A | 88 | 0 | 3.379 | 56.770 | 12.720 | 1.00 | 23.93 |
| ATOM | 663 | N | PRO | A | 89 | 0 | 3.778 | 53.752 | 9.514 | 1.00 | 23.60 |
| ATOM | 664 | CA | PRO | A | 89 | 0 | 3.955 | 53.382 | 8.116 | 1.00 | 25.19 |
| ATOM | 665 | C | PRO | A | 89 | 0 | 4.579 | 54.556 | 7.361 | 1.00 | 26.58 |
| ATOM | 666 | O | PRO | A | 89 | 0 | 4.177 | 55.699 | 7.585 | 1.00 | 26.66 |

APPENDIX 1-continued

| ATOM | 667 | CB | PRO | A | 89 | 0 | 2.566 | 53.065 | 7.555 | 1.00 | 23.59 |
|---|---|---|---|---|---|---|---|---|---|---|---|
| ATOM | 668 | CG | PRO | A | 89 | 0 | 1.740 | 52.856 | 8.798 | 1.00 | 22.37 |
| ATOM | 669 | CD | PRO | A | 89 | 0 | 2.415 | 53.513 | 9.970 | 1.00 | 23.25 |
| ATOM | 670 | N | GLY | A | 90 | 0 | 5.588 | 54.311 | 6.550 | 1.00 | 27.73 |
| ATOM | 671 | CA | GLY | A | 90 | 0 | 6.223 | 55.338 | 5.748 | 1.00 | 30.55 |
| ATOM | 672 | C | GLY | A | 90 | 0 | 7.384 | 56.032 | 6.438 | 1.00 | 32.38 |
| ATOM | 673 | O | GLY | A | 90 | 0 | 8.050 | 56.894 | 5.879 | 1.00 | 32.53 |
| ATOM | 674 | N | HIS | A | 91 | 0 | 7.639 | 55.693 | 7.702 | 1.00 | 32.77 |
| ATOM | 675 | CA | HIS | A | 91 | 0 | 8.691 | 56.283 | 8.494 | 1.00 | 32.55 |
| ATOM | 676 | C | HIS | A | 91 | 0 | 9.649 | 55.179 | 8.982 | 1.00 | 32.36 |
| ATOM | 677 | O | HIS | A | 91 | 0 | 9.381 | 53.972 | 8.961 | 1.00 | 31.30 |
| ATOM | 678 | CB | HIS | A | 91 | 0 | 8.118 | 57.016 | 9.722 | 1.00 | 33.75 |
| ATOM | 679 | CG | HIS | A | 91 | 0 | 7.147 | 58.073 | 9.295 | 1.00 | 34.64 |
| ATOM | 680 | ND1 | HIS | A | 91 | 0 | 7.519 | 59.381 | 9.072 | 1.00 | 34.41 |
| ATOM | 681 | CD2 | HIS | A | 91 | 0 | 5.822 | 57.977 | 9.002 | 1.00 | 34.89 |
| ATOM | 682 | CE1 | HIS | A | 91 | 0 | 6.450 | 60.050 | 8.679 | 1.00 | 34.87 |
| ATOM | 683 | NE2 | HIS | A | 91 | 0 | 5.410 | 59.233 | 8.628 | 1.00 | 35.14 |
| ATOM | 684 | N | ALA | A | 92 | 0 | 10.786 | 55.668 | 9.437 | 1.00 | 29.57 |
| ATOM | 685 | CA | ALA | A | 92 | 0 | 11.895 | 54.898 | 9.937 | 1.00 | 27.71 |
| ATOM | 686 | C | ALA | A | 92 | 0 | 12.316 | 55.347 | 11.337 | 1.00 | 27.41 |
| ATOM | 687 | O | ALA | A | 92 | 0 | 12.076 | 56.484 | 11.741 | 1.00 | 26.12 |
| ATOM | 688 | CB | ALA | A | 92 | 0 | 13.051 | 55.057 | 8.967 | 1.00 | 25.23 |
| ATOM | 689 | N | PHE | A | 93 | 0 | 12.931 | 54.418 | 12.081 | 1.00 | 26.87 |
| ATOM | 690 | CA | PHE | A | 93 | 0 | 13.441 | 54.760 | 13.405 | 1.00 | 25.87 |
| ATOM | 691 | C | PHE | A | 93 | 0 | 14.746 | 54.008 | 13.632 | 1.00 | 25.21 |
| ATOM | 692 | O | PHE | A | 93 | 0 | 14.797 | 52.810 | 13.347 | 1.00 | 25.80 |
| ATOM | 693 | CB | PHE | A | 93 | 0 | 12.457 | 54.456 | 14.526 | 1.00 | 25.30 |
| ATOM | 694 | CG | PHE | A | 93 | 0 | 12.964 | 54.955 | 15.847 | 1.00 | 25.41 |
| ATOM | 695 | CD1 | PHE | A | 93 | 0 | 13.154 | 56.309 | 16.061 | 1.00 | 25.36 |
| ATOM | 696 | CD2 | PHE | A | 93 | 0 | 13.276 | 54.057 | 16.853 | 1.00 | 25.31 |
| ATOM | 697 | CE1 | PHE | A | 93 | 0 | 13.637 | 56.753 | 17.285 | 1.00 | 26.54 |
| ATOM | 698 | CE2 | PHE | A | 93 | 0 | 13.754 | 54.503 | 18.078 | 1.00 | 25.39 |
| ATOM | 699 | CZ | PHE | A | 93 | 0 | 13.935 | 55.857 | 18.302 | 1.00 | 25.01 |
| ATOM | 700 | N | LEU | A | 94 | 0 | 15.756 | 54.699 | 14.136 | 1.00 | 23.39 |
| ATOM | 701 | CA | LEU | A | 94 | 0 | 17.046 | 54.058 | 14.361 | 1.00 | 23.35 |
| ATOM | 702 | C | LEU | A | 94 | 0 | 17.191 | 53.611 | 15.804 | 1.00 | 23.22 |
| ATOM | 703 | O | LEU | A | 94 | 0 | 17.261 | 54.431 | 16.714 | 1.00 | 23.47 |
| ATOM | 704 | CB | LEU | A | 94 | 0 | 18.186 | 54.994 | 13.943 | 1.00 | 24.96 |
| ATOM | 705 | CG | LEU | A | 94 | 0 | 19.630 | 54.555 | 14.170 | 1.00 | 26.28 |
| ATOM | 706 | CD1 | LEU | A | 94 | 0 | 19.979 | 53.313 | 13.352 | 1.00 | 25.99 |
| ATOM | 707 | CD2 | LEU | A | 94 | 0 | 20.627 | 55.678 | 13.887 | 1.00 | 26.06 |
| ATOM | 708 | N | TYR | A | 95 | 0 | 17.261 | 52.293 | 16.023 | 1.00 | 21.81 |
| ATOM | 709 | CA | TYR | A | 95 | 0 | 17.481 | 51.780 | 17.379 | 1.00 | 19.72 |
| ATOM | 710 | C | TYR | A | 95 | 0 | 18.991 | 51.663 | 17.585 | 1.00 | 20.90 |
| ATOM | 711 | O | TYR | A | 95 | 0 | 19.690 | 51.248 | 16.656 | 1.00 | 20.74 |
| ATOM | 712 | CB | TYR | A | 95 | 0 | 16.831 | 50.448 | 17.609 | 1.00 | 17.86 |
| ATOM | 713 | CG | TYR | A | 95 | 0 | 15.329 | 50.411 | 17.691 | 1.00 | 16.35 |
| ATOM | 714 | CD1 | TYR | A | 95 | 0 | 14.541 | 50.288 | 16.535 | 1.00 | 16.89 |
| ATOM | 715 | CD2 | TYR | A | 95 | 0 | 14.701 | 50.442 | 18.911 | 1.00 | 15.71 |
| ATOM | 716 | CE1 | TYR | A | 95 | 0 | 13.157 | 50.205 | 16.621 | 1.00 | 17.21 |
| ATOM | 717 | CE2 | TYR | A | 95 | 0 | 13.325 | 50.362 | 19.033 | 1.00 | 16.25 |
| ATOM | 718 | CZ | TYR | A | 95 | 0 | 12.568 | 50.266 | 17.874 | 1.00 | 17.97 |
| ATOM | 719 | OH | TYR | A | 95 | 0 | 11.205 | 50.189 | 18.001 | 1.00 | 18.61 |
| ATOM | 720 | N | LYS | A | 96 | 0 | 19.475 | 52.105 | 18.752 | 1.00 | 20.56 |
| ATOM | 721 | CA | LYS | A | 96 | 0 | 20.917 | 52.058 | 18.975 | 1.00 | 21.77 |
| ATOM | 722 | C | LYS | A | 96 | 0 | 21.139 | 51.519 | 20.386 | 1.00 | 20.91 |
| ATOM | 723 | O | LYS | A | 96 | 0 | 20.558 | 52.122 | 21.286 | 1.00 | 21.98 |
| ATOM | 724 | CB | LYS | A | 96 | 0 | 21.565 | 53.427 | 18.960 | 1.00 | 22.89 |
| ATOM | 725 | CG | LYS | A | 96 | 0 | 21.857 | 54.046 | 17.609 | 1.00 | 26.39 |
| ATOM | 726 | CD | LYS | A | 96 | 0 | 22.749 | 55.251 | 17.923 | 1.00 | 30.80 |
| ATOM | 727 | CE | LYS | A | 96 | 0 | 22.732 | 56.348 | 16.884 | 1.00 | 32.90 |
| ATOM | 728 | NZ | LYS | A | 96 | 0 | 23.767 | 57.378 | 17.277 | 1.00 | 36.06 |
| ATOM | 729 | N | PHE | A | 97 | 0 | 21.871 | 50.437 | 20.520 | 1.00 | 18.14 |
| ATOM | 730 | CA | PHE | A | 97 | 0 | 22.062 | 49.863 | 21.854 | 1.00 | 18.19 |
| ATOM | 731 | C | PHE | A | 97 | 0 | 23.276 | 48.928 | 21.805 | 1.00 | 16.76 |
| ATOM | 732 | O | PHE | A | 97 | 0 | 23.870 | 48.700 | 20.747 | 1.00 | 14.19 |
| ATOM | 733 | CB | PHE | A | 97 | 0 | 20.816 | 49.067 | 22.307 | 1.00 | 17.34 |
| ATOM | 734 | CG | PHE | A | 97 | 0 | 20.379 | 48.026 | 21.304 | 1.00 | 17.56 |
| ATOM | 735 | CD1 | PHE | A | 97 | 0 | 20.873 | 46.732 | 21.348 | 1.00 | 16.27 |
| ATOM | 736 | CD2 | PHE | A | 97 | 0 | 19.451 | 48.343 | 20.326 | 1.00 | 18.65 |
| ATOM | 737 | CE1 | PHE | A | 97 | 0 | 20.476 | 45.801 | 20.398 | 1.00 | 17.76 |
| ATOM | 738 | CE2 | PHE | A | 97 | 0 | 19.026 | 47.408 | 19.386 | 1.00 | 18.64 |
| ATOM | 739 | CZ | PHE | A | 97 | 0 | 19.546 | 46.120 | 19.416 | 1.00 | 17.55 |
| ATOM | 740 | N | THR | A | 98 | 0 | 23.552 | 48.348 | 22.971 | 1.00 | 17.45 |
| ATOM | 741 | CA | THR | A | 98 | 0 | 24.644 | 47.359 | 22.992 | 1.00 | 17.00 |
| ATOM | 742 | C | THR | A | 98 | 0 | 24.304 | 46.333 | 24.042 | 1.00 | 16.63 |
| ATOM | 743 | O | THR | A | 98 | 0 | 23.725 | 46.631 | 25.090 | 1.00 | 15.86 |
| ATOM | 744 | CB | THR | A | 98 | 0 | 26.028 | 47.990 | 23.256 | 1.00 | 17.53 |
| ATOM | 745 | OG1 | THR | A | 98 | 0 | 27.017 | 46.924 | 23.372 | 1.00 | 19.01 |

APPENDIX 1-continued

| | | | | | | | | | | | |
|---|---|---|---|---|---|---|---|---|---|---|---|
| ATOM | 746 | CG2 | THR | A | 98 | 0 | 26.088 | 48.807 | 24.525 | 1.00 | 14.85 |
| ATOM | 747 | N | PRO | A | 99 | 0 | 24.740 | 45.097 | 23.831 | 1.00 | 15.98 |
| ATOM | 748 | CA | PRO | A | 99 | 0 | 24.601 | 44.019 | 24.787 | 1.00 | 15.11 |
| ATOM | 749 | C | PRO | A | 99 | 0 | 25.445 | 44.270 | 26.020 | 1.00 | 15.99 |
| ATOM | 750 | O | PRO | A | 99 | 0 | 25.260 | 43.633 | 27.064 | 1.00 | 15.94 |
| ATOM | 751 | CB | PRO | A | 99 | 0 | 25.025 | 42.717 | 24.098 | 1.00 | 15.83 |
| ATOM | 752 | CG | PRO | A | 99 | 0 | 25.042 | 43.140 | 22.644 | 1.00 | 17.12 |
| ATOM | 753 | CD | PRO | A | 99 | 0 | 25.362 | 44.627 | 22.601 | 1.00 | 15.68 |
| ATOM | 754 | N | ALA | A | 100 | 0 | 26.452 | 45.149 | 25.932 | 1.00 | 17.29 |
| ATOM | 755 | CA | ALA | A | 100 | 0 | 27.316 | 45.501 | 27.050 | 1.00 | 16.88 |
| ATOM | 756 | C | ALA | A | 100 | 0 | 27.919 | 44.293 | 27.754 | 1.00 | 16.16 |
| ATOM | 757 | O | ALA | A | 100 | 0 | 27.779 | 44.187 | 28.977 | 1.00 | 18.13 |
| ATOM | 758 | CB | ALA | A | 100 | 0 | 26.498 | 46.292 | 28.084 | 1.00 | 14.96 |
| ATOM | 759 | N | GLY | A | 101 | 0 | 28.474 | 43.360 | 27.033 | 1.00 | 16.41 |
| ATOM | 760 | CA | GLY | A | 101 | 0 | 29.063 | 42.172 | 27.599 | 1.00 | 17.49 |
| ATOM | 761 | C | GLY | A | 101 | 0 | 28.130 | 40.994 | 27.769 | 1.00 | 16.15 |
| ATOM | 762 | O | GLY | A | 101 | 0 | 28.593 | 39.930 | 28.137 | 1.00 | 16.57 |
| ATOM | 763 | N | HIS | A | 102 | 0 | 26.838 | 41.120 | 27.521 | 1.00 | 17.58 |
| ATOM | 764 | CA | HIS | A | 102 | 0 | 25.858 | 40.058 | 27.804 | 1.00 | 15.77 |
| ATOM | 765 | C | HIS | A | 102 | 0 | 25.707 | 39.165 | 26.600 | 1.00 | 15.28 |
| ATOM | 766 | O | HIS | A | 102 | 0 | 25.087 | 39.641 | 25.662 | 1.00 | 17.64 |
| ATOM | 767 | CB | HIS | A | 102 | 0 | 24.498 | 40.666 | 28.186 | 1.00 | 17.95 |
| ATOM | 768 | CG | HIS | A | 102 | 0 | 23.432 | 39.661 | 28.493 | 1.00 | 20.00 |
| ATOM | 769 | ND1 | HIS | A | 102 | 0 | 22.099 | 40.005 | 28.547 | 1.00 | 20.59 |
| ATOM | 770 | CD2 | HIS | A | 102 | 0 | 23.475 | 38.323 | 28.772 | 1.00 | 20.09 |
| ATOM | 771 | CE1 | HIS | A | 102 | 0 | 21.398 | 38.937 | 28.866 | 1.00 | 20.77 |
| ATOM | 772 | NE2 | HIS | A | 102 | 0 | 22.201 | 37.896 | 29.016 | 1.00 | 20.56 |
| ATOM | 773 | N | ALA | A | 103 | 0 | 26.277 | 37.958 | 26.584 | 1.00 | 13.32 |
| ATOM | 774 | CA | ALA | A | 103 | 0 | 26.141 | 37.127 | 25.415 | 1.00 | 13.99 |
| ATOM | 775 | C | ALA | A | 103 | 0 | 24.974 | 36.156 | 25.649 | 1.00 | 13.43 |
| ATOM | 776 | O | ALA | A | 103 | 0 | 24.571 | 35.905 | 26.784 | 1.00 | 11.81 |
| ATOM | 777 | CB | ALA | A | 103 | 0 | 27.418 | 36.329 | 25.151 | 1.00 | 16.36 |
| ATOM | 778 | N | GLY | A | 104 | 0 | 24.459 | 35.610 | 24.554 | 1.00 | 12.38 |
| ATOM | 779 | CA | GLY | A | 104 | 0 | 23.381 | 34.632 | 24.778 | 1.00 | 12.85 |
| ATOM | 780 | C | GLY | A | 104 | 0 | 22.480 | 34.451 | 23.581 | 1.00 | 11.06 |
| ATOM | 781 | O | GLY | A | 104 | 0 | 22.674 | 35.057 | 22.515 | 1.00 | 10.91 |
| ATOM | 782 | N | THR | A | 105 | 0 | 21.442 | 33.650 | 23.794 | 1.00 | 10.14 |
| ATOM | 783 | CA | THR | A | 105 | 0 | 20.490 | 33.394 | 22.704 | 1.00 | 10.04 |
| ATOM | 784 | C | THR | A | 105 | 0 | 19.238 | 34.236 | 22.989 | 1.00 | 9.52 |
| ATOM | 785 | O | THR | A | 105 | 0 | 18.738 | 34.194 | 24.125 | 1.00 | 7.52 |
| ATOM | 786 | CB | THR | A | 105 | 0 | 20.114 | 31.913 | 22.665 | 1.00 | 12.67 |
| ATOM | 787 | OG1 | THR | A | 105 | 0 | 21.273 | 31.075 | 22.593 | 1.00 | 13.47 |
| ATOM | 788 | CG2 | THR | A | 105 | 0 | 19.187 | 31.684 | 21.468 | 1.00 | 12.75 |
| ATOM | 789 | N | PHE | A | 106 | 0 | 18.842 | 35.065 | 22.044 | 1.00 | 7.76 |
| ATOM | 790 | CA | PHE | A | 106 | 0 | 17.731 | 35.992 | 22.243 | 1.00 | 10.15 |
| ATOM | 791 | C | PHE | A | 106 | 0 | 16.756 | 35.910 | 21.068 | 1.00 | 8.42 |
| ATOM | 792 | O | PHE | A | 106 | 0 | 16.941 | 35.083 | 20.166 | 1.00 | 8.33 |
| ATOM | 793 | CB | PHE | A | 106 | 0 | 18.283 | 37.460 | 22.369 | 1.00 | 10.19 |
| ATOM | 794 | CG | PHE | A | 106 | 0 | 19.291 | 37.577 | 23.506 | 1.00 | 12.95 |
| ATOM | 795 | CD1 | PHE | A | 106 | 0 | 18.905 | 37.443 | 24.815 | 1.00 | 11.44 |
| ATOM | 796 | CD2 | PHE | A | 106 | 0 | 20.654 | 37.775 | 23.230 | 1.00 | 12.37 |
| ATOM | 797 | CE1 | PHE | A | 106 | 0 | 19.855 | 37.531 | 25.822 | 1.00 | 14.20 |
| ATOM | 798 | CE2 | PHE | A | 106 | 0 | 21.574 | 37.857 | 24.273 | 1.00 | 11.56 |
| ATOM | 799 | CZ | PHE | A | 106 | 0 | 21.202 | 37.733 | 25.599 | 1.00 | 9.45 |
| ATOM | 800 | N | TRP | A | 107 | 0 | 15.869 | 36.887 | 20.917 | 1.00 | 6.61 |
| ATOM | 801 | CA | TRP | A | 107 | 0 | 15.062 | 36.977 | 19.713 | 1.00 | 10.20 |
| ATOM | 802 | C | TRP | A | 107 | 0 | 14.511 | 38.398 | 19.495 | 1.00 | 10.63 |
| ATOM | 803 | O | TRP | A | 107 | 0 | 14.463 | 39.036 | 20.657 | 1.00 | 13.71 |
| ATOM | 804 | CB | TRP | A | 107 | 0 | 13.928 | 35.966 | 19.636 | 1.00 | 7.49 |
| ATOM | 805 | CG | TRP | A | 107 | 0 | 12.945 | 35.916 | 20.755 | 1.00 | 9.41 |
| ATOM | 806 | CD1 | TRP | A | 107 | 0 | 13.136 | 35.804 | 22.106 | 1.00 | 10.53 |
| ATOM | 807 | CD2 | TRP | A | 107 | 0 | 11.509 | 36.004 | 20.581 | 1.00 | 9.17 |
| ATOM | 808 | NE1 | TRP | A | 107 | 0 | 11.929 | 35.784 | 22.768 | 1.00 | 10.63 |
| ATOM | 809 | CE2 | TRP | A | 107 | 0 | 10.924 | 35.926 | 21.842 | 1.00 | 9.90 |
| ATOM | 810 | CE3 | TRP | A | 107 | 0 | 10.698 | 36.144 | 19.444 | 1.00 | 8.77 |
| ATOM | 811 | CZ2 | TRP | A | 107 | 0 | 9.538 | 35.947 | 22.025 | 1.00 | 10.01 |
| ATOM | 812 | CZ3 | TRP | A | 107 | 0 | 9.336 | 36.167 | 19.613 | 1.00 | 8.60 |
| ATOM | 813 | CH2 | TRP | A | 107 | 0 | 8.774 | 36.061 | 20.890 | 1.00 | 10.09 |
| ATOM | 814 | N | TYR | A | 108 | 0 | 14.117 | 38.847 | 18.464 | 1.00 | 10.72 |
| ATOM | 815 | CA | TYR | A | 108 | 0 | 13.498 | 40.148 | 18.302 | 1.00 | 12.19 |
| ATOM | 816 | C | TYR | A | 108 | 0 | 12.030 | 39.869 | 17.875 | 1.00 | 13.62 |
| ATOM | 817 | O | TYR | A | 108 | 0 | 11.752 | 38.837 | 17.245 | 1.00 | 13.85 |
| ATOM | 818 | CB | TYR | A | 108 | 0 | 14.182 | 40.994 | 17.259 | 1.00 | 11.05 |
| ATOM | 819 | CG | TYR | A | 108 | 0 | 14.176 | 40.413 | 15.857 | 1.00 | 13.89 |
| ATOM | 820 | CD1 | TYR | A | 108 | 0 | 15.087 | 39.464 | 15.423 | 1.00 | 12.99 |
| ATOM | 821 | CD2 | TYR | A | 108 | 0 | 13.257 | 40.897 | 14.920 | 1.00 | 14.94 |
| ATOM | 822 | CE1 | TYR | A | 108 | 0 | 15.064 | 38.979 | 14.130 | 1.00 | 13.64 |
| ATOM | 823 | CE2 | TYR | A | 108 | 0 | 13.216 | 40.409 | 13.624 | 1.00 | 15.34 |
| ATOM | 824 | CZ | TYR | A | 108 | 0 | 14.123 | 39.443 | 13.236 | 1.00 | 14.99 |

APPENDIX 1-continued

| | | | | | | | | | | | |
|---|---|---|---|---|---|---|---|---|---|---|---|
| ATOM | 825 | OH | TYR | A | 108 | 0 | 14.063 | 38.960 | 11.946 | 1.00 | 16.68 |
| ATOM | 826 | N | HIS | A | 109 | 0 | 11.123 | 40.752 | 18.254 | 1.00 | 12.81 |
| ATOM | 827 | CA | HIS | A | 109 | 0 | 9.735 | 40.630 | 17.826 | 1.00 | 14.92 |
| ATOM | 828 | C | HIS | A | 109 | 0 | 9.057 | 41.988 | 17.991 | 1.00 | 15.96 |
| ATOM | 829 | O | HIS | A | 109 | 0 | 9.392 | 42.800 | 18.875 | 1.00 | 15.67 |
| ATOM | 830 | CB | HIS | A | 109 | 0 | 8.903 | 39.566 | 18.550 | 1.00 | 12.30 |
| ATOM | 831 | CG | HIS | A | 109 | 0 | 8.804 | 39.727 | 20.036 | 1.00 | 12.30 |
| ATOM | 832 | ND1 | HIS | A | 109 | 0 | 7.788 | 40.429 | 20.666 | 1.00 | 9.89 |
| ATOM | 833 | CD2 | HIS | A | 109 | 0 | 9.614 | 39.264 | 21.034 | 1.00 | 10.76 |
| ATOM | 834 | CE1 | HIS | A | 109 | 0 | 7.982 | 40.379 | 21.971 | 1.00 | 8.49 |
| ATOM | 835 | NE2 | HIS | A | 109 | 0 | 9.086 | 39.679 | 22.224 | 1.00 | 7.92 |
| ATOM | 836 | N | SER | A | 110 | 0 | 8.070 | 42.203 | 17.122 | 1.00 | 16.26 |
| ATOM | 837 | CA | SER | A | 110 | 0 | 7.244 | 43.404 | 17.300 | 1.00 | 14.55 |
| ATOM | 838 | C | SER | A | 110 | 0 | 6.548 | 43.283 | 18.646 | 1.00 | 13.56 |
| ATOM | 839 | O | SER | A | 110 | 0 | 6.219 | 42.191 | 19.140 | 1.00 | 13.54 |
| ATOM | 840 | CB | SER | A | 110 | 0 | 6.219 | 43.543 | 16.159 | 1.00 | 16.69 |
| ATOM | 841 | OG | SER | A | 110 | 0 | 5.212 | 44.481 | 16.508 | 1.00 | 15.32 |
| ATOM | 842 | N | HIS | A | 111 | 0 | 6.396 | 44.395 | 19.359 | 1.00 | 14.60 |
| ATOM | 843 | CA | HIS | A | 111 | 0 | 5.724 | 44.397 | 20.645 | 1.00 | 16.23 |
| ATOM | 844 | C | HIS | A | 111 | 0 | 4.349 | 45.070 | 20.478 | 1.00 | 18.61 |
| ATOM | 845 | O | HIS | A | 111 | 0 | 3.713 | 45.391 | 21.473 | 1.00 | 21.72 |
| ATOM | 846 | CB | HIS | A | 111 | 0 | 6.478 | 45.166 | 21.721 | 1.00 | 14.37 |
| ATOM | 847 | CG | HIS | A | 111 | 0 | 6.392 | 44.519 | 23.077 | 1.00 | 15.33 |
| ATOM | 848 | ND1 | HIS | A | 111 | 0 | 5.341 | 44.660 | 23.947 | 1.00 | 14.55 |
| ATOM | 849 | CD2 | HIS | A | 111 | 0 | 7.265 | 43.676 | 23.680 | 1.00 | 14.72 |
| ATOM | 850 | CE1 | HIS | A | 111 | 0 | 5.589 | 43.936 | 25.040 | 1.00 | 16.29 |
| ATOM | 851 | NE2 | HIS | A | 111 | 0 | 6.773 | 43.326 | 24.920 | 1.00 | 15.35 |
| ATOM | 852 | N | PHE | A | 112 | 0 | 3.950 | 45.382 | 19.258 | 1.00 | 18.67 |
| ATOM | 853 | CA | PHE | A | 112 | 0 | 2.725 | 46.139 | 19.037 | 1.00 | 19.61 |
| ATOM | 854 | C | PHE | A | 112 | 0 | 1.540 | 45.219 | 18.777 | 1.00 | 19.06 |
| ATOM | 855 | O | PHE | A | 112 | 0 | 1.521 | 44.630 | 17.707 | 1.00 | 17.50 |
| ATOM | 856 | CB | PHE | A | 112 | 0 | 2.971 | 47.113 | 17.875 | 1.00 | 21.16 |
| ATOM | 857 | CG | PHE | A | 112 | 0 | 1.798 | 48.019 | 17.611 | 1.00 | 23.12 |
| ATOM | 858 | CD1 | PHE | A | 112 | 0 | 1.456 | 49.007 | 18.509 | 1.00 | 24.59 |
| ATOM | 859 | CD2 | PHE | A | 112 | 0 | 1.034 | 47.886 | 16.466 | 1.00 | 24.82 |
| ATOM | 860 | CE1 | PHE | A | 112 | 0 | G.387 | 49.852 | 18.312 | 1.00 | 24.29 |
| ATOM | 861 | CE2 | PHE | A | 112 | 0 | -0.063 | 48.714 | 16.243 | 1.00 | 25.87 |
| ATOM | 862 | CZ | PHE | A | 112 | 0 | -0.378 | 49.698 | 17.161 | 1.00 | 25.17 |
| ATOM | 863 | N | GLY | A | 113 | 0 | 0.599 | 45.092 | 19.707 | 1.00 | 18.05 |
| ATOM | 864 | CA | GLY | A | 113 | 0 | -0.554 | 44.236 | 19.433 | 1.00 | 19.69 |
| ATOM | 865 | C | GLY | A | 113 | 0 | -0.085 | 42.819 | 19.096 | 1.00 | 22.25 |
| ATOM | 866 | O | GLY | A | 113 | 0 | 0.937 | 42.333 | 19.593 | 1.00 | 20.55 |
| ATOM | 867 | N | THR | A | 114 | 0 | -0.817 | 42.173 | 18.186 | 1.00 | 20.91 |
| ATOM | 868 | CA | THR | A | 114 | 0 | -0.493 | 40.816 | 17.749 | 1.00 | 20.85 |
| ATOM | 869 | C | THR | A | 114 | 0 | 0.296 | 40.774 | 16.471 | 1.00 | 18.04 |
| ATOM | 870 | O | THR | A | 114 | 0 | 0.243 | 39.783 | 15.743 | 1.00 | 18.26 |
| ATOM | 871 | CB | THR | A | 114 | 0 | -1.847 | 40.095 | 17.487 | 1.00 | 23.93 |
| ATOM | 872 | OG1 | THR | A | 114 | 0 | -2.609 | 40.910 | 16.554 | 1.00 | 25.68 |
| ATOM | 873 | CG2 | THR | A | 114 | 0 | -2.571 | 39.926 | 18.792 | 1.00 | 23.72 |
| ATOM | 874 | N | GLN | A | 115 | 0 | 1.023 | 41.819 | 16.095 | 1.00 | 17.04 |
| ATOM | 875 | CA | GLN | A | 115 | 0 | 1.792 | 41.842 | 14.853 | 1.00 | 16.88 |
| ATOM | 876 | C | GLN | A | 115 | 0 | 2.881 | 40.775 | 14.744 | 1.00 | 17.94 |
| ATOM | 877 | O | GLN | A | 115 | 0 | 3.203 | 40.263 | 13.649 | 1.00 | 17.18 |
| ATOM | 878 | CB | GLN | A | 115 | 0 | 2.391 | 43.244 | 14.757 | 1.00 | 17.55 |
| ATOM | 879 | CG | GLN | A | 115 | 0 | 3.026 | 43.601 | 13.418 | 1.00 | 17.65 |
| ATOM | 880 | CD | GLN | A | 115 | 0 | 3.558 | 45.024 | 13.418 | 1.00 | 17.73 |
| ATOM | 881 | OE1 | GLN | A | 115 | 0 | 3.257 | 45.782 | 12.482 | 1.00 | 19.19 |
| ATOM | 882 | NE2 | GLN | A | 115 | 0 | 4.334 | 45.421 | 14.422 | 1.00 | 14.70 |
| ATOM | 883 | N | TYR | A | 116 | 0 | 3.515 | 40.416 | 15.881 | 1.00 | 16.32 |
| ATOM | 884 | CA | TYR | A | 116 | 0 | 4.561 | 39.386 | 15.859 | 1.00 | 15.92 |
| ATOM | 885 | C | TYR | A | 116 | 0 | 3.935 | 38.042 | 15.479 | 1.00 | 17.17 |
| ATOM | 886 | O | TYR | A | 116 | 0 | 4.584 | 37.258 | 14.786 | 1.00 | 16.70 |
| ATOM | 887 | CB | TYR | A | 116 | 0 | 5.411 | 39.312 | 17.096 | 1.00 | 13.45 |
| ATOM | 888 | CG | TYR | A | 116 | 0 | 5.209 | 38.487 | 18.314 | 1.00 | 10.97 |
| ATOM | 889 | CD1 | TYR | A | 116 | 0 | 5.581 | 37.146 | 18.394 | 1.00 | 11.02 |
| ATOM | 890 | CD2 | TYR | A | 116 | 0 | 4.665 | 39.052 | 19.460 | 1.00 | 12.18 |
| ATOM | 891 | CE1 | TYR | A | 116 | 0 | 5.364 | 36.399 | 19.532 | 1.00 | 10.02 |
| ATOM | 892 | CE2 | TYR | A | 116 | 0 | 4.491 | 38.345 | 20.642 | 1.00 | 12.25 |
| ATOM | 893 | CZ | TYR | A | 116 | 0 | 4.838 | 36.996 | 20.649 | 1.00 | 11.73 |
| ATOM | 894 | OH | TYR | A | 116 | 0 | 4.642 | 36.295 | 21.821 | 1.00 | 12.72 |
| ATOM | 895 | N | CYS | A | 117 | 0 | 2.654 | 37.829 | 15.842 | 1.00 | 17.70 |
| ATOM | 896 | CA | CYS | A | 117 | 0 | 1.965 | 36.617 | 15.424 | 1.00 | 18.01 |
| ATOM | 897 | C | CYS | A | 117 | 0 | 1.883 | 36.496 | 13.911 | 1.00 | 17.55 |
| ATOM | 898 | O | CYS | A | 117 | 0 | 1.796 | 35.352 | 13.450 | 1.00 | 17.50 |
| ATOM | 899 | CB | CYS | A | 117 | 0 | 0.565 | 36.528 | 16.042 | 1.00 | 17.90 |
| ATOM | 900 | SG | CYS | A | 117 | 0 | 0.463 | 36.895 | 17.810 | 1.00 | 19.72 |
| ATOM | 901 | N | ASP | A | 118 | 0 | 2.001 | 37.568 | 13.136 | 1.00 | 15.51 |
| ATOM | 902 | CA | ASP | A | 118 | 0 | 1.953 | 37.509 | 11.696 | 1.00 | 17.74 |
| ATOM | 903 | C | ASP | A | 118 | 0 | 3.341 | 37.445 | 11.061 | 1.00 | 18.72 |

APPENDIX 1-continued

| ATOM | 904 | O   | ASP | A | 118 | 0 |  3.494 | 37.770 |  9.865 | 1.00 | 17.47 |
|------|-----|-----|-----|---|-----|---|--------|--------|--------|------|-------|
| ATOM | 905 | CB  | ASP | A | 118 | 0 |  1.142 | 38.696 | 11.131 | 1.00 | 18.61 |
| ATOM | 906 | CG  | ASP | A | 118 | 0 | -0.356 | 38.448 | 11.378 | 1.00 | 21.44 |
| ATOM | 907 | OD1 | ASP | A | 118 | 0 | -0.826 | 37.331 | 11.082 | 1.00 | 21.55 |
| ATOM | 908 | OD2 | ASP | A | 118 | 0 | -1.064 | 39.333 | 11.885 | 1.00 | 21.54 |
| ATOM | 909 | N   | GLY | A | 119 | 0 |  4.355 | 37.095 | 11.882 | 1.00 | 18.19 |
| ATOM | 910 | CA  | GLY | A | 119 | 0 |  5.671 | 36.889 | 11.313 | 1.00 | 19.00 |
| ATOM | 911 | C   | GLY | A | 119 | 0 |  6.751 | 37.898 | 11.590 | 1.00 | 19.79 |
| ATOM | 912 | O   | GLY | A | 119 | 0 |  7.909 | 37.640 | 11.213 | 1.00 | 19.97 |
| ATOM | 913 | N   | LEU | A | 120 | 0 |  6.445 | 39.011 | 12.280 | 1.00 | 18.24 |
| ATOM | 914 | CA  | LEU | A | 120 | 0 |  7.484 | 39.991 | 12.569 | 1.00 | 16.08 |
| ATOM | 915 | C   | LEU | A | 120 | 0 |  8.210 | 39.565 | 13.848 | 1.00 | 16.53 |
| ATOM | 916 | O   | LEU | A | 120 | 0 |  7.933 | 40.051 | 14.939 | 1.00 | 15.31 |
| ATOM | 917 | CB  | LEU | A | 120 | 0 |  6.918 | 41.389 | 12.654 | 1.00 | 16.22 |
| ATOM | 918 | CG  | LEU | A | 120 | 0 |  7.916 | 42.540 | 12.830 | 1.00 | 17.73 |
| ATOM | 919 | CD1 | LEU | A | 120 | 0 |  9.188 | 42.293 | 12.043 | 1.00 | 17.73 |
| ATOM | 920 | CD2 | LEU | A | 120 | 0 |  7.302 | 43.880 | 12.448 | 1.00 | 16.66 |
| ATOM | 921 | N   | ARG | A | 121 | 0 |  9.144 | 38.622 | 13.682 | 1.00 | 14.23 |
| ATOM | 922 | CA  | ARG | A | 121 | 0 |  9.859 | 37.985 | 14.773 | 1.00 | 14.19 |
| ATOM | 923 | C   | ARG | A | 121 | 0 | 11.007 | 37.152 | 14.159 | 1.00 | 14.09 |
| ATOM | 924 | O   | ARG | A | 121 | 0 | 10.936 | 36.787 | 12.978 | 1.00 | 13.72 |
| ATOM | 925 | CB  | ARG | A | 121 | 0 |   8934 | 37.061 | 15.581 | 1.00 | 12.30 |
| ATOM | 926 | CG  | ARG | A | 121 | 0 |  8.253 | 35.999 | 14.728 | 1.00 | 12.44 |
| ATOM | 927 | CD  | ARG | A | 121 | 0 |  7.303 | 35.098 | 15.518 | 1.00 | 11.94 |
| ATOM | 928 | NE  | ARG | A | 121 | 0 |  6.507 | 34.269 | 14.604 | 1.00 | 12.92 |
| ATOM | 929 | CZ  | ARG | A | 121 | 0 |  5.413 | 33.570 | 14.933 | 1.00 | 10.55 |
| ATOM | 930 | NH1 | ARG | A | 121 | 0 |  4.897 | 33.483 | 16.137 | 1.00 |  8.12 |
| ATOM | 931 | NH2 | ARG | A | 121 | 0 |  4.803 | 32.946 | 13.930 | 1.00 | 10.40 |
| ATOM | 932 | N   | GLY | A | 122 | 0 | 12.045 | 36.848 | 14.937 | 1.00 | 12.29 |
| ATOM | 933 | CA  | GLY | A | 122 | 0 | 13.162 | 36.078 | 14.364 | 1.00 | 11.42 |
| ATOM | 934 | C   | GLY | A | 122 | 0 | 14.185 | 35.918 | 15.486 | 1.00 | 12.42 |
| ATOM | 935 | O   | GLY | A | 122 | 0 | 14.095 | 36.604 | 16.509 | 1.00 | 11.47 |
| ATOM | 936 | N   | PRO | A | 123 | 0 | 15.164 | 35.075 | 15.246 | 1.00 | 11.82 |
| ATOM | 937 | CA  | PRO | A | 123 | 0 | 16.226 | 34.778 | 16.190 | 1.00 | 12.81 |
| ATOM | 938 | C   | PRO | A | 123 | 0 | 17.288 | 35.857 | 16.258 | 1.00 | 12.41 |
| ATOM | 939 | O   | PRO | A | 123 | 0 | 17.565 | 36.580 | 15.302 | 1.00 | 12.03 |
| ATOM | 940 | CB  | PRO | A | 123 | 0 | 16.833 | 33.416 | 15.713 | 1.00 | 12.34 |
| ATOM | 941 | CG  | PRO | A | 123 | 0 | 16.567 | 33.494 | 14.223 | 1.00 | 12.19 |
| ATOM | 942 | CD  | PRO | A | 123 | 0 | 15.283 | 34.289 | 14.021 | 1.00 | 11.35 |
| ATOM | 943 | N   | MET | A | 124 | 0 | 17.903 | 36.027 | 17.431 | 1.00 | 14.30 |
| ATOM | 944 | CA  | MET | A | 124 | 0 | 18.959 | 37.024 | 17.628 | 1.00 | 14.19 |
| ATOM | 945 | C   | MET | A | 124 | 0 | 20.040 | 36.414 | 18.528 | 1.00 | 15.37 |
| ATOM | 946 | O   | MET | A | 124 | 0 | 19.788 | 36.067 | 19.690 | 1.00 | 15.41 |
| ATOM | 947 | CB  | MET | A | 124 | 0 | 18.411 | 38.290 | 18.242 | 1.00 | 15.94 |
| ATOM | 948 | CG  | MET | A | 124 | 0 | 19.464 | 39.345 | 18.604 | 1.00 | 19.30 |
| ATOM | 949 | SD  | MET | A | 124 | 0 | 18.646 | 40.875 | 19.164 | 1.00 | 21.94 |
| ATOM | 950 | CE  | MET | A | 124 | 0 | 19.918 | 42.061 | 18.729 | 1.00 | 23.64 |
| ATOM | 951 | N   | VAL | A | 125 | 0 | 21.212 | 36.178 | 17.939 | 1.00 | 13.74 |
| ATOM | 952 | CA  | VAL | A | 125 | 0 | 22.282 | 35.479 | 18.658 | 1.00 | 13.87 |
| ATOM | 953 | C   | VAL | A | 125 | 0 | 23.478 | 36.390 | 18.872 | 1.00 | 13.68 |
| ATOM | 954 | O   | VAL | A | 125 | 0 | 24.004 | 36.976 | 17.945 | 1.00 | 14.01 |
| ATOM | 955 | CB  | VAL | A | 125 | 0 | 22.672 | 34.139 | 18.005 | 1.00 | 12.58 |
| ATOM | 956 | CG1 | VAL | A | 125 | 0 | 23.787 | 33.383 | 18.749 | 1.00 | 11.23 |
| ATOM | 957 | CG2 | VAL | A | 125 | 0 | 21.448 | 33.212 | 18.033 | 1.00 | 12.14 |
| ATOM | 958 | N   | ILE | A | 126 | 0 | 23.860 | 36.535 | 20.135 | 1.00 | 14.48 |
| ATOM | 959 | CA  | ILE | A | 126 | 0 | 25.016 | 37.295 | 20.557 | 1.00 | 14.53 |
| ATOM | 960 | C   | ILE | A | 126 | 0 | 26.131 | 36.348 | 21.054 | 1.00 | 13.58 |
| ATOM | 961 | O   | ILE | A | 126 | 0 | 26.061 | 35.791 | 22.154 | 1.00 | 12.93 |
| ATOM | 962 | CB  | ILE | A | 126 | 0 | 24.649 | 38.295 | 21.662 | 1.00 | 14.95 |
| ATOM | 963 | CG1 | ILE | A | 126 | 0 | 23.563 | 39.302 | 21.254 | 1.00 | 15.29 |
| ATOM | 964 | CG2 | ILE | A | 126 | 0 | 25.901 | 39.014 | 22.174 | 1.00 | 14.24 |
| ATOM | 965 | CD1 | ILE | A | 126 | 0 | 23.703 | 39.905 | 19.896 | 1.00 | 15.84 |
| ATOM | 966 | N   | TYR | A | 127 | 0 | 27.142 | 36.146 | 20.236 | 1.00 | 13.66 |
| ATOM | 967 | CA  | TYR | A | 127 | 0 | 28.278 | 35.258 | 20.529 | 1.00 | 14.62 |
| ATOM | 968 | C   | TYR | A | 127 | 0 | 29.328 | 35.778 | 21.507 | 1.00 | 15.97 |
| ATOM | 969 | O   | TYR | A | 127 | 0 | 29.626 | 36.977 | 21.669 | 1.00 | 15.27 |
| ATOM | 970 | CB  | TYR | A | 127 | 0 | 28.965 | 34.939 | 19.176 | 1.00 | 14.97 |
| ATOM | 971 | CG  | TYR | A | 127 | 0 | 28.057 | 34.136 | 18.272 | 1.00 | 16.10 |
| ATOM | 972 | CD1 | TYR | A | 127 | 0 | 27.823 | 32.782 | 18.496 | 1.00 | 14.96 |
| ATOM | 973 | CD2 | TYR | A | 127 | 0 | 27.428 | 34.753 | 17.177 | 1.00 | 16.64 |
| ATOM | 974 | CE1 | TYR | A | 127 | 0 | 26.995 | 32.057 | 17.650 | 1.00 | 16.16 |
| ATOM | 975 | CE2 | TYR | A | 127 | 0 | 26.576 | 34.039 | 16.356 | 1.00 | 17.32 |
| ATOM | 976 | CZ  | TYR | A | 127 | 0 | 26.374 | 32.692 | 16.592 | 1.00 | 18.16 |
| ATOM | 977 | OH  | TYR | A | 127 | 0 | 25.540 | 31.971 | 15.756 | 1.00 | 20.32 |
| ATOM | 978 | N   | ASP | A | 128 | 0 | 29.892 | 34.895 | 22.312 | 1.00 | 14.36 |
| ATOM | 979 | CA  | ASP | A | 128 | 0 | 30.825 | 35.269 | 23.365 | 1.00 | 16.80 |
| ATOM | 980 | C   | ASP | A | 128 | 0 | 32.222 | 34.863 | 22.939 | 1.00 | 20.11 |
| ATOM | 981 | O   | ASP | A | 128 | 0 | 32.508 | 33.656 | 22.777 | 1.00 | 21.41 |
| ATOM | 982 | CB  | ASP | A | 128 | 0 | 30.398 | 34.568 | 24.649 | 1.00 | 16.65 |

APPENDIX 1-continued

| | | | | | | | | | | | |
|---|---|---|---|---|---|---|---|---|---|---|---|
| ATOM | 983 | CG | ASP | A | 128 | 0 | 31.136 | 35.055 | 25.874 | 1.00 | 18.36 |
| ATOM | 984 | OD1 | ASP | A | 128 | 0 | 32.194 | 35.708 | 25.750 | 1.00 | 18.72 |
| ATOM | 985 | OD2 | ASP | A | 128 | 0 | 30.710 | 34.819 | 27.024 | 1.00 | 20.03 |
| ATOM | 986 | N | ASP | A | 129 | 0 | 33.148 | 35.798 | 22.771 | 1.00 | 22.30 |
| ATOM | 987 | CA | ASP | A | 129 | 0 | 34.511 | 35.389 | 22.377 | 1.00 | 24.39 |
| ATOM | 988 | C | ASP | A | 129 | 0 | 35.282 | 34.740 | 23.509 | 1.00 | 22.47 |
| ATOM | 989 | O | ASP | A | 129 | 0 | 36.275 | 34.096 | 23.209 | 1.00 | 23.18 |
| ATOM | 990 | CB | ASP | A | 129 | 0 | 35.298 | 36.490 | 21.707 | 1.00 | 28.46 |
| ATOM | 991 | CG | ASP | A | 129 | 0 | 35.372 | 37.764 | 22.516 | 1.00 | 31.10 |
| ATOM | 992 | OD1 | ASP | A | 129 | 0 | 35.254 | 37.652 | 23.747 | 1.00 | 32.87 |
| ATOM | 993 | OD2 | ASP | A | 129 | 0 | 35.553 | 38.824 | 21.891 | 1.00 | 34.70 |
| ATOM | 994 | N | ASN | A | 130 | 0 | 34.829 | 34.684 | 24.736 | 1.00 | 21.92 |
| ATOM | 995 | CA | ASN | A | 130 | 0 | 35.368 | 34.015 | 25.874 | 1.00 | 23.74 |
| ATOM | 996 | C | ASN | A | 130 | 0 | 34.382 | 32.976 | 26.417 | 1.00 | 23.02 |
| ATOM | 997 | O | ASN | A | 130 | 0 | 34.352 | 32.684 | 27.616 | 1.00 | 20.14 |
| ATOM | 998 | CB | ASN | A | 130 | 0 | 35.686 | 35.002 | 27.028 | 1.00 | 26.41 |
| ATOM | 999 | CG | ASN | A | 130 | 0 | 36.583 | 36.127 | 26.550 | 1.00 | 30.99 |
| ATOM | 1000 | OD1 | ASN | A | 130 | 0 | 36.187 | 37.309 | 26.486 | 1.00 | 33.20 |
| ATOM | 1001 | ND2 | ASN | A | 130 | 0 | 37.818 | 35.769 | 26.175 | 1.00 | 30.96 |
| ATOM | 1002 | N | ASP | A | 131 | 0 | 33.533 | 32.401 | 25.561 | 1.00 | 23.32 |
| ATOM | 1003 | CA | ASP | A | 131 | 0 | 32.476 | 31.543 | 26.127 | 1.00 | 21.63 |
| ATOM | 1004 | C | ASP | A | 131 | 0 | 33.010 | 30.514 | 27.103 | 1.00 | 19.56 |
| ATOM | 1005 | O | ASP | A | 131 | 0 | 33.704 | 29.569 | 26.766 | 1.00 | 19.71 |
| ATOM | 1006 | CB | ASP | A | 131 | 0 | 31.594 | 30.877 | 25.063 | 1.00 | 22.97 |
| ATOM | 1007 | CG | ASP | A | 131 | 0 | 30.220 | 30.487 | 25.591 | 1.00 | 24.48 |
| ATOM | 1008 | OD1 | ASP | A | 131 | 0 | 30.181 | 29.525 | 26.397 | 1.00 | 26.42 |
| ATOM | 1009 | OD2 | ASP | A | 131 | 0 | 29.166 | 31.051 | 25.212 | 1.00 | 22.66 |
| ATOM | 1010 | N | PRO | A | 132 | 0 | 32.491 | 30.548 | 28.315 | 1.00 | 18.77 |
| ATOM | 1011 | CA | PRO | A | 132 | 0 | 32.759 | 29.611 | 29.381 | 1.00 | 19.41 |
| ATOM | 1012 | C | PRO | A | 132 | 0 | 32.523 | 28.141 | 29.031 | 1.00 | 20.89 |
| ATOM | 1013 | O | PRO | A | 132 | 0 | 33.112 | 27.250 | 29.672 | 1.00 | 19.99 |
| ATOM | 1014 | CB | PRO | A | 132 | 0 | 31.799 | 29.990 | 30.531 | 1.00 | 18.42 |
| ATOM | 1015 | CG | PRO | A | 132 | 0 | 31.589 | 31.470 | 30.263 | 1.00 | 16.87 |
| ATOM | 1016 | CD | PRO | A | 132 | 0 | 31.645 | 31.673 | 28.778 | 1.00 | 16.73 |
| ATOM | 1017 | N | HIS | A | 133 | 0 | 31.668 | 27.836 | 28.063 | 1.00 | 19.47 |
| ATOM | 1018 | CA | HIS | A | 133 | 0 | 31.331 | 26.465 | 27.700 | 1.00 | 18.79 |
| ATOM | 1019 | C | HIS | A | 133 | 0 | 31.887 | 26.014 | 26.372 | 1.00 | 19.35 |
| ATOM | 1020 | O | HIS | A | 133 | 0 | 31.503 | 24.954 | 25.826 | 1.00 | 18.60 |
| ATOM | 1021 | CB | HIS | A | 133 | 0 | 29.789 | 26.428 | 27.536 | 1.00 | 18.91 |
| ATOM | 1022 | CG | HIS | A | 133 | 0 | 29.065 | 26.242 | 28.815 | 1.00 | 18.13 |
| ATOM | 1023 | ND1 | HIS | A | 133 | 0 | 29.566 | 25.551 | 29.877 | 1.00 | 19.52 |
| ATOM | 1024 | CD2 | HIS | A | 133 | 0 | 27.817 | 26.625 | 29.183 | 1.00 | 19.38 |
| ATOM | 1025 | CE1 | HIS | A | 133 | 0 | 28.679 | 25.530 | 30.855 | 1.00 | 20.08 |
| ATOM | 1026 | NE2 | HIS | A | 133 | 0 | 27.587 | 26.180 | 30.457 | 1.00 | 19.60 |
| ATOM | 1027 | N | ALA | A | 134 | 0 | 32.840 | 26.801 | 25.852 | 1.00 | 19.40 |
| ATOM | 1028 | CA | ALA | A | 134 | 0 | 33.413 | 26.465 | 24.552 | 1.00 | 21.88 |
| ATOM | 1029 | C | ALA | A | 134 | 0 | 34.080 | 25.107 | 24.525 | 1.00 | 21.69 |
| ATOM | 1030 | O | ALA | A | 134 | 0 | 34.120 | 24.514 | 23.439 | 1.00 | 21.61 |
| ATOM | 1031 | CB | ALA | A | 134 | 0 | 34.418 | 27.548 | 24.128 | 1.00 | 22.55 |
| ATOM | 1032 | N | ALA | A | 135 | 0 | 34.582 | 24.527 | 25.622 | 1.00 | 21.96 |
| ATOM | 1033 | CA | ALA | A | 135 | 0 | 35.178 | 23.192 | 25.483 | 1.00 | 23.53 |
| ATOM | 1034 | C | ALA | A | 135 | 0 | 34.144 | 22.096 | 25.232 | 1.00 | 24.47 |
| ATOM | 1035 | O | ALA | A | 135 | 0 | 34.488 | 20.936 | 24.989 | 1.00 | 24.77 |
| ATOM | 1036 | CB | ALA | A | 135 | 0 | 35.910 | 22.820 | 26.776 | 1.00 | 21.92 |
| ATOM | 1037 | N | LEU | A | 136 | 0 | 32.862 | 22.375 | 25.457 | 1.00 | 24.95 |
| ATOM | 1038 | CA | LEU | A | 136 | 0 | 31.800 | 21.376 | 25.404 | 1.00 | 23.15 |
| ATOM | 1039 | C | LEU | A | 136 | 0 | 31.284 | 21.076 | 24.016 | 1.00 | 20.31 |
| ATOM | 1040 | O | LEU | A | 136 | 0 | 30.609 | 20.054 | 23.924 | 1.00 | 19.62 |
| ATOM | 1041 | CB | LEU | A | 136 | 0 | 30.665 | 21.845 | 26.318 | 1.00 | 24.43 |
| ATOM | 1042 | CG | LEU | A | 136 | 0 | 30.501 | 21.211 | 27.686 | 1.00 | 27.55 |
| ATOM | 1043 | CD1 | LEU | A | 136 | 0 | 31.803 | 20.721 | 28.285 | 1.00 | 25.75 |
| ATOM | 1044 | CD2 | LEU | A | 136 | 0 | 29.747 | 22.129 | 28.644 | 1.00 | 26.92 |
| ATOM | 1045 | N | TYR | A | 137 | 0 | 31.565 | 21.888 | 22.998 | 1.00 | 17.05 |
| ATOM | 1046 | CA | TYR | A | 137 | 0 | 31.085 | 21.612 | 21.662 | 1.00 | 16.65 |
| ATOM | 1047 | C | TYR | A | 137 | 0 | 32.076 | 22.054 | 20.599 | 1.00 | 17.99 |
| ATOM | 1048 | O | TYR | A | 137 | 0 | 32.965 | 22.891 | 20.794 | 1.00 | 18.69 |
| ATOM | 1049 | CB | TYR | A | 137 | 0 | 29.724 | 22.319 | 21.402 | 1.00 | 16.73 |
| ATOM | 1050 | CG | TYR | A | 137 | 0 | 29.711 | 23.760 | 21.857 | 1.00 | 16.24 |
| ATOM | 1051 | CD1 | TYR | A | 137 | 0 | 29.302 | 24.108 | 23.150 | 1.00 | 16.00 |
| ATOM | 1052 | CD2 | TYR | A | 137 | 0 | 30.159 | 24.754 | 21.001 | 1.00 | 14.76 |
| ATOM | 1053 | CE1 | TYR | A | 137 | 0 | 29.355 | 25.448 | 23.551 | 1.00 | 15.32 |
| ATOM | 1054 | CE2 | TYR | A | 137 | 0 | 30.165 | 26.081 | 21.396 | 1.00 | 15.52 |
| ATOM | 1055 | CZ | TYR | A | 137 | 0 | 29.759 | 26.410 | 22.675 | 1.00 | 15.61 |
| ATOM | 1056 | OH | TYR | A | 137 | 0 | 29.782 | 27.731 | 23.055 | 1.00 | 17.56 |
| ATOM | 1057 | N | ASP | A | 138 | 0 | 31.903 | 21.549 | 19.393 | 1.00 | 19.04 |
| ATOM | 1058 | CA | ASP | A | 138 | 0 | 32.733 | 21.859 | 18.253 | 1.00 | 20.02 |
| ATOM | 1059 | C | ASP | A | 138 | 0 | 32.139 | 22.933 | 17.364 | 1.00 | 21.05 |
| ATOM | 1060 | O | ASP | A | 138 | 0 | 32.911 | 23.553 | 16.631 | 1.00 | 21.98 |
| ATOM | 1061 | CB | ASP | A | 138 | 0 | 32.836 | 20.628 | 17.315 | 1.00 | 20.66 |

APPENDIX 1-continued

| ATOM | 1062 | CG | ASP | A | 138 | 0 | 33.355 | 19.455 | 18.089 | 1.00 | 22.79 |
| --- | --- | --- | --- | --- | --- | --- | --- | --- | --- | --- | --- |
| ATOM | 1063 | OD1 | ASP | A | 138 | 0 | 32.744 | 18.404 | 18.318 | 1.00 | 24.88 |
| ATOM | 1064 | OD2 | ASP | A | 138 | 0 | 34.481 | 19.675 | 18.581 | 1.00 | 25.34 |
| ATOM | 1065 | N | GLU | A | 139 | 0 | 30.825 | 22.957 | 17.184 | 1.00 | 19.73 |
| ATOM | 1066 | CA | GLU | A | 139 | 0 | 30.223 | 23.865 | 16.213 | 1.00 | 21.27 |
| ATOM | 1067 | C | GLU | A | 139 | 0 | 29.086 | 24.668 | 16.825 | 1.00 | 18.97 |
| ATOM | 1068 | O | GLU | A | 139 | 0 | 28.306 | 24.143 | 17.608 | 1.00 | 16.95 |
| ATOM | 1069 | CB | GLU | A | 139 | 0 | 29.617 | 23.164 | 15.000 | 1.00 | 24.71 |
| ATOM | 1070 | CG | GLU | A | 139 | 0 | 30.509 | 22.149 | 14.311 | 1.00 | 30.89 |
| ATOM | 1071 | CD | GLU | A | 139 | 0 | 31.633 | 22.868 | 13.587 | 1.00 | 34.42 |
| ATOM | 1072 | OE1 | GLU | A | 139 | 0 | 31.340 | 23.869 | 12.898 | 1.00 | 36.87 |
| ATOM | 1073 | OE2 | GLU | A | 139 | 0 | 32.794 | 22.457 | 13.705 | 1.00 | 37.60 |
| ATOM | 1074 | N | ASP | A | 140 | 0 | 29.057 | 25.933 | 16.408 | 1.00 | 19.38 |
| ATOM | 1075 | CA | ASP | A | 140 | 0 | 28.026 | 26.847 | 16.912 | 1.00 | 17.89 |
| ATOM | 1076 | C | ASP | A | 140 | 0 | 27.858 | 27.901 | 15.837 | 1.00 | 18.87 |
| ATOM | 1077 | O | ASP | A | 140 | 0 | 28.705 | 28.780 | 15.768 | 1.00 | 21.31 |
| ATOM | 1078 | CB | ASP | A | 140 | 0 | 28.438 | 27.399 | 18.268 | 1.00 | 16.26 |
| ATOM | 1079 | CG | ASP | A | 140 | 0 | 27.445 | 28.399 | 18.858 | 1.00 | 16.73 |
| ATOM | 1080 | OD1 | ASP | A | 140 | 0 | 27.854 | 29.143 | 19.781 | 1.00 | 14.86 |
| ATOM | 1081 | OD2 | ASP | A | 140 | 0 | 26.287 | 28.446 | 18.401 | 1.00 | 13.82 |
| ATOM | 1082 | N | ASP | A | 141 | 0 | 26.862 | 27.844 | 14.972 | 1.00 | 17.34 |
| ATOM | 1083 | CA | ASP | A | 141 | 0 | 26.750 | 28.859 | 13.937 | 1.00 | 19.52 |
| ATOM | 1084 | C | ASP | A | 141 | 0 | 25.301 | 29.031 | 13.520 | 1.00 | 19.33 |
| ATOM | 1085 | O | ASP | A | 141 | 0 | 24.342 | 28.513 | 14.115 | 1.00 | 17.91 |
| ATOM | 1086 | CB | ASP | A | 141 | 0 | 27.681 | 28.509 | 12.772 | 1.00 | 21.66 |
| ATOM | 1087 | CG | ASP | A | 141 | 0 | 27.384 | 27.151 | 12.193 | 1.00 | 24.87 |
| ATOM | 1088 | OD1 | ASP | A | 141 | 0 | 28.280 | 26.521 | 11.567 | 1.00 | 28.90 |
| ATOM | 1089 | OD2 | ASP | A | 141 | 0 | 26.271 | 26.604 | 12.302 | 1.00 | 25.89 |
| ATOM | 1090 | N | GLU | A | 142 | 0 | 25.102 | 29.688 | 12.387 | 1.00 | 19.21 |
| ATOM | 1091 | CA | GLU | A | 142 | 0 | 23.775 | 29.945 | 11.880 | 1.00 | 20.84 |
| ATOM | 1092 | C | GLU | A | 142 | 0 | 23.052 | 28.636 | 11.592 | 1.00 | 19.95 |
| ATOM | 1093 | O | GLU | A | 142 | 0 | 21.844 | 28.656 | 11.665 | 1.00 | 18.73 |
| ATOM | 1094 | CB | GLU | A | 142 | 0 | 23.771 | 30.894 | 10.699 | 1.00 | 23.40 |
| ATOM | 1095 | CG | GLU | A | 142 | 0 | 24.295 | 30.301 | 9.407 | 1.00 | 27.22 |
| ATOM | 1096 | CD | GLU | A | 142 | 0 | 25.718 | 30.826 | 9.221 | 1.00 | 32.36 |
| ATOM | 1097 | OE1 | GLU | A | 142 | 0 | 26.513 | 30.920 | 10.206 | 1.00 | 31.87 |
| ATOM | 1098 | OE2 | GLU | A | 142 | 0 | 25.968 | 31.136 | 8.023 | 1.00 | 35.76 |
| ATOM | 1099 | N | ASN | A | 143 | 0 | 23.723 | 27.508 | 11.378 | 1.00 | 20.40 |
| ATOM | 1100 | CA | ASN | A | 143 | 0 | 23.105 | 26.227 | 11.151 | 1.00 | 19.61 |
| ATOM | 1101 | C | ASN | A | 143 | 0 | 22.785 | 25.468 | 12.421 | 1.00 | 18.35 |
| ATOM | 1102 | O | ASN | A | 143 | 0 | 22.317 | 24.337 | 12.325 | 1.00 | 15.65 |
| ATOM | 1103 | CB | ASN | A | 143 | 0 | 24.024 | 25.401 | 10.229 | 1.00 | 23.57 |
| ATOM | 1104 | CG | ASN | A | 143 | 0 | 24.133 | 26.067 | 8.857 | 1.00 | 26.63 |
| ATOM | 1105 | OD1 | ASN | A | 143 | 0 | 25.220 | 26.376 | 8.356 | 1.00 | 29.89 |
| ATOM | 1106 | ND2 | ASN | A | 143 | 0 | 23.049 | 26.342 | 8.175 | 1.00 | 25.46 |
| ATOM | 1107 | N | THR | A | 144 | 0 | 23.067 | 25.974 | 13.632 | 1.00 | 16.76 |
| ATOM | 1108 | CA | THR | A | 144 | 0 | 22.678 | 25.257 | 14.825 | 1.00 | 15.40 |
| ATOM | 1109 | C | THR | A | 144 | 0 | 21.556 | 25.976 | 15.577 | 1.00 | 15.58 |
| ATOM | 1110 | O | THR | A | 144 | 0 | 21.361 | 25.776 | 16.789 | 1.00 | 17.88 |
| ATOM | 1111 | CB | THR | A | 144 | 0 | 23.848 | 25.018 | 15.785 | 1.00 | 16.43 |
| ATOM | 1112 | OG1 | THR | A | 144 | 0 | 24.296 | 26.270 | 16.297 | 1.00 | 14.82 |
| ATOM | 1113 | CG2 | THR | A | 144 | 0 | 24.935 | 24.215 | 15.104 | 1.00 | 15.98 |
| ATOM | 1114 | N | ILE | A | 145 | 0 | 20.821 | 26.834 | 14.898 | 1.00 | 13.92 |
| ATOM | 1115 | CA | ILE | A | 145 | 0 | 19.697 | 27.550 | 15.500 | 1.00 | 14.31 |
| ATOM | 1116 | C | ILE | A | 145 | 0 | 18.392 | 26.835 | 15.139 | 1.00 | 13.84 |
| ATOM | 1117 | O | ILE | A | 145 | 0 | 18.127 | 26.478 | 13.996 | 1.00 | 12.32 |
| ATOM | 1118 | CB | ILE | A | 145 | 0 | 19.641 | 29.016 | 15.011 | 1.00 | 15.15 |
| ATOM | 1119 | CG1 | ILE | A | 145 | 0 | 20.881 | 29.726 | 15.608 | 1.00 | 16.27 |
| ATOM | 1120 | CG2 | ILE | A | 145 | 0 | 18.346 | 29.736 | 15.375 | 1.00 | 13.14 |
| ATOM | 1121 | CD1 | ILE | A | 145 | 0 | 21.256 | 31.006 | 14.892 | 1.00 | 16.72 |
| ATOM | 1122 | N | ILE | A | 146 | 0 | 17.550 | 26.644 | 16.141 | 1.00 | 13.54 |
| ATOM | 1123 | CA | ILE | A | 146 | 0 | 16.263 | 25.983 | 15.926 | 1.00 | 13.70 |
| ATOM | 1124 | C | ILE | A | 146 | 0 | 15.167 | 26.899 | 16.494 | 1.00 | 12.67 |
| ATOM | 1125 | O | ILE | A | 146 | 0 | 15.155 | 27.082 | 17.714 | 1.00 | 10.09 |
| ATOM | 1126 | CB | ILE | A | 146 | 0 | 16.183 | 24.580 | 16.553 | 1.00 | 15.97 |
| ATOM | 1127 | CG1 | ILE | A | 146 | 0 | 17.280 | 23.621 | 16.012 | 1.00 | 17.29 |
| ATOM | 1128 | CG2 | ILE | A | 146 | 0 | 14.831 | 23.937 | 16.207 | 1.00 | 14.52 |
| ATOM | 1129 | CD1 | ILE | A | 146 | 0 | 17.359 | 22.340 | 16.832 | 1.00 | 18.45 |
| ATOM | 1130 | N | THR | A | 147 | 0 | 14.360 | 27.507 | 15.610 | 1.00 | 10.81 |
| ATOM | 1131 | CA | THR | A | 147 | 0 | 13.240 | 28.310 | 16.102 | 1.00 | 12.54 |
| ATOM | 1132 | C | THR | A | 147 | 0 | 11.912 | 27.526 | 15.988 | 1.00 | 13.55 |
| ATOM | 1133 | O | THR | A | 147 | 0 | 11.655 | 26.724 | 15.076 | 1.00 | 12.65 |
| ATOM | 1134 | CB | THR | A | 147 | 0 | 13.078 | 29.642 | 15.351 | 1.00 | 12.37 |
| ATOM | 1135 | OG1 | THR | A | 147 | 0 | 12.728 | 29.311 | 14.005 | 1.00 | 10.17 |
| ATOM | 1136 | CG2 | THR | A | 147 | 0 | 14.381 | 30.479 | 15.402 | 1.00 | 11.93 |
| ATOM | 1137 | N | LEU | A | 148 | 0 | 11.062 | 27.715 | 16.972 | 1.00 | 12.48 |
| ATOM | 1138 | CA | LEU | A | 148 | 0 | 9.719 | 27.171 | 17.039 | 1.00 | 13.90 |
| ATOM | 1139 | C | LEU | A | 148 | 0 | 8.719 | 28.350 | 16.916 | 1.00 | 15.44 |
| ATOM | 1140 | O | LEU | A | 148 | 0 | 8.860 | 29.383 | 17.579 | 1.00 | 15.28 |

APPENDIX 1-continued

| ATOM | 1141 | CB  | LEU | A | 148 | 0 | 9.501  | 26.419 | 18.340 | 1.00 | 12.83 |
|------|------|-----|-----|---|-----|---|--------|--------|--------|------|-------|
| ATOM | 1142 | CG  | LEU | A | 148 | 0 | 10.502 | 25.293 | 18.669 | 1.00 | 12.45 |
| ATOM | 1143 | CD1 | LEU | A | 148 | 0 | 10.154 | 24.669 | 19.997 | 1.00 | 11.49 |
| ATOM | 1144 | CD2 | LEU | A | 148 | 0 | 10.552 | 24.203 | 17.597 | 1.00 | 11.82 |
| ATOM | 1145 | N   | ALA | A | 149 | 0 | 7.726  | 28.241 | 16.053 | 1.00 | 14.08 |
| ATOM | 1146 | CA  | ALA | A | 149 | 0 | 6.725  | 29.256 | 15.825 | 1.00 | 15.37 |
| ATOM | 1147 | C   | ALA | A | 149 | 0 | 5.336  | 28.658 | 15.521 | 1.00 | 16.78 |
| ATOM | 1148 | O   | ALA | A | 149 | 0 | 5.198  | 27.637 | 14.841 | 1.00 | 15.78 |
| ATOM | 1149 | CB  | ALA | A | 149 | 0 | 7.068  | 30.127 | 14.628 | 1.00 | 13.22 |
| ATOM | 1150 | N   | ASP | A | 150 | 0 | 4.337  | 29.344 | 16.065 | 1.00 | 16.39 |
| ATOM | 1151 | CA  | ASP | A | 150 | 0 | 2.941  | 28.995 | 15.864 | 1.00 | 15.96 |
| ATOM | 1152 | C   | ASP | A | 150 | 0 | 2.515  | 29.758 | 14.624 | 1.00 | 16.53 |
| ATOM | 1153 | O   | ASP | A | 150 | 0 | 2.960  | 30.905 | 14.483 | 1.00 | 18.17 |
| ATOM | 1154 | CB  | ASP | A | 150 | 0 | 2.066  | 29.440 | 17.027 | 1.00 | 16.78 |
| ATOM | 1155 | CG  | ASP | A | 150 | 0 | 2.345  | 30.836 | 17.561 | 1.00 | 18.15 |
| ATOM | 1156 | OD1 | ASP | A | 150 | 0 | 3.410  | 31.472 | 17.347 | 1.00 | 16.29 |
| ATOM | 1157 | OD2 | ASP | A | 150 | 0 | 1.414  | 31.311 | 18.264 | 1.00 | 17.83 |
| ATOM | 1158 | N   | TRP | A | 151 | 0 | 1.776  | 29.157 | 13.726 | 1.00 | 15.62 |
| ATOM | 1159 | CA  | TRP | A | 151 | 0 | 1.366  | 29.828 | 12.499 | 1.00 | 14.37 |
| ATOM | 1160 | C   | TRP | A | 151 | 0 | -0.140 | 29.688 | 12.226 | 1.00 | 14.78 |
| ATOM | 1161 | O   | TRP | A | 151 | 0 | -0.679 | 28.607 | 12.425 | 1.00 | 13.41 |
| ATOM | 1162 | CB  | TRP | A | 151 | 0 | 2.229  | 29.239 | 11.373 | 1.00 | 13.56 |
| ATOM | 1163 | CG  | TRP | A | 151 | 0 | 2.046  | 30.004 | 10.097 | 1.00 | 13.31 |
| ATOM | 1164 | CD1 | TRP | A | 151 | 0 | 1.385  | 29.545 | 8.991  | 1.00 | 13.60 |
| ATOM | 1165 | CD2 | TRP | A | 151 | 0 | 2.484  | 31.316 | 9.806  | 1.00 | 15.46 |
| ATOM | 1166 | NE1 | TRP | A | 151 | 0 | 1.412  | 30.497 | 8.017  | 1.00 | 14.49 |
| ATOM | 1167 | CE2 | TRP | A | 151 | 0 | 2.061  | 31.605 | 8.473  | 1.00 | 15.53 |
| ATOM | 1168 | CE3 | TRP | A | 151 | 0 | 3.189  | 32.294 | 10.522 | 1.00 | 16.28 |
| ATOM | 1169 | CZ2 | TRP | A | 151 | 0 | 2.306  | 32.822 | 7.846  | 1.00 | 16.57 |
| ATOM | 1170 | CZ3 | TRP | A | 151 | 0 | 3.436  | 33.505 | 9.881  | 1.00 | 18.22 |
| ATOM | 1171 | CH2 | TRP | A | 151 | 0 | 3.003  | 33.766 | 8.560  | 1.00 | 18.00 |
| ATOM | 1172 | N   | TYR | A | 152 | 0 | -0.818 | 30.745 | 11.812 | 1.00 | 15.59 |
| ATOM | 1173 | CA  | TYR | A | 152 | 0 | -2.266 | 30.813 | 11.614 | 1.00 | 17.47 |
| ATOM | 1174 | C   | TYR | A | 152 | 0 | -2.556 | 31.086 | 10.149 | 1.00 | 18.79 |
| ATOM | 1175 | O   | TYR | A | 152 | 0 | -1.830 | 31.856 | 9.521  | 1.00 | 19.15 |
| ATOM | 1176 | CB  | TYR | A | 152 | 0 | -2.981 | 31.930 | 12.434 | 1.00 | 16.37 |
| ATOM | 1177 | CG  | TYR | A | 152 | 0 | -2.539 | 31.776 | 13.887 | 1.00 | 16.24 |
| ATOM | 1178 | CD1 | TYR | A | 152 | 0 | -1.313 | 32.303 | 14.318 | 1.00 | 15.22 |
| ATOM | 1179 | CD2 | TYR | A | 152 | 0 | -3.267 | 30.998 | 14.767 | 1.00 | 15.29 |
| ATOM | 1180 | CE1 | TYR | A | 152 | 0 | -0.889 | 32.135 | 15.626 | 1.00 | 14.67 |
| ATOM | 1181 | CE2 | TYR | A | 152 | 0 | -2.831 | 30.799 | 16.054 | 1.00 | 16.52 |
| ATOM | 1182 | CZ  | TYR | A | 152 | 0 | -1.632 | 31.369 | 16.474 | 1.00 | 16.12 |
| ATOM | 1183 | OH  | TYR | A | 152 | 0 | -1.219 | 31.139 | 17.771 | 1.00 | 16.36 |
| ATOM | 1184 | N   | HIS | A | 153 | 0 | -3.590 | 30.445 | 9.599  | 1.00 | 20.39 |
| ATOM | 1185 | CA  | HIS | A | 153 | 0 | -3.899 | 30.683 | 8.181  | 1.00 | 21.90 |
| ATOM | 1186 | C   | HIS | A | 153 | 0 | -4.642 | 31.988 | 7.952  | 1.00 | 21.94 |
| ATOM | 1187 | O   | HIS | A | 153 | 0 | -4.750 | 32.386 | 6.784  | 1.00 | 22.32 |
| ATOM | 1188 | CB  | HIS | A | 153 | 0 | -4.592 | 29.483 | 7.549  | 1.00 | 22.29 |
| ATOM | 1189 | CG  | HIS | A | 153 | 0 | -3.651 | 28.319 | 7.385  | 1.00 | 24.52 |
| ATOM | 1190 | ND1 | HIS | A | 153 | 0 | -4.071 | 27.022 | 7.258  | 1.00 | 24.25 |
| ATOM | 1191 | CD2 | HIS | A | 153 | 0 | -2.286 | 28.274 | 7.338  | 1.00 | 23.32 |
| ATOM | 1192 | CE1 | HIS | A | 153 | 0 | -3.034 | 26.220 | 7.124  | 1.00 | 24.15 |
| ATOM | 1193 | NE2 | HIS | A | 153 | 0 | -1.956 | 26.965 | 7.178  | 1.00 | 24.30 |
| ATOM | 1194 | N   | ILE | A | 154 | 0 | -5.084 | 32.718 | 8.972  | 1.00 | 21.86 |
| ATOM | 1195 | CA  | ILE | A | 154 | 0 | -5.611 | 34.046 | 8.686  | 1.00 | 24.39 |
| ATOM | 1196 | C   | ILE | A | 154 | 0 | 4.904  | 35.051 | 9.597  | 1.00 | 22.15 |
| ATOM | 1197 | O   | ILE | A | 154 | 0 | 4.517  | 34.732 | 10.698 | 1.00 | 20.15 |
| ATOM | 1198 | CB  | ILE | A | 154 | 0 | -7.120 | 34.281 | 8.693  | 1.00 | 26.43 |
| ATOM | 1199 | CG1 | ILE | A | 154 | 0 | -7.682 | 34.498 | 10.099 | 1.00 | 27.66 |
| ATOM | 1200 | CG2 | ILE | A | 154 | 0 | -7.947 | 33.251 | 7.928  | 1.00 | 26.60 |
| ATOM | 1201 | CD1 | ILE | A | 154 | 0 | -7.312 | 33.468 | 11.125 | 1.00 | 28.86 |
| ATOM | 1202 | N   | PRO | A | 155 | 0 | -4.723 | 36.255 | 9.105  | 1.00 | 23.79 |
| ATOM | 1203 | CA  | PRO | A | 155 | 0 | -4.108 | 37.361 | 9.816  | 1.00 | 23.66 |
| ATOM | 1204 | C   | PRO | A | 155 | 0 | -4.604 | 37.435 | 11.252 | 1.00 | 24.59 |
| ATOM | 1205 | O   | PRO | A | 155 | 0 | -5.814 | 37.317 | 11.539 | 1.00 | 24.53 |
| ATOM | 1206 | CB  | PRO | A | 155 | 0 | -4.546 | 38.634 | 9.077  | 1.00 | 24.20 |
| ATOM | 1207 | CG  | PRO | A | 155 | 0 | -4.990 | 38.162 | 7.733  | 1.00 | 23.40 |
| ATOM | 1208 | CD  | PRO | A | 155 | 0 | -5.207 | 36.672 | 7.776  | 1.00 | 23.41 |
| ATOM | 1209 | N   | ALA | A | 156 | 0 | -3.704 | 37.776 | 12.178 | 1.00 | 24.03 |
| ATOM | 1210 | CA  | ALA | A | 156 | 0 | -4.066 | 37.806 | 13.588 | 1.00 | 25.45 |
| ATOM | 1211 | C   | ALA | A | 156 | 0 | -5.262 | 38.667 | 13.992 | 1.00 | 24.85 |
| ATOM | 1212 | O   | ALA | A | 156 | 0 | -6.083 | 38.217 | 14.798 | 1.00 | 22.79 |
| ATOM | 1213 | CB  | ALA | A | 156 | 0 | -2.866 | 38.045 | 14.492 | 1.00 | 24.30 |
| ATOM | 1214 | N   | PRO | A | 157 | 0 | -5.393 | 39.873 | 13.518 | 1.00 | 25.98 |
| ATOM | 1215 | CA  | PRO | A | 157 | 0 | -6.521 | 40.741 | 13.807 | 1.00 | 28.77 |
| ATOM | 1216 | C   | PRO | A | 157 | 0 | -7.840 | 40.092 | 13.406 | 1.00 | 30.78 |
| ATOM | 1217 | O   | PRO | A | 157 | 0 | -8.798 | 40.416 | 14.105 | 1.00 | 34.62 |
| ATOM | 1218 | CB  | PRO | A | 157 | 0 | -6.324 | 42.071 | 13.068 | 1.00 | 26.56 |
| ATOM | 1219 | CG  | PRO | A | 157 | 0 | -4.859 | 42.013 | 12.762 | 1.00 | 25.98 |

APPENDIX 1-continued

| | | | | | | | | | | |
|---|---|---|---|---|---|---|---|---|---|---|
| ATOM | 1220 | CD | PRO | A | 157 | 0 | −4.480 | 40.547 | 12.585 | 1.00 | 25.96 |
| ATOM | 1221 | N | SER | A | 158 | 0 | −7.950 | 39.207 | 12.430 | 1.00 | 30.95 |
| ATOM | 1222 | CA | SER | A | 158 | 0 | −9.174 | 38.549 | 12.047 | 1.00 | 31.32 |
| ATOM | 1223 | C | SER | A | 158 | 0 | −9.450 | 37.288 | 12.851 | 1.00 | 33.61 |
| ATOM | 1224 | O | SER | A | 158 | 0 | −10.472 | 36.633 | 12.575 | 1.00 | 34.71 |
| ATOM | 1225 | CB | SER | A | 158 | 0 | −9.176 | 38.118 | 10.577 | 1.00 | 30.14 |
| ATOM | 1226 | OG | SER | A | 158 | 0 | −8.942 | 39.187 | 9.665 | 1.00 | 31.20 |
| ATOM | 1227 | N | ILE | A | 159 | 0 | −8.588 | 36.875 | 13.773 | 1.00 | 34.23 |
| ATOM | 1228 | CA | ILE | A | 159 | 0 | −8.918 | 35.642 | 14.491 | 1.00 | 36.40 |
| ATOM | 1229 | C | ILE | A | 159 | 0 | −10.189 | 35.896 | 15.309 | 1.00 | 39.20 |
| ATOM | 1230 | O | ILE | A | 159 | 0 | −10.294 | 36.875 | 16.046 | 1.00 | 39.00 |
| ATOM | 1231 | CB | ILE | A | 159 | 0 | −7.769 | 35.121 | 15.360 | 1.00 | 35.56 |
| ATOM | 1232 | CG1 | ILE | A | 159 | 0 | −6.713 | 34.408 | 14.485 | 1.00 | 35.58 |
| ATOM | 1233 | CG2 | ILE | A | 159 | 0 | −8.262 | 34.184 | 16.452 | 1.00 | 34.97 |
| ATOM | 1234 | CD1 | ILE | A | 159 | 0 | −5.388 | 34.268 | 15.212 | 1.00 | 34.91 |
| ATOM | 1235 | N | GLN | A | 160 | 0 | −11.137 | 34.969 | 15.196 | 1.00 | 41.53 |
| ATOM | 1236 | CA | GLN | A | 160 | 0 | −12.398 | 35.056 | 15.946 | 1.00 | 42.57 |
| ATOM | 1237 | C | GLN | A | 160 | 0 | −12.466 | 33.914 | 16.949 | 1.00 | 40.51 |
| ATOM | 1238 | O | GLN | A | 160 | 0 | −12.308 | 32.741 | 16.585 | 1.00 | 41.96 |
| ATOM | 1239 | CB | GLN | A | 160 | 0 | −13.542 | 35.062 | 14.937 | 1.00 | 45.52 |
| ATOM | 1240 | CG | GLN | A | 160 | 0 | −14.814 | 34.319 | 15.267 | 1.00 | 48.48 |
| ATOM | 1241 | CD | GLN | A | 160 | 0 | −15.570 | 33.799 | 14.055 | 1.00 | 50.12 |
| ATOM | 1242 | OE1 | GLN | A | 160 | 0 | −16.204 | 32.737 | 14.118 | 1.00 | 50.77 |
| ATOM | 1243 | NE2 | GLN | A | 160 | 0 | −15.504 | 34.520 | 12.940 | 1.00 | 51.22 |
| ATOM | 1244 | N | GLY | A | 161 | 0 | −12.667 | 34.191 | 18.225 | 1.00 | 37.10 |
| ATOM | 1245 | CA | GLY | A | 161 | 0 | −12.722 | 33.112 | 19.208 | 1.00 | 34.91 |
| ATOM | 1246 | C | GLY | A | 161 | 0 | −11.305 | 32.826 | 19.696 | 1.00 | 34.13 |
| ATOM | 1247 | O | GLY | A | 161 | 0 | −10.412 | 33.648 | 19.451 | 1.00 | 32.40 |
| ATOM | 1248 | N | ALA | A | 162 | 0 | −11.158 | 31.738 | 20.433 | 1.00 | 33.01 |
| ATOM | 1249 | CA | ALA | A | 162 | 0 | −9.864 | 31.355 | 20.988 | 1.00 | 32.39 |
| ATOM | 1250 | C | ALA | A | 162 | 0 | −8.927 | 30.902 | 19.880 | 1.00 | 31.53 |
| ATOM | 1251 | O | ALA | A | 162 | 0 | −9.285 | 30.132 | 19.013 | 1.00 | 30.73 |
| ATOM | 1252 | CB | ALA | A | 162 | 0 | −10.058 | 30.263 | 22.010 | 1.00 | 34.12 |
| ATOM | 1253 | N | ALA | A | 163 | 0 | −7.731 | 31.475 | 19.851 | 1.00 | 32.06 |
| ATOM | 1254 | CA | ALA | A | 163 | 0 | −6.740 | 31.202 | 18.814 | 1.00 | 30.85 |
| ATOM | 1255 | C | ALA | A | 163 | 0 | −6.219 | 29.774 | 18.897 | 1.00 | 29.40 |
| ATOM | 1256 | O | ALA | A | 163 | 0 | −5.967 | 29.223 | 19.965 | 1.00 | 30.49 |
| ATOM | 1257 | CB | ALA | A | 163 | 0 | −5.607 | 32.217 | 18.911 | 1.00 | 30.29 |
| ATOM | 1258 | N | GLN | A | 164 | 0 | −6.101 | 29.130 | 17.754 | 1.00 | 28.69 |
| ATOM | 1259 | CA | GLN | A | 164 | 0 | −5.616 | 27.769 | 17.612 | 1.00 | 28.24 |
| ATOM | 1260 | C | GLN | A | 164 | 0 | −4.720 | 27.744 | 16.370 | 1.00 | 25.02 |
| ATOM | 1261 | O | GLN | A | 164 | 0 | −5.157 | 28.046 | 15.260 | 1.00 | 23.64 |
| ATOM | 1262 | CB | GLN | A | 164 | 0 | −6.732 | 26.756 | 17.361 | 1.00 | 31.99 |
| ATOM | 1263 | CG | GLN | A | 164 | 0 | −7.885 | 26.640 | 18.319 | 1.00 | 36.24 |
| ATOM | 1264 | CD | GLN | A | 164 | 0 | −7.535 | 25.809 | 19.540 | 1.00 | 40.95 |
| ATOM | 1265 | OE1 | GLN | A | 164 | 0 | −7.863 | 26.166 | 20.684 | 1.00 | 43.34 |
| ATOM | 1266 | NE2 | GLN | A | 164 | 0 | −6.864 | 24.672 | 19.328 | 1.00 | 41.86 |
| ATOM | 1267 | N | PRO | A | 165 | 0 | −3.446 | 27.406 | 16.549 | 1.00 | 22.68 |
| ATOM | 1268 | CA | PRO | A | 165 | 0 | −2.501 | 27.360 | 15.463 | 1.00 | 20.43 |
| ATOM | 1269 | C | PRO | A | 165 | 0 | −2.856 | 26.294 | 14.429 | 1.00 | 18.89 |
| ATOM | 1270 | O | PRO | A | 165 | 0 | −3.286 | 25.176 | 14.715 | 1.00 | 18.00 |
| ATOM | 1271 | CB | PRO | A | 165 | 0 | −1.126 | 27.075 | 16.088 | 1.00 | 20.83 |
| ATOM | 1272 | CG | PRO | A | 165 | 0 | −1.476 | 26.651 | 17.479 | 1.00 | 22.05 |
| ATOM | 1273 | CD | PRO | A | 165 | 0 | −2.873 | 27.081 | 17.851 | 1.00 | 21.57 |
| ATOM | 1274 | N | ASP | A | 166 | 0 | −2.667 | 26.608 | 13.169 | 1.00 | 17.50 |
| ATOM | 1275 | CA | ASP | A | 166 | 0 | −2.829 | 25.677 | 12.059 | 1.00 | 19.82 |
| ATOM | 1276 | C | ASP | A | 166 | 0 | −1.591 | 24.788 | 11.930 | 1.00 | 19.47 |
| ATOM | 1277 | O | ASP | A | 166 | 0 | −1.692 | 23.649 | 11.506 | 1.00 | 19.38 |
| ATOM | 1278 | CB | ASP | A | 166 | 0 | −3.005 | 26.413 | 10.727 | 1.00 | 19.75 |
| ATOM | 1279 | CG | ASP | A | 166 | 0 | −4.347 | 27.162 | 10.728 | 1.00 | 21.69 |
| ATOM | 1280 | OD1 | ASP | A | 166 | 0 | −5.376 | 26.480 | 10.593 | 1.00 | 22.24 |
| ATOM | 1281 | OD2 | ASP | A | 166 | 0 | −4.384 | 28.392 | 10.885 | 1.00 | 22.13 |
| ATOM | 1282 | N | ALA | A | 167 | 0 | −0.435 | 25.386 | 12.231 | 1.00 | 18.54 |
| ATOM | 1283 | CA | ALA | A | 167 | 0 | 0.806 | 24.614 | 12.142 | 1.00 | 18.74 |
| ATOM | 1284 | C | ALA | A | 167 | 0 | 1.867 | 25.056 | 13.148 | 1.00 | 17.69 |
| ATOM | 1285 | O | ALA | A | 167 | 0 | 1.874 | 26.147 | 13.715 | 1.00 | 15.83 |
| ATOM | 1286 | CB | ALA | A | 167 | 0 | 1.387 | 24.767 | 10.735 | 1.00 | 17.32 |
| ATOM | 1287 | N | THR | A | 168 | 0 | 2.826 | 24.166 | 13.335 | 1.00 | 18.40 |
| ATOM | 1288 | CA | THR | A | 168 | 0 | 4.087 | 24.402 | 14.027 | 1.00 | 14.85 |
| ATOM | 1289 | C | THR | A | 168 | 0 | 5.180 | 24.553 | 12.955 | 1.00 | 15.24 |
| ATOM | 1290 | O | THR | A | 168 | 0 | 5.402 | 23.737 | 12.071 | 1.00 | 12.99 |
| ATOM | 1291 | CB | THR | A | 168 | 0 | 4.530 | 23.235 | 14.900 | 1.00 | 14.31 |
| ATOM | 1292 | OG1 | THR | A | 168 | 0 | 3.558 | 23.068 | 15.920 | 1.00 | 12.30 |
| ATOM | 1293 | CG2 | THR | A | 168 | 0 | 5.921 | 23.516 | 15.524 | 1.00 | 13.60 |
| ATOM | 1294 | N | LEU | A | 169 | 0 | 5.867 | 25.686 | 12.973 | 1.00 | 16.69 |
| ATOM | 1295 | CA | LEU | A | 169 | 0 | 6.976 | 26.002 | 12.071 | 1.00 | 14.74 |
| ATOM | 1296 | C | LEU | A | 169 | 0 | 8.285 | 25.747 | 12.833 | 1.00 | 14.34 |
| ATOM | 1297 | O | LEU | A | 169 | 0 | 8.497 | 26.259 | 13.942 | 1.00 | 12.34 |
| ATOM | 1298 | CB | LEU | A | 169 | 0 | 6.890 | 27.471 | 11.652 | 1.00 | 14.90 |

APPENDIX 1-continued

| ATOM | 1299 | CG | LEU | A | 169 | 0 | 6.071 | 27.845 | 10.428 | 1.00 | 17.83 |
|---|---|---|---|---|---|---|---|---|---|---|---|
| ATOM | 1300 | CD1 | LEU | A | 169 | 0 | 4.978 | 26.825 | 10.133 | 1.00 | 15.89 |
| ATOM | 1301 | CD2 | LEU | A | 169 | 0 | 5.500 | 29.254 | 10.443 | 1.00 | 16.43 |
| ATOM | 1302 | N | ILE | A | 170 | 0 | 9.141 | 24.923 | 12.255 | 1.00 | 14.06 |
| ATOM | 1303 | CA | ILE | A | 170 | 0 | 10.472 | 24.659 | 12.819 | 1.00 | 14.01 |
| ATOM | 1304 | C | ILE | A | 170 | 0 | 11.397 | 25.312 | 11.784 | 1.00 | 15.19 |
| ATOM | 1305 | O | ILE | A | 170 | 0 | 11.307 | 25.009 | 10.585 | 1.00 | 14.73 |
| ATOM | 1306 | CB | ILE | A | 170 | 0 | 10.807 | 23.179 | 13.025 | 1.00 | 14.75 |
| ATOM | 1307 | CG1 | ILE | A | 170 | 0 | 9.849 | 22.605 | 14.069 | 1.00 | 13.74 |
| ATOM | 1308 | CG2 | ILE | A | 170 | 0 | 12.268 | 22.983 | 13.468 | 1.00 | 13.47 |
| ATOM | 1309 | CD1 | ILE | A | 170 | 0 | 9.915 | 21.134 | 14.385 | 1.00 | 15.26 |
| ATOM | 1310 | N | ASN | A | 171 | 0 | 12.166 | 26.317 | 12.208 | 1.00 | 13.13 |
| ATOM | 1311 | CA | ASN | A | 171 | 0 | 12.992 | 27.042 | 11.250 | 1.00 | 13.74 |
| ATOM | 1312 | C | ASN | A | 171 | 0 | 12.163 | 27.517 | 10.083 | 1.00 | 13.71 |
| ATOM | 1313 | O | ASN | A | 171 | 0 | 12.562 | 27.381 | 8.921 | 1.00 | 13.20 |
| ATOM | 1314 | CB | ASN | A | 171 | 0 | 14.220 | 26.209 | 10.793 | 1.00 | 14.42 |
| ATOM | 1315 | CG | ASN | A | 171 | 0 | 15.236 | 26.157 | 11.940 | 1.00 | 16.29 |
| ATOM | 1316 | OD1 | ASN | A | 171 | 0 | 15.123 | 26.983 | 12.875 | 1.00 | 16.78 |
| ATOM | 1317 | ND2 | ASN | A | 171 | 0 | 16.203 | 25.259 | 11.964 | 1.00 | 14.32 |
| ATOM | 1318 | N | GLY | A | 172 | 0 | 10.967 | 28.074 | 10.337 | 1.00 | 14.17 |
| ATOM | 1319 | CA | GLY | A | 172 | 0 | 10.157 | 28.619 | 9.270 | 1.00 | 11.74 |
| ATOM | 1320 | C | GLY | A | 172 | 0 | 9.387 | 27.636 | 8.433 | 1.00 | 14.40 |
| ATOM | 1321 | O | GLY | A | 172 | 0 | 8.783 | 28.064 | 7.441 | 1.00 | 15.60 |
| ATOM | 1322 | N | LYS | A | 173 | 0 | 9.430 | 26.319 | 8.669 | 1.00 | 13.84 |
| ATOM | 1323 | CA | LYS | A | 173 | 0 | 8.777 | 25.363 | 7.794 | 1.00 | 13.67 |
| ATOM | 1324 | C | LYS | A | 173 | 0 | 8.038 | 24.303 | 8.589 | 1.00 | 13.59 |
| ATOM | 1325 | O | LYS | A | 173 | 0 | 8.445 | 24.027 | 9.723 | 1.00 | 11.70 |
| ATOM | 1326 | CB | LYS | A | 173 | 0 | 9.775 | 24.645 | 6.875 | 1.00 | 17.03 |
| ATOM | 1327 | CG | LYS | A | 173 | 0 | 10.704 | 25.577 | 6.118 | 1.00 | 17.63 |
| ATOM | 1328 | CD | LYS | A | 173 | 0 | 11.508 | 24.796 | 5.094 | 1.00 | 20.84 |
| ATOM | 1329 | CE | LYS | A | 173 | 0 | 12.213 | 25.821 | 4.198 | 1.00 | 22.63 |
| ATOM | 1330 | NZ | LYS | A | 173 | 0 | 13.304 | 25.087 | 3.499 | 1.00 | 28.08 |
| ATOM | 1331 | N | GLY | A | 174 | 0 | 6.922 | 23.821 | 8.014 | 1.00 | 12.28 |
| ATOM | 1332 | CA | GLY | A | 174 | 0 | 6.178 | 22.768 | 8.753 | 1.00 | 11.45 |
| ATOM | 1333 | C | GLY | A | 174 | 0 | 4.958 | 22.409 | 7.896 | 1.00 | 13.55 |
| ATOM | 1334 | O | GLY | A | 174 | 0 | 4.823 | 22.877 | 6.760 | 1.00 | 13.37 |
| ATOM | 1335 | N | ARG | A | 175 | 0 | 4.042 | 21.619 | 8.432 | 1.00 | 14.54 |
| ATOM | 1336 | CA | ARG | A | 175 | 0 | 2.859 | 21.201 | 7.687 | 1.00 | 16.62 |
| ATOM | 1337 | C | ARG | A | 175 | 0 | 1.598 | 21.336 | 8.541 | 1.00 | 17.67 |
| ATOM | 1338 | O | ARG | A | 175 | 0 | 1.727 | 21.264 | 9.769 | 1.00 | 18.41 |
| ATOM | 1339 | CB | ARG | A | 175 | 0 | 2.985 | 19.718 | 7.292 | 1.00 | 16.05 |
| ATOM | 1340 | CG | ARG | A | 175 | 0 | 3.894 | 19.472 | 6.116 | 1.00 | 16.55 |
| ATOM | 1341 | CD | ARG | A | 175 | 0 | 4.358 | 18.009 | 6.108 | 1.00 | 17.70 |
| ATOM | 1342 | NE | ARG | A | 175 | 0 | 5.421 | 17.861 | 5.097 | 1.00 | 17.74 |
| ATOM | 1343 | CZ | ARG | A | 175 | 0 | 5.971 | 16.667 | 4.792 | 1.00 | 17.63 |
| ATOM | 1344 | NH1 | ARG | A | 175 | 0 | 6.918 | 16.665 | 3.866 | 1.00 | 17.25 |
| ATOM | 1345 | NH2 | ARG | A | 175 | 0 | 5.594 | 15.538 | 5.375 | 1.00 | 14.80 |
| ATOM | 1346 | N | TYR | A | 176 | 0 | 0.429 | 21.438 | 7.908 | 1.00 | 18.08 |
| ATOM | 1347 | CA | TYR | A | 176 | 0 | -0.800 | 21.481 | 8.746 | 1.00 | 18.67 |
| ATOM | 1348 | C | TYR | A | 176 | 0 | -1.613 | 20.200 | 8.509 | 1.00 | 18.24 |
| ATOM | 1349 | O | TYR | A | 176 | 0 | -1.417 | 19.534 | 7.483 | 1.00 | 17.67 |
| ATOM | 1350 | CB | TYR | A | 176 | 0 | -1.635 | 22.709 | 8.462 | 1.00 | 17.21 |
| ATOM | 1351 | CG | TYR | A | 176 | 0 | -2.102 | 22.931 | 7.053 | 1.00 | 16.36 |
| ATOM | 1352 | CD1 | TYR | A | 176 | 0 | -1.246 | 23.433 | 6.089 | 1.00 | 14.84 |
| ATOM | 1353 | CD2 | TYR | A | 176 | 0 | -3.441 | 22.676 | 6.677 | 1.00 | 17.26 |
| ATOM | 1354 | CE1 | TYR | A | 176 | 0 | -1.640 | 23.686 | 4.796 | 1.00 | 16.01 |
| ATOM | 1355 | CE2 | TYR | A | 176 | 0 | -3.862 | 22.908 | 5.361 | 1.00 | 16.65 |
| ATOM | 1356 | CZ | TYR | A | 176 | 0 | -2.967 | 23.407 | 4.432 | 1.00 | 17.65 |
| ATOM | 1357 | OH | TYR | A | 176 | 0 | -3.347 | 23.678 | 3.131 | 1.00 | 17.81 |
| ATOM | 1358 | N | VAL | A | 177 | 0 | -2.427 | 19.815 | 9.464 | 1.00 | 18.46 |
| ATOM | 1359 | CA | VAL | A | 177 | 0 | -3.200 | 18.571 | 9.303 | 1.00 | 21.18 |
| ATOM | 1360 | C | VAL | A | 177 | 0 | -4.090 | 18.639 | 8.073 | 1.00 | 21.50 |
| ATOM | 1361 | O | VAL | A | 177 | 0 | -4.788 | 19.620 | 7.858 | 1.00 | 21.85 |
| ATOM | 1362 | CB | VAL | A | 177 | 0 | -4.072 | 18.306 | 10.532 | 1.00 | 22.29 |
| ATOM | 1363 | CG1 | VAL | A | 177 | 0 | -4.802 | 16.974 | 10.370 | 1.00 | 21.70 |
| ATOM | 1364 | CG2 | VAL | A | 177 | 0 | -3.205 | 18.289 | 11.784 | 1.00 | 22.43 |
| ATOM | 1365 | N | GLY | A | 178 | 0 | -3.989 | 17.707 | 7.142 | 1.00 | 21.84 |
| ATOM | 1366 | CA | GLY | A | 178 | 0 | -4.761 | 17.742 | 5.918 | 1.00 | 20.35 |
| ATOM | 1367 | C | GLY | A | 178 | 0 | -4.047 | 18.602 | 4.900 | 1.00 | 22.84 |
| ATOM | 1368 | O | GLY | A | 178 | 0 | -4.576 | 18.673 | 3.774 | 1.00 | 23.86 |
| ATOM | 1369 | N | GLY | A | 179 | 0 | -2.887 | 19.220 | 5.210 | 1.00 | 21.49 |
| ATOM | 1370 | CA | GLY | A | 179 | 0 | -2.291 | 20.060 | 4.149 | 1.00 | 19.94 |
| ATOM | 1371 | C | GLY | A | 179 | 0 | -1.389 | 19.250 | 3.242 | 1.00 | 18.86 |
| ATOM | 1372 | O | GLY | A | 179 | 0 | -1.192 | 18.052 | 3.399 | 1.00 | 19.35 |
| ATOM | 1373 | N | PRO | A | 180 | 0 | -0.800 | 19.905 | 2.268 | 1.00 | 19.42 |
| ATOM | 1374 | CA | PRO | A | 180 | 0 | 0.150 | 19.328 | 1.335 | 1.00 | 19.92 |
| ATOM | 1375 | C | PRO | A | 180 | 0 | 1.430 | 18.922 | 2.041 | 1.00 | 20.56 |
| ATOM | 1376 | O | PRO | A | 180 | 0 | 1.731 | 19.399 | 3.145 | 1.00 | 20.66 |
| ATOM | 1377 | CB | PRO | A | 180 | 0 | 0.503 | 20.399 | 0.298 | 1.00 | 19.52 |

APPENDIX 1-continued

| | | | | | | | | | | |
|---|---|---|---|---|---|---|---|---|---|---|
| ATOM | 1378 | CG | PRO | A | 180 | 0 | -0.144 | 21.639 | 0.829 | 1.00 | 19.70 |
| ATOM | 1379 | CD | PRO | A | 180 | 0 | -0.930 | 21.356 | 2.081 | 1.00 | 19.79 |
| ATOM | 1380 | N | ALA | A | 181 | 0 | 2.213 | 18.059 | 1.403 | 1.00 | 21.19 |
| ATOM | 1381 | CA | ALA | A | 181 | 0 | 3.489 | 17.644 | 2.007 | 1.00 | 23.04 |
| ATOM | 1382 | C | ALA | A | 181 | 0 | 4.548 | 18.723 | 1.772 | 1.00 | 21.24 |
| ATOM | 1383 | O | ALA | A | 181 | 0 | 5.465 | 18.522 | 0.986 | 1.00 | 23.93 |
| ATOM | 1384 | CB | ALA | A | 181 | 0 | 3.928 | 16.305 | 1.435 | 1.00 | 21.73 |
| ATOM | 1385 | N | ALA | A | 182 | 0 | 4.398 | 19.905 | 2.315 | 1.00 | 19.30 |
| ATOM | 1386 | CA | ALA | A | 182 | 0 | 5.357 | 20.987 | 2.183 | 1.00 | 18.39 |
| ATOM | 1387 | C | ALA | A | 182 | 0 | 6.706 | 20.549 | 2.791 | 1.00 | 17.36 |
| ATOM | 1388 | O | ALA | A | 182 | 0 | 6.858 | 19.712 | 3.701 | 1.00 | 16.16 |
| ATOM | 1389 | CB | ALA | A | 182 | 0 | 4.826 | 22.209 | 2.932 | 1.00 | 17.68 |
| ATOM | 1390 | N | GLU | A | 183 | 0 | 7.739 | 21.103 | 2.210 | 1.00 | 18.23 |
| ATOM | 1391 | CA | GLU | A | 183 | 0 | 9.134 | 20.882 | 2.599 | 1.00 | 20.90 |
| ATOM | 1392 | C | GLU | A | 183 | 0 | 9.381 | 21.078 | 4.093 | 1.00 | 18.87 |
| ATOM | 1393 | O | GLU | A | 183 | 0 | 8.976 | 22.073 | 4.699 | 1.00 | 17.80 |
| ATOM | 1394 | CB | GLU | A | 183 | 0 | 9.990 | 21.875 | 1.820 | 1.00 | 25.16 |
| ATOM | 1395 | CG | GLU | A | 183 | 0 | 11.508 | 21.760 | 1.962 | 1.00 | 31.31 |
| ATOM | 1396 | CD | GLU | A | 183 | 0 | 12.075 | 22.803 | 0.998 | 1.00 | 34.38 |
| ATOM | 1397 | OE1 | GLU | A | 183 | 0 | 11.901 | 22.609 | -0.229 | 1.00 | 36.88 |
| ATOM | 1398 | OE2 | GLU | A | 183 | 0 | 12.619 | 23.809 | 1.484 | 1.00 | 36.18 |
| ATOM | 1399 | N | LEU | A | 184 | 0 | 10.010 | 20.093 | 4.691 | 1.00 | 17.33 |
| ATOM | 1400 | CA | LEU | A | 184 | 0 | 10.388 | 20.155 | 6.098 | 1.00 | 18.77 |
| ATOM | 1401 | C | LEU | A | 184 | 0 | 11.780 | 20.743 | 6.255 | 1.00 | 19.44 |
| ATOM | 1402 | O | LEU | A | 184 | 0 | 12.582 | 20.687 | 5.314 | 1.00 | 20.95 |
| ATOM | 1403 | CB | LEU | A | 184 | 0 | 10.331 | 18.735 | 6.673 | 1.00 | 18.11 |
| ATOM | 1404 | CG | LEU | A | 184 | 0 | 8.915 | 18.125 | 6.577 | 1.00 | 19.10 |
| ATOM | 1405 | CD1 | LEU | A | 184 | 0 | 8.887 | 16.734 | 7.178 | 1.00 | 18.87 |
| ATOM | 1406 | CD2 | LEU | A | 184 | 0 | 7.868 | 19.026 | 7.229 | 1.00 | 18.69 |
| ATOM | 1407 | N | SER | A | 185 | 0 | 12.054 | 21.342 | 7.398 | 1.00 | 18.46 |
| ATOM | 1408 | CA | SER | A | 185 | 0 | 13.366 | 21.883 | 7.699 | 1.00 | 17.73 |
| ATOM | 1409 | C | SER | A | 185 | 0 | 14.298 | 20.699 | 8.018 | 1.00 | 16.95 |
| ATOM | 1410 | O | SER | A | 185 | 0 | 13.883 | 19.710 | 8.629 | 1.00 | 15.84 |
| ATOM | 1411 | CB | SER | A | 185 | 0 | 13.303 | 22.786 | 8.934 | 1.00 | 17.34 |
| ATOM | 1412 | OG | SER | A | 185 | 0 | 12.846 | 24.073 | 8.560 | 1.00 | 18.09 |
| ATOM | 1413 | N | ILE | A | 186 | 0 | 15.533 | 20.845 | 7.587 | 1.00 | 16.43 |
| ATOM | 1414 | CA | ILE | A | 186 | 0 | 16.595 | 19.858 | 7.821 | 1.00 | 16.85 |
| ATOM | 1415 | C | ILE | A | 186 | 0 | 17.725 | 20.491 | 8.626 | 1.00 | 15.86 |
| ATOM | 1416 | O | ILE | A | 186 | 0 | 18.178 | 21.605 | 8.387 | 1.00 | 11.67 |
| ATOM | 1417 | CB | ILE | A | 186 | 0 | 17.193 | 19.390 | 6.471 | 1.00 | 18.77 |
| ATOM | 1418 | CG1 | ILE | A | 186 | 0 | 16.048 | 18.895 | 5.557 | 1.00 | 19.78 |
| ATOM | 1419 | CG2 | ILE | A | 186 | 0 | 18.167 | 18.241 | 6.697 | 1.00 | 18.53 |
| ATOM | 1420 | CD1 | ILE | A | 186 | 0 | 16.44 | 18.731 | 4.110 | 1.00 | 22.35 |
| ATOM | 1421 | N | VAL | A | 187 | 0 | 18.114 | 19.840 | 9.703 | 1.00 | 16.18 |
| ATOM | 1422 | CA | VAL | A | 187 | 0 | 19.243 | 20.287 | 10.505 | 1.00 | 16.63 |
| ATOM | 1423 | C | VAL | A | 187 | 0 | 20.362 | 19.239 | 10.231 | 1.00 | 17.36 |
| ATOM | 1424 | O | VAL | A | 187 | 0 | 20.158 | 18.046 | 10.505 | 1.00 | 15.19 |
| ATOM | 1425 | CB | VAL | A | 187 | 0 | 18.928 | 20.323 | 11.984 | 1.00 | 16.68 |
| ATOM | 1426 | CG1 | VAL | A | 187 | 0 | 20.198 | 20.622 | 12.796 | 1.00 | 16.82 |
| ATOM | 1427 | CG2 | VAL | A | 187 | 0 | 17.874 | 21.375 | 12.275 | 1.00 | 17.07 |
| ATOM | 1428 | N | ASN | A | 188 | 0 | 21.449 | 19.695 | 9.634 | 1.00 | 16.45 |
| ATOM | 1429 | CA | ASN | A | 188 | 0 | 22.528 | 18.766 | 9.272 | 1.00 | 19.84 |
| ATOM | 1430 | C | ASN | A | 188 | 0 | 23.598 | 18.597 | 10.349 | 1.00 | 19.41 |
| ATOM | 1431 | O | ASN | A | 188 | 0 | 24.051 | 19.618 | 10.862 | 1.00 | 21.31 |
| ATOM | 1432 | CB | ASN | A | 188 | 0 | 23.209 | 19.246 | 7.976 | 1.00 | 18.78 |
| ATOM | 1433 | CG | ASN | A | 188 | 0 | 22.249 | 19.186 | 6.797 | 1.00 | 20.77 |
| ATOM | 1434 | OD1 | ASN | A | 188 | 0 | 21.734 | 20.201 | 6.305 | 1.00 | 21.70 |
| ATOM | 1435 | ND2 | ASN | A | 188 | 0 | 21.995 | 17.985 | 6.286 | 1.00 | 20.52 |
| ATOM | 1436 | N | VAL | A | 189 | 0 | 24.024 | 17.389 | 10.681 | 1.00 | 17.35 |
| ATOM | 1437 | CA | VAL | A | 189 | 0 | 25.098 | 17.164 | 11.617 | 1.00 | 17.93 |
| ATOM | 1438 | C | VAL | A | 189 | 0 | 26.091 | 16.135 | 11.046 | 1.00 | 19.82 |
| ATOM | 1439 | O | VAL | A | 189 | 0 | 25.773 | 15.392 | 10.109 | 1.00 | 18.90 |
| ATOM | 1440 | CB | VAL | A | 189 | 0 | 24.660 | 16.684 | 13.009 | 1.00 | 18.43 |
| ATOM | 1441 | CG1 | VAL | A | 189 | 0 | 23.931 | 17.796 | 13.766 | 1.00 | 18.89 |
| ATOM | 1442 | CG2 | VAL | A | 189 | 0 | 23.760 | 15.449 | 12.965 | 1.00 | 15.94 |
| ATOM | 1443 | N | GLU | A | 190 | 0 | 27.242 | 15.993 | 11.688 | 1.00 | 21.48 |
| ATOM | 1444 | CA | GLU | A | 190 | 0 | 28.220 | 14.972 | 11.274 | 1.00 | 24.63 |
| ATOM | 1445 | C | GLU | A | 190 | 0 | 28.514 | 14.065 | 12.469 | 1.00 | 23.06 |
| ATOM | 1446 | O | GLU | A | 190 | 0 | 28.797 | 14.650 | 13.522 | 1.00 | 21.04 |
| ATOM | 1447 | CB | GLU | A | 190 | 0 | 29.569 | 15.551 | 10.860 | 1.00 | 26.79 |
| ATOM | 1448 | CG | GLU | A | 190 | 0 | 29.571 | 16.355 | 9.567 | 1.00 | 32.24 |
| ATOM | 1449 | CD | GLU | A | 190 | 0 | 30.951 | 16.990 | 9.351 | 1.00 | 34.67 |
| ATOM | 1450 | OE1 | GLU | A | 190 | 0 | 31.927 | 16.199 | 9.305 | 1.00 | 35.41 |
| ATOM | 1451 | OE2 | GLU | A | 190 | 0 | 30.999 | 18.236 | 9.264 | 1.00 | 35.78 |
| ATOM | 1452 | N | GLN | A | 191 | 0 | 28.490 | 12.752 | 12.256 | 1.00 | 21.94 |
| ATOM | 1453 | CA | GLN | A | 191 | 0 | 28.768 | 11.824 | 13.357 | 1.00 | 21.92 |
| ATOM | 1454 | C | GLN | A | 191 | 0 | 30.121 | 12.151 | 13.984 | 1.00 | 22.68 |
| ATOM | 1455 | O | GLN | A | 191 | 0 | 31.052 | 12.516 | 13.251 | 1.00 | 23.08 |
| ATOM | 1456 | CB | GLN | A | 191 | 0 | 28.797 | 10.400 | 12.820 | 1.00 | 22.01 |

APPENDIX 1-continued

| ATOM | 1457 | CG | GLN | A | 191 | 0 | 28.795 | 9.347 | 13.917 | 1.00 | 23.87 |
|---|---|---|---|---|---|---|---|---|---|---|---|
| ATOM | 1458 | CD | GLN | A | 191 | 0 | 28.846 | 7.966 | 13.259 | 1.00 | 26.64 |
| ATOM | 1459 | OE1 | GLN | A | 191 | 0 | 29.745 | 7.761 | 12.427 | 1.00 | 28.86 |
| ATOM | 1460 | NE2 | GLN | A | 191 | 0 | 27.909 | 7.080 | 13.563 | 1.00 | 26.40 |
| ATOM | 1461 | N | GLY | A | 192 | 0 | 30.224 | 12.119 | 15.290 | 1.00 | 21.84 |
| ATOM | 1462 | CA | GLY | A | 192 | 0 | 31.418 | 12.469 | 15.996 | 1.00 | 22.91 |
| ATOM | 1463 | C | GLY | A | 192 | 0 | 31.564 | 13.910 | 16.446 | 1.00 | 23.87 |
| ATOM | 1464 | O | GLY | A | 192 | 0 | 32.394 | 14.174 | 17.322 | 1.00 | 25.80 |
| ATOM | 1465 | N | LYS | A | 193 | 0 | 30.839 | 14.867 | 15.922 | 1.00 | 23.54 |
| ATOM | 1466 | CA | LYS | A | 193 | 0 | 30.899 | 16.259 | 16.362 | 1.00 | 22.84 |
| ATOM | 1467 | C | LYS | A | 193 | 0 | 29.840 | 16.584 | 17.404 | 1.00 | 21.67 |
| ATOM | 1468 | O | LYS | A | 193 | 0 | 28.826 | 15.882 | 17.538 | 1.00 | 20.99 |
| ATOM | 1469 | CB | LYS | A | 193 | 0 | 30.682 | 17.155 | 15.143 | 1.00 | 24.53 |
| ATOM | 1470 | CG | LYS | A | 193 | 0 | 31.900 | 17.149 | 14.217 | 1.00 | 27.82 |
| ATOM | 1471 | CD | LYS | A | 193 | 0 | 31.739 | 18.261 | 13.199 | 1.00 | 30.02 |
| ATOM | 1472 | CE | LYS | A | 193 | 0 | 33.060 | 19.001 | 12.990 | 1.00 | 31.93 |
| ATOM | 1473 | NZ | LYS | A | 193 | 0 | 33.392 | 18.906 | 11.540 | 1.00 | 33.14 |
| ATOM | 1474 | N | LYS | A | 194 | 0 | 30.067 | 17.626 | 18.169 | 1.00 | 19.25 |
| ATOM | 1475 | CA | LYS | A | 194 | 0 | 29.168 | 18.115 | 19.187 | 1.00 | 19.49 |
| ATOM | 1476 | C | LYS | A | 194 | 0 | 28.722 | 19.523 | 18.780 | 1.00 | 19.40 |
| ATOM | 1477 | O | LYS | A | 194 | 0 | 29.512 | 20.285 | 18.235 | 1.00 | 19.29 |
| ATOM | 1478 | CB | LYS | A | 194 | 0 | 29.771 | 18.115 | 20.576 | 1.00 | 21.88 |
| ATOM | 1479 | CG | LYS | A | 194 | 0 | 30.338 | 16.748 | 20.999 | 1.00 | 25.59 |
| ATOM | 1480 | CD | LYS | A | 194 | 0 | 31.054 | 16.902 | 22.331 | 1.00 | 29.48 |
| ATOM | 1481 | CE | LYS | A | 194 | 0 | 31.455 | 15.582 | 22.970 | 1.00 | 33.58 |
| ATOM | 1482 | NZ | LYS | A | 194 | 0 | 30.363 | 15.049 | 23.868 | 1.00 | 35.93 |
| ATOM | 1483 | N | TYR | A | 195 | 0 | 27.418 | 19.818 | 18.910 | 1.00 | 16.92 |
| ATOM | 1484 | CA | TYR | A | 195 | 0 | 26.858 | 21.068 | 18.431 | 1.00 | 15.60 |
| ATOM | 1485 | C | TYR | A | 195 | 0 | 26.143 | 21.838 | 19.530 | 1.00 | 14.20 |
| ATOM | 1486 | O | TYR | A | 195 | 0 | 25.394 | 21.232 | 20.295 | 1.00 | 13.75 |
| ATOM | 1487 | CB | TYR | A | 195 | 0 | 25.814 | 20.880 | 17.300 | 1.00 | 16.13 |
| ATOM | 1488 | CG | TYR | A | 195 | 0 | 26.424 | 20.225 | 16.066 | 1.00 | 15.41 |
| ATOM | 1489 | CD1 | TYR | A | 195 | 0 | 26.663 | 18.851 | 16.091 | 1.00 | 15.91 |
| ATOM | 1490 | CD2 | TYR | A | 195 | 0 | 26.786 | 20.942 | 14.945 | 1.00 | 14.73 |
| ATOM | 1491 | CE1 | TYR | A | 195 | 0 | 27.244 | 18.204 | 15.010 | 1.00 | 16.55 |
| ATOM | 1492 | CE2 | TYR | A | 195 | 0 | 27.331 | 20.312 | 13.839 | 1.00 | 15.60 |
| ATOM | 1493 | CZ | TYR | A | 195 | 0 | 27.570 | 18.947 | 13.888 | 1.00 | 16.18 |
| ATOM | 1494 | OH | TYR | A | 195 | 0 | 28.144 | 18.287 | 12.831 | 1.00 | 15.64 |
| ATOM | 1495 | N | ARG | A | 196 | 0 | 26.366 | 23.136 | 19.561 | 1.00 | 12.74 |
| ATOM | 1496 | CA | ARG | A | 196 | 0 | 25.619 | 23.980 | 20.482 | 1.00 | 13.63 |
| ATOM | 1497 | C | ARG | A | 196 | 0 | 24.343 | 24.369 | 19.711 | 1.00 | 13.86 |
| ATOM | 1498 | O | ARG | A | 196 | 0 | 24.343 | 25.218 | 18.802 | 1.00 | 13.81 |
| ATOM | 1499 | CB | ARG | A | 196 | 0 | 26.379 | 25.187 | 20.991 | 1.00 | 13.96 |
| ATOM | 1500 | CG | ARG | A | 196 | 0 | 25.520 | 26.162 | 21.796 | 1.00 | 14.22 |
| ATOM | 1501 | CD | ARG | A | 196 | 0 | 26.337 | 27.238 | 22.438 | 1.00 | 15.27 |
| ATOM | 1502 | NE | ARG | A | 196 | 0 | 25.649 | 28.138 | 23.319 | 1.00 | 17.38 |
| ATOM | 1503 | CZ | ARG | A | 196 | 0 | 26.203 | 29.034 | 24.140 | 1.00 | 18.86 |
| ATOM | 1504 | NH1 | ARG | A | 196 | 0 | 27.540 | 29.141 | 24.217 | 1.00 | 16.30 |
| ATOM | 1505 | NH2 | ARG | A | 196 | 0 | 25.377 | 29.788 | 24.869 | 1.00 | 16.73 |
| ATOM | 1506 | N | MET | A | 197 | 0 | 23.266 | 23.624 | 20.002 | 1.00 | 13.86 |
| ATOM | 1507 | CA | MET | A | 197 | 0 | 21.980 | 23.932 | 19.340 | 1.00 | 12.98 |
| ATOM | 1508 | C | MET | A | 197 | 0 | 21.293 | 25.055 | 20.127 | 1.00 | 12.50 |
| ATOM | 1509 | O | MET | A | 197 | 0 | 21.285 | 24.997 | 21.359 | 1.00 | 13.93 |
| ATOM | 1510 | CB | MET | A | 197 | 0 | 21.118 | 22.693 | 19.266 | 1.00 | 12.50 |
| ATOM | 1511 | CG | MET | A | 197 | 0 | 21.762 | 21.567 | 18.447 | 1.00 | 13.94 |
| ATOM | 1512 | SD | MET | A | 197 | 0 | 21.860 | 22.033 | 16.735 | 1.00 | 16.62 |
| ATOM | 1513 | CE | MET | A | 197 | 0 | 22.157 | 20.467 | 15.927 | 1.00 | 16.37 |
| ATOM | 1514 | N | ARG | A | 198 | 0 | 20.768 | 26.064 | 19.450 | 1.00 | 11.00 |
| ATOM | 1515 | CA | ARG | A | 198 | 0 | 20.131 | 27.191 | 20.137 | 1.00 | 11.83 |
| ATOM | 1516 | C | ARG | A | 198 | 0 | 18.624 | 27.130 | 19.868 | 1.00 | 12.36 |
| ATOM | 1517 | O | ARG | A | 198 | 0 | 18.145 | 27.304 | 18.731 | 1.00 | 10.03 |
| ATOM | 1518 | CB | ARG | A | 198 | 0 | 20.804 | 28.460 | 19.629 | 1.00 | 13.98 |
| ATOM | 1519 | CG | ARG | A | 198 | 0 | 22.282 | 28.567 | 20.065 | 1.00 | 16.25 |
| ATOM | 1520 | CD | ARG | A | 198 | 0 | 22.932 | 29.863 | 19.626 | 1.00 | 16.68 |
| ATOM | 1521 | NE | ARG | A | 198 | 0 | 24.350 | 29.957 | 20.042 | 1.00 | 16.91 |
| ATOM | 1522 | CZ | ARG | A | 198 | 0 | 24.812 | 30.691 | 21.055 | 1.00 | 15.76 |
| ATOM | 1523 | NH1 | ARG | A | 198 | 0 | 24.031 | 31.456 | 21.820 | 1.00 | 13.44 |
| ATOM | 1524 | NH2 | ARG | A | 198 | 0 | 26.123 | 30.721 | 21.316 | 1.00 | 15.41 |
| ATOM | 1525 | N | LEU | A | 199 | 0 | 17.871 | 26.807 | 20.908 | 1.00 | 10.44 |
| ATOM | 1526 | CA | LEU | A | 199 | 0 | 16.426 | 26.568 | 20.708 | 1.00 | 10.69 |
| ATOM | 1527 | C | LEU | A | 199 | 0 | 15.598 | 27.772 | 21.169 | 1.00 | 10.07 |
| ATOM | 1528 | O | LEU | A | 199 | 0 | 15.682 | 28.216 | 22.317 | 1.00 | 10.07 |
| ATOM | 1529 | CB | LEU | A | 199 | 0 | 16.003 | 25.317 | 21.491 | 1.00 | 8.67 |
| ATOM | 1530 | CG | LEU | A | 199 | 0 | 14.499 | 24.942 | 21.391 | 1.00 | 10.33 |
| ATOM | 1531 | CD1 | LEU | A | 199 | 0 | 14.193 | 24.333 | 20.023 | 1.00 | 8.13 |
| ATOM | 1532 | CD2 | LEU | A | 199 | 0 | 14.170 | 23.907 | 22.485 | 1.00 | 9.10 |
| ATOM | 1533 | N | ILE | A | 200 | 0 | 14.857 | 28.370 | 20.242 | 1.00 | 10.46 |
| ATOM | 1534 | CA | ILE | A | 200 | 0 | 14.104 | 29.572 | 20.585 | 1.00 | 11.72 |
| ATOM | 1535 | C | ILE | A | 200 | 0 | 12.627 | 29.428 | 20.310 | 1.00 | 13.84 |

APPENDIX 1-continued

| ATOM | 1536 | O | ILE | A | 200 | 0 | 12.254 | 29.059 | 19.192 | 1.00 | 13.22 |
|---|---|---|---|---|---|---|---|---|---|---|---|
| ATOM | 1537 | CB | ILE | A | 200 | 0 | 14.628 | 30.755 | 19.735 | 1.00 | 12.89 |
| ATOM | 1538 | CG1 | ILE | A | 200 | 0 | 16.165 | 30.899 | 19.824 | 1.00 | 12.38 |
| ATOM | 1539 | CG2 | ILE | A | 200 | 0 | 13.998 | 32.091 | 20.065 | 1.00 | 13.13 |
| ATOM | 1540 | CD1 | ILE | A | 200 | 0 | 16.811 | 31.634 | 18.671 | 1.00 | 12.54 |
| ATOM | 1541 | N | SER | A | 201 | 0 | 11.829 | 29.825 | 21.312 | 1.00 | 14.64 |
| ATOM | 1542 | CA | SER | A | 201 | 0 | 10.379 | 29.849 | 21.023 | 1.00 | 13.89 |
| ATOM | 1543 | C | SER | A | 201 | 0 | 10.018 | 31.280 | 20.608 | 1.00 | 11.10 |
| ATOM | 1544 | O | SER | A | 201 | 0 | 10.250 | 32.261 | 21.320 | 1.00 | 8.85 |
| ATOM | 1545 | CB | SER | A | 201 | 0 | 9.539 | 29.367 | 22.202 | 1.00 | 13.01 |
| ATOM | 1546 | OG | SER | A | 201 | 0 | 8.313 | 30.047 | 22.207 | 1.00 | 12.19 |
| ATOM | 1547 | N | LEU | A | 202 | 0 | 9.428 | 31.376 | 19.438 | 1.00 | 9.64 |
| ATOM | 1548 | CA | LEU | A | 202 | 0 | 8.959 | 32.637 | 18.881 | 1.00 | 9.06 |
| ATOM | 1549 | C | LEU | A | 202 | 0 | 7.415 | 32.740 | 19.046 | 1.00 | 10.40 |
| ATOM | 1550 | O | LEU | A | 202 | 0 | 6.802 | 33.528 | 18.351 | 1.00 | 9.36 |
| ATOM | 1551 | CB | LEU | A | 202 | 0 | 9.239 | 32.618 | 17.379 | 1.00 | 9.09 |
| ATOM | 1552 | CG | LEU | A | 202 | 0 | 10.691 | 32.451 | 16.888 | 1.00 | 10.90 |
| ATOM | 1553 | CD1 | LEU | A | 202 | 0 | 10.637 | 32.470 | 15.367 | 1.00 | 10.05 |
| ATOM | 1554 | CD2 | LEU | A | 202 | 0 | 11.617 | 33.559 | 17.414 | 1.00 | 8.56 |
| ATOM | 1555 | N | SER | A | 203 | 0 | 6.821 | 31.942 | 19.892 | 1.00 | 9.59 |
| ATOM | 1556 | CA | SER | A | 203 | 0 | 5.414 | 31.756 | 20.017 | 1.00 | 15.31 |
| ATOM | 1557 | C | SER | A | 203 | 0 | 4.624 | 32.960 | 20.544 | 1.00 | 16.67 |
| ATOM | 1558 | O | SER | A | 203 | 0 | 4.964 | 33.676 | 21.483 | 1.00 | 16.42 |
| ATOM | 1559 | CB | SER | A | 203 | 0 | 5.130 | 30.505 | 20.867 | 1.00 | 15.21 |
| ATOM | 1560 | OG | SER | A | 203 | 0 | 3.742 | 30.240 | 21.004 | 1.00 | 17.14 |
| ATOM | 1561 | N | CYS | A | 204 | 0 | 3.428 | 33.051 | 19.984 | 1.00 | 17.18 |
| ATOM | 1562 | CA | CYS | A | 204 | 0 | 2.442 | 34.018 | 20.470 | 1.00 | 18.43 |
| ATOM | 1563 | C | CYS | A | 204 | 0 | 1.599 | 33.316 | 21.522 | 1.00 | 17.02 |
| ATOM | 1564 | O | CYS | A | 204 | 0 | 0.867 | 34.039 | 22.200 | 1.00 | 17.27 |
| ATOM | 1565 | CB | CYS | A | 204 | 0 | 1.524 | 34.508 | 19.334 | 1.00 | 18.60 |
| ATOM | 1566 | SG | CYS | A | 204 | 0 | 2.135 | 36.038 | 18.612 | 1.00 | 20.23 |
| ATOM | 1567 | N | ASP | A | 205 | 0 | 1.687 | 31.989 | 21.665 | 1.00 | 16.38 |
| ATOM | 1568 | CA | ASP | A | 205 | 0 | 0.776 | 31.392 | 22.683 | 1.00 | 12.26 |
| ATOM | 1569 | C | ASP | A | 205 | 0 | 1.123 | 30.002 | 23.087 | 1.00 | 11.34 |
| ATOM | 1570 | O | ASP | A | 205 | 0 | 1.432 | 29.687 | 24.255 | 1.00 | 11.40 |
| ATOM | 1571 | CB | ASP | A | 205 | 0 | -0.622 | 31.516 | 22.076 | 1.00 | 14.87 |
| ATOM | 1572 | CG | ASP | A | 205 | 0 | -1.729 | 30.881 | 22.892 | 1.00 | 16.61 |
| ATOM | 1573 | OD1 | ASP | A | 205 | 0 | -2.884 | 30.999 | 22.433 | 1.00 | 18.48 |
| ATOM | 1574 | OD2 | ASP | A | 205 | 0 | -1.534 | 30.263 | 23.966 | 1.00 | 17.48 |
| ATOM | 1575 | N | PRO | A | 206 | 0 | 1.036 | 29.030 | 22.205 | 1.00 | 11.79 |
| ATOM | 1576 | CA | PRO | A | 206 | 0 | 1.313 | 27.639 | 22.542 | 1.00 | 11.91 |
| ATOM | 1577 | C | PRO | A | 206 | 0 | 2.739 | 27.411 | 23.045 | 1.00 | 14.01 |
| ATOM | 1578 | O | PRO | A | 206 | 0 | 3.676 | 28.135 | 22.661 | 1.00 | 14.38 |
| ATOM | 1579 | CB | PRO | A | 206 | 0 | 1.124 | 26.816 | 21.262 | 1.00 | 11.87 |
| ATOM | 1580 | CG | PRO | A | 206 | 0 | 1.112 | 27.893 | 20.191 | 1.00 | 12.83 |
| ATOM | 1581 | CD | PRO | A | 206 | 0 | 0.749 | 29.241 | 20.766 | 1.00 | 11.09 |
| ATOM | 1582 | N | ASN | A | 207 | 0 | 2.888 | 26.439 | 23.911 | 1.00 | 13.06 |
| ATOM | 1583 | CA | ASN | A | 207 | 0 | 4.128 | 25.919 | 24.429 | 1.00 | 15.01 |
| ATOM | 1584 | C | ASN | A | 207 | 0 | 4.332 | 24.591 | 23.677 | 1.00 | 15.84 |
| ATOM | 1585 | O | ASN | A | 207 | 0 | 3.376 | 24.095 | 23.038 | 1.00 | 16.22 |
| ATOM | 1586 | CB | ASN | A | 207 | 0 | 4.144 | 25.682 | 25.933 | 1.00 | 15.12 |
| ATOM | 1587 | CG | ASN | A | 207 | 0 | 3.054 | 24.708 | 26.395 | 1.00 | 19.36 |
| ATOM | 1588 | OD1 | ASN | A | 207 | 0 | 2.062 | 25.161 | 27.014 | 1.00 | 19.36 |
| ATOM | 1589 | ND2 | ASN | A | 207 | 0 | 3.174 | 23.408 | 26.203 | 1.00 | 16.49 |
| ATOM | 1590 | N | TRP | A | 208 | 0 | 5.557 | 24.077 | 23.634 | 1.00 | 14.46 |
| ATOM | 1591 | CA | TRP | A | 208 | 0 | 5.827 | 22.865 | 22.892 | 1.00 | 12.04 |
| ATOM | 1592 | C | TRP | A | 208 | 0 | 6.638 | 21.921 | 23.783 | 1.00 | 13.85 |
| ATOM | 1593 | O | TRP | A | 208 | 0 | 7.482 | 22.385 | 24.558 | 1.00 | 13.02 |
| ATOM | 1594 | CB | TRP | A | 208 | 0 | 6.654 | 23.136 | 21.628 | 1.00 | 11.91 |
| ATOM | 1595 | CG | TRP | A | 208 | 0 | 5.951 | 23.769 | 20.465 | 1.00 | 11.27 |
| ATOM | 1596 | CD1 | TRP | A | 208 | 0 | 5.149 | 23.164 | 19.561 | 1.00 | 10.33 |
| ATOM | 1597 | CD2 | TRP | A | 208 | 0 | 5.988 | 25.158 | 20.092 | 1.00 | 10.29 |
| ATOM | 1598 | NE1 | TRP | A | 208 | 0 | 4.698 | 24.078 | 18.625 | 1.00 | 10.91 |
| ATOM | 1599 | CE2 | TRP | A | 208 | 0 | 5.201 | 25.313 | 18.954 | 1.00 | 9.64 |
| ATOM | 1600 | CE3 | TRP | A | 208 | 0 | 6.634 | 26.294 | 20.625 | 1.00 | 10.25 |
| ATOM | 1601 | CZ2 | TRP | A | 208 | 0 | 5.011 | 26.553 | 18.344 | 1.00 | 8.53 |
| ATOM | 1602 | CZ3 | TRP | A | 208 | 0 | 6.494 | 27.514 | 20.019 | 1.00 | 10.02 |
| ATOM | 1603 | CH2 | TRP | A | 208 | 0 | 5.668 | 27.633 | 18.881 | 1.00 | 11.79 |
| ATOM | 1604 | N | GLN | A | 209 | 0 | 6.420 | 20.620 | 23.580 | 1.00 | 13.82 |
| ATOM | 1605 | CA | GLN | A | 209 | 0 | 7.240 | 19.588 | 24.192 | 1.00 | 13.83 |
| ATOM | 1606 | C | GLN | A | 209 | 0 | 8.251 | 19.281 | 23.075 | 1.00 | 13.07 |
| ATOM | 1607 | O | GLN | A | 209 | 0 | 7.848 | 18.968 | 21.948 | 1.00 | 14.18 |
| ATOM | 1608 | CB | GLN | A | 209 | 0 | 6.441 | 18.319 | 24.487 | 1.00 | 15.65 |
| ATOM | 1609 | CG | GLN | A | 209 | 0 | 5.449 | 18.481 | 25.649 | 1.00 | 17.26 |
| ATOM | 1610 | CD | GLN | A | 209 | 0 | 6.177 | 18.514 | 26.975 | 1.00 | 18.17 |
| ATOM | 1611 | OE1 | GLN | A | 209 | 0 | 7.414 | 18.471 | 27.002 | 1.00 | 20.00 |
| ATOM | 1612 | NE2 | GLN | A | 209 | 0 | 5.462 | 18.570 | 28.085 | 1.00 | 16.89 |
| ATOM | 1613 | N | PHE | A | 210 | 0 | 9.538 | 19.461 | 23.351 | 1.00 | 11.26 |
| ATOM | 1614 | CA | PHE | A | 210 | 0 | 10.526 | 19.329 | 22.287 | 1.00 | 10.01 |

APPENDIX 1-continued

| | | | | | | | | | | |
|---|---|---|---|---|---|---|---|---|---|---|
| ATOM | 1615 | C   | PHE | A | 210 | 0 | 11.457 | 18.153 | 22.585 | 1.00 | 9.18 |
| ATOM | 1616 | O   | PHE | A | 210 | 0 | 11.894 | 17.999 | 23.732 | 1.00 | 10.07 |
| ATOM | 1617 | CB  | PHE | A | 210 | 0 | 11.370 | 20.629 | 22.292 | 1.00 | 10.86 |
| ATOM | 1618 | CG  | PHE | A | 210 | 0 | 12.489 | 20.581 | 21.292 | 1.00 | 9.63 |
| ATOM | 1619 | CD1 | PHE | A | 210 | 0 | 13.760 | 20.179 | 21.674 | 1.00 | 9.95 |
| ATOM | 1620 | CD2 | PHE | A | 210 | 0 | 12.251 | 20.922 | 19.984 | 1.00 | 8.54 |
| ATOM | 1621 | CE1 | PHE | A | 210 | 0 | 14.778 | 20.150 | 20.738 | 1.00 | 9.23 |
| ATOM | 1622 | CE2 | PHE | A | 210 | 0 | 13.243 | 20.862 | 19.023 | 1.00 | 7.93 |
| ATOM | 1623 | CZ  | PHE | A | 210 | 0 | 14.520 | 20.491 | 19.426 | 1.00 | 8.71 |
| ATOM | 1624 | N   | SER | A | 211 | 0 | 11.741 | 17.384 | 21.545 | 1.00 | 8.62 |
| ATOM | 1625 | CA  | SER | A | 211 | 0 | 12.645 | 16.255 | 21.716 | 1.00 | 10.71 |
| ATOM | 1626 | C   | SER | A | 211 | 0 | 13.142 | 15.844 | 20.347 | 1.00 | 11.36 |
| ATOM | 1627 | O   | SER | A | 211 | 0 | 12.661 | 16.323 | 19.315 | 1.00 | 9.99 |
| ATOM | 1628 | CB  | SER | A | 211 | 0 | 11.970 | 15.070 | 22.427 | 1.00 | 10.56 |
| ATOM | 1629 | OG  | SER | A | 211 | 0 | 10.899 | 14.731 | 21.513 | 1.00 | 12.92 |
| ATOM | 1630 | N   | ILE | A | 212 | 0 | 14.268 | 15.122 | 20.390 | 1.00 | 13.67 |
| ATOM | 1631 | CA  | ILE | A | 212 | 0 | 14.883 | 14.680 | 19.131 | 1.00 | 14.79 |
| ATOM | 1632 | C   | ILE | A | 212 | 0 | 15.013 | 13.166 | 19.220 | 1.00 | 15.44 |
| ATOM | 1633 | O   | ILE | A | 212 | 0 | 15.624 | 12.689 | 20.177 | 1.00 | 15.98 |
| ATOM | 1634 | CB  | ILE | A | 212 | 0 | 16.255 | 15.341 | 18.887 | 1.00 | 17.04 |
| ATOM | 1635 | CG1 | ILE | A | 212 | 0 | 16.082 | 16.859 | 18.756 | 1.00 | 15.64 |
| ATOM | 1636 | CG2 | ILE | A | 212 | 0 | 16.935 | 14.722 | 17.648 | 1.00 | 15.24 |
| ATOM | 1637 | CD1 | ILE | A | 212 | 0 | 17.352 | 17.648 | 18.553 | 1.00 | 16.57 |
| ATOM | 1638 | N   | ASP | A | 213 | 0 | 14.453 | 12.418 | 18.281 | 1.00 | 15.53 |
| ATOM | 1639 | CA  | ASP | A | 213 | 0 | 14.549 | 10.952 | 18.401 | 1.00 | 16.50 |
| ATOM | 1640 | C   | ASP | A | 213 | 0 | 16.004 | 10.469 | 18.541 | 1.00 | 16.69 |
| ATOM | 1641 | O   | ASP | A | 213 | 0 | 16.948 | 10.902 | 17.851 | 1.00 | 14.36 |
| ATOM | 1642 | CB  | ASP | A | 213 | 0 | 13.884 | 10.359 | 17.173 | 1.00 | 17.15 |
| ATOM | 1643 | CG  | ASP | A | 213 | 0 | 12.369 | 10.467 | 17.144 | 1.00 | 18.12 |
| ATOM | 1644 | OD1 | ASP | A | 213 | 0 | 11.751 | 10.995 | 18.092 | 1.00 | 16.90 |
| ATOM | 1645 | OD2 | ASP | A | 213 | 0 | 11.801 | 9.990  | 16.129 | 1.00 | 17.35 |
| ATOM | 1646 | N   | GLY | A | 214 | 0 | 16.198 | 9.559  | 19.477 | 1.00 | 15.76 |
| ATOM | 1647 | CA  | GLY | A | 214 | 0 | 17.457 | 8.900  | 19.747 | 1.00 | 17.22 |
| ATOM | 1648 | C   | GLY | A | 214 | 0 | 18.548 | 9.757  | 20.368 | 1.00 | 18.54 |
| ATOM | 1649 | O   | GLY | A | 214 | 0 | 19.680 | 9.277  | 20.404 | 1.00 | 18.20 |
| ATOM | 1650 | N   | HIS | A | 215 | 0 | 18.341 | 11.024 | 20.738 | 1.00 | 18.17 |
| ATOM | 1651 | CA  | HIS | A | 215 | 0 | 19.422 | 11.880 | 21.229 | 1.00 | 17.59 |
| ATOM | 1652 | C   | HIS | A | 215 | 0 | 19.096 | 12.505 | 22.577 | 1.00 | 17.92 |
| ATOM | 1653 | O   | HIS | A | 215 | 0 | 17.917 | 12.696 | 22.898 | 1.00 | 20.45 |
| ATOM | 1654 | CB  | HIS | A | 215 | 0 | 19.705 | 13.008 | 20.221 | 1.00 | 15.73 |
| ATOM | 1655 | CG  | HIS | A | 215 | 0 | 20.309 | 12.543 | 18.936 | 1.00 | 16.90 |
| ATOM | 1656 | ND1 | HIS | A | 215 | 0 | 19.589 | 11.864 | 17.963 | 1.00 | 17.35 |
| ATOM | 1657 | CD2 | HIS | A | 215 | 0 | 21.574 | 12.658 | 18.444 | 1.00 | 16.15 |
| ATOM | 1658 | CE1 | HIS | A | 215 | 0 | 20.376 | 11.576 | 16.933 | 1.00 | 17.63 |
| ATOM | 1659 | NE2 | HIS | A | 215 | 0 | 21.599 | 12.046 | 17.216 | 1.00 | 17.73 |
| ATOM | 1660 | N   | GLU | A | 216 | 0 | 20.104 | 12.815 | 23.382 | 1.00 | 17.22 |
| ATOM | 1661 | CA  | GLU | A | 216 | 0 | 19.876 | 13.479 | 24.665 | 1.00 | 15.86 |
| ATOM | 1662 | C   | GLU | A | 216 | 0 | 20.070 | 14.976 | 24.456 | 1.00 | 15.61 |
| ATOM | 1663 | O   | GLU | A | 216 | 0 | 20.684 | 15.386 | 23.453 | 1.00 | 14.96 |
| ATOM | 1664 | CB  | GLU | A | 216 | 0 | 20.817 | 12.901 | 25.694 | 1.00 | 15.38 |
| ATOM | 1665 | CG  | GLU | A | 216 | 0 | 20.440 | 11.520 | 26.166 | 1.00 | 16.53 |
| ATOM | 1666 | CD  | GLU | A | 216 | 0 | 21.242 | 11.058 | 27.357 | 1.00 | 17.23 |
| ATOM | 1667 | OE1 | GLU | A | 216 | 0 | 22.378 | 10.619 | 27.129 | 1.00 | 20.31 |
| ATOM | 1668 | OE2 | GLU | A | 216 | 0 | 20.813 | 11.119 | 28.519 | 1.00 | 16.06 |
| ATOM | 1669 | N   | LEU | A | 217 | 0 | 19.623 | 15.792 | 25.394 | 1.00 | 14.64 |
| ATOM | 1670 | CA  | LEU | A | 217 | 0 | 19.738 | 17.243 | 25.251 | 1.00 | 14.91 |
| ATOM | 1671 | C   | LEU | A | 217 | 0 | 20.512 | 17.792 | 26.446 | 1.00 | 14.71 |
| ATOM | 1672 | O   | LEU | A | 217 | 0 | 19.950 | 17.734 | 27.539 | 1.00 | 15.67 |
| ATOM | 1673 | CB  | LEU | A | 217 | 0 | 18.362 | 17.931 | 25.229 | 1.00 | 14.75 |
| ATOM | 1674 | CG  | LEU | A | 217 | 0 | 17.276 | 17.349 | 24.306 | 1.00 | 15.40 |
| ATOM | 1675 | CD1 | LEU | A | 217 | 0 | 15.939 | 18.075 | 24.505 | 1.00 | 15.08 |
| ATOM | 1676 | CD2 | LEU | A | 217 | 0 | 17.723 | 17.453 | 22.849 | 1.00 | 15.22 |
| ATOM | 1677 | N   | THR | A | 218 | 0 | 21.732 | 18.278 | 26.229 | 1.00 | 13.65 |
| ATOM | 1678 | CA  | THR | A | 218 | 0 | 22.507 | 18.714 | 27.402 | 1.00 | 13.26 |
| ATOM | 1679 | C   | THR | A | 218 | 0 | 22.427 | 20.232 | 27.505 | 1.00 | 13..27 |
| ATOM | 1680 | O   | THR | A | 218 | 0 | 23.142 | 20.955 | 26.805 | 1.00 | 12.91 |
| ATOM | 1681 | CB  | THR | A | 218 | 0 | 23.955 | 18.216 | 27.304 | 1.00 | 12.08 |
| ATOM | 1682 | OG1 | THR | A | 218 | 0 | 23.935 | 16.782 | 27.331 | 1.00 | 15.48 |
| ATOM | 1683 | CG2 | THR | A | 218 | 0 | 24.767 | 18.721 | 28.470 | 1.00 | 11.46 |
| ATOM | 1684 | N   | ILE | A | 219 | 0 | 21.522 | 20.649 | 28.385 | 1.00 | 13.30 |
| ATOM | 1685 | CA  | ILE | A | 219 | 0 | 21.259 | 22.068 | 28.547 | 1.00 | 14.53 |
| ATOM | 1686 | C   | ILE | A | 219 | 0 | 22.420 | 22.818 | 29.180 | 1.00 | 12.72 |
| ATOM | 1687 | O   | ILE | A | 219 | 0 | 22.795 | 22.492 | 30.292 | 1.00 | 13.08 |
| ATOM | 1688 | CB  | ILE | A | 219 | 0 | 19.930 | 22.268 | 29.323 | 1.00 | 14.74 |
| ATOM | 1689 | CG1 | ILE | A | 219 | 0 | 18.761 | 21.699 | 28.441 | 1.00 | 17.33 |
| ATOM | 1690 | CG2 | ILE | A | 219 | 0 | 19.666 | 23.717 | 29.656 | 1.00 | 13.40 |
| ATOM | 1691 | CD1 | ILE | A | 219 | 0 | 17.597 | 21.481 | 29.412 | 1.00 | 19.42 |
| ATOM | 1692 | N   | ILE | A | 220 | 0 | 22.898 | 23.869 | 28.510 | 1.00 | 12.55 |
| ATOM | 1693 | CA  | ILE | A | 220 | 0 | 23.994 | 24.696 | 29.019 | 1.00 | 13.25 |

APPENDIX 1-continued

| ATOM | 1694 | C   | ILE | A | 220 | 0 | 23.686 | 26.193 | 29.085 | 1.00 | 15.11 |
| ATOM | 1695 | O   | ILE | A | 220 | 0 | 24.477 | 27.001 | 29.618 | 1.00 | 14.73 |
| ATOM | 1696 | CB  | ILE | A | 220 | 0 | 25.239 | 24.507 | 28.125 | 1.00 | 11.80 |
| ATOM | 1697 | CG1 | ILE | A | 220 | 0 | 24.954 | 24.871 | 26.671 | 1.00 | 10.93 |
| ATOM | 1698 | CG2 | ILE | A | 220 | 0 | 25.770 | 23.072 | 28.291 | 1.00 | 9.59  |
| ATOM | 1699 | CD1 | ILE | A | 220 | 0 | 26.249 | 25.231 | 25.928 | 1.00 | 12.07 |
| ATOM | 1700 | N   | GLU | A | 221 | 0 | 22.490 | 26.573 | 28.597 | 1.00 | 13.30 |
| ATOM | 1701 | CA  | GLU | A | 221 | 0 | 22.048 | 27.951 | 28.624 | 1.00 | 12.96 |
| ATOM | 1702 | C   | GLU | A | 221 | 0 | 20.522 | 28.066 | 28.727 | 1.00 | 13.77 |
| ATOM | 1703 | O   | GLU | A | 221 | 0 | 19.799 | 27.301 | 28.068 | 1.00 | 14.06 |
| ATOM | 1704 | CB  | GLU | A | 221 | 0 | 22.436 | 28.666 | 27.318 | 1.00 | 12.73 |
| ATOM | 1705 | CG  | GLU | A | 221 | 0 | 22.280 | 30.178 | 27.325 | 1.00 | 12.94 |
| ATOM | 1706 | CD  | GLU | A | 221 | 0 | 22.018 | 30.783 | 25.969 | 1.00 | 13.84 |
| ATOM | 1707 | OE1 | GLU | A | 221 | 0 | 22.345 | 30.269 | 24.887 | 1.00 | 12.66 |
| ATOM | 1708 | OE2 | GLU | A | 221 | 0 | 21.386 | 31.862 | 25.936 | 1.00 | 14.80 |
| ATOM | 1709 | N   | VAL | A | 222 | 0 | 20.062 | 29.091 | 29.434 | 1.00 | 13.89 |
| ATOM | 1710 | CA  | VAL | A | 222 | 0 | 18.632 | 29.350 | 29.534 | 1.00 | 14.13 |
| ATOM | 1711 | C   | VAL | A | 222 | 0 | 18.409 | 30.853 | 29.493 | 1.00 | 13.87 |
| ATOM | 1712 | O   | VAL | A | 222 | 0 | 18.900 | 31.657 | 30.300 | 1.00 | 11.55 |
| ATOM | 1713 | CB  | VAL | A | 222 | 0 | 18.003 | 28.649 | 30.737 | 1.00 | 16.86 |
| ATOM | 1714 | CG1 | VAL | A | 222 | 0 | 18.730 | 28.941 | 32.017 | 1.00 | 19.16 |
| ATOM | 1715 | CG2 | VAL | A | 222 | 0 | 16.575 | 29.120 | 31.033 | 1.00 | 18.45 |
| ATOM | 1716 | N   | ASP | A | 223 | 0 | 17.631 | 31.267 | 28.481 | 1.00 | 11.69 |
| ATOM | 1717 | CA  | ASP | A | 223 | 0 | 17.245 | 32.673 | 28.386 | 1.00 | 13.60 |
| ATOM | 1718 | C   | ASP | A | 223 | 0 | 18.472 | 33.598 | 28.548 | 1.00 | 14.44 |
| ATOM | 1719 | O   | ASP | A | 223 | 0 | 18.423 | 34.552 | 29.336 | 1.00 | 12.75 |
| ATOM | 1720 | CB  | ASP | A | 223 | 0 | 16.161 | 33.033 | 29.417 | 1.00 | 12.59 |
| ATOM | 1721 | CG  | ASP | A | 223 | 0 | 14.845 | 32.279 | 29.364 | 1.00 | 14.64 |
| ATOM | 1722 | OD1 | ASP | A | 223 | 0 | 14.697 | 31.397 | 28.493 | 1.00 | 13.34 |
| ATOM | 1723 | OD2 | ASP | A | 223 | 0 | 13.858 | 32.463 | 30.156 | 1.00 | 13.85 |
| ATOM | 1724 | N   | GLY | A | 224 | 0 | 19.544 | 33.372 | 27.767 | 1.00 | 13.49 |
| ATOM | 1725 | CA  | GLY | A | 224 | 0 | 20.728 | 34.213 | 27.770 | 1.00 | 12.85 |
| ATOM | 1726 | C   | GLY | A | 224 | 0 | 21.562 | 34.112 | 29.049 | 1.00 | 13.00 |
| ATOM | 1727 | O   | GLY | A | 224 | 0 | 22.326 | 35.040 | 29.317 | 1.00 | 13.97 |
| ATOM | 1728 | N   | GLU | A | 225 | 0 | 21.370 | 33.105 | 29.875 | 1.00 | 11.78 |
| ATOM | 1729 | CA  | GLU | A | 225 | 0 | 22.068 | 32.888 | 31.114 | 1.00 | 14.97 |
| ATOM | 1730 | C   | GLU | A | 225 | 0 | 22.609 | 31.447 | 31.106 | 1.00 | 16.73 |
| ATOM | 1731 | O   | GLU | A | 225 | 0 | 21.858 | 30.498 | 30.849 | 1.00 | 15.88 |
| ATOM | 1732 | CB  | GLU | A | 225 | 0 | 21.174 | 33.062 | 32.358 | 1.00 | 16.54 |
| ATOM | 1733 | CG  | GLU | A | 225 | 0 | 20.509 | 34.424 | 32.534 | 1.00 | 16.30 |
| ATOM | 1734 | CD  | GLU | A | 225 | 0 | 21.492 | 35.546 | 32.823 | 1.00 | 17.57 |
| ATOM | 1735 | OE1 | GLU | A | 225 | 0 | 22.450 | 35.254 | 33.561 | 1.00 | 18.76 |
| ATOM | 1736 | OE2 | GLU | A | 225 | 0 | 21.360 | 36.711 | 32.360 | 1.00 | 17.77 |
| ATOM | 1737 | N   | LEU | A | 226 | 0 | 23.922 | 31.285 | 31.324 | 1.00 | 16.90 |
| ATOM | 1738 | CA  | LEU | A | 226 | 0 | 24.526 | 29.955 | 31.318 | 1.00 | 15.50 |
| ATOM | 1739 | C   | LEU | A | 226 | 0 | 24.183 | 29.127 | 32.540 | 1.00 | 15.04 |
| ATOM | 1740 | O   | LEU | A | 226 | 0 | 24.002 | 29.648 | 33.652 | 1.00 | 15.17 |
| ATOM | 1741 | CB  | LEU | A | 226 | 0 | 26.062 | 30.008 | 31.216 | 1.00 | 15.36 |
| ATOM | 1742 | CG  | LEU | A | 226 | 0 | 26.567 | 30.741 | 29.958 | 1.00 | 17.95 |
| ATOM | 1743 | CD1 | LEU | A | 226 | 0 | 28.076 | 30.876 | 29.979 | 1.00 | 18.77 |
| ATOM | 1744 | CD2 | LEU | A | 226 | 0 | 26.111 | 30.029 | 28.687 | 1.00 | 17.36 |
| ATOM | 1745 | N   | THR | A | 227 | 0 | 24.119 | 27.799 | 32.332 | 1.00 | 13.62 |
| ATOM | 1746 | CA  | THR | A | 227 | 0 | 23.848 | 26.930 | 33.472 | 1.00 | 13.72 |
| ATOM | 1747 | C   | THR | A | 227 | 0 | 24.936 | 25.851 | 33.528 | 1.00 | 14.30 |
| ATOM | 1748 | O   | THR | A | 227 | 0 | 25.732 | 25.629 | 32.592 | 1.00 | 14.28 |
| ATOM | 1749 | CB  | THR | A | 227 | 0 | 22.478 | 26.217 | 33.352 | 1.00 | 14.35 |
| ATOM | 1750 | OG1 | THR | A | 227 | 0 | 22.506 | 25.385 | 32.178 | 1.00 | 13.68 |
| ATOM | 1751 | CG2 | THR | A | 227 | 0 | 21.284 | 27.161 | 33.180 | 1.00 | 12.29 |
| ATOM | 1752 | N   | GLU | A | 228 | 0 | 24.960 | 25.136 | 34.625 | 1.00 | 14.73 |
| ATOM | 1753 | CA  | GLU | A | 228 | 0 | 25.765 | 23.907 | 34.714 | 1.00 | 17.32 |
| ATOM | 1754 | C   | GLU | A | 228 | 0 | 25.110 | 22.971 | 33.680 | 1.00 | 17.30 |
| ATOM | 1755 | O   | GLU | A | 228 | 0 | 23.917 | 23.035 | 33.472 | 1.00 | 16.97 |
| ATOM | 1756 | CB  | GLU | A | 228 | 0 | 25.617 | 23.315 | 36.114 | 1.00 | 16.58 |
| ATOM | 1757 | CG  | GLU | A | 228 | 0 | 26.493 | 23.979 | 37.186 | 1.00 | 18.10 |
| ATOM | 1758 | CD  | GLU | A | 228 | 0 | 26.236 | 23.458 | 38.575 | 1.00 | 20.92 |
| ATOM | 1759 | OE1 | GLU | A | 228 | 0 | 25.469 | 22.470 | 38.755 | 1.00 | 23.38 |
| ATOM | 1760 | OE2 | GLU | A | 228 | 0 | 26.769 | 23.997 | 39.564 | 1.00 | 21.26 |
| ATOM | 1761 | N   | PRO | A | 229 | 0 | 25.867 | 22.158 | 32.984 | 1.00 | 16.91 |
| ATOM | 1762 | CA  | PRO | A | 229 | 0 | 25.369 | 21.207 | 31.992 | 1.00 | 16.37 |
| ATOM | 1763 | C   | PRO | A | 229 | 0 | 24.351 | 20.275 | 32.599 | 1.00 | 16.24 |
| ATOM | 1764 | O   | PRO | A | 229 | 0 | 24.624 | 19.652 | 33.619 | 1.00 | 15.76 |
| ATOM | 1765 | CB  | PRO | A | 229 | 0 | 26.612 | 20.469 | 31.419 | 1.00 | 15.97 |
| ATOM | 1766 | CG  | PRO | A | 229 | 0 | 27.701 | 21.509 | 31.741 | 1.00 | 15.92 |
| ATOM | 1767 | CD  | PRO | A | 229 | 0 | 27.337 | 22.141 | 33.083 | 1.00 | 14.86 |
| ATOM | 1768 | N   | HIS | A | 230 | 0 | 23.140 | 20.164 | 32.038 | 1.00 | 15.58 |
| ATOM | 1769 | CA  | HIS | A | 230 | 0 | 22.090 | 19.325 | 32.618 | 1.00 | 15.01 |
| ATOM | 1770 | C   | HIS | A | 230 | 0 | 21.354 | 18.610 | 31.488 | 1.00 | 13.55 |
| ATOM | 1771 | O   | HIS | A | 230 | 0 | 20.756 | 19.192 | 30.590 | 1.00 | 13.47 |
| ATOM | 1772 | CB  | HIS | A | 230 | 0 | 21.172 | 20.164 | 33.510 | 1.00 | 15.89 |

APPENDIX 1-continued

| | | | | | | | | | | |
|---|---|---|---|---|---|---|---|---|---|---|
| ATOM | 1773 | CG | HIS | A | 230 | 0 | 20.045 | 19.341 | 34.064 | 1.00 | 18.32 |
| ATOM | 1774 | ND1 | HIS | A | 230 | 0 | 20.252 | 18.347 | 35.004 | 1.00 | 18.14 |
| ATOM | 1775 | CD2 | HIS | A | 230 | 0 | 18.713 | 19.328 | 33.791 | 1.00 | 17.75 |
| ATOM | 1776 | CE1 | HIS | A | 230 | 0 | 19.121 | 17.768 | 35.310 | 1.00 | 16.33 |
| ATOM | 1777 | NE2 | HIS | A | 230 | 0 | 18.173 | 18.344 | 34.609 | 1.00 | 17.85 |
| ATOM | 1778 | N | THR | A | 231 | 0 | 21.496 | 17.304 | 31.458 | 1.00 | 12.94 |
| ATOM | 1779 | CA | THR | A | 231 | 0 | 20.995 | 16.474 | 30.346 | 1.00 | 14.15 |
| ATOM | 1780 | C | THR | A | 231 | 0 | 19.620 | 15.890 | 30.547 | 1.00 | 13.41 |
| ATOM | 1781 | O | THR | A | 231 | 0 | 19.293 | 15.401 | 31.616 | 1.00 | 14.89 |
| ATOM | 1782 | CB | THR | A | 231 | 0 | 22.040 | 15.364 | 30.060 | 1.00 | 13.73 |
| ATOM | 1783 | OG1 | THR | A | 231 | 0 | 23.314 | 16.023 | 29.852 | 1.00 | 14.77 |
| ATOM | 1784 | CG2 | THR | A | 231 | 0 | 21.655 | 14.600 | 28.818 | 1.00 | 13.06 |
| ATOM | 1785 | N | VAL | A | 232 | 0 | 18.776 | 15.954 | 29.549 | 1.00 | 12.86 |
| ATOM | 1786 | CA | VAL | A | 232 | 0 | 17.374 | 15.505 | 29.665 | 1.00 | 13.44 |
| ATOM | 1787 | C | VAL | A | 232 | 0 | 16.999 | 14.966 | 28.319 | 1.00 | 14.96 |
| ATOM | 1788 | O | VAL | A | 232 | 0 | 17.790 | 15.258 | 27.390 | 1.00 | 14.12 |
| ATOM | 1789 | CB | VAL | A | 232 | 0 | 16.771 | 16.910 | 30.000 | 1.00 | 17.41 |
| ATOM | 1790 | CG1 | VAL | A | 232 | 0 | 16.075 | 17.587 | 28.856 | 1.00 | 14.66 |
| ATOM | 1791 | CG2 | VAL | A | 232 | 0 | 16.158 | 16.935 | 31.371 | 1.00 | 15.66 |
| ATOM | 1792 | N | ASP | A | 233 | 0 | 15.874 | 14.277 | 28.153 | 1.00 | 14.01 |
| ATOM | 1793 | CA | ASP | A | 233 | 0 | 15.405 | 13.803 | 26.874 | 1.00 | 14.73 |
| ATOM | 1794 | C | ASP | A | 233 | 0 | 14.353 | 14.718 | 26.245 | 1.00 | 14.74 |
| ATOM | 1795 | O | ASP | A | 233 | 0 | 14.187 | 14.731 | 25.027 | 1.00 | 13.41 |
| ATOM | 1796 | CB | ASP | A | 233 | 0 | 14.640 | 12.465 | 27.046 | 1.00 | 16.54 |
| ATOM | 1797 | CG | ASP | A | 233 | 0 | 15.637 | 11.417 | 27.536 | 1.00 | 19.27 |
| ATOM | 1798 | OD1 | ASP | A | 233 | 0 | 16.543 | 11.145 | 26.732 | 1.00 | 20.98 |
| ATOM | 1799 | OD2 | ASP | A | 233 | 0 | 15.536 | 10.945 | 28.667 | 1.00 | 19.27 |
| ATOM | 1800 | N | ARG | A | 234 | 0 | 13.595 | 15.386 | 27.122 | 1.00 | 13.79 |
| ATOM | 1801 | CA | ARG | A | 234 | 0 | 12.514 | 16.199 | 26.598 | 1.00 | 16.36 |
| ATOM | 1802 | C | ARG | A | 234 | 0 | 12.258 | 17.426 | 27.472 | 1.00 | 15.17 |
| ATOM | 1803 | O | ARG | A | 234 | 0 | 12.418 | 17.390 | 28.686 | 1.00 | 13.96 |
| ATOM | 1804 | CB | ARG | A | 234 | 0 | 11.265 | 15.330 | 26.482 | 1.00 | 19.23 |
| ATOM | 1805 | CG | ARG | A | 234 | 0 | 10.104 | 16.036 | 25.788 | 1.00 | 22.25 |
| ATOM | 1806 | CD | ARG | A | 234 | 0 | 8.981 | 15.023 | 25.506 | 1.00 | 24.68 |
| ATOM | 1807 | NE | ARG | A | 234 | 0 | 8.157 | 14.983 | 26.705 | 1.00 | 28.27 |
| ATOM | 1808 | CZ | ARG | A | 234 | 0 | 6.845 | 14.828 | 26.719 | 1.00 | 28.66 |
| ATOM | 1809 | NH1 | ARG | A | 234 | 0 | 6.291 | 14.833 | 27.909 | 1.00 | 30.08 |
| ATOM | 1810 | NH2 | ARG | A | 234 | 0 | 6.191 | 14.662 | 25.587 | 1.00 | 30.24 |
| ATOM | 1811 | N | LEU | A | 235 | 0 | 11.874 | 18.524 | 26.816 | 1.00 | 13.90 |
| ATOM | 1812 | CA | LEU | A | 235 | 0 | 11.619 | 19.742 | 27.607 | 1.00 | 13.15 |
| ATOM | 1813 | C | LEU | A | 235 | 0 | 10.390 | 20.430 | 27.041 | 1.00 | 11.49 |
| ATOM | 1814 | O | LEU | A | 235 | 0 | 10.025 | 20.304 | 25.873 | 1.00 | 11.08 |
| ATOM | 1815 | CB | LEU | A | 235 | 0 | 12.825 | 20.630 | 27.695 | 1.00 | 14.39 |
| ATOM | 1816 | CG | LEU | A | 235 | 0 | 13.459 | 21.645 | 26.801 | 1.00 | 17.19 |
| ATOM | 1817 | CD1 | LEU | A | 235 | 0 | 14.795 | 21.218 | 26.197 | 1.00 | 16.98 |
| ATOM | 1818 | CD2 | LEU | A | 235 | 0 | 12.586 | 22.219 | 25.685 | 1.00 | 18.24 |
| ATOM | 1819 | N | GLN | A | 236 | 0 | 9.769 | 21.152 | 27.949 | 1.00 | 12.74 |
| ATOM | 1820 | CA | GLN | A | 236 | 0 | 8.576 | 21.944 | 27.616 | 1.00 | 13.45 |
| ATOM | 1821 | C | GLN | A | 236 | 0 | 9.005 | 23.390 | 27.459 | 1.00 | 12.21 |
| ATOM | 1822 | O | GLN | A | 236 | 0 | 9.606 | 23.939 | 28.406 | 1.00 | 13.90 |
| ATOM | 1823 | CB | GLN | A | 236 | 0 | 7.525 | 21.770 | 28.741 | 1.00 | 12.06 |
| ATOM | 1824 | CG | GLN | A | 236 | 0 | 6.197 | 22.276 | 28.238 | 1.00 | 14.12 |
| ATOM | 1825 | CD | GLN | A | 236 | 0 | 5.025 | 22.108 | 29.205 | 1.00 | 13.35 |
| ATOM | 1826 | OE1 | GLN | A | 236 | 0 | 3.893 | 22.215 | 28.721 | 1.00 | 15.61 |
| ATOM | 1827 | NE2 | GLN | A | 236 | 0 | 5.226 | 21.912 | 30.463 | 1.00 | 12.00 |
| ATOM | 1828 | N | ILE | A | 237 | 0 | 8.748 | 24.011 | 26.311 | 1.00 | 12.17 |
| ATOM | 1829 | CA | ILE | A | 237 | 0 | 9.213 | 25.390 | 26.156 | 1.00 | 12.41 |
| ATOM | 1830 | C | ILE | A | 237 | 0 | 8.061 | 26.376 | 25.953 | 1.00 | 13.14 |
| ATOM | 1831 | O | ILE | A | 237 | 0 | 7.283 | 26.310 | 24.990 | 1.00 | 13.64 |
| ATOM | 1832 | CB | ILE | A | 237 | 0 | 10.255 | 25.437 | 25.022 | 1.00 | 11.03 |
| ATOM | 1833 | CG1 | ILE | A | 237 | 0 | 10.947 | 26.793 | 24.960 | 1.00 | 11.84 |
| ATOM | 1834 | CG2 | ILE | A | 237 | 0 | 9.615 | 25.086 | 23.662 | 1.00 | 10.02 |
| ATOM | 1835 | CD1 | ILE | A | 237 | 0 | 12.041 | 26.953 | 23.902 | 1.00 | 11.23 |
| ATOM | 1836 | N | PHE | A | 238 | 0 | 8.037 | 27.414 | 26.765 | 1.00 | 12.83 |
| ATOM | 1837 | CA | PHE | A | 238 | 0 | 6.979 | 28.431 | 26.714 | 1.00 | 13.23 |
| ATOM | 1838 | C | PHE | A | 238 | 0 | 7.382 | 29.683 | 25.957 | 1.00 | 13.99 |
| ATOM | 1839 | O | PHE | A | 238 | 0 | 8.530 | 29.848 | 25.545 | 1.00 | 13.87 |
| ATOM | 1840 | CB | PHE | A | 238 | 0 | 6.592 | 28.848 | 28.145 | 1.00 | 12.72 |
| ATOM | 1841 | CG | PHE | A | 238 | 0 | 6.176 | 27.691 | 28.993 | 1.00 | 14.51 |
| ATOM | 1842 | CD1 | PHE | A | 238 | 0 | 7.098 | 26.957 | 29.710 | 1.00 | 14.84 |
| ATOM | 1843 | CD2 | PHE | A | 238 | 0 | 4.836 | 27.314 | 29.078 | 1.00 | 15.50 |
| ATOM | 1844 | CE1 | PHE | A | 238 | 0 | 6.748 | 25.882 | 30.497 | 1.00 | 13.87 |
| ATOM | 1845 | CE2 | PHE | A | 238 | 0 | 4.468 | 26.236 | 29.862 | 1.00 | 14.62 |
| ATOM | 1846 | CZ | PHE | A | 238 | 0 | 5.423 | 25.528 | 30.568 | 1.00 | 15.15 |
| ATOM | 1847 | N | THR | A | 239 | 0 | 6.388 | 30.494 | 25.604 | 1.00 | 14.16 |
| ATOM | 1848 | CA | THR | A | 239 | 0 | 6.543 | 31.678 | 24.806 | 1.00 | 13.44 |
| ATOM | 1849 | C | THR | A | 239 | 0 | 7.832 | 32.453 | 25.106 | 1.00 | 11.74 |
| ATOM | 1850 | O | THR | A | 239 | 0 | 8.012 | 32.950 | 26.218 | 1.00 | 10.47 |
| ATOM | 1851 | CB | THR | A | 239 | 0 | 5.381 | 32.695 | 24.978 | 1.00 | 15.55 |

APPENDIX 1-continued

| ATOM | 1852 | OG1 | THR | A | 239 | 0 | 5.258 | 33.008 | 26.359 | 1.00 | 17.88 |
|------|------|-----|-----|---|-----|---|-------|--------|--------|------|-------|
| ATOM | 1853 | CG2 | THR | A | 239 | 0 | 4.055 | 32.131 | 24.478 | 1.00 | 16.75 |
| ATOM | 1854 | N | GLY | A | 240 | 0 | 8.672 | 32.593 | 24.078 | 1.00 | 7.94 |
| ATOM | 1855 | CA | GLY | A | 240 | 0 | 9.877 | 33.348 | 24.193 | 1.00 | 10.08 |
| ATOM | 1856 | C | GLY | A | 240 | 0 | 11.039 | 32.865 | 25.041 | 1.00 | 11.34 |
| ATOM | 1857 | O | GLY | A | 240 | 0 | 11.977 | 33.650 | 25.216 | 1.00 | 11.02 |
| ATOM | 1858 | N | GLN | A | 241 | 0 | 10.990 | 31.646 | 25.592 | 1.00 | 9.73 |
| ATOM | 1859 | CA | GLN | A | 241 | 0 | 12.067 | 31.090 | 26.364 | 1.00 | 9.59 |
| ATOM | 1860 | C | GLN | A | 241 | 0 | 13.114 | 30.587 | 25.342 | 1.00 | 10.56 |
| ATOM | 1861 | O | GLN | A | 241 | 0 | 12.823 | 30.467 | 24.126 | 1.00 | 8.44 |
| ATOM | 1862 | CB | GLN | A | 241 | 0 | 11.604 | 29.965 | 27.285 | 1.00 | 10.57 |
| ATOM | 1863 | CG | GLN | A | 241 | 0 | 10.820 | 30.363 | 28.523 | 1.00 | 10.54 |
| ATOM | 1864 | CD | GLN | A | 241 | 0 | 10.341 | 29.190 | 29.341 | 1.00 | 12.22 |
| ATOM | 1865 | OE1 | GLN | A | 241 | 0 | 10.118 | 28.077 | 28.815 | 1.00 | 13.21 |
| ATOM | 1866 | NE2 | GLN | A | 241 | 0 | 10.220 | 29.466 | 30.639 | 1.00 | 11.74 |
| ATOM | 1867 | N | ARG | A | 242 | 0 | 14.372 | 30.492 | 25.774 | 1.00 | 9.00 |
| ATOM | 1868 | CA | ARG | A | 242 | 0 | 15.388 | 29.992 | 24.834 | 1.00 | 11.01 |
| ATOM | 1869 | C | ARG | A | 242 | 0 | 16.210 | 28.966 | 25.609 | 1.00 | 11.30 |
| ATOM | 1870 | O | ARG | A | 242 | 0 | 16.292 | 29.133 | 26.816 | 1.00 | 9.51 |
| ATOM | 1871 | CB | ARG | A | 242 | 0 | 16.324 | 31.043 | 24.265 | 1.00 | 12.77 |
| ATOM | 1872 | CG | ARG | A | 242 | 0 | 15.694 | 32.128 | 23.364 | 1.00 | 12.52 |
| ATOM | 1873 | CD | ARG | A | 242 | 0 | 15.066 | 33.249 | 24.138 | 1.00 | 10.81 |
| ATOM | 1874 | NE | ARG | A | 242 | 0 | 15.957 | 34.126 | 24.892 | 1.00 | 10.80 |
| ATOM | 1875 | CZ | ARG | A | 242 | 0 | 15.630 | 34.761 | 26.002 | 1.00 | 11.36 |
| ATOM | 1876 | NH1 | ARG | A | 242 | 0 | 16.486 | 35.548 | 26.648 | 1.00 | 7.98 |
| ATOM | 1877 | NH2 | ARG | A | 242 | 0 | 14.365 | 34.589 | 26.489 | 1.00 | 12.78 |
| ATOM | 1878 | N | TYR | A | 243 | 0 | 16.717 | 27.934 | 24.942 | 1.00 | 11.61 |
| ATOM | 1879 | CA | TYR | A | 243 | 0 | 17.631 | 27.009 | 25.610 | 1.00 | 12.54 |
| ATOM | 1880 | C | TYR | A | 243 | 0 | 18.819 | 26.762 | 24.650 | 1.00 | 14.46 |
| ATOM | 1881 | O | TYR | A | 243 | 0 | 18.568 | 26.656 | 23.435 | 1.00 | 16.11 |
| ATOM | 1882 | CB | TYR | A | 243 | 0 | 17.015 | 25.638 | 25.934 | 1.00 | 11.09 |
| ATOM | 1883 | CG | TYR | A | 243 | 0 | 16.007 | 25.667 | 27.054 | 1.00 | 12.11 |
| ATOM | 1884 | CD1 | TYR | A | 243 | 0 | 14.641 | 25.825 | 26.843 | 1.00 | 12.88 |
| ATOM | 1885 | CD2 | TYR | A | 243 | 0 | 16.440 | 25.575 | 28.371 | 1.00 | 12.11 |
| ATOM | 1886 | CE1 | TYR | A | 243 | 0 | 13.748 | 25.869 | 27.915 | 1.00 | 12.71 |
| ATOM | 1887 | CE2 | TYR | A | 243 | 0 | 15.560 | 25.582 | 29.436 | 1.00 | 12.50 |
| ATOM | 1888 | CZ | TYR | A | 243 | 0 | 14.205 | 25.738 | 29.188 | 1.00 | 12.29 |
| ATOM | 1889 | OH | TYR | A | 243 | 0 | 13.379 | 25.789 | 30.286 | 1.00 | 13.65 |
| ATOM | 1890 | N | SER | A | 244 | 0 | 20.059 | 26.734 | 25.144 | 1.00 | 12.78 |
| ATOM | 1891 | CA | SER | A | 244 | 0 | 21.117 | 26.212 | 24.268 | 1.00 | 13.22 |
| ATOM | 1892 | C | SER | A | 244 | 0 | 21.333 | 24.779 | 24.814 | 1.00 | 11.06 |
| ATOM | 1893 | O | SER | A | 244 | 0 | 21.377 | 24.604 | 26.018 | 1.00 | 11.27 |
| ATOM | 1894 | CB | SER | A | 244 | 0 | 22.485 | 26.907 | 24.308 | 1.00 | 14.46 |
| ATOM | 1895 | OG | SER | A | 244 | 0 | 22.551 | 28.029 | 23.463 | 1.00 | 13.59 |
| ATOM | 1896 | N | PHE | A | 245 | 0 | 21.484 | 23.780 | 23.983 | 1.00 | 11.89 |
| ATOM | 1897 | CA | PHE | A | 245 | 0 | 21.772 | 22.437 | 24.452 | 1.00 | 13.14 |
| ATOM | 1898 | C | PHE | A | 245 | 0 | 22.867 | 21.857 | 23.546 | 1.00 | 12.32 |
| ATOM | 1899 | O | PHE | A | 245 | 0 | 22.890 | 22.128 | 22.354 | 1.00 | 11.11 |
| ATOM | 1900 | CB | PHE | A | 245 | 0 | 20.554 | 21.495 | 24.526 | 1.00 | 11.40 |
| ATOM | 1901 | CG | PHE | A | 245 | 0 | 19.915 | 21.236 | 23.195 | 1.00 | 11.98 |
| ATOM | 1902 | CD1 | PHE | A | 245 | 0 | 18.815 | 21.993 | 22.813 | 1.00 | 13.38 |
| ATOM | 1903 | CD2 | PHE | A | 245 | 0 | 20.349 | 20.236 | 22.351 | 1.00 | 11.45 |
| ATOM | 1904 | CE1 | PHE | A | 245 | 0 | 18.216 | 21.773 | 21.588 | 1.00 | 12.84 |
| ATOM | 1905 | CE2 | PHE | A | 245 | 0 | 19.759 | 20.000 | 21.129 | 1.00 | 11.48 |
| ATOM | 1906 | CZ | PHE | A | 245 | 0 | 18.705 | 20.796 | 20.743 | 1.00 | 12.65 |
| ATOM | 1907 | N | VAL | A | 246 | 0 | 23.742 | 21.073 | 24.169 | 1.00 | 13.51 |
| ATOM | 1908 | CA | VAL | A | 246 | 0 | 24.775 | 20.427 | 23.341 | 1.00 | 13.37 |
| ATOM | 1909 | C | VAL | A | 246 | 0 | 24.096 | 19.177 | 22.783 | 1.00 | 12.47 |
| ATOM | 1910 | O | VAL | A | 246 | 0 | 23.505 | 18.425 | 23.540 | 1.00 | 11.41 |
| ATOM | 1911 | CB | VAL | A | 246 | 0 | 25.990 | 19.984 | 24.190 | 1.00 | 14.96 |
| ATOM | 1912 | CG1 | VAL | A | 246 | 0 | 26.995 | 19.186 | 23.364 | 1.00 | 13.75 |
| ATOM | 1913 | CG2 | VAL | A | 246 | 0 | 26.681 | 21.165 | 24.841 | 1.00 | 15.92 |
| ATOM | 1914 | N | LEU | A | 247 | 0 | 24.160 | 18.996 | 21.490 | 1.00 | 12.97 |
| ATOM | 1915 | CA | LEU | A | 247 | 0 | 23.766 | 17.833 | 20.785 | 1.00 | 14.32 |
| ATOM | 1916 | C | LEU | A | 247 | 0 | 25.071 | 17.077 | 20.395 | 1.00 | 14.22 |
| ATOM | 1917 | O | LEU | A | 247 | 0 | 25.954 | 17.529 | 19.664 | 1.00 | 12.45 |
| ATOM | 1918 | CB | LEU | A | 247 | 0 | 22.980 | 18.109 | 19.505 | 1.00 | 16.00 |
| ATOM | 1919 | CG | LEU | A | 247 | 0 | 22.514 | 16.786 | 18.835 | 1.00 | 16.80 |
| ATOM | 1920 | CD1 | LEU | A | 247 | 0 | 21.266 | 16.306 | 19.513 | 1.00 | 18.30 |
| ATOM | 1921 | CD2 | LEU | A | 247 | 0 | 22.207 | 16.988 | 17.373 | 1.00 | 18.70 |
| ATOM | 1922 | N | ASP | A | 248 | 0 | 25.144 | 15.886 | 20.926 | 1.00 | 13.56 |
| ATOM | 1923 | CA | ASP | A | 248 | 0 | 26.278 | 14.980 | 20.727 | 1.00 | 16.65 |
| ATOM | 1924 | C | ASP | A | 248 | 0 | 25.916 | 14.072 | 19.581 | 1.00 | 16.18 |
| ATOM | 1925 | O | ASP | A | 248 | 0 | 25.095 | 13.166 | 19.813 | 1.00 | 17.60 |
| ATOM | 1926 | CB | ASP | A | 248 | 0 | 26.536 | 14.229 | 22.036 | 1.00 | 17.83 |
| ATOM | 1927 | CG | ASP | A | 248 | 0 | 27.798 | 13.359 | 22.024 | 1.00 | 21.77 |
| ATOM | 1928 | OD1 | ASP | A | 248 | 0 | 28.231 | 12.967 | 23.140 | 1.00 | 24.11 |
| ATOM | 1929 | OD2 | ASP | A | 248 | 0 | 28.345 | 13.060 | 20.950 | 1.00 | 21.25 |
| ATOM | 1930 | N | ALA | A | 249 | 0 | 26.414 | 14.277 | 18.369 | 1.00 | 15.85 |

APPENDIX 1-continued

| | | | | | | | | | | |
|---|---|---|---|---|---|---|---|---|---|---|
| ATOM | 1931 | CA | ALA | A | 249 | 0 | 25.982 | 13.416 | 17.255 | 1.00 | 17.99 |
| ATOM | 1932 | C | ALA | A | 249 | 0 | 26.698 | 12.049 | 17.306 | 1.00 | 20.21 |
| ATOM | 1933 | O | ALA | A | 249 | 0 | 27.569 | 11.766 | 16.485 | 1.00 | 19.11 |
| ATOM | 1934 | CB | ALA | A | 249 | 0 | 26.165 | 14.126 | 15.930 | 1.00 | 14.57 |
| ATOM | 1935 | N | ASN | A | 250 | 0 | 26.273 | 11.223 | 18.253 | 1.00 | 21.66 |
| ATOM | 1936 | CA | ASN | A | 250 | 0 | 26.861 | 9.961 | 18.581 | 1.00 | 25.53 |
| ATOM | 1937 | C | ASN | A | 250 | 0 | 26.061 | 8.721 | 18.202 | 1.00 | 27.30 |
| ATOM | 1938 | O | ASN | A | 250 | 0 | 26.344 | 7.645 | 18.756 | 1.00 | 29.42 |
| ATOM | 1939 | CB | ASN | A | 250 | 0 | 27.108 | 9.912 | 20.104 | 1.00 | 25.83 |
| ATOM | 1940 | CG | ASN | A | 250 | 0 | 25.888 | 9.968 | 20.978 | 1.00 | 28.76 |
| ATOM | 1941 | OD1 | ASN | A | 250 | 0 | 24.757 | 10.156 | 20.527 | 1.00 | 29.90 |
| ATOM | 1942 | ND2 | ASN | A | 250 | 0 | 26.042 | 9.826 | 22.306 | 1.00 | 29.52 |
| ATOM | 1943 | N | GLN | A | 251 | 0 | 25.089 | 8.841 | 17.302 | 1.00 | 26.74 |
| ATOM | 1944 | CA | GLN | A | 251 | 0 | 24.239 | 7.712 | 16.934 | 1.00 | 23.48 |
| ATOM | 1945 | C | GLN | A | 251 | 0 | 24.583 | 7.311 | 15.510 | 1.00 | 21.73 |
| ATOM | 1946 | O | GLN | A | 251 | 0 | 25.333 | 8.009 | 14.843 | 1.00 | 19.39 |
| ATOM | 1947 | CB | GLN | A | 251 | 0 | 22.757 | 8.104 | 17.022 | 1.00 | 24.79 |
| ATOM | 1948 | CG | GLN | A | 251 | 0 | 22.333 | 8.701 | 18.360 | 1.00 | 25.14 |
| ATOM | 1949 | CD | GLN | A | 251 | 0 | 22.430 | 7.693 | 19.480 | 1.00 | 26.76 |
| ATOM | 1950 | OE1 | GLN | A | 251 | 0 | 21.762 | 6.654 | 19.405 | 1.00 | 28.78 |
| ATOM | 1951 | NE2 | GLN | A | 251 | 0 | 23.202 | 7.986 | 20.514 | 1.00 | 26.02 |
| ATOM | 1952 | N | PRO | A | 252 | 0 | 24.058 | 6.177 | 15.076 | 1.00 | 20.53 |
| ATOM | 1953 | CA | PRO | A | 252 | 0 | 24.293 | 5.637 | 13.755 | 1.00 | 20.06 |
| ATOM | 1954 | C | PRO | A | 252 | 0 | 23.940 | 6.671 | 12.702 | 1.00 | 21.83 |
| ATOM | 1955 | O | PRO | A | 252 | 0 | 22.973 | 7.424 | 12.940 | 1.00 | 22.51 |
| ATOM | 1956 | CB | PRO | A | 252 | 0 | 23.417 | 4.367 | 13.647 | 1.00 | 19.98 |
| ATOM | 1957 | CG | PRO | A | 252 | 0 | 23.288 | 3.997 | 15.096 | 1.00 | 19.94 |
| ATOM | 1958 | CD | PRO | A | 252 | 0 | 23.223 | 5.289 | 15.902 | 1.00 | 19.68 |
| ATOM | 1959 | N | VAL | A | 253 | 0 | 24.663 | 6.728 | 11.584 | 1.00 | 20.85 |
| ATOM | 1960 | CA | VAL | A | 253 | 0 | 24.302 | 7.741 | 10.604 | 1.00 | 22.29 |
| ATOM | 1961 | C | VAL | A | 253 | 0 | 22.897 | 7.414 | 10.108 | 1.00 | 23.02 |
| ATOM | 1962 | O | VAL | A | 253 | 0 | 22.593 | 6.289 | 9.753 | 1.00 | 21.37 |
| ATOM | 1963 | CB | VAL | A | 253 | 0 | 25.298 | 8.065 | 9.494 | 1.00 | 23.22 |
| ATOM | 1964 | CG1 | VAL | A | 253 | 0 | 26.696 | 7.582 | 9.827 | 1.00 | 22.25 |
| ATOM | 1965 | CG2 | VAL | A | 253 | 0 | 24.859 | 7.680 | 8.101 | 1.00 | 22.26 |
| ATOM | 1966 | N | ASP | A | 254 | 0 | 22.012 | 8.422 | 10.159 | 1.00 | 24.32 |
| ATOM | 1967 | CA | ASP | A | 254 | 0 | 20.613 | 8.176 | 9.786 | 1.00 | 22.09 |
| ATOM | 1968 | C | ASP | A | 254 | 0 | 19.782 | 9.448 | 9.821 | 1.00 | 20.71 |
| ATOM | 1969 | O | ASP | A | 254 | 0 | 20.365 | 10.481 | 10.099 | 1.00 | 18.92 |
| ATOM | 1970 | CB | ASP | A | 254 | 0 | 20.048 | 7.211 | 10.830 | 1.00 | 23.39 |
| ATOM | 1971 | CG | ASP | A | 254 | 0 | 18.964 | 6.331 | 10.251 | 1.00 | 24.43 |
| ATOM | 1972 | OD1 | ASP | A | 254 | 0 | 18.355 | 6.663 | 9.239 | 1.00 | 23.21 |
| ATOM | 1973 | OD2 | ASP | A | 254 | 0 | 18.736 | 5.244 | 10.816 | 1.00 | 28.26 |
| ATOM | 1974 | N | ASN | A | 255 | 0 | 18.485 | 9.338 | 9.496 | 1.00 | 18.97 |
| ATOM | 1975 | CA | ASN | A | 255 | 0 | 17.583 | 10.479 | 9.599 | 1.00 | 17.69 |
| ATOM | 1976 | C | ASN | A | 255 | 0 | 16.785 | 10.335 | 10.889 | 1.00 | 17.64 |
| ATOM | 1977 | O | ASN | A | 255 | 0 | 16.390 | 9.204 | 11.249 | 1.00 | 17.75 |
| ATOM | 1978 | CB | ASN | A | 255 | 0 | 16.663 | 10.554 | 8.386 | 1.00 | 17.19 |
| ATOM | 1979 | CG | ASN | A | 255 | 0 | 17.467 | 10.882 | 7.143 | 1.00 | 17.33 |
| ATOM | 1980 | OD1 | ASN | A | 255 | 0 | 17.891 | 12.023 | 6.932 | 1.00 | 18.05 |
| ATOM | 1981 | ND2 | ASN | A | 255 | 0 | 17.649 | 9.913 | 6.263 | 1.00 | 15.98 |
| ATOM | 1982 | N | TYR | A | 256 | 0 | 16.657 | 11.403 | 11.684 | 1.00 | 14.89 |
| ATOM | 1983 | CA | TYR | A | 256 | 0 | 15.983 | 11.364 | 12.961 | 1.00 | 12.56 |
| ATOM | 1984 | C | TYR | A | 256 | 0 | 14.966 | 12.520 | 12.991 | 1.00 | 15.02 |
| ATOM | 1985 | O | TYR | A | 256 | 0 | 15.208 | 13.637 | 12.509 | 1.00 | 14.49 |
| ATOM | 1986 | CB | TYR | A | 256 | 0 | 16.867 | 11.479 | 14.216 | 1.00 | 14.85 |
| ATOM | 1987 | CG | TYR | A | 256 | 0 | 17.883 | 10.349 | 14.316 | 1.00 | 13.96 |
| ATOM | 1988 | CD1 | TYR | A | 256 | 0 | 19.030 | 10.427 | 13.529 | 1.00 | 13.97 |
| ATOM | 1989 | CD2 | TYR | A | 256 | 0 | 17.712 | 9.245 | 15.129 | 1.00 | 14.62 |
| ATOM | 1990 | CE1 | TYR | A | 256 | 0 | 19.986 | 9.422 | 13.534 | 1.00 | 13.83 |
| ATOM | 1991 | CE2 | TYR | A | 256 | 0 | 18.667 | 8.224 | 15.170 | 1.00 | 15.31 |
| ATOM | 1992 | CZ | TYR | A | 256 | 0 | 19.795 | 8.336 | 14.346 | 1.00 | 15.90 |
| ATOM | 1993 | OH | TYR | A | 256 | 0 | 20.763 | 7.341 | 14.337 | 1.00 | 17.15 |
| ATOM | 1994 | N | TRP | A | 257 | 0 | 13.801 | 12.198 | 13.564 | 1.00 | 13.58 |
| ATOM | 1995 | CA | TRP | A | 257 | 0 | 12.742 | 13.196 | 13.657 | 1.00 | 14.21 |
| ATOM | 1996 | C | TRP | A | 257 | 0 | 13.041 | 14.198 | 14.769 | 1.00 | 12.04 |
| ATOM | 1997 | O | TRP | A | 257 | 0 | 13.382 | 13.811 | 15.878 | 1.00 | 10.46 |
| ATOM | 1998 | CB | TRP | A | 257 | 0 | 11.363 | 12.592 | 13.988 | 1.00 | 12.49 |
| ATOM | 1999 | CG | TRP | A | 257 | 0 | 10.648 | 11.906 | 12.865 | 1.00 | 13.06 |
| ATOM | 2000 | CD1 | TRP | A | 257 | 0 | 10.315 | 10.568 | 12.879 | 1.00 | 12.86 |
| ATOM | 2001 | CD2 | TRP | A | 257 | 0 | 10.161 | 12.437 | 11.633 | 1.00 | 12.33 |
| ATOM | 2002 | NE1 | TRP | A | 257 | 0 | 9.640 | 10.267 | 11.720 | 1.00 | 13.75 |
| ATOM | 2003 | CE2 | TRP | A | 257 | 0 | 9.530 | 11.388 | 10.940 | 1.00 | 13.78 |
| ATOM | 2004 | CE3 | TRP | A | 257 | 0 | 10.173 | 13.691 | 11.035 | 1.00 | 14.13 |
| ATOM | 2005 | CZ2 | TRP | A | 257 | 0 | 8.940 | 11.538 | 9.681 | 1.00 | 13.24 |
| ATOM | 2006 | CZ3 | TRP | A | 257 | 0 | 9.590 | 13.868 | 9.786 | 1.00 | 14.34 |
| ATOM | 2007 | CH2 | TRP | A | 257 | 0 | 8.963 | 12.789 | 9.127 | 1.00 | 13.64 |
| ATOM | 2008 | N | ILE | A | 258 | 0 | 12.790 | 15.463 | 14.454 | 1.00 | 12.29 |
| ATOM | 2009 | CA | ILE | A | 258 | 0 | 12.886 | 16.498 | 15.508 | 1.00 | 12.44 |

APPENDIX 1-continued

| | | | | | | | | | | | |
|---|---|---|---|---|---|---|---|---|---|---|---|
| ATOM | 2010 | C | ILE | A | 258 | 0 | 11.391 | 16.840 | 15.769 | 1.00 | 12.40 |
| ATOM | 2011 | O | ILE | A | 258 | 0 | 10.629 | 17.039 | 14.812 | 1.00 | 12.43 |
| ATOM | 2012 | CB | ILE | A | 258 | 0 | 13.617 | 17.777 | 15.048 | 1.00 | 13.32 |
| ATOM | 2013 | CG1 | ILE | A | 258 | 0 | 15.107 | 17.477 | 14.854 | 1.00 | 14.52 |
| ATOM | 2014 | CG2 | ILE | A | 258 | 0 | 13.365 | 18.888 | 16.052 | 1.00 | 12.32 |
| ATOM | 2015 | CD1 | ILE | A | 258 | 0 | 15.839 | 18.474 | 13.994 | 1.00 | 14.35 |
| ATOM | 2016 | N | ARG | A | 259 | 0 | 11.017 | 16.764 | 17.013 | 1.00 | 11.51 |
| ATOM | 2017 | CA | ARG | A | 259 | 0 | 9.610 | 16.832 | 17.407 | 1.00 | 13.43 |
| ATOM | 2018 | C | ARG | A | 259 | 0 | 9.254 | 18.019 | 18.274 | 1.00 | 12.74 |
| ATOM | 2019 | O | ARG | A | 259 | 0 | 9.931 | 18.246 | 19.280 | 1.00 | 12.62 |
| ATOM | 2020 | CB | ARG | A | 259 | 0 | 9.326 | 15.567 | 18.253 | 1.00 | 12.43 |
| ATOM | 2021 | CG | ARG | A | 259 | 0 | 9.308 | 14.290 | 17.414 | 1.00 | 15.81 |
| ATOM | 2022 | CD | ARG | A | 259 | 0 | 8.910 | 13.054 | 18.244 | 1.00 | 16.58 |
| ATOM | 2023 | NE | ARG | A | 259 | 0 | 9.204 | 11.818 | 17.528 | 1.00 | 16.91 |
| ATOM | 2024 | CZ | ARG | A | 259 | 0 | 8.475 | 11.187 | 16.616 | 1.00 | 18.43 |
| ATOM | 2025 | NH1 | ARG | A | 259 | 0 | 7.285 | 11.657 | 16.239 | 1.00 | 19.39 |
| ATOM | 2026 | NH2 | ARG | A | 259 | 0 | 8.907 | 10.070 | 16.045 | 1.00 | 17.95 |
| ATOM | 2027 | N | ALA | A | 260 | 0 | 8.226 | 18.764 | 17.884 | 1.00 | 13.12 |
| ATOM | 2028 | CA | ALA | A | 260 | 0 | 7.768 | 19.882 | 18.727 | 1.00 | 12.65 |
| ATOM | 2029 | C | ALA | A | 260 | 0 | 6.237 | 19.763 | 18.802 | 1.00 | 14.47 |
| ATOM | 2030 | O | ALA | A | 260 | 0 | 5.545 | 20.140 | 17.868 | 1.00 | 14.73 |
| ATOM | 2031 | CB | ALA | A | 260 | 0 | 8.281 | 21.188 | 18.165 | 1.00 | 9.58 |
| ATOM | 2032 | N | GLN | A | 261 | 0 | 5.690 | 19.225 | 19.870 | 1.00 | 14.78 |
| ATOM | 2033 | CA | GLN | A | 261 | 0 | 4.272 | 19.004 | 20.060 | 1.00 | 16.99 |
| ATOM | 2034 | C | GLN | A | 261 | 0 | 3.606 | 20.154 | 20.803 | 1.00 | 15.01 |
| ATOM | 2035 | O | GLN | A | 261 | 0 | 3.914 | 20.389 | 21.961 | 1.00 | 13.86 |
| ATOM | 2036 | CB | GLN | A | 261 | 0 | 4.118 | 17.747 | 20.924 | 1.00 | 20.94 |
| ATOM | 2037 | CG | GLN | A | 261 | 0 | 2.717 | 17.131 | 20.940 | 1.00 | 27.53 |
| ATOM | 2038 | CD | GLN | A | 261 | 0 | 2.721 | 15.991 | 21.947 | 1.00 | 29.63 |
| ATOM | 2039 | OE1 | GLN | A | 261 | 0 | 3.152 | 14.887 | 21.682 | 1.00 | 31.60 |
| ATOM | 2040 | NE2 | GLN | A | 261 | 0 | 2.331 | 16.255 | 23.188 | 1.00 | 34.91 |
| ATOM | 2041 | N | PRO | A | 262 | 0 | 2.663 | 20.820 | 20.167 | 1.00 | 14.60 |
| ATOM | 2042 | CA | PRO | A | 262 | 0 | 1.974 | 21.969 | 20.739 | 1.00 | 15.72 |
| ATOM | 2043 | C | PRO | A | 262 | 0 | 0.921 | 21.568 | 21.757 | 1.00 | 16.25 |
| ATOM | 2044 | O | PRO | A | 262 | 0 | 0.498 | 20.409 | 21.814 | 1.00 | 15.61 |
| ATOM | 2045 | CB | PRO | A | 262 | 0 | 1.401 | 22.752 | 19.539 | 1.00 | 13.88 |
| ATOM | 2046 | CG | PRO | A | 262 | 0 | 1.168 | 21.608 | 18.563 | 1.00 | 13.62 |
| ATOM | 2047 | CD | PRO | A | 262 | 0 | 2.257 | 20.570 | 18.772 | 1.00 | 13.23 |
| ATOM | 2048 | N | ASN | A | 263 | 0 | 0.570 | 22.481 | 22.665 | 1.00 | 17.25 |
| ATOM | 2049 | CA | ASN | A | 263 | 0 | -0.471 | 22.203 | 23.648 | 1.00 | 17.50 |
| ATOM | 2050 | C | ASN | A | 263 | 0 | -1.834 | 22.460 | 22.981 | 1.00 | 18.43 |
| ATOM | 2051 | O | ASN | A | 263 | 0 | -2.810 | 22.121 | 23.608 | 1.00 | 19.35 |
| ATOM | 2052 | CB | ASN | A | 263 | 0 | -0.422 | 22.990 | 24.954 | 1.00 | 16.12 |
| ATOM | 2053 | CG | ASN | A | 263 | 0 | -0.333 | 24.493 | 24.728 | 1.00 | 16.97 |
| ATOM | 2054 | OD1 | ASN | A | 263 | 0 | 0.236 | 25.002 | 23.751 | 1.00 | 15.54 |
| ATOM | 2055 | ND2 | ASN | A | 263 | 0 | -0.905 | 25.269 | 25.653 | 1.00 | 16.31 |
| ATOM | 2056 | N | LYS | A | 264 | 0 | -1.947 | 23.055 | 21.818 | 1.00 | 20.51 |
| ATOM | 2057 | CA | LYS | A | 264 | 0 | -3.256 | 23.208 | 21.180 | 1.00 | 24.76 |
| ATOM | 2058 | C | LYS | A | 264 | 0 | -3.055 | 23.395 | 19.683 | 1.00 | 23.64 |
| ATOM | 2059 | O | LYS | A | 264 | 0 | -1.909 | 23.572 | 19.267 | 1.00 | 24.23 |
| ATOM | 2060 | CB | LYS | A | 264 | 0 | -4.038 | 24.393 | 21.775 | 1.00 | 25.87 |
| ATOM | 2061 | CG | LYS | A | 264 | 0 | -3.266 | 25.702 | 21.602 | 1.00 | 28.62 |
| ATOM | 2062 | CD | LYS | A | 264 | 0 | -3.579 | 26.624 | 22.772 | 1.00 | 30.65 |
| ATOM | 2063 | CE | LYS | A | 264 | 0 | -4.114 | 27.960 | 22.283 | 1.00 | 32.62 |
| ATOM | 2064 | NZ | LYS | A | 264 | 0 | -4.593 | 28.753 | 23.459 | 1.00 | 34.39 |
| ATOM | 2065 | N | GLY | A | 265 | 0 | -4.112 | 23.386 | 18.892 | 1.00 | 22.60 |
| ATOM | 2066 | CA | GLY | A | 265 | 0 | -3.959 | 23.591 | 17.452 | 1.00 | 22.98 |
| ATOM | 2067 | C | GLY | A | 265 | 0 | -5.190 | 23.002 | 16.758 | 1.00 | 23.95 |
| ATOM | 2068 | O | GLY | A | 265 | 0 | -5.904 | 22.202 | 17.362 | 1.00 | 22.64 |
| ATOM | 2069 | N | ARG | A | 266 | 0 | -5.398 | 23.434 | 15.537 | 1.00 | 24.60 |
| ATOM | 2070 | CA | ARG | A | 266 | 0 | -6.527 | 23.051 | 14.734 | 1.00 | 26.24 |
| ATOM | 2071 | C | ARG | A | 266 | 0 | -6.412 | 21.605 | 14.272 | 1.00 | 27.29 |
| ATOM | 2072 | O | ARG | A | 266 | 0 | -5.329 | 21.074 | 14.015 | 1.00 | 25.41 |
| ATOM | 2073 | CB | ARG | A | 266 | 0 | -6.628 | 23.903 | 13.469 | 1.00 | 30.71 |
| ATOM | 2074 | CG | ARG | A | 266 | 0 | -7.065 | 25.334 | 13.563 | 1.00 | 35.66 |
| ATOM | 2075 | CD | ARG | A | 266 | 0 | -8.161 | 25.673 | 12.539 | 1.00 | 40.48 |
| ATOM | 2076 | NE | ARG | A | 266 | 0 | -9.379 | 25.957 | 13.286 | 1.00 | 45.08 |
| ATOM | 2077 | CZ | ARG | A | 266 | 0 | -10.551 | 25.334 | 13.319 | 1.00 | 47.09 |
| ATOM | 2078 | NH1 | ARG | A | 266 | 0 | -10.921 | 24.294 | 12.577 | 1.00 | 48.10 |
| ATOM | 2079 | NH2 | ARG | A | 266 | 0 | -11.452 | 25.828 | 14.165 | 1.00 | 47.80 |
| ATOM | 2080 | N | ASN | A | 267 | 0 | -7.586 | 20.983 | 14.141 | 1.00 | 25.17 |
| ATOM | 2081 | CA | ASN | A | 267 | 0 | -7.727 | 19.669 | 13.602 | 1.00 | 23.96 |
| ATOM | 2082 | C | ASN | A | 267 | 0 | -6.859 | 18.625 | 14.244 | 1.00 | 22.35 |
| ATOM | 2083 | O | ASN | A | 267 | 0 | -6.306 | 17.864 | 13.448 | 1.00 | 23.57 |
| ATOM | 2084 | CB | ASN | A | 267 | 0 | -7.390 | 19.695 | 12.098 | 1.00 | 26.46 |
| ATOM | 2085 | CG | ASN | A | 267 | 0 | -8.461 | 20.426 | 11.309 | 1.00 | 29.21 |
| ATOM | 2086 | OD1 | ASN | A | 267 | 0 | -8.190 | 21.226 | 10.405 | 1.00 | 30.18 |
| ATOM | 2087 | ND2 | ASN | A | 267 | 0 | -9.681 | 20.075 | 11.701 | 1.00 | 28.77 |
| ATOM | 2088 | N | GLY | A | 268 | 0 | -6.706 | 18.594 | 15.550 | 1.00 | 21.85 |

APPENDIX 1-continued

| | | | | | | | | | | |
|---|---|---|---|---|---|---|---|---|---|---|
| ATOM | 2089 | CA | GLY | A | 268 | 0 | -5.890 | 17.533 | 16.121 | 1.00 | 22.47 |
| ATOM | 2090 | C | GLY | A | 268 | 0 | -4.383 | 17.760 | 16.118 | 1.00 | 23.29 |
| ATOM | 2091 | O | GLY | A | 268 | 0 | -3.652 | 16.898 | 16.632 | 1.00 | 23.28 |
| ATOM | 2092 | N | LEU | A | 269 | 0 | -3.880 | 18.901 | 15.676 | 1.00 | 22.69 |
| ATOM | 2093 | CA | LEU | A | 269 | 0 | -2.454 | 19.222 | 15.684 | 1.00 | 22.62 |
| ATOM | 2094 | C | LEU | A | 269 | 0 | -1.753 | 18.890 | 16.990 | 1.00 | 23.26 |
| ATOM | 2095 | O | LEU | A | 269 | 0 | -0.650 | 18.335 | 17.035 | 1.00 | 23.42 |
| ATOM | 2096 | CB | LEU | A | 269 | 0 | -2.311 | 20.713 | 15.472 | 1.00 | 22.28 |
| ATOM | 2097 | CG | LEU | A | 269 | 0 | -1.183 | 21.414 | 14.745 | 1.00 | 23.42 |
| ATOM | 2098 | CD1 | LEU | A | 269 | 0 | -0.508 | 22.380 | 15.682 | 1.00 | 19.64 |
| ATOM | 2099 | CD2 | LEU | A | 269 | 0 | -0.213 | 20.492 | 14.009 | 1.00 | 21.26 |
| ATOM | 2100 | N | ALA | A | 270 | 0 | -2.371 | 19.199 | 18.135 | 1.00 | 21.51 |
| ATOM | 2101 | CA | ALA | A | 270 | 0 | -1.784 | 18.899 | 19.419 | 1.00 | 22.26 |
| ATOM | 2102 | C | ALA | A | 270 | 0 | -1.612 | 17.415 | 19.680 | 1.00 | 23.22 |
| ATOM | 2103 | O | ALA | A | 270 | 0 | -0.898 | 17.077 | 20.637 | 1.00 | 21.81 |
| ATOM | 2104 | CB | ALA | A | 270 | 0 | -2.632 | 19.518 | 20.542 | 1.00 | 21.06 |
| ATOM | 2105 | N | GLY | A | 271 | 0 | -2.337 | 16.521 | 18.996 | 1.00 | 23.75 |
| ATOM | 2106 | CA | GLY | A | 271 | 0 | -2.190 | 15.125 | 19.372 | 1.00 | 24.98 |
| ATOM | 2107 | C | GLY | A | 271 | 0 | -1.507 | 14.267 | 18.328 | 1.00 | 26.07 |
| ATOM | 2108 | O | GLY | A | 271 | 0 | -1.501 | 13.045 | 18.523 | 1.00 | 26.26 |
| ATOM | 2109 | N | THR | A | 272 | 0 | -0.906 | 14.825 | 17.278 | 1.00 | 26.48 |
| ATOM | 2110 | CA | THR | A | 272 | 0 | -0.327 | 13.901 | 16.294 | 1.00 | 25.27 |
| ATOM | 2111 | C | THR | A | 272 | 0 | 0.986 | 14.362 | 15.701 | 1.00 | 25.58 |
| ATOM | 2112 | O | THR | A | 272 | 0 | 1.216 | 15.567 | 15.701 | 1.00 | 24.46 |
| ATOM | 2113 | CB | THR | A | 272 | 0 | -1.380 | 13.759 | 15.164 | 1.00 | 24.40 |
| ATOM | 2114 | OG1 | THR | A | 272 | 0 | -0.931 | 12.737 | 14.275 | 1.00 | 26.32 |
| ATOM | 2115 | CG2 | THR | A | 272 | 0 | -1.575 | 15.022 | 14.347 | 1.00 | 22.50 |
| ATOM | 2116 | N | PHE | A | 273 | 0 | 1.714 | 13.443 | 15.062 | 1.00 | 24.01 |
| ATOM | 2117 | CA | PHE | A | 273 | 0 | 2.897 | 13.755 | 14.271 | 1.00 | 23.99 |
| ATOM | 2118 | C | PHE | A | 273 | 0 | 2.663 | 13.201 | 12.858 | 1.00 | 24.84 |
| ATOM | 2119 | O | PHE | A | 273 | 0 | 3.534 | 13.207 | 11.987 | 1.00 | 24.73 |
| ATOM | 2120 | CB | PHE | A | 273 | 0 | 4.175 | 13.094 | 14.812 | 1.00 | 22.16 |
| ATOM | 2121 | CG | PHE | A | 273 | 0 | 4.550 | 13.676 | 16.153 | 1.00 | 21.84 |
| ATOM | 2122 | CD1 | PHE | A | 273 | 0 | 4.190 | 13.037 | 17.327 | 1.00 | 20.67 |
| ATOM | 2123 | CD2 | PHE | A | 273 | 0 | 5.221 | 14.881 | 16.216 | 1.00 | 20.98 |
| ATOM | 2124 | CE1 | PHE | A | 273 | 0 | 4.538 | 13.574 | 18.554 | 1.00 | 21.75 |
| ATOM | 2125 | CE2 | PHE | A | 273 | 0 | 5.559 | 15.428 | 17.440 | 1.00 | 21.65 |
| ATOM | 2126 | CZ | PHE | A | 273 | 0 | 5.216 | 14.787 | 18.616 | 1.00 | 22.38 |
| ATOM | 2127 | N | ALA | A | 274 | 0 | 1.440 | 12.718 | 12.647 | 1.00 | 24.38 |
| ATOM | 2128 | CA | ALA | A | 274 | 0 | 1.094 | 12.053 | 11.397 | 1.00 | 24.29 |
| ATOM | 2129 | C | ALA | A | 274 | 0 | 1.399 | 12.920 | 10.194 | 1.00 | 24.15 |
| ATOM | 2130 | O | ALA | A | 274 | 0 | 0.990 | 14.078 | 10.161 | 1.00 | 23.07 |
| ATOM | 2131 | CB | ALA | A | 274 | 0 | -0.385 | 11.681 | 11.387 | 1.00 | 23.53 |
| ATOM | 2132 | N | ASN | A | 275 | 0 | 2.075 | 12.355 | 9.204 | 1.00 | 23.41 |
| ATOM | 2133 | CA | ASN | A | 275 | 0 | 2.389 | 13.068 | 7.987 | 1.00 | 24.88 |
| ATOM | 2134 | C | ASN | A | 275 | 0 | 3.498 | 14.093 | 8.191 | 1.00 | 22.73 |
| ATOM | 2135 | O | ASN | A | 275 | 0 | 3.708 | 14.947 | 7.337 | 1.00 | 21.57 |
| ATOM | 2136 | CB | ASN | A | 275 | 0 | 1.138 | 13.806 | 7.516 | 1.00 | 30.04 |
| ATOM | 2137 | CG | ASN | A | 275 | 0 | 0.194 | 13.070 | 6.633 | 1.00 | 35.28 |
| ATOM | 2138 | OD1 | ASN | A | 275 | 0 | -0.458 | 12.071 | 6.985 | 1.00 | 36.92 |
| ATOM | 2139 | ND2 | ASN | A | 275 | 0 | 0.156 | 13.655 | 5.427 | 1.00 | 37.87 |
| ATOM | 2140 | N | GLY | A | 276 | 0 | 4.185 | 14.083 | 9.322 | 1.00 | 22.10 |
| ATOM | 2141 | CA | GLY | A | 276 | 0 | 5.278 | 15.025 | 9.503 | 1.00 | 20.95 |
| ATOM | 2142 | C | GLY | A | 276 | 0 | 4.801 | 16.392 | 9.962 | 1.00 | 19.61 |
| ATOM | 2143 | O | GLY | A | 276 | 0 | 5.587 | 17.325 | 9.816 | 1.00 | 19.96 |
| ATOM | 2144 | N | VAL | A | 277 | 0 | 3.600 | 16.504 | 10.540 | 1.00 | 16.82 |
| ATOM | 2145 | CA | VAL | A | 277 | 0 | 3.207 | 17.796 | 11.107 | 1.00 | 15.06 |
| ATOM | 2146 | C | VAL | A | 277 | 0 | 4.033 | 17.942 | 12.379 | 1.00 | 13.80 |
| ATOM | 2147 | O | VAL | A | 277 | 0 | 4.454 | 16.912 | 12.926 | 1.00 | 13.80 |
| ATOM | 2148 | CB | VAL | A | 277 | 0 | 1.676 | 17.849 | 11.397 | 1.00 | 14.37 |
| ATOM | 2149 | CG1 | VAL | A | 277 | 0 | 0.882 | 17.824 | 10.099 | 1.00 | 13.37 |
| ATOM | 2150 | CG2 | VAL | A | 277 | 0 | 1.213 | 16.763 | 12.330 | 1.00 | 11.77 |
| ATOM | 2151 | N | ASN | A | 278 | 0 | 4.307 | 19.100 | 12.936 | 1.00 | 14.25 |
| ATOM | 2152 | CA | ASN | A | 278 | 0 | 5.026 | 19.262 | 14.209 | 1.00 | 13.80 |
| ATOM | 2153 | C | ASN | A | 278 | 0 | 6.443 | 18.640 | 14.209 | 1.00 | 13.80 |
| ATOM | 2154 | O | ASN | A | 278 | 0 | 7.020 | 18.228 | 15.229 | 1.00 | 11.81 |
| ATOM | 2155 | CB | ASN | A | 278 | 0 | 4.216 | 18.607 | 15.312 | 1.00 | 14.24 |
| ATOM | 2156 | CG | ASN | A | 278 | 0 | 2.890 | 19.288 | 15.659 | 1.00 | 15.35 |
| ATOM | 2157 | OD1 | ASN | A | 278 | 0 | 1.952 | 18.531 | 16.009 | 1.00 | 14.81 |
| ATOM | 2158 | ND2 | ASN | A | 278 | 0 | 2.821 | 20.591 | 15.593 | 1.00 | 10.69 |
| ATOM | 2159 | N | SER | A | 279 | 0 | 7.044 | 18.595 | 13.025 | 1.00 | 12.68 |
| ATOM | 2160 | CA | SER | A | 279 | 0 | 8.296 | 17.892 | 12.860 | 1.00 | 15.48 |
| ATOM | 2161 | C | SER | A | 279 | 0 | 9.323 | 18.571 | 11.964 | 1.00 | 15.07 |
| ATOM | 2162 | O | SER | A | 279 | 0 | 8.995 | 19.309 | 11.044 | 1.00 | 12.20 |
| ATOM | 2163 | CB | SER | A | 279 | 0 | 7.976 | 16.549 | 12.122 | 1.00 | 14.76 |
| ATOM | 2164 | CG | SER | A | 279 | 0 | 7.268 | 15.722 | 13.054 | 1.00 | 19.57 |
| ATOM | 2165 | N | ALA | A | 280 | 0 | 10.570 | 18.152 | 12.229 | 1.00 | 15.67 |
| ATOM | 2166 | CA | ALA | A | 280 | 0 | 11.664 | 18.548 | 11.327 | 1.00 | 16.75 |
| ATOM | 2167 | C | ALA | A | 280 | 0 | 12.620 | 17.341 | 11.287 | 1.00 | 15.83 |

APPENDIX 1-continued

| ATOM | 2168 | O   | ALA | A | 280 | 0 | 12.438 | 16.346 | 11.997 | 1.00 | 15.55 |
|------|------|-----|-----|---|-----|---|--------|--------|--------|------|-------|
| ATOM | 2169 | CB  | ALA | A | 280 | 0 | 12.363 | 19.828 | 11.745 | 1.00 | 16.40 |
| ATOM | 2170 | N   | ILE | A | 281 | 0 | 13.669 | 17.478 | 10.485 | 1.00 | 14.79 |
| ATOM | 2171 | CA  | ILE | A | 281 | 0 | 14.569 | 16.346 | 10.257 | 1.00 | 15.55 |
| ATOM | 2172 | C   | ILE | A | 281 | 0 | 16.002 | 16.610 | 10.699 | 1.00 | 15.92 |
| ATOM | 2173 | O   | ILE | A | 281 | 0 | 16.649 | 17.577 | 10.284 | 1.00 | 14.96 |
| ATOM | 2174 | CB  | ILE | A | 281 | 0 | 14.557 | 16.013 | 8.735  | 1.00 | 16.44 |
| ATOM | 2175 | CG1 | ILE | A | 281 | 0 | 13.147 | 15.573 | 8.275  | 1.00 | 16.42 |
| ATOM | 2176 | CG2 | ILE | A | 281 | 0 | 15.615 | 14.959 | 8.421  | 1.00 | 15.71 |
| ATOM | 2177 | CD1 | ILE | A | 281 | 0 | 12.981 | 15.376 | 6.771  | 1.00 | 14.22 |
| ATOM | 2178 | N   | LEU | A | 282 | 0 | 16.505 | 15.698 | 11.515 | 1.00 | 16.76 |
| ATOM | 2179 | CA  | LEU | A | 282 | 0 | 17.920 | 15.736 | 11.912 | 1.00 | 15.82 |
| ATOM | 2180 | C   | LEU | A | 282 | 0 | 18.655 | 14.747 | 10.990 | 1.00 | 16.16 |
| ATOM | 2181 | O   | LEU | A | 282 | 0 | 18.409 | 13.530 | 11.034 | 1.00 | 16.41 |
| ATOM | 2182 | CB  | LEU | A | 282 | 0 | 18.129 | 15.400 | 13.379 | 1.00 | 14.54 |
| ATOM | 2183 | CG  | LEU | A | 282 | 0 | 19.632 | 15.346 | 13.773 | 1.00 | 16.00 |
| ATOM | 2184 | CD1 | LEU | A | 282 | 0 | 20.100 | 16.767 | 14.052 | 1.00 | 16.10 |
| ATOM | 2185 | CD2 | LEU | A | 282 | 0 | 19.865 | 14.469 | 14.970 | 1.00 | 13.21 |
| ATOM | 2186 | N   | ARG | A | 283 | 0 | 19.490 | 15.254 | 10.100 | 1.00 | 15.20 |
| ATOM | 2187 | CA  | ARG | A | 283 | 0 | 20.160 | 14.377 | 9.141  | 1.00 | 16.98 |
| ATOM | 2188 | C   | ARG | A | 283 | 0 | 21.683 | 14.326 | 9.279  | 1.00 | 17.31 |
| ATOM | 2189 | O   | ARG | A | 283 | 0 | 22.398 | 15.330 | 9.203  | 1.00 | 17.82 |
| ATOM | 2190 | CB  | ARG | A | 283 | 0 | 19.844 | 14.861 | 7.736  | 1.00 | 17.30 |
| ATOM | 2191 | CG  | ARG | A | 283 | 0 | 20.417 | 13.978 | 6.641  | 1.00 | 19.94 |
| ATOM | 2192 | CD  | ARG | A | 283 | 0 | 19.860 | 14.446 | 5.301  | 1.00 | 20.04 |
| ATOM | 2193 | NE  | ARG | A | 283 | 0 | 18.474 | 14.010 | 5.208  | 1.00 | 21.56 |
| ATOM | 2194 | CZ  | ARG | A | 283 | 0 | 17.479 | 14.530 | 4.505  | 1.00 | 21.81 |
| ATOM | 2195 | NH1 | ARG | A | 283 | 0 | 16.287 | 13.922 | 4.564  | 1.00 | 21.52 |
| ATOM | 2196 | NH2 | ARG | A | 283 | 0 | 17.653 | 15.634 | 3.797  | 1.00 | 21.84 |
| ATOM | 2197 | N   | TYR | A | 284 | 0 | 22.163 | 13.136 | 9.567  | 1.00 | 16.79 |
| ATOM | 2198 | CA  | TYR | A | 284 | 0 | 23.581 | 12.821 | 9.620  | 1.00 | 16.35 |
| ATOM | 2199 | C   | TYR | A | 284 | 0 | 24.155 | 12.787 | 8.198  | 1.00 | 16.52 |
| ATOM | 2200 | O   | TYR | A | 284 | 0 | 23.556 | 12.226 | 7.271  | 1.00 | 16.33 |
| ATOM | 2201 | CB  | TYR | A | 284 | 0 | 23.730 | 11.444 | 10.252 | 1.00 | 16.51 |
| ATOM | 2202 | CG  | TYR | A | 284 | 0 | 23.727 | 11.460 | 11.755 | 1.00 | 17.09 |
| ATOM | 2203 | CD1 | TYR | A | 284 | 0 | 24.910 | 11.178 | 12.437 | 1.00 | 17.37 |
| ATOM | 2204 | CD2 | TYR | A | 284 | 0 | 22.601 | 11.753 | 12.504 | 1.00 | 17.15 |
| ATOM | 2205 | CE1 | TYR | A | 284 | 0 | 24.937 | 11.163 | 13.817 | 1.00 | 17.64 |
| ATOM | 2206 | CE2 | TYR | A | 284 | 0 | 22.623 | 11.770 | 13.892 | 1.00 | 15.66 |
| ATOM | 2207 | CZ  | TYR | A | 284 | 0 | 23.796 | 11.476 | 14.542 | 1.00 | 15.99 |
| ATOM | 2208 | OH  | TYR | A | 284 | 0 | 23.873 | 11.448 | 15.919 | 1.00 | 14.03 |
| ATOM | 2209 | N   | ALA | A | 285 | 0 | 25.276 | 13.463 | 7.992  | 1.00 | 17.42 |
| ATOM | 2210 | CA  | ALA | A | 285 | 0 | 25.950 | 13.461 | 6.692  | 1.00 | 19.35 |
| ATOM | 2211 | C   | ALA | A | 285 | 0 | 26.186 | 11.994 | 6.328  | 1.00 | 19.20 |
| ATOM | 2212 | O   | ALA | A | 285 | 0 | 26.692 | 11.237 | 7.146  | 1.00 | 17.18 |
| ATOM | 2213 | CB  | ALA | A | 285 | 0 | 27.293 | 14.194 | 6.770  | 1.00 | 19.86 |
| ATOM | 2214 | N   | GLY | A | 286 | 0 | 25.724 | 11.614 | 5.153  | 1.00 | 20.01 |
| ATOM | 2215 | CA  | GLY | A | 286 | 0 | 25.851 | 10.224 | 4.747  | 1.00 | 21.88 |
| ATOM | 2216 | C   | GLY | A | 286 | 0 | 24.507 | 9.510  | 4.754  | 1.00 | 22.87 |
| ATOM | 2217 | O   | GLY | A | 286 | 0 | 24.406 | 8.418  | 4.197  | 1.00 | 23.06 |
| ATOM | 2218 | N   | ALA | A | 287 | 0 | 23.504 | 10.076 | 5.423  | 1.00 | 22.81 |
| ATOM | 2219 | CA  | ALA | A | 287 | 0 | 22.176 | 9.449  | 5.364  | 1.00 | 21.50 |
| ATOM | 2220 | C   | ALA | A | 287 | 0 | 21.482 | 9.880  | 4.079  | 1.00 | 20.58 |
| ATOM | 2221 | O   | ALA | A | 287 | 0 | 21.647 | 11.032 | 3.629  | 1.00 | 19.44 |
| ATOM | 2222 | CB  | ALA | A | 287 | 0 | 21.340 | 9.890  | 6.562  | 1.00 | 21.34 |
| ATOM | 2223 | N   | ALA | A | 288 | 0 | 20.632 | 9.041  | 3.523  | 1.00 | 21.20 |
| ATOM | 2224 | CA  | ALA | A | 288 | 0 | 19.899 | 9.450  | 2.310  | 1.00 | 23.46 |
| ATOM | 2225 | C   | ALA | A | 288 | 0 | 18.965 | 10.629 | 2.513  | 1.00 | 24.70 |
| ATOM | 2226 | O   | ALA | A | 288 | 0 | 18.494 | 10.929 | 3.621  | 1.00 | 25.30 |
| ATOM | 2227 | CB  | ALA | A | 288 | 0 | 19.012 | 8.298  | 1.827  | 1.00 | 24.84 |
| ATOM | 2228 | N   | ASN | A | 289 | 0 | 18.638 | 11.300 | 1.411  | 1.00 | 25.98 |
| ATOM | 2229 | CA  | ASN | A | 289 | 0 | 17.674 | 12.398 | 1.439  | 1.00 | 27.16 |
| ATOM | 2230 | C   | ASN | A | 289 | 0 | 16.303 | 11.707 | 1.505  | 1.00 | 27.36 |
| ATOM | 2231 | O   | ASN | A | 289 | 0 | 15.761 | 11.330 | 0.477  | 1.00 | 27.56 |
| ATOM | 2232 | CB  | ASN | A | 289 | 0 | 17.784 | 13.250 | 0.189  | 1.00 | 29.01 |
| ATOM | 2233 | CG  | ASN | A | 289 | 0 | 18.808 | 14.364 | 0.299  | 1.00 | 30.44 |
| ATOM | 2234 | OD1 | ASN | A | 289 | 0 | 20.005 | 14.168 | 0.545  | 1.00 | 30.40 |
| ATOM | 2235 | ND2 | ASN | A | 289 | 0 | 18.340 | 15.591 | 0.121  | 1.00 | 31.98 |
| ATOM | 2236 | N   | ALA | A | 290 | 0 | 15.837 | 11.426 | 2.703  | 1.00 | 25.22 |
| ATOM | 2237 | CA  | ALA | A | 290 | 0 | 14.600 | 10.727 | 2.955  | 1.00 | 25.09 |
| ATOM | 2238 | C   | ALA | A | 290 | 0 | 14.087 | 11.057 | 4.363  | 1.00 | 22.98 |
| ATOM | 2239 | O   | ALA | A | 290 | 0 | 14.830 | 11.555 | 5.205  | 1.00 | 22.02 |
| ATOM | 2240 | CB  | ALA | A | 290 | 0 | 14.764 | 9.210  | 2.823  | 1.00 | 24.89 |
| ATOM | 2241 | N   | ASP | A | 291 | 0 | 12.822 | 10.718 | 4.597  | 1.00 | 21.88 |
| ATOM | 2242 | CA  | ASP | A | 291 | 0 | 12.223 | 10.985 | 5.907  | 1.00 | 21.71 |
| ATOM | 2243 | C   | ASP | A | 291 | 0 | 12.724 | 9.965  | 6.916  | 1.00 | 18.93 |
| ATOM | 2244 | O   | ASP | A | 291 | 0 | 12.911 | 8.814  | 6.596  | 1.00 | 19.66 |
| ATOM | 2245 | CB  | ASP | A | 291 | 0 | 10.695 | 10.862 | 5.834  | 1.00 | 22.63 |
| ATOM | 2246 | CG  | ASP | A | 291 | 0 | 10.088 | 12.005 | 5.076  | 1.00 | 25.41 |

APPENDIX 1-continued

| ATOM | 2247 | OD1 | ASP | A | 291 | 0 | 10.781 | 12.988 | 4.735 | 1.00 | 27.11 |
| --- | --- | --- | --- | --- | --- | --- | --- | --- | --- | --- | --- |
| ATOM | 2248 | OD2 | ASP | A | 291 | 0 | 8.885 | 11.932 | 4.812 | 1.00 | 27.47 |
| ATOM | 2249 | N | PRO | A | 292 | 0 | 12.863 | 10.362 | 8.164 | 1.00 | 16.14 |
| ATOM | 2250 | CA | PRO | A | 292 | 0 | 13.229 | 9.473 | 9.230 | 1.00 | 15.27 |
| ATOM | 2251 | C | PRO | A | 292 | 0 | 12.087 | 8.484 | 9.389 | 1.00 | 19.40 |
| ATOM | 2252 | O | PRO | A | 292 | 0 | 10.925 | 8.785 | 9.063 | 1.00 | 20.36 |
| ATOM | 2253 | CB | PRO | A | 292 | 0 | 13.257 | 10.335 | 10.511 | 1.00 | 14.68 |
| ATOM | 2254 | CG | PRO | A | 292 | 0 | 13.291 | 11.739 | 9.941 | 1.00 | 14.39 |
| ATOM | 2255 | CD | PRO | A | 292 | 0 | 12.606 | 11.735 | 8.593 | 1.00 | 14.02 |
| ATOM | 2256 | N | THR | A | 293 | 0 | 12.357 | 7.361 | 10.024 | 1.00 | 19.91 |
| ATOM | 2257 | CA | THR | A | 293 | 0 | 11.360 | 6.379 | 10.373 | 1.00 | 20.62 |
| ATOM | 2258 | C | THR | A | 293 | 0 | 11.589 | 6.055 | 11.847 | 1.00 | 20.83 |
| ATOM | 2259 | O | THR | A | 293 | 0 | 11.323 | 4.943 | 12.287 | 1.00 | 23.91 |
| ATOM | 2260 | CB | THR | A | 293 | 0 | 11.556 | 5.088 | 9.557 | 1.00 | 23.41 |
| ATOM | 2261 | OG1 | THR | A | 293 | 0 | 12.874 | 4.577 | 9.836 | 1.00 | 24.50 |
| ATOM | 2262 | CG2 | THR | A | 293 | 0 | 11.438 | 5.341 | 8.058 | 1.00 | 23.72 |
| ATOM | 2263 | N | THR | A | 294 | 0 | 12.172 | 6.958 | 12.624 | 1.00 | 19.30 |
| ATOM | 2264 | CA | THR | A | 294 | 0 | 12.440 | 6.634 | 14.017 | 1.00 | 19.42 |
| ATOM | 2265 | C | THR | A | 294 | 0 | 11.214 | 6.896 | 14.878 | 1.00 | 20.66 |
| ATOM | 2266 | O | THR | A | 294 | 0 | 10.240 | 7.485 | 14.411 | 1.00 | 19.89 |
| ATOM | 2267 | CB | THR | A | 294 | 0 | 13.565 | 7.548 | 14.553 | 1.00 | 19.28 |
| ATOM | 2268 | OG1 | THR | A | 294 | 0 | 13.174 | 8.889 | 14.251 | 1.00 | 17.55 |
| ATOM | 2269 | CG2 | THR | A | 294 | 0 | 14.860 | 7.214 | 13.822 | 1.00 | 19.27 |
| ATOM | 2270 | N | SER | A | 295 | 0 | 11.359 | 6.576 | 16.159 | 1.00 | 23.85 |
| ATOM | 2271 | CA | SER | A | 295 | 0 | 10.274 | 6.851 | 17.095 | 1.00 | 27.18 |
| ATOM | 2272 | C | SER | A | 295 | 0 | 10.781 | 7.484 | 18.375 | 1.00 | 27.92 |
| ATOM | 2273 | O | SER | A | 295 | 0 | 11.900 | 7.292 | 18.844 | 1.00 | 27.09 |
| ATOM | 2274 | CB | SER | A | 295 | 0 | 9.513 | 5.546 | 17.367 | 1.00 | 28.92 |
| ATOM | 2275 | OG | SER | A | 295 | 0 | 10.389 | 4.761 | 18.160 | 1.00 | 33.04 |
| ATOM | 2276 | N | ALA | A | 296 | 0 | 9.930 | 8.331 | 18.965 | 1.00 | 30.04 |
| ATOM | 2277 | CA | ALA | A | 296 | 0 | 10.295 | 9.003 | 20.207 | 1.00 | 29.82 |
| ATOM | 2278 | C | ALA | A | 296 | 0 | 10.552 | 8.011 | 21.327 | 1.00 | 30.83 |
| ATOM | 2279 | O | ALA | A | 296 | 0 | 10.114 | 6.861 | 21.328 | 1.00 | 30.67 |
| ATOM | 2280 | CB | ALA | A | 296 | 0 | 9.187 | 9.968 | 20.599 | 1.00 | 30.16 |
| ATOM | 2281 | N | ASN | A | 297 | 0 | 11.286 | 8.489 | 22.328 | 1.00 | 31.65 |
| ATOM | 2282 | CA | ASN | A | 297 | 0 | 11.543 | 7.750 | 23.549 | 1.00 | 32.16 |
| ATOM | 2283 | C | ASN | A | 297 | 0 | 10.200 | 7.650 | 24.285 | 1.00 | 32.80 |
| ATOM | 2284 | O | ASN | A | 297 | 0 | 9.492 | 8.616 | 24.565 | 1.00 | 31.30 |
| ATOM | 2285 | CB | ASN | A | 297 | 0 | 12.522 | 8.497 | 24.443 | 1.00 | 33.07 |
| ATOM | 2286 | CG | ASN | A | 297 | 0 | 12.869 | 7.742 | 25.706 | 1.00 | 35.21 |
| ATOM | 2287 | OD1 | ASN | A | 297 | 0 | 12.116 | 6.965 | 26.284 | 1.00 | 35.45 |
| ATOM | 2288 | ND2 | ASN | A | 297 | 0 | 14.106 | 7.982 | 26.162 | 1.00 | 37.10 |
| ATOM | 2289 | N | PRO | A | 298 | 0 | 9.865 | 6.430 | 24.647 | 1.00 | 33.40 |
| ATOM | 2290 | CA | PRO | A | 298 | 0 | 8.626 | 6.116 | 25.331 | 1.00 | 33.89 |
| ATOM | 2291 | C | PRO | A | 298 | 0 | 8.580 | 6.690 | 26.732 | 1.00 | 32.60 |
| ATOM | 2292 | O | PRO | A | 298 | 0 | 7.522 | 7.155 | 27.173 | 1.00 | 32.72 |
| ATOM | 2293 | CB | PRO | A | 298 | 0 | 8.505 | 4.576 | 25.358 | 1.00 | 35.13 |
| ATOM | 2294 | CG | PRO | A | 298 | 0 | 9.932 | 4.147 | 25.128 | 1.00 | 34.52 |
| ATOM | 2295 | CD | PRO | A | 298 | 0 | 10.630 | 5.222 | 24.323 | 1.00 | 34.10 |
| ATOM | 2296 | N | ASN | A | 299 | 0 | 9.689 | 6.721 | 27.461 | 1.00 | 29.60 |
| ATOM | 2297 | CA | ASN | A | 299 | 0 | 9.701 | 7.229 | 28.834 | 1.00 | 28.47 |
| ATOM | 2298 | C | ASN | A | 299 | 0 | 10.818 | 8.251 | 29.006 | 1.00 | 27.18 |
| ATOM | 2299 | O | ASN | A | 299 | 0 | 11.906 | 7.967 | 29.528 | 1.00 | 25.69 |
| ATOM | 2300 | CB | ASN | A | 299 | 0 | 9.964 | 6.017 | 29.747 | 1.00 | 29.50 |
| ATOM | 2301 | CG | ASN | A | 299 | 0 | 8.907 | 4.935 | 29.673 | 1.00 | 32.34 |
| ATOM | 2302 | OD1 | ASN | A | 299 | 0 | 9.090 | 3.873 | 29.075 | 1.00 | 33.50 |
| ATOM | 2303 | ND2 | ASN | A | 299 | 0 | 7.735 | 5.182 | 30.251 | 1.00 | 33.04 |
| ATOM | 2304 | N | PRO | A | 300 | 0 | 10.629 | 9.450 | 28.498 | 1.00 | 26.02 |
| ATOM | 2305 | CA | PRO | A | 300 | 0 | 11.668 | 10.486 | 28.498 | 1.00 | 23.99 |
| ATOM | 2306 | C | PRO | A | 300 | 0 | 11.987 | 11.054 | 29.860 | 1.00 | 21.16 |
| ATOM | 2307 | O | PRO | A | 300 | 0 | 11.051 | 11.174 | 30.649 | 1.00 | 20.81 |
| ATOM | 2308 | CB | PRO | A | 300 | 0 | 11.137 | 11.623 | 27.594 | 1.00 | 23.33 |
| ATOM | 2309 | CG | PRO | A | 300 | 0 | 9.645 | 11.422 | 27.729 | 1.00 | 24.68 |
| ATOM | 2310 | CD | PRO | A | 300 | 0 | 9.387 | 9.918 | 27.882 | 1.00 | 25.22 |
| ATOM | 2311 | N | ALA | A | 301 | 0 | 13.242 | 11.361 | 30.179 | 1.00 | 19.17 |
| ATOM | 2312 | CA | ALA | A | 301 | 0 | 13.538 | 12.139 | 31.410 | 1.00 | 17.57 |
| ATOM | 2313 | C | ALA | A | 301 | 0 | 13.159 | 13.588 | 31.084 | 1.00 | 16.53 |
| ATOM | 2314 | O | ALA | A | 301 | 0 | 13.613 | 14.235 | 30.131 | 1.00 | 16.24 |
| ATOM | 2315 | CB | ALA | A | 301 | 0 | 15.006 | 11.982 | 31.774 | 1.00 | 17.17 |
| ATOM | 2316 | N | GLN | A | 302 | 0 | 12.139 | 14.131 | 31.723 | 1.00 | 18.15 |
| ATOM | 2317 | CA | GLN | A | 302 | 0 | 11.580 | 15.446 | 31.441 | 1.00 | 19.34 |
| ATOM | 2318 | C | GLN | A | 302 | 0 | 12.335 | 16.580 | 32.124 | 1.00 | 19.16 |
| ATOM | 2319 | O | GLN | A | 302 | 0 | 12.577 | 16.444 | 33.324 | 1.00 | 19.07 |
| ATOM | 2320 | CB | GLN | A | 302 | 0 | 10.122 | 15.483 | 31.937 | 1.00 | 19.10 |
| ATOM | 2321 | CG | GLN | A | 302 | 0 | 9.304 | 16.666 | 31.478 | 1.00 | 20.55 |
| ATOM | 2322 | CD | GLN | A | 302 | 0 | 8.960 | 16.738 | 30.009 | 1.00 | 20.18 |
| ATOM | 2323 | OE1 | GLN | A | 302 | 0 | 8.843 | 15.721 | 29.331 | 1.00 | 22.29 |
| ATOM | 2324 | NE2 | GLN | A | 302 | 0 | 8.813 | 17.936 | 29.436 | 1.00 | 18.46 |
| ATOM | 2325 | N | LEU | A | 303 | 0 | 12.629 | 17.681 | 31.444 | 1.00 | 17.92 |

APPENDIX 1-continued

| ATOM | 2326 | CA | LEU | A | 303 | 0 | 13.241 | 18.824 | 32.139 | 1.00 | 17.32 |
|---|---|---|---|---|---|---|---|---|---|---|---|
| ATOM | 2327 | C | LEU | A | 303 | 0 | 12.316 | 19.357 | 33.232 | 1.00 | 17.65 |
| ATOM | 2328 | O | LEU | A | 303 | 0 | 11.140 | 19.664 | 33.021 | 1.00 | 17.55 |
| ATOM | 2329 | CB | LEU | A | 303 | 0 | 13.489 | 19.988 | 31.168 | 1.00 | 15.14 |
| ATOM | 2330 | CG | LEU | A | 303 | 0 | 13.919 | 21.317 | 31.797 | 1.00 | 16.94 |
| ATOM | 2331 | CD1 | LEU | A | 303 | 0 | 15.262 | 21.146 | 32.504 | 1.00 | 17.30 |
| ATOM | 2332 | CD2 | LEU | A | 303 | 0 | 13.988 | 22.432 | 30.764 | 1.00 | 12.82 |
| ATOM | 2333 | N | ASN | A | 304 | 0 | 12.868 | 19.580 | 34.399 | 1.00 | 17.34 |
| ATOM | 2334 | CA | ASN | A | 304 | 0 | 12.199 | 20.212 | 35.531 | 1.00 | 19.12 |
| ATOM | 2335 | C | ASN | A | 304 | 0 | 13.071 | 21.435 | 35.833 | 1.00 | 19.06 |
| ATOM | 2336 | O | ASN | A | 304 | 0 | 14.265 | 21.349 | 36.122 | 1.00 | 20.37 |
| ATOM | 2337 | CB | ASN | A | 304 | 0 | 12.073 | 19.244 | 36.704 | 1.00 | 22.16 |
| ATOM | 2338 | CG | ASN | A | 304 | 0 | 11.748 | 19.900 | 38.024 | 1.00 | 25.02 |
| ATOM | 2339 | OD1 | ASN | A | 304 | 0 | 11.506 | 21.111 | 38.146 | 1.00 | 26.72 |
| ATOM | 2340 | ND2 | ASN | A | 304 | 0 | 11.766 | 19.133 | 39.114 | 1.00 | 25.99 |
| ATOM | 2341 | N | GLU | A | 305 | 0 | 12.541 | 22.629 | 35.662 | 1.00 | 17.64 |
| ATOM | 2342 | CA | GLU | A | 305 | 0 | 13.204 | 23.890 | 35.840 | 1.00 | 16.64 |
| ATOM | 2343 | C | GLU | A | 305 | 0 | 13.884 | 23.977 | 37.194 | 1.00 | 16.06 |
| ATOM | 2344 | O | GLU | A | 305 | 0 | 14.965 | 24.564 | 37.208 | 1.00 | 14.78 |
| ATOM | 2345 | CB | GLU | A | 305 | 0 | 12.286 | 25.085 | 35.567 | 1.00 | 15.91 |
| ATOM | 2346 | CG | GLU | A | 305 | 0 | 12.898 | 26.484 | 35.831 | 1.00 | 14.81 |
| ATOM | 2347 | CD | GLU | A | 305 | 0 | 11.794 | 27.546 | 35.666 | 1.00 | 15.72 |
| ATOM | 2348 | OE1 | GLU | A | 305 | 0 | 11.584 | 28.026 | 34.527 | 1.00 | 14.63 |
| ATOM | 2349 | OE2 | GLU | A | 305 | 0 | 11.154 | 27.861 | 36.685 | 1.00 | 13.05 |
| ATOM | 2350 | N | ALA | A | 306 | 0 | 13.416 | 23.432 | 38.298 | 1.00 | 15.83 |
| ATOM | 2351 | CA | ALA | A | 306 | 0 | 14.131 | 23.509 | 39.565 | 1.00 | 17.92 |
| ATOM | 2352 | C | ALA | A | 306 | 0 | 15.437 | 22.682 | 39.532 | 1.00 | 18.62 |
| ATOM | 2353 | O | ALA | A | 306 | 0 | 16.213 | 22.867 | 40.464 | 1.00 | 18.37 |
| ATOM | 2354 | CB | ALA | A | 306 | 0 | 13.283 | 22.993 | 40.711 | 1.00 | 16.23 |
| ATOM | 2355 | N | ASP | A | 307 | 0 | 15.721 | 21.860 | 38.523 | 1.00 | 18.04 |
| ATOM | 2356 | CA | ASP | A | 307 | 0 | 16.988 | 21.164 | 38.409 | 1.00 | 18.68 |
| ATOM | 2357 | C | ASP | A | 307 | 0 | 18.035 | 22.039 | 37.707 | 1.00 | 19.89 |
| ATOM | 2358 | O | ASP | A | 307 | 0 | 19.239 | 21.695 | 37.739 | 1.00 | 20.36 |
| ATOM | 2359 | CB | ASP | A | 307 | 0 | 16.904 | 19.863 | 37.592 | 1.00 | 17.64 |
| ATOM | 2360 | CG | ASP | A | 307 | 0 | 15.980 | 18.873 | 38.290 | 1.00 | 18.17 |
| ATOM | 2361 | OD1 | ASP | A | 307 | 0 | 15.918 | 18.919 | 39.535 | 1.00 | 18.27 |
| ATOM | 2362 | OD2 | ASP | A | 307 | 0 | 15.311 | 18.094 | 37.592 | 1.00 | 17.32 |
| ATOM | 2363 | N | LEU | A | 308 | 0 | 17.583 | 23.110 | 37.052 | 1.00 | 16.43 |
| ATOM | 2364 | CA | LEU | A | 308 | 0 | 18.581 | 23.962 | 36.377 | 1.00 | 16.80 |
| ATOM | 2365 | C | LEU | A | 308 | 0 | 19.327 | 24.827 | 37.384 | 1.00 | 16.94 |
| ATOM | 2366 | O | LEU | A | 308 | 0 | 18.784 | 25.320 | 38.380 | 1.00 | 17.28 |
| ATOM | 2367 | CB | LEU | A | 308 | 0 | 17.925 | 24.775 | 35.257 | 1.00 | 12.52 |
| ATOM | 2368 | CG | LEU | A | 308 | 0 | 17.436 | 23.936 | 34.073 | 1.00 | 12.15 |
| ATOM | 2369 | CD1 | LEU | A | 308 | 0 | 16.692 | 24.834 | 33.101 | 1.00 | 11.67 |
| ATOM | 2370 | CD2 | LEU | A | 308 | 0 | 18.547 | 23.186 | 33.341 | 1.00 | 12.23 |
| ATOM | 2371 | N | HIS | A | 309 | 0 | 20.640 | 24.968 | 37.243 | 1.00 | 18.01 |
| ATOM | 2372 | CA | HIS | A | 309 | 0 | 21.430 | 25.802 | 38.158 | 1.00 | 18.47 |
| ATOM | 2373 | C | HIS | A | 309 | 0 | 22.328 | 26.770 | 37.394 | 1.00 | 17.36 |
| ATOM | 2374 | O | HIS | A | 309 | 0 | 23.015 | 26.378 | 36.459 | 1.00 | 17.82 |
| ATOM | 2375 | CB | HIS | A | 309 | 0 | 22.267 | 24.997 | 39.140 | 1.00 | 18.51 |
| ATOM | 2376 | CG | HIS | A | 309 | 0 | 21.470 | 24.052 | 39.965 | 1.00 | 20.71 |
| ATOM | 2377 | ND1 | HIS | A | 309 | 0 | 21.526 | 22.684 | 39.790 | 1.00 | 21.77 |
| ATOM | 2378 | CD2 | HIS | A | 309 | 0 | 20.578 | 24.285 | 40.956 | 1.00 | 22.07 |
| ATOM | 2379 | CE1 | HIS | A | 309 | 0 | 20.701 | 22.115 | 40.657 | 1.00 | 22.85 |
| ATOM | 2380 | NE2 | HIS | A | 309 | 0 | 20.120 | 23.059 | 41.377 | 1.00 | 22.67 |
| ATOM | 2381 | N | ALA | A | 310 | 0 | 22.352 | 28.005 | 37.837 | 1.00 | 17.27 |
| ATOM | 2382 | CA | ALA | A | 310 | 0 | 23.173 | 29.068 | 37.228 | 1.00 | 17.74 |
| ATOM | 2383 | C | ALA | A | 310 | 0 | 24.663 | 28.775 | 37.342 | 1.00 | 18.13 |
| ATOM | 2384 | O | ALA | A | 310 | 0 | 25.103 | 28.233 | 38.369 | 1.00 | 19.61 |
| ATOM | 2385 | CB | ALA | A | 310 | 0 | 22.869 | 30.356 | 37.985 | 1.00 | 16.92 |
| ATOM | 2386 | N | LEU | A | 311 | 0 | 25.427 | 29.021 | 36.304 | 1.00 | 19.30 |
| ATOM | 2387 | CA | LEU | A | 311 | 0 | 26.856 | 28.762 | 36.277 | 1.00 | 20.71 |
| ATOM | 2388 | C | LEU | A | 311 | 0 | 27.655 | 29.922 | 36.881 | 1.00 | 22.67 |
| ATOM | 2389 | O | LEU | A | 311 | 0 | 28.581 | 29.788 | 37.682 | 1.00 | 23.06 |
| ATOM | 2390 | CB | LEU | A | 311 | 0 | 27.305 | 28.591 | 34.817 | 1.00 | 20.57 |
| ATOM | 2391 | CG | LEU | A | 311 | 0 | 28.796 | 28.196 | 34.684 | 1.00 | 21.52 |
| ATOM | 2392 | CD1 | LEU | A | 311 | 0 | 28.993 | 26.783 | 35.229 | 1.00 | 20.80 |
| ATOM | 2393 | CD2 | LEU | A | 311 | 0 | 29.319 | 28.282 | 33.254 | 1.00 | 20.17 |
| ATOM | 2394 | N | ILE | A | 312 | 0 | 27.333 | 31.142 | 36.449 | 1.00 | 23.42 |
| ATOM | 2395 | CA | ILE | A | 312 | 0 | 28.092 | 32.311 | 36.899 | 1.00 | 24.86 |
| ATOM | 2396 | C | ILE | A | 312 | 0 | 27.337 | 33.157 | 37.914 | 1.00 | 26.54 |
| ATOM | 2397 | O | ILE | A | 312 | 0 | 26.154 | 33.467 | 37.739 | 1.00 | 25.31 |
| ATOM | 2398 | CB | ILE | A | 312 | 0 | 28.397 | 33.179 | 35.670 | 1.00 | 24.45 |
| ATOM | 2399 | CG1 | ILE | A | 312 | 0 | 28.998 | 32.330 | 34.576 | 1.00 | 25.60 |
| ATOM | 2400 | CG2 | ILE | A | 312 | 0 | 29.261 | 34.373 | 36.075 | 1.00 | 26.44 |
| ATOM | 2401 | CD1 | ILE | A | 312 | 0 | 30.462 | 32.026 | 34.512 | 1.00 | 24.51 |
| ATOM | 2402 | N | ASP | A | 313 | 0 | 28.008 | 33.523 | 39.003 | 1.00 | 28.70 |
| ATOM | 2403 | CA | ASP | A | 313 | 0 | 27.432 | 34.339 | 40.071 | 1.00 | 30.99 |
| ATOM | 2404 | C | ASP | A | 313 | 0 | 26.065 | 33.763 | 40.417 | 1.00 | 29.83 |

APPENDIX 1-continued

| | | | | | | | | | | | |
|---|---|---|---|---|---|---|---|---|---|---|---|
| ATOM | 2405 | O | ASP | A | 313 | 0 | 25.024 | 34.385 | 40.235 | 1.00 | 28.51 |
| ATOM | 2406 | CB | ASP | A | 313 | 0 | 27.266 | 35.777 | 39.576 | 1.00 | 35.88 |
| ATOM | 2407 | CG | ASP | A | 313 | 0 | 28.532 | 36.505 | 39.187 | 1.00 | 40.21 |
| ATOM | 2408 | OD1 | ASP | A | 313 | 0 | 29.577 | 36.243 | 39.847 | 1.00 | 42.99 |
| ATOM | 2409 | OD2 | ASP | A | 313 | 0 | 28.525 | 37.346 | 38.252 | 1.00 | 40.95 |
| ATOM | 2410 | N | PRO | A | 314 | 0 | 26.041 | 32.517 | 40.863 | 1.00 | 28.77 |
| ATOM | 2411 | CA | PRO | A | 314 | 0 | 24.841 | 31.743 | 41.074 | 1.00 | 27.80 |
| ATOM | 2412 | C | PRO | A | 314 | 0 | 23.865 | 32.198 | 42.137 | 1.00 | 26.49 |
| ATOM | 2413 | O | PRO | A | 314 | 0 | 22.671 | 31.857 | 42.032 | 1.00 | 27.17 |
| ATOM | 2414 | CB | PRO | A | 314 | 0 | 25.297 | 30.311 | 41.479 | 1.00 | 27.61 |
| ATOM | 2415 | CG | PRO | A | 314 | 0 | 26.711 | 30.573 | 41.929 | 1.00 | 29.37 |
| ATOM | 2416 | CD | PRO | A | 314 | 0 | 27.248 | 31.726 | 41.111 | 1.00 | 28.10 |
| ATOM | 2417 | N | ALA | A | 315 | 0 | 24.364 | 32.818 | 43.206 | 1.00 | 23.45 |
| ATOM | 2418 | CA | ALA | A | 315 | 0 | 23.505 | 33.092 | 44.336 | 1.00 | 22.34 |
| ATOM | 2419 | C | ALA | A | 315 | 0 | 22.414 | 34.111 | 44.008 | 1.00 | 22.46 |
| ATOM | 2420 | O | ALA | A | 315 | 0 | 22.678 | 35.127 | 43.370 | 1.00 | 22.52 |
| ATOM | 2421 | CB | ALA | A | 315 | 0 | 24.294 | 33.617 | 45.532 | 1.00 | 21.68 |
| ATOM | 2422 | N | ALA | A | 316 | 0 | 21.226 | 33.838 | 44.534 | 1.00 | 20.85 |
| ATOM | 2423 | CA | ALA | A | 316 | 0 | 20.133 | 34.805 | 44.422 | 1.00 | 20.78 |
| ATOM | 2424 | C | ALA | A | 316 | 0 | 20.547 | 36.010 | 45.271 | 1.00 | 20.55 |
| ATOM | 2425 | O | ALA | A | 316 | 0 | 21.143 | 35.846 | 46.333 | 1.00 | 21.47 |
| ATOM | 2426 | CB | ALA | A | 316 | 0 | 18.897 | 34.166 | 45.043 | 1.00 | 18.32 |
| ATOM | 2427 | N | PRO | A | 317 | 0 | 20.237 | 37.212 | 44.864 | 1.00 | 20.84 |
| ATOM | 2428 | CA | PRO | A | 317 | 0 | 20.539 | 38.410 | 45.634 | 1.00 | 20.82 |
| ATOM | 2429 | C | PRO | A | 317 | 0 | 19.766 | 38.449 | 46.945 | 1.00 | 20.96 |
| ATOM | 2430 | O | PRO | A | 317 | 0 | 18.668 | 37.885 | 47.030 | 1.00 | 21.42 |
| ATOM | 2431 | CB | PRO | A | 317 | 0 | 20.064 | 39.590 | 44.758 | 1.00 | 21.64 |
| ATOM | 2432 | CG | PRO | A | 317 | 0 | 19.178 | 38.938 | 43.746 | 1.00 | 21.69 |
| ATOM | 2433 | CD | PRO | A | 317 | 0 | 19.517 | 37.466 | 43.619 | 1.00 | 20.10 |
| ATOM | 2434 | N | GLY | A | 318 | 0 | 20.269 | 39.080 | 47.988 | 1.00 | 20.69 |
| ATOM | 2435 | CA | GLY | A | 318 | 0 | 19.533 | 39.282 | 49.225 | 1.00 | 21.68 |
| ATOM | 2436 | C | GLY | A | 318 | 0 | 19.631 | 38.218 | 50.283 | 1.00 | 22.93 |
| ATOM | 2437 | O | GLY | A | 318 | 0 | 20.344 | 37.221 | 50.101 | 1.00 | 23.87 |
| ATOM | 2438 | N | ILE | A | 319 | 0 | 18.895 | 38.398 | 51.368 | 1.00 | 22.20 |
| ATOM | 2439 | CA | ILE | A | 319 | 0 | 18.879 | 37.432 | 52.454 | 1.00 | 24.16 |
| ATOM | 2440 | C | ILE | A | 319 | 0 | 18.169 | 36.189 | 51.956 | 1.00 | 25.28 |
| ATOM | 2441 | O | ILE | A | 319 | 0 | 17.071 | 36.271 | 51.405 | 1.00 | 26.26 |
| ATOM | 2442 | CB | ILE | A | 319 | 0 | 18.208 | 38.030 | 53.704 | 1.00 | 24.54 |
| ATOM | 2443 | CG1 | ILE | A | 319 | 0 | 19.075 | 39.176 | 54.213 | 1.00 | 25.08 |
| ATOM | 2444 | CG2 | ILE | A | 319 | 0 | 17.944 | 37.012 | 54.793 | 1.00 | 24.03 |
| ATOM | 2445 | CD1 | ILE | A | 319 | 0 | 18.262 | 40.183 | 55.006 | 1.00 | 27.56 |
| ATOM | 2446 | N | PRO | A | 320 | 0 | 18.762 | 35.030 | 52.159 | 1.00 | 26.23 |
| ATOM | 2447 | CA | PRO | A | 320 | 0 | 18.273 | 33.748 | 51.684 | 1.00 | 26.64 |
| ATOM | 2448 | C | PRO | A | 320 | 0 | 17.105 | 33.172 | 52.453 | 1.00 | 26.74 |
| ATOM | 2449 | O | PRO | A | 320 | 0 | 17.140 | 32.025 | 52.896 | 1.00 | 27.54 |
| ATOM | 2450 | CB | PRO | A | 320 | 0 | 19.501 | 32.801 | 51.772 | 1.00 | 27.16 |
| ATOM | 2451 | CG | PRO | A | 320 | 0 | 20.216 | 33.388 | 52.985 | 1.00 | 25.20 |
| ATOM | 2452 | CD | PRO | A | 320 | 0 | 20.061 | 34.891 | 52.837 | 1.00 | 25.62 |
| ATOM | 2453 | N | THR | A | 321 | 0 | 16.022 | 33.909 | 52.611 | 1.00 | 27.35 |
| ATOM | 2454 | CA | THR | A | 321 | 0 | 14.820 | 33.550 | 53.329 | 1.00 | 28.07 |
| ATOM | 2455 | C | THR | A | 321 | 0 | 13.632 | 34.190 | 52.603 | 1.00 | 27.48 |
| ATOM | 2456 | O | THR | A | 321 | 0 | 13.597 | 35.383 | 52.302 | 1.00 | 27.13 |
| ATOM | 2457 | CB | THR | A | 321 | 0 | 14.824 | 34.085 | 54.780 | 1.00 | 29.87 |
| ATOM | 2458 | OG1 | THR | A | 321 | 0 | 15.957 | 33.582 | 55.511 | 1.00 | 31.85 |
| ATOM | 2459 | CG2 | THR | A | 321 | 0 | 13.548 | 33.687 | 55.507 | 1.00 | 31.06 |
| ATOM | 2460 | N | PRO | A | 322 | 0 | 12.630 | 33.378 | 52.326 | 1.00 | 26.63 |
| ATOM | 2461 | CA | PRO | A | 322 | 0 | 11.428 | 33.824 | 51.637 | 1.00 | 25.91 |
| ATOM | 2462 | C | PRO | A | 322 | 0 | 10.892 | 35.072 | 52.313 | 1.00 | 25.37 |
| ATOM | 2463 | O | PRO | A | 322 | 0 | 10.945 | 35.194 | 53.542 | 1.00 | 25.02 |
| ATOM | 2464 | CB | PRO | A | 322 | 0 | 10.456 | 32.638 | 51.661 | 1.00 | 26.11 |
| ATOM | 2465 | CG | PRO | A | 322 | 0 | 11.370 | 31.477 | 51.931 | 1.00 | 26.67 |
| ATOM | 2466 | CD | PRO | A | 322 | 0 | 12.592 | 31.961 | 52.691 | 1.00 | 26.21 |
| ATOM | 2467 | N | GLY | A | 323 | 0 | 10.432 | 36.075 | 51.573 | 1.00 | 24.30 |
| ATOM | 2468 | CA | GLY | A | 323 | 0 | 9.943 | 37.288 | 52.197 | 1.00 | 24.13 |
| ATOM | 2469 | C | GLY | A | 323 | 0 | 11.013 | 38.161 | 52.842 | 1.00 | 25.48 |
| ATOM | 2470 | O | GLY | A | 323 | 0 | 10.603 | 39.128 | 53.512 | 1.00 | 25.28 |
| ATOM | 2471 | N | ALA | A | 324 | 0 | 12.320 | 37.959 | 52.688 | 1.00 | 24.80 |
| ATOM | 2472 | CA | ALA | A | 324 | 0 | 13.278 | 38.831 | 53.377 | 1.00 | 24.61 |
| ATOM | 2473 | C | ALA | A | 324 | 0 | 14.034 | 39.773 | 52.451 | 1.00 | 23.92 |
| ATOM | 2474 | O | ALA | A | 324 | 0 | 15.148 | 40.225 | 52.748 | 1.00 | 24.53 |
| ATOM | 2475 | CB | ALA | A | 324 | 0 | 14.255 | 38.012 | 54.204 | 1.00 | 23.79 |
| ATOM | 2476 | N | ALA | A | 325 | 0 | 13.423 | 40.081 | 51.315 | 1.00 | 22.22 |
| ATOM | 2477 | CA | ALA | A | 325 | 0 | 14.033 | 40.985 | 50.341 | 1.00 | 20.42 |
| ATOM | 2478 | C | ALA | A | 325 | 0 | 13.825 | 42.423 | 50.803 | 1.00 | 19.97 |
| ATOM | 2479 | O | ALA | A | 325 | 0 | 12.987 | 42.648 | 51.677 | 1.00 | 18.14 |
| ATOM | 2480 | CB | ALA | A | 325 | 0 | 13.272 | 40.763 | 49.018 | 1.00 | 19.40 |
| ATOM | 2481 | N | ASP | A | 326 | 0 | 14.422 | 43.421 | 50.161 | 1.00 | 20.69 |
| ATOM | 2482 | CA | ASP | A | 326 | 0 | 14.141 | 44.804 | 50.529 | 1.00 | 22.54 |
| ATOM | 2483 | C | ASP | A | 326 | 0 | 12.702 | 45.158 | 50.220 | 1.00 | 22.83 |

APPENDIX 1-continued

| | | | | | | | | | | | |
|---|---|---|---|---|---|---|---|---|---|---|---|
| ATOM | 2484 | O | ASP | A | 326 | 0 | 12.015 | 45.754 | 51.030 | 1.00 | 23.68 |
| ATOM | 2485 | CB | ASP | A | 326 | 0 | 15.089 | 45.767 | 49.789 | 1.00 | 22.32 |
| ATOM | 2486 | CG | ASP | A | 326 | 0 | 16.494 | 45.378 | 50.238 | 1.00 | 23.83 |
| ATOM | 2487 | OD1 | ASP | A | 326 | 0 | 16.650 | 45.284 | 51.475 | 1.00 | 24.78 |
| ATOM | 2488 | OD2 | ASP | A | 326 | 0 | 17.393 | 45.171 | 49.409 | 1.00 | 24.90 |
| ATOM | 2489 | N | VAL | A | 327 | 0 | 12.254 | 44.821 | 49.026 | 1.00 | 24.29 |
| ATOM | 2490 | CA | VAL | A | 327 | 0 | 10.914 | 45.064 | 48.503 | 1.00 | 23.57 |
| ATOM | 2491 | C | VAL | A | 327 | 0 | 10.246 | 43.721 | 48.170 | 1.00 | 23.46 |
| ATOM | 2492 | O | VAL | A | 327 | 0 | 10.785 | 42.933 | 47.386 | 1.00 | 22.62 |
| ATOM | 2493 | CB | VAL | A | 327 | 0 | 10.946 | 45.898 | 47.220 | 1.00 | 24.70 |
| ATOM | 2494 | CG1 | VAL | A | 327 | 0 | 9.554 | 46.274 | 46.751 | 1.00 | 24.11 |
| ATOM | 2495 | CG2 | VAL | A | 327 | 0 | 11.773 | 47.173 | 47.420 | 1.00 | 26.30 |
| ATOM | 2496 | N | ASN | A | 328 | 0 | 9.113 | 43.463 | 48.811 | 1.00 | 21.44 |
| ATOM | 2497 | CA | ASN | A | 328 | 0 | 8.390 | 42.212 | 48.717 | 1.00 | 23.21 |
| ATOM | 2498 | C | ASN | A | 328 | 0 | 6.986 | 42.410 | 48.158 | 1.00 | 23.12 |
| ATOM | 2499 | O | ASN | A | 328 | 0 | 6.140 | 43.030 | 48.799 | 1.00 | 22.76 |
| ATOM | 2500 | CB | ASN | A | 328 | 0 | 8.223 | 41.603 | 50.121 | 1.00 | 23.09 |
| ATOM | 2501 | CG | ASN | A | 328 | 0 | 9.569 | 41.204 | 50.693 | 1.00 | 24.61 |
| ATOM | 2502 | OD1 | ASN | A | 328 | 0 | 10.181 | 40.188 | 50.295 | 1.00 | 25.87 |
| ATOM | 2503 | ND2 | ASN | A | 328 | 0 | 10.017 | 42.029 | 51.617 | 1.00 | 21.47 |
| ATOM | 2504 | N | LEU | A | 329 | 0 | 6.776 | 42.000 | 46.923 | 1.00 | 23.14 |
| ATOM | 2505 | CA | LEU | A | 329 | 0 | 5.497 | 42.179 | 46.268 | 1.00 | 24.23 |
| ATOM | 2506 | C | LEU | A | 329 | 0 | 4.859 | 40.822 | 45.953 | 1.00 | 25.21 |
| ATOM | 2507 | O | LEU | A | 329 | 0 | 5.489 | 39.876 | 45.469 | 1.00 | 24.20 |
| ATOM | 2508 | CB | LEU | A | 329 | 0 | 5.622 | 42.963 | 44.948 | 1.00 | 24.33 |
| ATOM | 2509 | CG | LEU | A | 329 | 0 | 6.369 | 44.279 | 45.082 | 1.00 | 26.30 |
| ATOM | 2510 | CD1 | LEU | A | 329 | 0 | 6.778 | 44.884 | 43.757 | 1.00 | 26.24 |
| ATOM | 2511 | CD2 | LEU | A | 329 | 0 | 5.550 | 45.249 | 45.913 | 1.00 | 27.07 |
| ATOM | 2512 | N | ARG | A | 330 | 0 | 3.562 | 40.806 | 46.204 | 1.00 | 25.13 |
| ATOM | 2513 | CA | ARG | A | 330 | 0 | 2.74039 | .641 | 45.899 | 1.00 | 27.48 |
| ATOM | 2514 | C | ARG | A | 330 | 0 | 1.628 | 40.116 | 44.965 | 1.00 | 27.52 |
| ATOM | 2515 | O | ARG | A | 330 | 0 | 0.988 | 41.132 | 45.257 | 1.00 | 27.17 |
| ATOM | 2516 | CB | ARG | A | 330 | 0 | 2.200 | 39.017 | 47.166 | 1.00 | 29.82 |
| ATOM | 2517 | CG | ARG | A | 330 | 0 | 1.351 | 37.794 | 46.932 | 1.00 | 33.18 |
| ATOM | 2518 | CD | ARG | A | 330 | 0 | 0.880 | 37.251 | 48.284 | 1.00 | 37.06 |
| ATOM | 2519 | NE | ARG | A | 330 | 0 | 0.305 | 35.914 | 48.038 | 1.00 | 40.34 |
| ATOM | 2520 | CZ | ARG | A | 330 | 0 | 1.009 | 34.803 | 48.298 | 1.00 | 40.82 |
| ATOM | 2521 | NH1 | ARG | A | 330 | 0 | 2.229 | 34.903 | 48.812 | 1.00 | 40.36 |
| ATOM | 2522 | NH2 | ARG | A | 330 | 0 | 0.415 | 33.642 | 48.040 | 1.00 | 41.33 |
| ATOM | 2523 | N | PHE | A | 331 | 0 | 1.507 | 39.481 | 43.795 | 1.00 | 25.88 |
| ATOM | 2524 | CA | PHE | A | 331 | 0 | 0.475 | 39.937 | 42.855 | 1.00 | 25.87 |
| ATOM | 2525 | C | PHE | A | 331 | 0 | −0.6573 | 8.919 | 42.779 | 1.00 | 25.94 |
| ATOM | 2526 | O | PHE | A | 331 | 0 | −0.441 | 37.697 | 42.824 | 1.00 | 24.61 |
| ATOM | 2527 | CB | PHE | A | 331 | 0 | 1.102 | 40.269 | 41.511 | 1.00 | 25.94 |
| ATOM | 2528 | CG | PHE | A | 331 | 0 | 1.884 | 41.565 | 41.496 | 1.00 | 28.66 |
| ATOM | 2529 | CD1 | PHE | A | 331 | 0 | 1.282 | 42.782 | 41.759 | 1.00 | 28.04 |
| ATOM | 2530 | CD2 | PHE | A | 331 | 0 | 3.246 | 41.569 | 41.214 | 1.00 | 29.71 |
| ATOM | 2531 | CE1 | PHE | A | 331 | 0 | 1.988 | 43.963 | 41.744 | 1.00 | 29.21 |
| ATOM | 2532 | CE2 | PHE | A | 331 | 0 | 3.975 | 42.753 | 41.181 | 1.00 | 30.61 |
| ATOM | 2533 | CZ | PHE | A | 331 | 0 | 3.348 | 43.965 | 41.453 | 1.00 | 30.66 |
| ATOM | 2534 | N | GLN | A | 332 | 0 | −1.873 | 39.446 | 42.676 | 1.00 | 25.58 |
| ATOM | 2535 | CA | GLN | A | 332 | 0 | −3.085 | 38.628 | 42.608 | 1.00 | 26.60 |
| ATOM | 2536 | C | GLN | A | 332 | 0 | −3.672 | 38.698 | 41.203 | 1.00 | 23.61 |
| ATOM | 2537 | O | GLN | A | 332 | 0 | −4.136 | 39.739 | 40.755 | 1.00 | 21.73 |
| ATOM | 2538 | CB | GLN | A | 332 | 0 | −4.110 | 39.094 | 43.630 | 1.00 | 30.32 |
| ATOM | 2539 | CG | GLN | A | 332 | 0 | −5.412 | 38.299 | 43.642 | 1.00 | 35.72 |
| ATOM | 2540 | CD | GLN | A | 332 | 0 | −5.199 | 36.961 | 44.325 | 1.00 | 39.98 |
| ATOM | 2541 | OE1 | GLN | A | 332 | 0 | −5.859 | 35.961 | 44.007 | 1.00 | 42.32 |
| ATOM | 2542 | NE2 | GLN | A | 332 | 0 | −4.257 | 36.915 | 45.270 | 1.00 | 42.27 |
| ATOM | 2543 | N | LEU | A | 333 | 0 | −3.612 | 37.576 | 40.504 | 1.00 | 23.60 |
| ATOM | 2544 | CA | LEU | A | 333 | 0 | −4.105 | 37.565 | 39.118 | 1.00 | 26.25 |
| ATOM | 2545 | C | LEU | A | 333 | 0 | −5.627 | 37.373 | 39.123 | 1.00 | 26.55 |
| ATOM | 2546 | O | LEU | A | 333 | 0 | −6.107 | 36.655 | 39.998 | 1.00 | 25.70 |
| ATOM | 2547 | CB | LEU | A | 333 | 0 | −3.424 | 36.465 | 38.304 | 1.00 | 25.25 |
| ATOM | 2548 | CG | LEU | A | 333 | 0 | −1.919 | 36.608 | 38.052 | 1.00 | 25.72 |
| ATOM | 2549 | CD1 | LEU | A | 333 | 0 | −1.431 | 35.565 | 37.067 | 1.00 | 23.66 |
| ATOM | 2550 | CD2 | LEU | A | 333 | 0 | −1.551 | 38.000 | 37.558 | 1.00 | 25.25 |
| ATOM | 2551 | N | GLY | A | 334 | 0 | −6.327 | 37.976 | 38.188 | 1.00 | 27.85 |
| ATOM | 2552 | CA | GLY | A | 334 | 0 | −7.770 | 37.782 | 38.118 | 1.00 | 29.96 |
| ATOM | 2553 | C | GLY | A | 334 | 0 | −8.253 | 37.802 | 36.672 | 1.00 | 32.36 |
| ATOM | 2554 | O | GLY | A | 334 | 0 | −7.559 | 38.175 | 35.719 | 1.00 | 30.74 |
| ATOM | 2555 | N | PHE | A | 335 | 0 | −9.502 | 37.377 | 36.544 | 1.00 | 34.76 |
| ATOM | 2556 | CA | PHE | A | 335 | 0 | −10.181 | 37.360 | 35.260 | 1.00 | 38.54 |
| ATOM | 2557 | C | PHE | A | 335 | 0 | −11.625 | 37.806 | 35.514 | 1.00 | 41.05 |
| ATOM | 2558 | O | PHE | A | 335 | 0 | −12.443 | 37.028 | 36.021 | 1.00 | 41.53 |
| ATOM | 2559 | CB | PHE | A | 335 | 0 | −10.183 | 36.003 | 34.586 | 1.00 | 39.00 |
| ATOM | 2560 | CG | PHE | A | 335 | 0 | −10.772 | 36.105 | 33.197 | 1.00 | 40.61 |
| ATOM | 2561 | CD1 | PHE | A | 335 | 0 | −10.052 | 36.686 | 32.175 | 1.00 | 40.45 |
| ATOM | 2562 | CD2 | PHE | A | 335 | 0 | −12.045 | 35.614 | 32.942 | 1.00 | 41.39 |

APPENDIX 1-continued

| | | | | | | | | | | |
|---|---|---|---|---|---|---|---|---|---|---|
| ATOM | 2563 | CE1 | PHE | A | 335 | 0 | -10.580 | 36.778 | 30.901 | 1.00 | 40.81 |
| ATOM | 2564 | CE2 | PHE | A | 335 | 0 | -12.588 | 35.697 | 31.671 | 1.00 | 41.51 |
| ATOM | 2565 | CZ | PHE | A | 335 | 0 | -11.849 | 36.281 | 30.652 | 1.00 | 41.87 |
| ATOM | 2566 | N | SER | A | 336 | 0 | -11.861 | 39.075 | 35.193 | 1.00 | 42.39 |
| ATOM | 2567 | CA | SER | A | 336 | 0 | -13.203 | 39.582 | 35.445 | 1.00 | 44.12 |
| ATOM | 2568 | C | SER | A | 336 | 0 | -13.704 | 40.525 | 34.370 | 1.00 | 44.31 |
| ATOM | 2569 | O | SER | A | 336 | 0 | -13.028 | 41.440 | 33.903 | 1.00 | 44.49 |
| ATOM | 2570 | CB | SER | A | 336 | 0 | -13.214 | 40.206 | 36.842 | 1.00 | 45.46 |
| ATOM | 2571 | OG | SER | A | 336 | 0 | -13.727 | 39.233 | 37.758 | 1.00 | 47.11 |
| ATOM | 2572 | N | GLY | A | 337 | 0 | -14.963 | 40.267 | 33.983 | 1.00 | 44.12 |
| ATOM | 2573 | CA | GLY | A | 337 | 0 | -15.630 | 41.067 | 32.959 | 1.00 | 41.89 |
| ATOM | 2574 | C | GLY | A | 337 | 0 | -14.963 | 40.920 | 31.608 | 1.00 | 40.08 |
| ATOM | 2575 | O | GLY | A | 337 | 0 | -14.712 | 41.891 | 30.888 | 1.00 | 41.35 |
| ATOM | 2576 | N | GLY | A | 338 | 0 | -14.583 | 39.699 | 31.263 | 1.00 | 39.12 |
| ATOM | 2577 | CA | GLY | A | 338 | 0 | -13.899 | 39.364 | 30.034 | 1.00 | 36.11 |
| ATOM | 2578 | C | GLY | A | 338 | 0 | -12.503 | 39.970 | 29.929 | 1.00 | 34.97 |
| ATOM | 2579 | O | GLY | A | 338 | 0 | -12.005 | 40.116 | 28.806 | 1.00 | 33.64 |
| ATOM | 2580 | N | ARG | A | 339 | 0 | -11.885 | 40.355 | 31.048 | 1.00 | 33.21 |
| ATOM | 2581 | CA | ARG | A | 339 | 0 | -10.538 | 40.916 | 30.982 | 1.00 | 32.04 |
| ATOM | 2582 | C | ARG | A | 339 | 0 | -9.724 | 40.397 | 32.164 | 1.00 | 29.23 |
| ATOM | 2583 | O | ARG | A | 339 | 0 | -10.260 | 40.053 | 33.210 | 1.00 | 26.38 |
| ATOM | 2584 | CB | ARG | A | 339 | 0 | -10.495 | 42.419 | 30.845 | 1.00 | 36.52 |
| ATOM | 2585 | CG | ARG | A | 339 | 0 | -11.291 | 43.281 | 31.790 | 1.00 | 42.08 |
| ATOM | 2586 | CD | ARG | A | 339 | 0 | -11.895 | 44.502 | 31.127 | 1.00 | 45.03 |
| ATOM | 2587 | NE | ARG | A | 339 | 0 | -11.046 | 45.380 | 30.351 | 1.00 | 47.77 |
| ATOM | 2588 | CZ | ARG | A | 339 | 0 | -10.635 | 46.616 | 30.664 | 1.00 | 49.55 |
| ATOM | 2589 | NH1 | ARG | A | 339 | 0 | -10.935 | 47.242 | 31.799 | 1.00 | 49.60 |
| ATOM | 2590 | NH2 | ARG | A | 339 | 0 | -9.862 | 47.295 | 29.805 | 1.00 | 49.96 |
| ATOM | 2591 | N | PHE | A | 340 | 0 | -8.425 | 40.181 | 31.900 | 1.00 | 25.50 |
| ATOM | 2592 | CA | PHE | A | 340 | 0 | -7.526 | 39.713 | 32.938 | 1.00 | 22.68 |
| ATOM | 2593 | C | PHE | A | 340 | 0 | -7.171 | 40.945 | 33.774 | 1.00 | 22.15 |
| ATOM | 2594 | O | PHE | A | 340 | 0 | -7.069 | 42.069 | 33.266 | 1.00 | 21.26 |
| ATOM | 2595 | CB | PHE | A | 340 | 0 | -6.210 | 39.135 | 32.397 | 1.00 | 22.39 |
| ATOM | 2596 | CG | PHE | A | 340 | 0 | -6.333 | 37.792 | 31.736 | 1.00 | 20.74 |
| ATOM | 2597 | CD1 | PHE | A | 340 | 0 | -6.338 | 37.710 | 30.357 | 1.00 | 20.97 |
| ATOM | 2598 | CD2 | PHE | A | 340 | 0 | -6.448 | 36.644 | 32.468 | 1.00 | 21.19 |
| ATOM | 2599 | CE1 | PHE | A | 340 | 0 | -6.449 | 36.488 | 29.721 | 1.00 | 21.61 |
| ATOM | 2600 | CE2 | PHE | A | 340 | 0 | -6.585 | 35.408 | 31.826 | 1.00 | 22.99 |
| ATOM | 2601 | CZ | PHE | A | 340 | 0 | -6.578 | 35.334 | 30.444 | 1.00 | 19.90 |
| ATOM | 2602 | N | THR | A | 341 | 0 | -7.000 | 40.736 | 35.069 | 1.00 | 20.76 |
| ATOM | 2603 | CA | THR | A | 341 | 0 | -6.605 | 41.879 | 35.889 | 1.00 | 21.55 |
| ATOM | 2604 | C | THR | A | 341 | 0 | -5.400 | 41.509 | 36.759 | 1.00 | 21.00 |
| ATOM | 2605 | O | THR | A | 341 | 0 | -5.236 | 40.329 | 37.089 | 1.00 | 20.70 |
| ATOM | 2606 | CB | THR | A | 341 | 0 | -7.757 | 42.255 | 36.853 | 1.00 | 21.12 |
| ATOM | 2607 | OG1 | THR | A | 341 | 0 | -8.014 | 41.102 | 37.668 | 1.00 | 21.26 |
| ATOM | 2608 | CG2 | THR | A | 341 | 0 | -9.050 | 42.630 | 36.150 | 1.00 | 21.74 |
| ATOM | 2609 | N | ILE | A | 342 | 0 | -4.750 | 42.529 | 37.308 | 1.00 | 20.28 |
| ATOM | 2610 | CA | ILE | A | 342 | 0 | -3.739 | 42.273 | 38.333 | 1.00 | 20.34 |
| ATOM | 2611 | C | ILE | A | 342 | 0 | -4.026 | 43.212 | 39.496 | 1.00 | 18.92 |
| ATOM | 2612 | O | ILE | A | 342 | 0 | -4.004 | 44.437 | 39.327 | 1.00 | 16.42 |
| ATOM | 2613 | CB | ILE | A | 342 | 0 | -2.306 | 42.439 | 37.820 | 1.00 | 21.04 |
| ATOM | 2614 | CG1 | ILE | A | 342 | 0 | -1.337 | 42.721 | 38.988 | 1.00 | 21.39 |
| ATOM | 2615 | CG2 | ILE | A | 342 | 0 | -2.250 | 43.540 | 36.800 | 1.00 | 24.57 |
| ATOM | 2616 | CD1 | ILE | A | 342 | 0 | -0.260 | 41.661 | 38.949 | 1.00 | 24.53 |
| ATOM | 2617 | N | ASN | A | 343 | 0 | -4.282 | 42.601 | 40.650 | 1.00 | 17.77 |
| ATOM | 2618 | CA | ASN | A | 343 | 0 | -4.702 | 43.413 | 41.782 | 1.00 | 21.51 |
| ATOM | 2619 | C | ASN | A | 343 | 0 | -5.881 | 44.287 | 41.394 | 1.00 | 21.43 |
| ATOM | 2620 | O | ASN | A | 343 | 0 | -5.903 | 45.495 | 41.598 | 1.00 | 20.26 |
| ATOM | 2621 | CB | ASN | A | 343 | 0 | -3.513 | 44.231 | 42.356 | 1.00 | 22.34 |
| ATOM | 2622 | CG | ASN | A | 343 | 0 | -2.685 | 43.190 | 43.073 | 1.00 | 25.38 |
| ATOM | 2623 | OD1 | ASN | A | 343 | 0 | -2.075 | 42.218 | 42.598 | 1.00 | 26.90 |
| ATOM | 2624 | ND2 | ASN | A | 343 | 0 | -2.652 | 43.238 | 44.425 | 1.00 | 25.34 |
| ATOM | 2625 | N | GLY | A | 344 | 0 | -6.875 | 43.703 | 40.730 | 1.00 | 23.77 |
| ATOM | 2626 | CA | GLY | A | 344 | 0 | -8.078 | 44.406 | 40.324 | 1.00 | 25.28 |
| ATOM | 2627 | C | GLY | A | 344 | 0 | -7.954 | 45.280 | 39.111 | 1.00 | 26.82 |
| ATOM | 2628 | O | GLY | A | 344 | 0 | -9.029 | 45.728 | 38.672 | 1.00 | 29.56 |
| ATOM | 2629 | N | THR | A | 345 | 0 | -6.798 | 45.561 | 38.527 | 1.00 | 26.28 |
| ATOM | 2630 | CA | THR | A | 345 | 0 | -6.766 | 46.440 | 37.366 | 1.00 | 25.48 |
| ATOM | 2631 | C | THR | A | 345 | 0 | -6.343 | 45.703 | 36.109 | 1.00 | 26.49 |
| ATOM | 2632 | O | THR | A | 345 | 0 | -5.385 | 44.925 | 36.122 | 1.00 | 28.22 |
| ATOM | 2633 | CB | THR | A | 345 | 0 | -5.829 | 47.648 | 37.589 | 1.00 | 26.17 |
| ATOM | 2634 | OG1 | THR | A | 345 | 0 | -6.191 | 48.334 | 38.788 | 1.00 | 25.32 |
| ATOM | 2635 | CG2 | THR | A | 345 | 0 | -5.867 | 48.677 | 36.462 | 1.00 | 24.83 |
| ATOM | 2636 | N | ALA | A | 346 | 0 | -7.017 | 46.012 | 35.008 | 1.00 | 24.80 |
| ATOM | 2637 | CA | ALA | A | 346 | 0 | -6.768 | 45.491 | 33.688 | 1.00 | 23.82 |
| ATOM | 2638 | C | ALA | A | 346 | 0 | -5.862 | 46.511 | 32.997 | 1.00 | 23.77 |
| ATOM | 2639 | O | ALA | A | 346 | 0 | -6.098 | 47.711 | 33.088 | 1.00 | 22.93 |
| ATOM | 2640 | CB | ALA | A | 346 | 0 | -8.031 | 45.353 | 32.841 | 1.00 | 24.13 |
| ATOM | 2641 | N | TYR | A | 347 | 0 | -4.793 | 46.023 | 32.392 | 1.00 | 22.69 |

APPENDIX 1-continued

| | | | | | | | | | | |
|---|---|---|---|---|---|---|---|---|---|---|
| ATOM | 2642 | CA | TYR | A | 347 | 0 | -3.862 | 46.949 | 31.792 | 1.00 | 22.75 |
| ATOM | 2643 | C | TYR | A | 347 | 0 | -4.483 | 47.532 | 30.527 | 1.00 | 23.42 |
| ATOM | 2644 | O | TYR | A | 347 | 0 | -4.954 | 46.753 | 29.709 | 1.00 | 22.19 |
| ATOM | 2645 | CB | TYR | A | 347 | 0 | -2.521 | 46.274 | 31.455 | 1.00 | 21.25 |
| ATOM | 2646 | CG | TYR | A | 347 | 0 | -1.584 | 47.221 | 30.732 | 1.00 | 18.93 |
| ATOM | 2647 | CD1 | TYR | A | 347 | 0 | -0.819 | 48.137 | 31.442 | 1.00 | 18.17 |
| ATOM | 2648 | CD2 | TYR | A | 347 | 0 | -1.473 | 47.176 | 29.353 | 1.00 | 19.30 |
| ATOM | 2649 | CE1 | TYR | A | 347 | 0 | 0.034 | 49.003 | 30.763 | 1.00 | 18.37 |
| ATOM | 2650 | CE2 | TYR | A | 347 | 0 | -0.650 | 48.063 | 28.664 | 1.00 | 18.40 |
| ATOM | 2651 | CZ | TYR | A | 347 | 0 | 0.102 | 48.962 | 29.394 | 1.00 | 18.99 |
| ATOM | 2652 | OH | TYR | A | 347 | 0 | 0.947 | 49.802 | 28.706 | 1.00 | 19.65 |
| ATOM | 2653 | N | GLU | A | 348 | 0 | -4.378 | 48.833 | 30.359 | 1.00 | 25.22 |
| ATOM | 2654 | CA | GLU | A | 348 | 0 | -4.769 | 49.453 | 29.098 | 1.00 | 28.77 |
| ATOM | 2655 | C | GLU | A | 348 | 0 | -3.659 | 50.470 | 28.805 | 1.00 | 27.38 |
| ATOM | 2656 | O | GLU | A | 348 | 0 | -3.297 | 51.229 | 29.704 | 1.00 | 28.49 |
| ATOM | 2657 | CB | GLU | A | 348 | 0 | -6.114 | 50.134 | 29.110 | 1.00 | 32.95 |
| ATOM | 2658 | CG | GLU | A | 348 | 0 | -7.391 | 49.302 | 29.072 | 1.00 | 39.29 |
| ATOM | 2659 | CD | GLU | A | 348 | 0 | -8.562 | 50.170 | 29.559 | 1.00 | 43.20 |
| ATOM | 2660 | OE1 | GLU | A | 348 | 0 | -8.825 | 51.211 | 28.900 | 1.00 | 45.31 |
| ATOM | 2661 | OE2 | GLU | A | 348 | 0 | -9.175 | 49.855 | 30.601 | 1.00 | 44.11 |
| ATOM | 2662 | N | SER | A | 349 | 0 | -3.168 | 50.541 | 27.621 | 1.00 | 25.73 |
| ATOM | 2663 | CA | SER | A | 349 | 0 | -2.080 | 51.410 | 27.201 | 1.00 | 28.25 |
| ATOM | 2664 | C | SER | A | 349 | 0 | -2.401 | 52.887 | 27.194 | 1.00 | 28.71 |
| ATOM | 2665 | O | SER | A | 349 | 0 | -3.279 | 53.399 | 26.526 | 1.00 | 29.13 |
| ATOM | 2666 | CB | SER | A | 349 | 0 | -1.743 | 50.818 | 25.838 | 1.00 | 28.54 |
| ATOM | 2667 | OG | SER | A | 349 | 0 | -0.850 | 51.499 | 25.026 | 1.00 | 33.31 |
| ATOM | 2668 | N | PRO | A | 350 | 0 | -1.623 | 53.700 | 27.898 | 1.00 | 29.56 |
| ATOM | 2669 | CA | PRO | A | 350 | 0 | -1.770 | 55.145 | 27.997 | 1.00 | 28.53 |
| ATOM | 2670 | C | PRO | A | 350 | 0 | -1.480 | 55.825 | 26.679 | 1.00 | 28.01 |
| ATOM | 2671 | O | PRO | A | 350 | 0 | -0.787 | 55.217 | 25.856 | 1.00 | 26.93 |
| ATOM | 2672 | CB | PRO | A | 350 | 0 | -0.752 | 55.632 | 29.063 | 1.00 | 27.91 |
| ATOM | 2673 | CG | PRO | A | 350 | 0 | 0.309 | 54.560 | 28.863 | 1.00 | 28.03 |
| ATOM | 2674 | CD | PRO | A | 350 | 0 | -0.461 | 53.245 | 28.688 | 1.00 | 28.76 |
| ATOM | 2675 | N | SER | A | 351 | 0 | -1.951 | 57.066 | 26.485 | 1.00 | 28.89 |
| ATOM | 2676 | CA | SER | A | 351 | 0 | -1.630 | 57.718 | 25.206 | 1.00 | 29.67 |
| ATOM | 2677 | C | SER | A | 351 | 0 | -0.213 | 58.287 | 25.257 | 1.00 | 27.67 |
| ATOM | 2678 | O | SER | A | 351 | 0 | 0.320 | 58.524 | 24.177 | 1.00 | 28.18 |
| ATOM | 2679 | CB | SER | A | 351 | 0 | -2.566 | 58.860 | 24.790 | 1.00 | 31.71 |
| ATOM | 2680 | OG | SER | A | 351 | 0 | -2.793 | 59.679 | 25.938 | 1.00 | 34.19 |
| ATOM | 2681 | N | VAL | A | 352 | 0 | 0.316 | 58.529 | 26.449 | 1.00 | 25.32 |
| ATOM | 2682 | CA | VAL | A | 352 | 0 | 1.703 | 58.997 | 26.534 | 1.00 | 25.27 |
| ATOM | 2683 | C | VAL | A | 352 | 0 | 2.503 | 57.872 | 27.211 | 1.00 | 23.63 |
| ATOM | 2684 | O | VAL | A | 352 | 0 | 2.181 | 57.493 | 28.323 | 1.00 | 23.26 |
| ATOM | 2685 | CB | VAL | A | 352 | 0 | 1.934 | 60.300 | 27.303 | 1.00 | 24.91 |
| ATOM | 2686 | CG1 | VAL | A | 352 | 0 | 1.129 | 61.436 | 26.658 | 1.00 | 24.41 |
| ATOM | 2687 | CG2 | VAL | A | 352 | 0 | 3.424 | 60.635 | 27.281 | 1.00 | 23.35 |
| ATOM | 2688 | N | PRO | A | 353 | 0 | 3.498 | 57.375 | 26.510 | 1.00 | 22.39 |
| ATOM | 2689 | CA | PRO | A | 353 | 0 | 4.342 | 56.300 | 26.983 | 1.00 | 21.86 |
| ATOM | 2690 | C | PRO | A | 353 | 0 | 4.978 | 56.699 | 28.300 | 1.00 | 20.91 |
| ATOM | 2691 | O | PRO | A | 353 | 0 | 5.393 | 57.852 | 28.483 | 1.00 | 21.91 |
| ATOM | 2692 | CB | PRO | A | 353 | 0 | 5.417 | 56.054 | 25.916 | 1.00 | 23.95 |
| ATOM | 2693 | CG | PRO | A | 353 | 0 | 5.181 | 57.123 | 24.878 | 1.00 | 23.79 |
| ATOM | 2694 | CD | PRO | A | 353 | 0 | 3.882 | 57.848 | 25.180 | 1.00 | 23.03 |
| ATOM | 2695 | N | THR | A | 354 | 0 | 5.043 | 55.778 | 29.234 | 1.00 | 18.66 |
| ATOM | 2696 | CA | THR | A | 354 | 0 | 5.646 | 56.015 | 30.530 | 1.00 | 18.05 |
| ATOM | 2697 | C | THR | A | 354 | 0 | 6.981 | 56.739 | 30.478 | 1.00 | 18.33 |
| ATOM | 2698 | O | THR | A | 354 | 0 | 7.168 | 57.630 | 31.319 | 1.00 | 19.46 |
| ATOM | 2699 | CB | THR | A | 354 | 0 | 5.871 | 54.661 | 31.242 | 1.00 | 17.10 |
| ATOM | 2700 | OG1 | THR | A | 354 | 0 | 4.903 | 53.710 | 30.797 | 1.00 | 17.24 |
| ATOM | 2701 | CG2 | THR | A | 354 | 0 | 5.772 | 54.852 | 32.741 | 1.00 | 16.43 |
| ATOM | 2702 | N | LEU | A | 355 | 0 | 7.940 | 56.380 | 29.618 | 1.00 | 17.49 |
| ATOM | 2703 | CA | LEU | A | 355 | 0 | 9.215 | 57.076 | 29.604 | 1.00 | 18.84 |
| ATOM | 2704 | C | LEU | A | 355 | 0 | 9.013 | 58.579 | 29.284 | 1.00 | 19.80 |
| ATOM | 2705 | O | LEU | A | 355 | 0 | 9.722 | 59.417 | 29.849 | 1.00 | 17.13 |
| ATOM | 2706 | CB | LEU | A | 355 | 0 | 10.200 | 56.498 | 28.622 | 1.00 | 17.89 |
| ATOM | 2707 | CG | LEU | A | 355 | 0 | 11.703 | 56.488 | 28.819 | 1.00 | 18.66 |
| ATOM | 2708 | CD1 | LEU | A | 355 | 0 | 12.436 | 56.851 | 27.547 | 1.00 | 18.37 |
| ATOM | 2709 | CD2 | LEU | A | 355 | 0 | 12.199 | 57.204 | 30.056 | 1.00 | 16.79 |
| ATOM | 2710 | N | LEU | A | 356 | 0 | 8.134 | 58.883 | 28.328 | 1.00 | 20.48 |
| ATOM | 2711 | CA | LEU | A | 356 | 0 | 7.812 | 60.274 | 27.993 | 1.00 | 21.62 |
| ATOM | 2712 | C | LEU | A | 356 | 0 | 7.085 | 60.932 | 29.163 | 1.00 | 21.28 |
| ATOM | 2713 | O | LEU | A | 356 | 0 | 7.497 | 62.042 | 29.506 | 1.00 | 22.01 |
| ATOM | 2714 | CB | LEU | A | 356 | 0 | 7.028 | 60.474 | 26.700 | 1.00 | 22.08 |
| ATOM | 2715 | CG | LEU | A | 356 | 0 | 6.850 | 61.939 | 26.239 | 1.00 | 23.98 |
| ATOM | 2716 | CD1 | LEU | A | 356 | 0 | 8.157 | 62.709 | 26.207 | 1.00 | 23.11 |
| ATOM | 2717 | CD2 | LEU | A | 356 | 0 | 6.191 | 61.985 | 24.864 | 1.00 | 24.74 |
| ATOM | 2718 | N | GLN | A | 357 | 0 | 6.219 | 60.267 | 29.922 | 1.00 | 21.37 |
| ATOM | 2719 | CA | GLN | A | 357 | 0 | 5.669 | 60.893 | 31.120 | 1.00 | 21.87 |
| ATOM | 2720 | C | GLN | A | 357 | 0 | 6.759 | 61.254 | 32.128 | 1.00 | 24.12 |

APPENDIX 1-continued

| ATOM | 2721 | O   | GLN | A | 357 | 0 |  6.674 | 62.277 | 32.811 | 1.00 | 24.92 |
|------|------|-----|-----|---|-----|---|--------|--------|--------|------|-------|
| ATOM | 2722 | CB  | GLN | A | 357 | 0 |  4.636 | 60.015 | 31.822 | 1.00 | 20.63 |
| ATOM | 2723 | CG  | GLN | A | 357 | 0 |  3.447 | 59.674 | 30.906 | 1.00 | 19.17 |
| ATOM | 2724 | CD  | GLN | A | 357 | 0 |  2.547 | 58.643 | 31.540 | 1.00 | 18.85 |
| ATOM | 2725 | OE1 | GLN | A | 357 | 0 |  2.162 | 58.748 | 32.713 | 1.00 | 19.06 |
| ATOM | 2726 | NE2 | GLN | A | 357 | 0 |  2.262 | 57.600 | 30.742 | 1.00 | 18.49 |
| ATOM | 2727 | N   | ILE | A | 358 | 0 |  7.735 | 60.371 | 32.346 | 1.00 | 25.66 |
| ATOM | 2728 | CA  | ILE | A | 358 | 0 |  8.822 | 60.651 | 33.263 | 1.00 | 26.19 |
| ATOM | 2729 | C   | ILE | A | 358 | 0 |  9.699 | 61.800 | 32.762 | 1.00 | 27.66 |
| ATOM | 2730 | O   | ILE | A | 358 | 0 |  9.940 | 62.725 | 33.551 | 1.00 | 26.65 |
| ATOM | 2731 | CB  | ILE | A | 358 | 0 |  9.692 | 59.420 | 33.578 | 1.00 | 24.79 |
| ATOM | 2732 | CG1 | ILE | A | 358 | 0 |  8.807 | 58.395 | 34.304 | 1.00 | 24.09 |
| ATOM | 2733 | CG2 | ILE | A | 358 | 0 | 10.865 | 59.841 | 34.451 | 1.00 | 23.78 |
| ATOM | 2734 | CD1 | ILE | A | 358 | 0 |  9.251 | 56.954 | 34.234 | 1.00 | 23.34 |
| ATOM | 2735 | N   | MET | A | 359 | 0 | 10.054 | 61.844 | 31.486 | 1.00 | 29.63 |
| ATOM | 2736 | CA  | MET | A | 359 | 0 | 10.893 | 62.910 | 30.965 | 1.00 | 33.02 |
| ATOM | 2737 | C   | MET | A | 359 | 0 | 10.174 | 64.260 | 31.027 | 1.00 | 34.46 |
| ATOM | 2738 | O   | MET | A | 359 | 0 | 10.801 | 65.324 | 31.026 | 1.00 | 33.77 |
| ATOM | 2739 | CB  | MET | A | 359 | 0 | 11.346 | 62.664 | 29.537 | 1.00 | 35.67 |
| ATOM | 2740 | CG  | MET | A | 359 | 0 | 12.065 | 61.403 | 29.138 | 1.00 | 40.75 |
| ATOM | 2741 | SD  | MET | A | 359 | 0 | 13.764 | 61.153 | 29.671 | 1.00 | 44.90 |
| ATOM | 2742 | CE  | MET | A | 359 | 0 | 14.594 | 62.592 | 29.007 | 1.00 | 44.24 |
| ATOM | 2743 | N   | SER | A | 360 | 0 |  8.835 | 64.238 | 31.070 | 1.00 | 33.43 |
| ATOM | 2744 | CA  | SER | A | 360 | 0 |  8.024 | 65.430 | 31.088 | 1.00 | 32.92 |
| ATOM | 2745 | C   | SER | A | 360 | 0 |  7.761 | 65.995 | 32.474 | 1.00 | 33.24 |
| ATOM | 2746 | O   | SER | A | 360 | 0 |  6.989 | 66.966 | 32.556 | 1.00 | 34.08 |
| ATOM | 2747 | CB  | SER | A | 360 | 0 |  6.678 | 65.134 | 30.393 | 1.00 | 31.34 |
| ATOM | 2748 | OG  | SER | A | 360 | 0 |  6.928 | 65.109 | 28.996 | 1.00 | 31.06 |
| ATOM | 2749 | N   | GLY | A | 361 | 0 |  8.288 | 65.360 | 33.517 | 1.00 | 32.06 |
| ATOM | 2750 | CA  | GLY | A | 361 | 0 |  8.072 | 65.868 | 34.847 | 1.00 | 31.80 |
| ATOM | 2751 | C   | GLY | A | 361 | 0 |  7.487 | 64.955 | 35.880 | 1.00 | 32.48 |
| ATOM | 2752 | O   | GLY | A | 361 | 0 |  7.420 | 65.377 | 37.043 | 1.00 | 33.20 |
| ATOM | 2753 | N   | ALA | A | 362 | 0 |  6.991 | 63.769 | 35.535 | 1.00 | 33.69 |
| ATOM | 2754 | CA  | ALA | A | 362 | 0 |  6.406 | 62.926 | 36.601 | 1.00 | 35.10 |
| ATOM | 2755 | C   | ALA | A | 362 | 0 |  7.475 | 62.615 | 37.650 | 1.00 | 34.45 |
| ATOM | 2756 | O   | ALA | A | 362 | 0 |  8.598 | 62.306 | 37.286 | 1.00 | 33.60 |
| ATOM | 2757 | CB  | ALA | A | 362 | 0 |  5.789 | 61.658 | 36.043 | 1.00 | 34.88 |
| ATOM | 2758 | N   | GLN | A | 363 | 0 |  7.146 | 62.676 | 38.920 | 1.00 | 36.22 |
| ATOM | 2759 | CA  | GLN | A | 363 | 0 |  8.083 | 62.458 | 40.007 | 1.00 | 37.87 |
| ATOM | 2760 | C   | GLN | A | 363 | 0 |  7.776 | 61.189 | 40.787 | 1.00 | 37.20 |
| ATOM | 2761 | O   | GLN | A | 363 | 0 |  8.620 | 60.777 | 41.587 | 1.00 | 36.79 |
| ATOM | 2762 | CB  | GLN | A | 363 | 0 |  8.012 | 63.619 | 41.022 | 1.00 | 40.41 |
| ATOM | 2763 | CG  | GLN | A | 363 | 0 |  8.986 | 64.740 | 40.721 | 1.00 | 44.07 |
| ATOM | 2764 | CD  | GLN | A | 363 | 0 |  8.586 | 66.154 | 41.092 | 1.00 | 45.77 |
| ATOM | 2765 | OE1 | GLN | A | 363 | 0 |  7.697 | 66.473 | 41.901 | 1.00 | 46.53 |
| ATOM | 2766 | NE2 | GLN | A | 363 | 0 |  9.294 | 67.089 | 40.435 | 1.00 | 46.12 |
| ATOM | 2767 | N   | SER | A | 364 | 0 |  6.579 | 60.632 | 40.610 | 1.00 | 35.74 |
| ATOM | 2768 | CA  | SER | A | 364 | 0 |  6.249 | 59.434 | 41.381 | 1.00 | 34.54 |
| ATOM | 2769 | C   | SER | A | 364 | 0 |  5.225 | 58.588 | 40.653 | 1.00 | 34.32 |
| ATOM | 2770 | O   | SER | A | 364 | 0 |  4.605 | 59.037 | 39.692 | 1.00 | 33.71 |
| ATOM | 2771 | CB  | SER | A | 364 | 0 |  5.774 | 59.835 | 42.769 | 1.00 | 35.68 |
| ATOM | 2772 | OG  | SER | A | 364 | 0 |  4.396 | 60.095 | 42.928 | 1.00 | 35.86 |
| ATOM | 2773 | N   | ALA | A | 365 | 0 |  5.015 | 57.372 | 41.146 | 1.00 | 33.95 |
| ATOM | 2774 | CA  | ALA | A | 365 | 0 |  4.017 | 56.486 | 40.564 | 1.00 | 34.62 |
| ATOM | 2775 | C   | ALA | A | 365 | 0 |  2.637 | 57.148 | 40.560 | 1.00 | 34.46 |
| ATOM | 2776 | O   | ALA | A | 365 | 0 |  1.906 | 56.995 | 39.582 | 1.00 | 34.37 |
| ATOM | 2777 | CB  | ALA | A | 365 | 0 |  3.963 | 55.155 | 41.301 | 1.00 | 33.51 |
| ATOM | 2778 | N   | ASN | A | 366 | 0 |  2.261 | 57.916 | 41.571 | 1.00 | 34.45 |
| ATOM | 2779 | CA  | ASN | A | 366 | 0 |  1.003 | 58.619 | 41.632 | 1.00 | 36.37 |
| ATOM | 2780 | C   | ASN | A | 366 | 0 |  0.708 | 59.524 | 40.447 | 1.00 | 35.60 |
| ATOM | 2781 | O   | ASN | A | 366 | 0 | -0.462 | 59.719 | 40.131 | 1.00 | 36.50 |
| ATOM | 2782 | CB  | ASN | A | 366 | 0 |  0.904 | 59.464 | 42.918 | 1.00 | 38.72 |
| ATOM | 2783 | CG  | ASN | A | 366 | 0 |  0.794 | 58.558 | 44.126 | 1.00 | 41.08 |
| ATOM | 2784 | OD1 | ASN | A | 366 | 0 |  0.863 | 58.966 | 45.284 | 1.00 | 43.39 |
| ATOM | 2785 | ND2 | ASN | A | 366 | 0 |  0.646 | 57.256 | 43.914 | 1.00 | 42.72 |
| ATOM | 2786 | N   | ASP | A | 367 | 0 |  1.694 | 60.046 | 39.752 | 1.00 | 34.06 |
| ATOM | 2787 | CA  | ASP | A | 367 | 0 |  1.571 | 60.899 | 38.610 | 1.00 | 33.37 |
| ATOM | 2788 | C   | ASP | A | 367 | 0 |  1.566 | 60.122 | 37.293 | 1.00 | 32.09 |
| ATOM | 2789 | O   | ASP | A | 367 | 0 |  1.430 | 60.762 | 36.247 | 1.00 | 31.74 |
| ATOM | 2790 | CB  | ASP | A | 367 | 0 |  2.768 | 61.841 | 38.483 | 1.00 | 35.96 |
| ATOM | 2791 | CG  | ASP | A | 367 | 0 |  3.048 | 62.818 | 39.602 | 1.00 | 37.69 |
| ATOM | 2792 | OD1 | ASP | A | 367 | 0 |  2.123 | 63.209 | 40.336 | 1.00 | 37.23 |
| ATOM | 2793 | OD2 | ASP | A | 367 | 0 |  4.258 | 63.194 | 39.705 | 1.00 | 39.62 |
| ATOM | 2794 | N   | LEU | A | 368 | 0 |  1.791 | 58.814 | 37.371 | 1.00 | 30.39 |
| ATOM | 2795 | CA  | LEU | A | 368 | 0 |  1.897 | 58.055 | 36.123 | 1.00 | 28.74 |
| ATOM | 2796 | C   | LEU | A | 368 | 0 |  0.586 | 57.386 | 35.745 | 1.00 | 28.85 |
| ATOM | 2797 | O   | LEU | A | 368 | 0 | -0.214 | 56.947 | 36.555 | 1.00 | 28.17 |
| ATOM | 2798 | CB  | LEU | A | 368 | 0 |  3.043 | 57.046 | 36.194 | 1.00 | 26.94 |
| ATOM | 2799 | CG  | LEU | A | 368 | 0 |  4.436 | 57.668 | 36.422 | 1.00 | 27.05 |

APPENDIX 1-continued

| | | | | | | | | | | |
|---|---|---|---|---|---|---|---|---|---|---|
| ATOM | 2800 | CD1 | LEU | A | 368 | 0 | 5.455 | 56.581 | 36.765 | 1.00 | 25.41 |
| ATOM | 2801 | CD2 | LEU | A | 368 | 0 | 4.882 | 58.499 | 35.236 | 1.00 | 24.44 |
| ATOM | 2802 | N | LEU | A | 369 | 0 | 0.392 | 57.332 | 34.446 | 1.00 | 28.81 |
| ATOM | 2803 | CA | LEU | A | 369 | 0 | −0.753 | 56.671 | 33.834 | 1.00 | 29.65 |
| ATOM | 2804 | C | LEU | A | 369 | 0 | −0.238 | 55.398 | 33.162 | 1.00 | 28.29 |
| ATOM | 2805 | O | LEU | A | 369 | 0 | 0.875 | 55.356 | 32.660 | 1.00 | 25.59 |
| ATOM | 2806 | CB | LEU | A | 369 | 0 | −1.333 | 57.668 | 32.821 | 1.00 | 30.27 |
| ATOM | 2807 | CG | LEU | A | 369 | 0 | −1.800 | 58.998 | 33.456 | 1.00 | 32.06 |
| ATOM | 2808 | CD1 | LEU | A | 369 | 0 | −2.220 | 59.979 | 32.370 | 1.00 | 31.87 |
| ATOM | 2809 | CD2 | LEU | A | 369 | 0 | −2.932 | 58.787 | 34.455 | 1.00 | 30.89 |
| ATOM | 2810 | N | PRO | A | 370 | 0 | −1.054 | 54.361 | 33.157 | 1.00 | 27.87 |
| ATOM | 2811 | CA | PRO | A | 370 | 0 | −2.396 | 54.379 | 33.688 | 1.00 | 26.71 |
| ATOM | 2812 | C | PRO | A | 370 | 0 | −2.513 | 54.112 | 35.169 | 1.00 | 26.73 |
| ATOM | 2813 | O | PRO | A | 370 | 0 | −1.872 | 53.184 | 35.668 | 1.00 | 26.55 |
| ATOM | 2814 | CB | PRO | A | 370 | 0 | −3.126 | 53.222 | 32.958 | 1.00 | 27.28 |
| ATOM | 2815 | CG | PRO | A | 370 | 0 | −2.003 | 52.317 | 32.557 | 1.00 | 27.38 |
| ATOM | 2816 | CD | PRO | A | 370 | 0 | −0.720 | 53.102 | 32.482 | 1.00 | 27.24 |
| ATOM | 2817 | N | ALA | A | 371 | 0 | −3.414 | 54.810 | 35.870 | 1.00 | 26.16 |
| ATOM | 2818 | CA | ALA | A | 371 | 0 | −3.581 | 54.556 | 37.302 | 1.00 | 25.73 |
| ATOM | 2819 | C | ALA | A | 371 | 0 | −3.892 | 53.103 | 37.616 | 1.00 | 24.59 |
| ATOM | 2820 | O | ALA | A | 371 | 0 | −4.758 | 52.533 | 36.946 | 1.00 | 25.05 |
| ATOM | 2821 | CB | ALA | A | 371 | 0 | −4.718 | 55.394 | 37.903 | 1.00 | 26.42 |
| ATOM | 2822 | N | GLY | A | 372 | 0 | −3.261 | 52.524 | 38.625 | 1.00 | 22.47 |
| ATOM | 2823 | CA | GLY | A | 372 | 0 | −3.519 | 51.187 | 39.087 | 1.00 | 21.06 |
| ATOM | 2824 | C | GLY | A | 372 | 0 | −2.691 | 50.096 | 38.427 | 1.00 | 23.01 |
| ATOM | 2825 | O | GLY | A | 372 | 0 | −2.758 | 48.928 | 38.831 | 1.00 | 23.85 |
| ATOM | 2826 | N | SER | A | 373 | 0 | −1.910 | 50.428 | 37.421 | 1.00 | 23.30 |
| ATOM | 2827 | CA | SER | A | 373 | 0 | −1.054 | 49.459 | 36.736 | 1.00 | 24.36 |
| ATOM | 2828 | C | SER | A | 373 | 0 | 0.429 | 49.746 | 36.919 | 1.00 | 24.76 |
| ATOM | 2829 | O | SER | A | 373 | 0 | 1.257 | 49.103 | 36.270 | 1.00 | 25.75 |
| ATOM | 2830 | CB | SER | A | 373 | 0 | −1.371 | 49.584 | 35.233 | 1.00 | 23.25 |
| ATOM | 2831 | OG | SER | A | 373 | 0 | −2.638 | 49.014 | 34.952 | 1.00 | 23.80 |
| ATOM | 2832 | N | VAL | A | 374 | 0 | 0.779 | 50.799 | 37.657 | 1.00 | 23.87 |
| ATOM | 2833 | CA | VAL | A | 374 | 0 | 2.176 | 51.255 | 37.706 | 1.00 | 22.95 |
| ATOM | 2834 | C | VAL | A | 374 | 0 | 2.739 | 51.109 | 39.105 | 1.00 | 21.72 |
| ATOM | 2835 | O | VAL | A | 374 | 0 | 2.093 | 51.518 | 40.059 | 1.00 | 21.03 |
| ATOM | 2836 | CB | VAL | A | 374 | 0 | 2.317 | 52.687 | 37.169 | 1.00 | 23.05 |
| ATOM | 2837 | CG1 | VAL | A | 374 | 0 | 3.720 | 53.273 | 37.323 | 1.00 | 24.13 |
| ATOM | 2838 | CG2 | VAL | A | 374 | 0 | 1.945 | 52.771 | 35.698 | 1.00 | 21.58 |
| ATOM | 2839 | N | TYR | A | 375 | 0 | 3.862 | 50.402 | 39.246 | 1.00 | 20.52 |
| ATOM | 2840 | CA | TYR | A | 375 | 0 | 4.445 | 50.184 | 40.573 | 1.00 | 22.02 |
| ATOM | 2841 | C | TYR | A | 375 | 0 | 5.873 | 50.743 | 40.549 | 1.00 | 22.56 |
| ATOM | 2842 | O | TYR | A | 375 | 0 | 6.665 | 50.524 | 39.639 | 1.00 | 21.82 |
| ATOM | 2843 | CB | TYR | A | 375 | 0 | 4.467 | 48.729 | 41.067 | 1.00 | 21.98 |
| ATOM | 2844 | CG | TYR | A | 375 | 0 | 3.042 | 48.217 | 41.226 | 1.00 | 24.04 |
| ATOM | 2845 | CD1 | TYR | A | 375 | 0 | 2.398 | 48.261 | 42.445 | 1.00 | 23.57 |
| ATOM | 2846 | CD2 | TYR | A | 375 | 0 | 2.339 | 47.760 | 40.115 | 1.00 | 24.92 |
| ATOM | 2847 | CE1 | TYR | A | 375 | 0 | 1.100 | 47.831 | 42.575 | 1.00 | 25.65 |
| ATOM | 2848 | CE2 | TYR | A | 375 | 0 | 1.034 | 47.327 | 40.220 | 1.00 | 25.89 |
| ATOM | 2849 | CZ | TYR | A | 375 | 0 | 0.429 | 47.352 | 41.464 | 1.00 | 26.65 |
| ATOM | 2850 | OH | TYR | A | 375 | 0 | −0.869 | 46.916 | 41.593 | 1.00 | 27.26 |
| ATOM | 2851 | N | GLU | A | 376 | 0 | 6.130 | 51.563 | 41.546 | 1.00 | 22.36 |
| ATOM | 2852 | CA | GLU | A | 376 | 0 | 7.403 | 52.214 | 41.718 | 1.00 | 23.62 |
| ATOM | 2853 | C | GLU | A | 376 | 0 | 8.411 | 51.289 | 42.387 | 1.00 | 22.40 |
| ATOM | 2854 | O | GLU | A | 376 | 0 | 8.062 | 50.578 | 43.324 | 1.00 | 21.88 |
| ATOM | 2855 | CB | GLU | A | 376 | 0 | 7.211 | 53.465 | 42.614 | 1.00 | 25.13 |
| ATOM | 2856 | CG | GLU | A | 376 | 0 | 8.500 | 54.255 | 42.720 | 1.00 | 27.91 |
| ATOM | 2857 | CD | GLU | A | 376 | 0 | 8.376 | 55.725 | 43.046 | 1.00 | 29.20 |
| ATOM | 2858 | OE1 | GLU | A | 376 | 0 | 7.247 | 56.268 | 43.109 | 1.00 | 30.01 |
| ATOM | 2859 | OE2 | GLU | A | 376 | 0 | 9.458 | 56.336 | 43.219 | 1.00 | 28.05 |
| ATOM | 2860 | N | LEU | A | 377 | 0 | 9.669 | 51.353 | 41.954 | 1.00 | 21.23 |
| ATOM | 2861 | CA | LEU | A | 377 | 0 | 10.705 | 50.535 | 42.626 | 1.00 | 19.95 |
| ATOM | 2862 | C | LEU | A | 377 | 0 | 11.838 | 51.478 | 42.982 | 1.00 | 20.30 |
| ATOM | 2863 | O | LEU | A | 377 | 0 | 12.220 | 52.350 | 42.197 | 1.00 | 20.12 |
| ATOM | 2864 | CB | LEU | A | 377 | 0 | 11.129 | 49.419 | 41.692 | 1.00 | 20.77 |
| ATOM | 2865 | CG | LEU | A | 377 | 0 | 10.668 | 47.964 | 41.818 | 1.00 | 20.49 |
| ATOM | 2866 | CD1 | LEU | A | 377 | 0 | 9.439 | 47.739 | 42.629 | 1.00 | 17.77 |
| ATOM | 2867 | CD2 | LEU | A | 377 | 0 | 10.617 | 47.242 | 40.483 | 1.00 | 19.28 |
| ATOM | 2868 | N | PRO | A | 378 | 0 | 12.407 | 51.334 | 44.162 | 1.00 | 19.69 |
| ATOM | 2869 | CA | PRO | A | 378 | 0 | 13.523 | 52.117 | 44.631 | 1.00 | 19.91 |
| ATOM | 2870 | C | PRO | A | 378 | 0 | 14.797 | 51.650 | 43.937 | 1.00 | 19.81 |
| ATOM | 2871 | O | PRO | A | 378 | 0 | 14.795 | 50.645 | 43.241 | 1.00 | 17.74 |
| ATOM | 2872 | CB | PRO | A | 378 | 0 | 13.611 | 51.893 | 46.157 | 1.00 | 20.21 |
| ATOM | 2873 | CG | PRO | A | 378 | 0 | 12.957 | 50.546 | 46.291 | 1.00 | 20.73 |
| ATOM | 2874 | CD | PRO | A | 378 | 0 | 12.050 | 50.292 | 45.114 | 1.00 | 19.74 |
| ATOM | 2875 | N | ARG | A | 379 | 0 | 15.877 | 52.410 | 44.059 | 1.00 | 19.68 |
| ATOM | 2876 | CA | ARG | A | 379 | 0 | 17.172 | 52.135 | 43.449 | 1.00 | 18.58 |
| ATOM | 2877 | C | ARG | A | 379 | 0 | 18.027 | 51.129 | 44.193 | 1.00 | 18.68 |
| ATOM | 2878 | O | ARG | A | 379 | 0 | 18.151 | 51.126 | 45.432 | 1.00 | 17.60 |

APPENDIX 1-continued

| | | | | | | | | | | |
|---|---|---|---|---|---|---|---|---|---|---|
| ATOM | 2879 | CB | ARG | A | 379 | 0 | 17.946 | 53.487 | 43.431 | 1.00 | 18.33 |
| ATOM | 2880 | CG | ARG | A | 379 | 0 | 19.406 | 53.348 | 43.030 | 1.00 | 19.33 |
| ATOM | 2881 | CD | ARG | A | 379 | 0 | 20.026 | 54.710 | 42.729 | 1.00 | 19.06 |
| ATOM | 2882 | NE | ARG | A | 379 | 0 | 21.413 | 54.561 | 42.295 | 1.00 | 16.65 |
| ATOM | 2883 | CZ | ARG | A | 379 | 0 | 21.794 | 54.681 | 41.031 | 1.00 | 15.60 |
| ATOM | 2884 | NH1 | ARG | A | 379 | 0 | 20.964 | 54.904 | 40.038 | 1.00 | 14.29 |
| ATOM | 2885 | NH2 | ARG | A | 379 | 0 | 23.096 | 54.505 | 40.783 | 1.00 | 17.29 |
| ATOM | 2886 | N | ASN | A | 380 | 0 | 18.701 | 50.263 | 43.441 | 1.00 | 20.11 |
| ATOM | 2887 | CA | ASN | A | 380 | 0 | 19.658 | 49.328 | 44.011 | 1.00 | 21.97 |
| ATOM | 2888 | C | ASN | A | 380 | 0 | 19.129 | 48.604 | 45.227 | 1.00 | 22.44 |
| ATOM | 2889 | O | ASN | A | 380 | 0 | 19.712 | 48.630 | 46.317 | 1.00 | 22.53 |
| ATOM | 2890 | CB | ASN | A | 380 | 0 | 20.995 | 50.045 | 44.345 | 1.00 | 23.30 |
| ATOM | 2891 | CG | ASN | A | 380 | 0 | 21.860 | 50.231 | 43.107 | 1.00 | 25.83 |
| ATOM | 2892 | OD1 | ASN | A | 380 | 0 | 22.636 | 51.186 | 42.877 | 1.00 | 27.14 |
| ATOM | 2893 | ND2 | ASN | A | 380 | 0 | 21.767 | 49.271 | 42.185 | 1.00 | 24.91 |
| ATOM | 2894 | N | GLN | A | 381 | 0 | 17.974 | 47.936 | 45.097 | 1.00 | 21.39 |
| ATOM | 2895 | CA | GLN | A | 381 | 0 | 17.468 | 47.162 | 46.220 | 1.00 | 20.88 |
| ATOM | 2896 | C | GLN | A | 381 | 0 | 17.169 | 45.760 | 45.679 | 1.00 | 19.96 |
| ATOM | 2897 | O | GLN | A | 381 | 0 | 17.000 | 45.635 | 44.471 | 1.00 | 19.90 |
| ATOM | 2898 | CB | GLN | A | 381 | 0 | 16.219 | 47.722 | 46.871 | 1.00 | 22.84 |
| ATOM | 2899 | CG | GLN | A | 381 | 0 | 16.326 | 49.172 | 47.318 | 1.00 | 27.28 |
| ATOM | 2900 | CD | GLN | A | 381 | 0 | 16.065 | 49.297 | 48.792 | 1.00 | 30.24 |
| ATOM | 2901 | OE1 | GLN | A | 381 | 0 | 15.067 | 49.917 | 49.171 | 1.00 | 34.48 |
| ATOM | 2902 | NE2 | GLN | A | 381 | 0 | 16.929 | 48.742 | 49.611 | 1.00 | 30.80 |
| ATOM | 2903 | N | VAL | A | 382 | 0 | 17.046 | 44.825 | 46.594 | 1.00 | 18.67 |
| ATOM | 2904 | CA | VAL | A | 382 | 0 | 16.665 | 43.472 | 46.248 | 1.00 | 18.98 |
| ATOM | 2905 | C | VAL | A | 382 | 0 | 15.139 | 43.327 | 46.212 | 1.00 | 19.75 |
| ATOM | 2906 | O | VAL | A | 382 | 0 | 14.443 | 43.550 | 47.225 | 1.00 | 18.76 |
| ATOM | 2907 | CB | VAL | A | 382 | 0 | 17.252 | 42.491 | 47.278 | 1.00 | 19.03 |
| ATOM | 2908 | CG1 | VAL | A | 382 | 0 | 16.811 | 41.065 | 46.960 | 1.00 | 18.87 |
| ATOM | 2909 | CG2 | VAL | A | 382 | 0 | 18.779 | 42.637 | 47.344 | 1.00 | 17.54 |
| ATOM | 2910 | N | VAL | A | 383 | 0 | 14.601 | 42.954 | 45.046 | 1.00 | 17.58 |
| ATOM | 2911 | CA | VAL | A | 383 | 0 | 13.151 | 42.715 | 45.037 | 1.00 | 17.76 |
| ATOM | 2912 | C | VAL | A | 383 | 0 | 12.777 | 41.254 | 44.883 | 1.00 | 17.50 |
| ATOM | 2913 | O | VAL | A | 383 | 0 | 13.348 | 40.472 | 44.153 | 1.00 | 16.42 |
| ATOM | 2914 | CB | VAL | A | 383 | 0 | 12.306 | 43.626 | 44.145 | 1.00 | 17.69 |
| ATOM | 2915 | CG1 | VAL | A | 383 | 0 | 13.111 | 44.759 | 43.585 | 1.00 | 15.33 |
| ATOM | 2916 | CG2 | VAL | A | 383 | 0 | 11.400 | 43.009 | 43.126 | 1.00 | 17.79 |
| ATOM | 2917 | N | GLU | A | 384 | 0 | 11.743 | 40.861 | 45.638 | 1.00 | 18.47 |
| ATOM | 2918 | CA | GLU | A | 384 | 0 | 11.173 | 39.529 | 45.542 | 1.00 | 18.27 |
| ATOM | 2919 | C | GLU | A | 384 | 0 | 9.711 | 39.683 | 45.096 | 1.00 | 18.94 |
| ATOM | 2920 | O | GLU | A | 384 | 0 | 8.956 | 40.311 | 45.816 | 1.00 | 19.06 |
| ATOM | 2921 | CB | GLU | A | 384 | 0 | 11.253 | 38.764 | 46.852 | 1.00 | 17.12 |
| ATOM | 2922 | CG | GLU | A | 384 | 0 | 10.717 | 37.345 | 46.738 | 1.00 | 17.52 |
| ATOM | 2923 | CD | GLU | A | 384 | 0 | 10.979 | 36.551 | 47.998 | 1.00 | 19.10 |
| ATOM | 2924 | OE1 | GLU | A | 384 | 0 | 12.101 | 36.050 | 48.218 | 1.00 | 20.69 |
| ATOM | 2925 | OE2 | GLU | A | 384 | 0 | 10.018 | 36.405 | 48.773 | 1.00 | 21.22 |
| ATOM | 2926 | N | LEU | A | 385 | 0 | 9.326 | 39.182 | 43.948 | 1.00 | 19.78 |
| ATOM | 2927 | CA | LEU | A | 385 | 0 | 7.966 | 39.153 | 43.463 | 1.00 | 21.07 |
| ATOM | 2928 | C | LEU | A | 385 | 0 | 7.391 | 37.738 | 43.591 | 1.00 | 20.91 |
| ATOM | 2929 | O | LEU | A | 385 | 0 | 8.043 | 36.790 | 43.113 | 1.00 | 21.40 |
| ATOM | 2930 | CB | LEU | A | 385 | 0 | 7.881 | 39.466 | 41.959 | 1.00 | 20.92 |
| ATOM | 2931 | CG | LEU | A | 385 | 0 | 8.393 | 40.795 | 41.457 | 1.00 | 23.75 |
| ATOM | 2932 | CD1 | LEU | A | 385 | 0 | 8.118 | 40.984 | 39.962 | 1.00 | 23.01 |
| ATOM | 2933 | CD2 | LEU | A | 385 | 0 | 7.827 | 41.977 | 42.244 | 1.00 | 22.40 |
| ATOM | 2934 | N | VAL | A | 386 | 0 | 6.182 | 37.574 | 44.099 | 1.00 | 20.91 |
| ATOM | 2935 | CA | VAL | A | 386 | 0 | 5.510 | 36.274 | 44.189 | 1.00 | 19.03 |
| ATOM | 2936 | C | VAL | A | 386 | 0 | 4.228 | 36.334 | 43.356 | 1.00 | 21.11 |
| ATOM | 2937 | O | VAL | A | 386 | 0 | 3.465 | 37.326 | 43.516 | 1.00 | 20.56 |
| ATOM | 2938 | CB | VAL | A | 386 | 0 | 5.159 | 35.967 | 45.654 | 1.00 | 20.91 |
| ATOM | 2939 | CG1 | VAL | A | 386 | 0 | 4.518 | 34.575 | 45.739 | 1.00 | 20.40 |
| ATOM | 2940 | CG2 | VAL | A | 386 | 0 | 6.321 | 36.044 | 46.625 | 1.00 | 19.89 |
| ATOM | 2941 | N | VAL | A | 387 | 0 | 4.011 | 35.469 | 42.358 | 1.00 | 20.02 |
| ATOM | 2942 | CA | VAL | A | 387 | 0 | 2.817 | 35.515 | 41.491 | 1.00 | 20.83 |
| ATOM | 2943 | C | VAL | A | 387 | 0 | 2.119 | 34.152 | 41.385 | 1.00 | 21.15 |
| ATOM | 2944 | O | VAL | A | 387 | 0 | 2.369 | 33.285 | 40.528 | 1.00 | 19.97 |
| ATOM | 2945 | CB | VAL | A | 387 | 0 | 3.163 | 36.076 | 40.104 | 1.00 | 20.91 |
| ATOM | 2946 | CG1 | VAL | A | 387 | 0 | 1.917 | 36.472 | 39.297 | 1.00 | 22.49 |
| ATOM | 2947 | CG2 | VAL | A | 387 | 0 | 3.959 | 37.393 | 40.171 | 1.00 | 22.24 |
| ATOM | 2948 | N | PRO | A | 388 | 0 | 1.262 | 33.832 | 42.358 | 1.00 | 20.55 |
| ATOM | 2949 | CA | PRO | A | 388 | 0 | 0.570 | 32.548 | 42.483 | 1.00 | 20.93 |
| ATOM | 2950 | C | PRO | A | 388 | 0 | −0.271 | 32.226 | 41.264 | 1.00 | 20.76 |
| ATOM | 2951 | O | PRO | A | 388 | 0 | −0.928 | 33.118 | 40.715 | 1.00 | 19.53 |
| ATOM | 2952 | CB | PRO | A | 388 | 0 | −0.310 | 32.559 | 43.757 | 1.00 | 20.54 |
| ATOM | 2953 | CG | PRO | A | 388 | 0 | 0.280 | 33.766 | 44.482 | 1.00 | 21.86 |
| ATOM | 2954 | CD | PRO | A | 388 | 0 | 0.841 | 34.707 | 43.438 | 1.00 | 20.83 |
| ATOM | 2955 | N | ALA | A | 389 | 0 | −0.160 | 30.986 | 40.807 | 1.00 | 21.68 |
| ATOM | 2956 | CA | ALA | A | 389 | 0 | −0.983 | 30.617 | 39.640 | 1.00 | 24.20 |
| ATOM | 2957 | C | ALA | A | 389 | 0 | −2.394 | 30.320 | 40.148 | 1.00 | 25.02 |

APPENDIX 1-continued

| ATOM | 2958 | O   | ALA | A | 389 | 0 | -2.619  | 30.162 | 41.350 | 1.00 | 24.19 |
|------|------|-----|-----|---|-----|---|---------|--------|--------|------|-------|
| ATOM | 2959 | CB  | ALA | A | 389 | 0 | -0.383  | 29.403 | 38.968 | 1.00 | 23.67 |
| ATOM | 2960 | N   | GLY | A | 390 | 0 | -3.309  | 30.143 | 39.222 | 1.00 | 28.43 |
| ATOM | 2961 | CA  | GLY | A | 390 | 0 | -4.713  | 29.811 | 39.539 | 1.00 | 28.47 |
| ATOM | 2962 | C   | GLY | A | 390 | 0 | -5.624  | 30.325 | 38.431 | 1.00 | 28.63 |
| ATOM | 2963 | O   | GLY | A | 390 | 0 | -6.512  | 29.630 | 37.937 | 1.00 | 31.26 |
| ATOM | 2964 | N   | VAL | A | 391 | 0 | -5.402  | 31.531 | 37.961 | 1.00 | 27.11 |
| ATOM | 2965 | CA  | VAL | A | 391 | 0 | -6.234  | 32.164 | 36.962 | 1.00 | 26.51 |
| ATOM | 2966 | C   | VAL | A | 391 | 0 | -6.246  | 31.377 | 35.666 | 1.00 | 29.59 |
| ATOM | 2967 | O   | VAL | A | 391 | 0 | -5.274  | 30.775 | 35.181 | 1.00 | 30.61 |
| ATOM | 2968 | CB  | VAL | A | 391 | 0 | -5.835  | 33.634 | 36.788 | 1.00 | 25.83 |
| ATOM | 2969 | CG1 | VAL | A | 391 | 0 | -4.584  | 33.787 | 35.937 | 1.00 | 24.18 |
| ATOM | 2970 | CG2 | VAL | A | 391 | 0 | -7.017  | 34.419 | 36.219 | 1.00 | 24.11 |
| ATOM | 2971 | N   | LEU | A | 392 | 0 | -7.439  | 31.392 | 35.058 | 1.00 | 30.83 |
| ATOM | 2972 | CA  | LEU | A | 392 | 0 | -7.705  | 30.604 | 33.867 | 1.00 | 30.29 |
| ATOM | 2973 | C   | LEU | A | 392 | 0 | -6.809  | 31.004 | 32.710 | 1.00 | 27.38 |
| ATOM | 2974 | O   | LEU | A | 392 | 0 | -6.316  | 32.113 | 32.665 | 1.00 | 24.62 |
| ATOM | 2975 | CB  | LEU | A | 392 | 0 | -9.173  | 30.726 | 33.436 | 1.00 | 32.58 |
| ATOM | 2976 | CG  | LEU | A | 392 | 0 | -9.711  | 32.126 | 33.189 | 1.00 | 33.97 |
| ATOM | 2977 | CD1 | LEU | A | 392 | 0 | -9.411  | 32.626 | 31.786 | 1.00 | 34.78 |
| ATOM | 2978 | CD2 | LEU | A | 392 | 0 | -11.225 | 32.122 | 33.463 | 1.00 | 36.03 |
| ATOM | 2979 | N   | GLY | A | 393 | 0 | -6.725  | 30.074 | 31.754 | 1.00 | 26.24 |
| ATOM | 2980 | CA  | GLY | A | 393 | 0 | -5.936  | 30.302 | 30.554 | 1.00 | 25.54 |
| ATOM | 2981 | C   | GLY | A | 393 | 0 | -4.458  | 29.994 | 30.710 | 1.00 | 25.81 |
| ATOM | 2982 | O   | GLY | A | 393 | 0 | -3.686  | 30.361 | 29.820 | 1.00 | 26.67 |
| ATOM | 2983 | N   | GLY | A | 394 | 0 | -4.033  | 29.379 | 31.803 | 1.00 | 25.84 |
| ATOM | 2984 | CA  | GLY | A | 394 | 0 | -2.615  | 29.112 | 32.035 | 1.00 | 25.94 |
| ATOM | 2985 | C   | GLY | A | 394 | 0 | -2.140  | 27.844 | 31.348 | 1.00 | 26.00 |
| ATOM | 2986 | O   | GLY | A | 394 | 0 | -2.884  | 27.193 | 30.625 | 1.00 | 25.18 |
| ATOM | 2987 | N   | PRO | A | 395 | 0 | -0.860  | 27.527 | 31.517 | 1.00 | 24.26 |
| ATOM | 2988 | CA  | PRO | A | 395 | 0 | 0.051   | 28.258 | 32.364 | 1.00 | 21.79 |
| ATOM | 2989 | C   | PRO | A | 395 | 0 | 0.517   | 29.518 | 31.660 | 1.00 | 19.29 |
| ATOM | 2990 | O   | PRO | A | 395 | 0 | 0.704   | 29.597 | 30.445 | 1.00 | 17.41 |
| ATOM | 2991 | CB  | PRO | A | 395 | 0 | 1.159   | 27.279 | 32.794 | 1.00 | 22.52 |
| ATOM | 2992 | CG  | PRO | A | 395 | 0 | 1.062   | 26.223 | 31.758 | 1.00 | 24.35 |
| ATOM | 2993 | CD  | PRO | A | 395 | 0 | -0.241  | 26.312 | 30.973 | 1.00 | 24.87 |
| ATOM | 2994 | N   | HIS | A | 396 | 0 | 0.586   | 30.591 | 32.451 | 1.00 | 16.97 |
| ATOM | 2995 | CA  | HIS | A | 396 | 0 | 0.970   | 31.917 | 31.980 | 1.00 | 15.05 |
| ATOM | 2996 | C   | HIS | A | 396 | 0 | 2.477   | 32.137 | 32.186 | 1.00 | 15.41 |
| ATOM | 2997 | O   | HIS | A | 396 | 0 | 3.039   | 32.025 | 33.275 | 1.00 | 14.21 |
| ATOM | 2998 | CB  | HIS | A | 396 | 0 | 0.288   | 32.989 | 32.842 | 1.00 | 15.40 |
| ATOM | 2999 | CG  | HIS | A | 396 | 0 | -1.224  | 32.924 | 32.737 | 1.00 | 18.23 |
| ATOM | 3000 | ND1 | HIS | A | 396 | 0 | -1.942  | 33.504 | 31.702 | 1.00 | 16.23 |
| ATOM | 3001 | CD2 | HIS | A | 396 | 0 | -2.109  | 32.319 | 33.557 | 1.00 | 17.00 |
| ATOM | 3002 | CE1 | HIS | A | 396 | 0 | -3.218  | 33.262 | 31.906 | 1.00 | 18.22 |
| ATOM | 3003 | NE2 | HIS | A | 396 | 0 | -3.343  | 32.526 | 33.014 | 1.00 | 19.08 |
| ATOM | 3004 | N   | PRO | A | 397 | 0 | 3.143   | 32.403 | 31.090 | 1.00 | 14.69 |
| ATOM | 3005 | CA  | PRO | A | 397 | 0 | 4.593   | 32.617 | 31.080 | 1.00 | 16.91 |
| ATOM | 3006 | C   | PRO | A | 397 | 0 | 4.818   | 34.129 | 31.202 | 1.00 | 17.59 |
| ATOM | 3007 | O   | PRO | A | 397 | 0 | 4.524   | 34.843 | 30.235 | 1.00 | 17.59 |
| ATOM | 3008 | CB  | PRO | A | 397 | 0 | 5.076   | 32.040 | 29.757 | 1.00 | 16.63 |
| ATOM | 3009 | CG  | PRO | A | 397 | 0 | 3.785   | 31.844 | 28.978 | 1.00 | 17.83 |
| ATOM | 3010 | CD  | PRO | A | 397 | 0 | 2.620   | 32.464 | 29.736 | 1.00 | 14.36 |
| ATOM | 3011 | N   | PHE | A | 398 | 0 | 5.242   | 34.590 | 32.377 | 1.00 | 16.39 |
| ATOM | 3012 | CA  | PHE | A | 398 | 0 | 5.462   | 36.019 | 32.529 | 1.00 | 15.95 |
| ATOM | 3013 | C   | PHE | A | 398 | 0 | 6.906   | 36.365 | 32.168 | 1.00 | 15.74 |
| ATOM | 3014 | O   | PHE | A | 398 | 0 | 7.846   | 35.619 | 32.444 | 1.00 | 15.78 |
| ATOM | 3015 | CB  | PHE | A | 398 | 0 | 5.173   | 36.455 | 33.963 | 1.00 | 17.20 |
| ATOM | 3016 | CG  | PHE | A | 398 | 0 | 3.817   | 37.073 | 34.169 | 1.00 | 19.23 |
| ATOM | 3017 | CD1 | PHE | A | 398 | 0 | 2.673   | 36.299 | 34.005 | 1.00 | 19.58 |
| ATOM | 3018 | CD2 | PHE | A | 398 | 0 | 3.688   | 38.403 | 34.537 | 1.00 | 19.42 |
| ATOM | 3019 | CE1 | PHE | A | 398 | 0 | 1.409   | 36.832 | 34.198 | 1.00 | 19.83 |
| ATOM | 3020 | CE2 | PHE | A | 398 | 0 | 2.405   | 38.933 | 34.709 | 1.00 | 21.46 |
| ATOM | 3021 | CZ  | PHE | A | 398 | 0 | 1.260   | 38.162 | 34.539 | 1.00 | 19.65 |
| ATOM | 3022 | N   | HIS | A | 399 | 0 | 7.080   | 37.562 | 31.640 | 1.00 | 14.77 |
| ATOM | 3023 | CA  | HIS | A | 399 | 0 | 8.374   | 38.089 | 31.333 | 1.00 | 14.75 |
| ATOM | 3024 | C   | HIS | A | 399 | 0 | 8.580   | 39.496 | 31.872 | 1.00 | 17.67 |
| ATOM | 3025 | O   | HIS | A | 399 | 0 | 7.635   | 40.308 | 31.925 | 1.00 | 18.29 |
| ATOM | 3026 | CB  | HIS | A | 399 | 0 | 8.582   | 37.968 | 29.861 | 1.00 | 14.01 |
| ATOM | 3027 | CG  | HIS | A | 399 | 0 | 8.747   | 39.105 | 28.962 | 1.00 | 16.26 |
| ATOM | 3028 | ND1 | HIS | A | 399 | 0 | 9.957   | 39.511 | 28.446 | 1.00 | 15.35 |
| ATOM | 3029 | CD2 | HIS | A | 399 | 0 | 7.788   | 39.903 | 28.386 | 1.00 | 17.58 |
| ATOM | 3030 | CE1 | HIS | A | 399 | 0 | 9.764   | 40.507 | 27.593 | 1.00 | 15.61 |
| ATOM | 3031 | NE2 | HIS | A | 399 | 0 | 8.457   | 40.770 | 27.548 | 1.00 | 17.52 |
| ATOM | 3032 | N   | LEU | A | 400 | 0 | 9.837   | 39.771 | 32.201 | 1.00 | 15.57 |
| ATOM | 3033 | CA  | LEU | A | 400 | 0 | 10.220  | 41.061 | 32.745 | 1.00 | 16.93 |
| ATOM | 3034 | C   | LEU | A | 400 | 0 | 11.207  | 41.732 | 31.788 | 1.00 | 16.51 |
| ATOM | 3035 | O   | LEU | A | 400 | 0 | 12.268  | 41.175 | 31.510 | 1.00 | 15.77 |
| ATOM | 3036 | CB  | LEU | A | 400 | 0 | 10.913  | 40.825 | 34.084 | 1.00 | 18.17 |

APPENDIX 1-continued

| ATOM | 3037 | CG  | LEU | A | 400 | 0 | 10.877 | 41.741 | 35.288 | 1.00 | 21.27 |
| ATOM | 3038 | CD1 | LEU | A | 400 | 0 | 12.130 | 41.638 | 36.151 | 1.00 | 19.27 |
| ATOM | 3039 | CD2 | LEU | A | 400 | 0 | 10.536 | 43.166 | 34.926 | 1.00 | 19.86 |
| ATOM | 3040 | N   | HIS | A | 401 | 0 | 10.945 | 42.916 | 31.321 | 1.00 | 14.34 |
| ATOM | 3041 | CA  | HIS | A | 401 | 0 | 11.830 | 43.707 | 30.506 | 1.00 | 16.06 |
| ATOM | 3042 | C   | HIS | A | 401 | 0 | 12.924 | 44.300 | 31.428 | 1.00 | 16.15 |
| ATOM | 3043 | O   | HIS | A | 401 | 0 | 12.644 | 44.543 | 32.600 | 1.00 | 13.61 |
| ATOM | 3044 | CB  | HIS | A | 401 | 0 | 11.105 | 44.884 | 29.843 | 1.00 | 13.27 |
| ATOM | 3045 | CG  | HIS | A | 401 | 0 | 10.184 | 44.441 | 28.751 | 1.00 | 14.50 |
| ATOM | 3046 | ND1 | HIS | A | 401 | 0 | 10.201 | 44.973 | 27.479 | 1.00 | 14.96 |
| ATOM | 3047 | CD2 | HIS | A | 401 | 0 |  9.202 | 43.492 | 28.750 | 1.00 | 12.35 |
| ATOM | 3048 | CE1 | HIS | A | 401 | 0 |  9.263 | 44.387 | 26.725 | 1.00 | 12.61 |
| ATOM | 3049 | NE2 | HIS | A | 401 | 0 |  8.677 | 43.507 | 27.492 | 1.00 | 12.41 |
| ATOM | 3050 | N   | GLY | A | 402 | 0 | 14.103 | 44.549 | 30.855 | 1.00 | 15.59 |
| ATOM | 3051 | CA  | GLY | A | 402 | 0 | 15.152 | 45.209 | 31.598 | 1.00 | 15.18 |
| ATOM | 3052 | C   | GLY | A | 402 | 0 | 16.009 | 44.351 | 32.510 | 1.00 | 15.96 |
| ATOM | 3053 | O   | GLY | A | 402 | 0 | 16.927 | 44.898 | 33.170 | 1.00 | 16.30 |
| ATOM | 3054 | N   | HIS | A | 403 | 0 | 15.618 | 43.147 | 32.893 | 1.00 | 12.96 |
| ATOM | 3055 | CA  | HIS | A | 403 | 0 | 16.282 | 42.337 | 33.873 | 1.00 | 15.00 |
| ATOM | 3056 | C   | HIS | A | 403 | 0 | 16.226 | 40.839 | 33.586 | 1.00 | 15.22 |
| ATOM | 3057 | O   | HIS | A | 403 | 0 | 15.253 | 40.381 | 32.971 | 1.00 | 16.16 |
| ATOM | 3058 | CB  | HIS | A | 403 | 0 | 15.525 | 42.478 | 35.227 | 1.00 | 14.13 |
| ATOM | 3059 | CG  | HIS | A | 403 | 0 | 15.571 | 43.829 | 35.827 | 1.00 | 16.69 |
| ATOM | 3060 | ND1 | HIS | A | 403 | 0 | 16.604 | 44.253 | 36.649 | 1.00 | 16.13 |
| ATOM | 3061 | CD2 | HIS | A | 403 | 0 | 14.744 | 44.911 | 35.659 | 1.00 | 15.50 |
| ATOM | 3062 | CE1 | HIS | A | 403 | 0 | 16.425 | 45.520 | 37.002 | 1.00 | 15.02 |
| ATOM | 3063 | NE2 | HIS | A | 403 | 0 | 15.285 | 45.905 | 36.430 | 1.00 | 16.15 |
| ATOM | 3064 | N   | ALA | A | 404 | 0 | 17.138 | 40.054 | 34.113 | 1.00 | 13.71 |
| ATOM | 3065 | CA  | ALA | A | 404 | 0 | 17.039 | 38.607 | 34.158 | 1.00 | 12.60 |
| ATOM | 3066 | C   | ALA | A | 404 | 0 | 16.771 | 38.370 | 35.649 | 1.00 | 12.31 |
| ATOM | 3067 | O   | ALA | A | 404 | 0 | 17.156 | 39.291 | 36.373 | 1.00 | 13.94 |
| ATOM | 3068 | CB  | ALA | A | 404 | 0 | 18.249 | 37.819 | 33.721 | 1.00 | 13.84 |
| ATOM | 3069 | N   | PHE | A | 405 | 0 | 16.085 | 37.356 | 36.126 | 1.00 | 12.21 |
| ATOM | 3070 | CA  | PHE | A | 405 | 0 | 15.813 | 37.235 | 37.559 | 1.00 | 11.64 |
| ATOM | 3071 | C   | PHE | A | 405 | 0 | 16.177 | 35.821 | 38.008 | 1.00 | 12.55 |
| ATOM | 3072 | O   | PHE | A | 405 | 0 | 16.196 | 34.883 | 37.201 | 1.00 | 12.23 |
| ATOM | 3073 | CB  | PHE | A | 405 | 0 | 14.325 | 37.487 | 37.907 | 1.00 | 11.82 |
| ATOM | 3074 | CG  | PHE | A | 405 | 0 | 13.382 | 36.893 | 36.879 | 1.00 | 11.75 |
| ATOM | 3075 | CD1 | PHE | A | 405 | 0 | 13.030 | 35.557 | 36.933 | 1.00 | 10.76 |
| ATOM | 3076 | CD2 | PHE | A | 405 | 0 | 12.917 | 37.663 | 35.824 | 1.00 | 11.55 |
| ATOM | 3077 | CE1 | PHE | A | 405 | 0 | 12.189 | 35.002 | 35.978 | 1.00 | 11.52 |
| ATOM | 3078 | CE2 | PHE | A | 405 | 0 | 12.087 | 37.112 | 34.862 | 1.00 | 13.32 |
| ATOM | 3079 | CZ  | PHE | A | 405 | 0 | 11.692 | 35.767 | 34.946 | 1.00 | 11.45 |
| ATOM | 3080 | N   | SER | A | 406 | 0 | 16.414 | 35.625 | 39.288 | 1.00 | 12.86 |
| ATOM | 3081 | CA  | SER | A | 406 | 0 | 16.660 | 34.286 | 39.796 | 1.00 | 13.43 |
| ATOM | 3082 | C   | SER | A | 406 | 0 | 15.276 | 33.712 | 40.130 | 1.00 | 13.49 |
| ATOM | 3083 | O   | SER | A | 406 | 0 | 14.518 | 34.375 | 40.847 | 1.00 | 10.13 |
| ATOM | 3084 | CB  | SER | A | 406 | 0 | 17.433 | 34.290 | 41.123 | 1.00 | 13.78 |
| ATOM | 3085 | OG  | SER | A | 406 | 0 | 18.708 | 34.834 | 40.938 | 1.00 | 16.72 |
| ATOM | 3086 | N   | VAL | A | 407 | 0 | 15.100 | 32.453 | 39.741 | 1.00 | 14.53 |
| ATOM | 3087 | CA  | VAL | A | 407 | 0 | 13.853 | 31.777 | 40.093 | 1.00 | 13.90 |
| ATOM | 3088 | C   | VAL | A | 407 | 0 | 14.160 | 30.943 | 41.325 | 1.00 | 14.53 |
| ATOM | 3089 | O   | VAL | A | 407 | 0 | 14.513 | 29.753 | 41.262 | 1.00 | 14.62 |
| ATOM | 3090 | CB  | VAL | A | 407 | 0 | 13.333 | 30.903 | 38.941 | 1.00 | 16.43 |
| ATOM | 3091 | CG1 | VAL | A | 407 | 0 | 11.969 | 30.317 | 39.341 | 1.00 | 16.69 |
| ATOM | 3092 | CG2 | VAL | A | 407 | 0 | 13.272 | 31.682 | 37.626 | 1.00 | 14.90 |
| ATOM | 3093 | N   | VAL | A | 408 | 0 | 13.971 | 31.544 | 42.485 | 1.00 | 14.32 |
| ATOM | 3094 | CA  | VAL | A | 408 | 0 | 14.173 | 30.947 | 43.780 | 1.00 | 15.47 |
| ATOM | 3095 | C   | VAL | A | 408 | 0 | 13.115 | 29.870 | 44.049 | 1.00 | 16.51 |
| ATOM | 3096 | O   | VAL | A | 408 | 0 | 13.387 | 28.927 | 44.812 | 1.00 | 17.39 |
| ATOM | 3097 | CB  | VAL | A | 408 | 0 | 14.280 | 31.967 | 44.932 | 1.00 | 15.75 |
| ATOM | 3098 | CG1 | VAL | A | 408 | 0 | 15.345 | 33.015 | 44.600 | 1.00 | 14.81 |
| ATOM | 3099 | CG2 | VAL | A | 408 | 0 | 12.952 | 32.693 | 45.189 | 1.00 | 15.99 |
| ATOM | 3100 | N   | ARG | A | 409 | 0 | 11.972 | 29.940 | 43.387 | 1.00 | 16.28 |
| ATOM | 3101 | CA  | ARG | A | 409 | 0 | 10.960 | 28.900 | 43.570 | 1.00 | 17.67 |
| ATOM | 3102 | C   | ARG | A | 409 | 0 | 10.217 | 28.757 | 42.236 | 1.00 | 17.09 |
| ATOM | 3103 | O   | ARG | A | 409 | 0 |  9.585 | 29.698 | 41.763 | 1.00 | 15.25 |
| ATOM | 3104 | CB  | ARG | A | 409 | 0 |  9.993 | 29.143 | 44.718 | 1.00 | 17.87 |
| ATOM | 3105 | CG  | ARG | A | 409 | 0 |  8.796 | 28.188 | 44.663 | 1.00 | 21.12 |
| ATOM | 3106 | CD  | ARG | A | 409 | 0 |  8.008 | 28.181 | 45.945 | 1.00 | 22.10 |
| ATOM | 3107 | NE  | ARG | A | 409 | 0 |  6.801 | 27.370 | 45.955 | 1.00 | 24.80 |
| ATOM | 3108 | CZ  | ARG | A | 409 | 0 |  5.918 | 27.361 | 46.961 | 1.00 | 25.93 |
| ATOM | 3109 | NH1 | ARG | A | 409 | 0 |  4.859 | 26.569 | 46.877 | 1.00 | 27.14 |
| ATOM | 3110 | NH2 | ARG | A | 409 | 0 |  6.068 | 28.117 | 48.046 | 1.00 | 25.44 |
| ATOM | 3111 | N   | SER | A | 410 | 0 | 10.366 | 27.576 | 41.668 | 1.00 | 16.33 |
| ATOM | 3112 | CA  | SER | A | 410 | 0 |  9.802 | 27.245 | 40.373 | 1.00 | 18.33 |
| ATOM | 3113 | C   | SER | A | 410 | 0 |  8.406 | 26.612 | 40.492 | 1.00 | 18.60 |
| ATOM | 3114 | O   | SER | A | 410 | 0 |  7.941 | 26.223 | 41.566 | 1.00 | 16.94 |
| ATOM | 3115 | CB  | SER | A | 410 | 0 | 10.724 | 26.199 | 39.705 | 1.00 | 19.51 |

APPENDIX 1-continued

| ATOM | 3116 | OG | SER | A | 410 | 0 | 11.718 | 26.865 | 38.933 | 1.00 | 20.28 |
|------|------|-----|-----|---|-----|---|--------|--------|--------|------|-------|
| ATOM | 3117 | N | ALA | A | 411 | 0 | 7.754 | 26.551 | 39.343 | 1.00 | 18.19 |
| ATOM | 3118 | CA | ALA | A | 411 | 0 | 6.458 | 25.899 | 39.231 | 1.00 | 19.76 |
| ATOM | 3119 | C | ALA | A | 411 | 0 | 6.667 | 24.406 | 39.474 | 1.00 | 22.62 |
| ATOM | 3120 | O | ALA | A | 411 | 0 | 7.636 | 23.759 | 39.067 | 1.00 | 20.97 |
| ATOM | 3121 | CB | ALA | A | 411 | 0 | 5.873 | 26.075 | 37.841 | 1.00 | 17.13 |
| ATOM | 3122 | N | GLY | A | 412 | 0 | 5.710 | 23.856 | 40.229 | 1.00 | 26.30 |
| ATOM | 3123 | CA | GLY | A | 412 | 0 | 5.714 | 22.442 | 40.558 | 1.00 | 27.05 |
| ATOM | 3124 | C | GLY | A | 412 | 0 | 6.692 | 22.150 | 41.677 | 1.00 | 29.22 |
| ATOM | 3125 | O | GLY | A | 412 | 0 | 6.917 | 20.959 | 41.944 | 1.00 | 32.10 |
| ATOM | 3126 | N | SER | A | 413 | 0 | 7.293 | 23.139 | 42.322 | 1.00 | 28.66 |
| ATOM | 3127 | CA | SER | A | 413 | 0 | 8.223 | 22.871 | 43.400 | 1.00 | 28.58 |
| ATOM | 3128 | C | SER | A | 413 | 0 | 7.757 | 23.600 | 44.642 | 1.00 | 29.64 |
| ATOM | 3129 | O | SER | A | 413 | 0 | 7.279 | 24.735 | 44.524 | 1.00 | 30.66 |
| ATOM | 3130 | CB | SER | A | 413 | 0 | 9.610 | 23.407 | 43.015 | 1.00 | 30.12 |
| ATOM | 3131 | OG | SER | A | 413 | 0 | 10.484 | 23.233 | 44.127 | 1.00 | 31.74 |
| ATOM | 3132 | N | SER | A | 414 | 0 | 7.902 | 23.031 | 45.819 | 1.00 | 29.19 |
| ATOM | 3133 | CA | SER | A | 414 | 0 | 7.523 | 23.753 | 47.033 | 1.00 | 30.71 |
| ATOM | 3134 | C | SER | A | 414 | 0 | 8.762 | 24.124 | 47.834 | 1.00 | 30.51 |
| ATOM | 3135 | O | SER | A | 414 | 0 | 8.746 | 24.453 | 49.017 | 1.00 | 31.90 |
| ATOM | 3136 | CB | SER | A | 414 | 0 | 6.612 | 22.832 | 47.853 | 1.00 | 31.10 |
| ATOM | 3137 | OG | SER | A | 414 | 0 | 7.438 | 21.764 | 48.299 | 1.00 | 34.24 |
| ATOM | 3138 | N | THR | A | 415 | 0 | 9.919 | 24.063 | 47.194 | 1.00 | 30.60 |
| ATOM | 3139 | CA | THR | A | 415 | 0 | 11.194 | 24.336 | 47.860 | 1.00 | 30.60 |
| ATOM | 3140 | C | THR | A | 415 | 0 | 11.819 | 25.614 | 47.291 | 1.00 | 27.71 |
| ATOM | 3141 | O | THR | A | 415 | 0 | 11.582 | 25.998 | 46.137 | 1.00 | 27.49 |
| ATOM | 3142 | CB | THR | A | 415 | 0 | 12.089 | 23.095 | 47.747 | 1.00 | 32.16 |
| ATOM | 3143 | OG1 | THR | A | 415 | 0 | 13.411 | 23.441 | 47.285 | 1.00 | 35.60 |
| ATOM | 3144 | CG2 | THR | A | 415 | 0 | 11.599 | 22.103 | 46.710 | 1.00 | 34.11 |
| ATOM | 3145 | N | TYR | A | 416 | 0 | 12.662 | 26.268 | 48.053 | 1.00 | 24.34 |
| ATOM | 3146 | CA | TYR | A | 416 | 0 | 13.288 | 27.513 | 47.621 | 1.00 | 25.69 |
| ATOM | 3147 | C | TYR | A | 416 | 0 | 14.782 | 27.297 | 47.392 | 1.00 | 24.69 |
| ATOM | 3148 | O | TYR | A | 416 | 0 | 15.364 | 26.603 | 48.211 | 1.00 | 25.96 |
| ATOM | 3149 | CB | TYR | A | 416 | 0 | 13.129 | 28.633 | 48.659 | 1.00 | 23.79 |
| ATOM | 3150 | CG | TYR | A | 416 | 0 | 11.690 | 29.091 | 48.794 | 1.00 | 24.53 |
| ATOM | 3151 | CD1 | TYR | A | 416 | 0 | 10.789 | 28.387 | 49.596 | 1.00 | 24.14 |
| ATOM | 3152 | CD2 | TYR | A | 416 | 0 | 11.230 | 30.219 | 48.131 | 1.00 | 23.99 |
| ATOM | 3153 | CE1 | TYR | A | 416 | 0 | 9.474 | 28.799 | 49.713 | 1.00 | 23.70 |
| ATOM | 3154 | CE2 | TYR | A | 416 | 0 | 9.922 | 30.641 | 48.248 | 1.00 | 23.96 |
| ATOM | 3155 | CZ | TYR | A | 416 | 0 | 9.050 | 29.929 | 49.054 | 1.00 | 23.73 |
| ATOM | 3156 | OH | TYR | A | 416 | 0 | 7.744 | 30.337 | 49.152 | 1.00 | 23.53 |
| ATOM | 3157 | N | ASN | A | 417 | 0 | 15.360 | 27.867 | 46.353 | 1.00 | 22.34 |
| ATOM | 3158 | CA | ASN | A | 417 | 0 | 16.810 | 27.702 | 46.223 | 1.00 | 20.83 |
| ATOM | 3159 | C | ASN | A | 417 | 0 | 17.425 | 29.089 | 46.092 | 1.00 | 20.43 |
| ATOM | 3160 | O | ASN | A | 417 | 0 | 17.247 | 29.761 | 45.082 | 1.00 | 20.00 |
| ATOM | 3161 | CB | ASN | A | 417 | 0 | 17.179 | 26.763 | 45.086 | 1.00 | 19.72 |
| ATOM | 3162 | CG | ASN | A | 417 | 0 | 18.660 | 26.716 | 44.758 | 1.00 | 19.50 |
| ATOM | 3163 | OD1 | ASN | A | 417 | 0 | 19.485 | 27.313 | 45.465 | 1.00 | 20.18 |
| ATOM | 3164 | ND2 | ASN | A | 417 | 0 | 18.981 | 26.043 | 43.660 | 1.00 | 17.21 |
| ATOM | 3165 | N | PHE | A | 418 | 0 | 18.153 | 29.508 | 47.119 | 1.00 | 20.79 |
| ATOM | 3166 | CA | PHE | A | 418 | 0 | 18.831 | 30.797 | 47.049 | 1.00 | 20.77 |
| ATOM | 3167 | C | PHE | A | 418 | 0 | 20.314 | 30.613 | 46.725 | 1.00 | 20.47 |
| ATOM | 3168 | O | PHE | A | 418 | 0 | 20.973 | 31.618 | 46.517 | 1.00 | 19.47 |
| ATOM | 3169 | CB | PHE | A | 418 | 0 | 18.764 | 31.542 | 48.384 | 1.00 | 20.52 |
| ATOM | 3170 | CG | PHE | A | 418 | 0 | 17.332 | 31.821 | 48.753 | 1.00 | 22.19 |
| ATOM | 3171 | CD1 | PHE | A | 418 | 0 | 16.644 | 30.947 | 49.578 | 1.00 | 21.36 |
| ATOM | 3172 | CD2 | PHE | A | 418 | 0 | 16.697 | 32.951 | 48.244 | 1.00 | 21.95 |
| ATOM | 3173 | CE1 | PHE | A | 418 | 0 | 15.320 | 31.208 | 49.919 | 1.00 | 21.64 |
| ATOM | 3174 | CE2 | PHE | A | 418 | 0 | 15.386 | 33.198 | 48.599 | 1.00 | 22.81 |
| ATOM | 3175 | CZ | PHE | A | 418 | 0 | 14.694 | 32.325 | 49.419 | 1.00 | 22.57 |
| ATOM | 3176 | N | VAL | A | 419 | 0 | 20.816 | 29.380 | 46.732 | 1.00 | 19.72 |
| ATOM | 3177 | CA | VAL | A | 419 | 0 | 22.272 | 29.235 | 46.564 | 1.00 | 19.96 |
| ATOM | 3178 | C | VAL | A | 419 | 0 | 22.682 | 29.261 | 45.114 | 1.00 | 20.65 |
| ATOM | 3179 | O | VAL | A | 419 | 0 | 23.634 | 29.875 | 44.671 | 1.00 | 21.02 |
| ATOM | 3180 | CB | VAL | A | 419 | 0 | 22.708 | 27.888 | 47.200 | 1.00 | 21.81 |
| ATOM | 3181 | CG1 | VAL | A | 419 | 0 | 23.954 | 27.291 | 46.588 | 1.00 | 21.97 |
| ATOM | 3182 | CG2 | VAL | A | 419 | 0 | 22.885 | 28.098 | 48.713 | 1.00 | 21.55 |
| ATOM | 3183 | N | ASN | A | 420 | 0 | 21.867 | 28.585 | 44.327 | 1.00 | 19.77 |
| ATOM | 3184 | CA | ASN | A | 420 | 0 | 22.076 | 28.232 | 42.967 | 1.00 | 21.81 |
| ATOM | 3185 | C | ASN | A | 420 | 0 | 21.028 | 28.263 | 41.891 | 1.00 | 20.21 |
| ATOM | 3186 | O | ASN | A | 420 | 0 | 21.046 | 27.407 | 41.004 | 1.00 | 20.13 |
| ATOM | 3187 | CB | ASN | A | 420 | 0 | 22.166 | 26.587 | 43.207 | 1.00 | 21.91 |
| ATOM | 3188 | CG | ASN | A | 420 | 0 | 23.441 | 26.231 | 42.529 | 1.00 | 24.12 |
| ATOM | 3189 | OD1 | ASN | A | 420 | 0 | 23.933 | 25.113 | 42.403 | 1.00 | 26.75 |
| ATOM | 3190 | ND2 | ASN | A | 420 | 0 | 24.051 | 27.318 | 42.027 | 1.00 | 25.42 |
| ATOM | 3191 | N | PRO | A | 421 | 0 | 19.987 | 29.034 | 42.038 | 1.00 | 20.27 |
| ATOM | 3192 | CA | PRO | A | 421 | 0 | 18.808 | 28.951 | 41.183 | 1.00 | 17.57 |
| ATOM | 3193 | C | PRO | A | 421 | 0 | 19.100 | 29.369 | 39.778 | 1.00 | 15.76 |
| ATOM | 3194 | O | PRO | A | 421 | 0 | 19.907 | 30.281 | 39.586 | 1.00 | 15.13 |

APPENDIX 1-continued

| ATOM | 3195 | CB  | PRO | A | 421 | 0 | 17.769 | 29.850 | 41.894 | 1.00 | 19.52 |
| ATOM | 3196 | CG  | PRO | A | 421 | 0 | 18.674 | 30.863 | 42.589 | 1.00 | 19.88 |
| ATOM | 3197 | CD  | PRO | A | 421 | 0 | 19.847 | 30.057 | 43.095 | 1.00 | 20.45 |
| ATOM | 3198 | N   | VAL | A | 422 | 0 | 18.385 | 28.803 | 38.820 | 1.00 | 15.28 |
| ATOM | 3199 | CA  | VAL | A | 422 | 0 | 18.502 | 29.239 | 37.420 | 1.00 | 13.48 |
| ATOM | 3200 | C   | VAL | A | 422 | 0 | 18.157 | 30.721 | 37.397 | 1.00 | 14.53 |
| ATOM | 3201 | O   | VAL | A | 422 | 0 | 17.340 | 31.208 | 38.183 | 1.00 | 14.44 |
| ATOM | 3202 | CB  | VAL | A | 422 | 0 | 17.498 | 28.435 | 36.585 | 1.00 | 15.23 |
| ATOM | 3203 | CG1 | VAL | A | 422 | 0 | 16.032 | 28.747 | 36.937 | 1.00 | 13.85 |
| ATOM | 3204 | CG2 | VAL | A | 422 | 0 | 17.681 | 28.514 | 35.089 | 1.00 | 13.26 |
| ATOM | 3205 | N   | LYS | A | 423 | 0 | 18.691 | 31.447 | 36.451 | 1.00 | 15.35 |
| ATOM | 3206 | CA  | LYS | A | 423 | 0 | 18.366 | 32.831 | 36.189 | 1.00 | 17.23 |
| ATOM | 3207 | C   | LYS | A | 423 | 0 | 17.759 | 32.891 | 34.784 | 1.00 | 16.55 |
| ATOM | 3208 | O   | LYS | A | 423 | 0 | 18.284 | 32.189 | 33.909 | 1.00 | 16.92 |
| ATOM | 3209 | CB  | LYS | A | 423 | 0 | 19.627 | 33.681 | 36.174 | 1.00 | 19.33 |
| ATOM | 3210 | CG  | LYS | A | 423 | 0 | 20.118 | 33.985 | 37.565 | 1.00 | 24.09 |
| ATOM | 3211 | CD  | LYS | A | 423 | 0 | 21.065 | 35.206 | 37.466 | 1.00 | 27.32 |
| ATOM | 3212 | CE  | LYS | A | 423 | 0 | 22.470 | 34.596 | 37.263 | 1.00 | 28.78 |
| ATOM | 3213 | NZ  | LYS | A | 423 | 0 | 23.128 | 34.482 | 38.595 | 1.00 | 29.50 |
| ATOM | 3214 | N   | ARG | A | 424 | 0 | 16.630 | 33.570 | 34.617 | 1.00 | 15.85 |
| ATOM | 3215 | CA  | ARG | A | 424 | 0 | 16.016 | 33.592 | 33.294 | 1.00 | 16.20 |
| ATOM | 3216 | C   | ARG | A | 424 | 0 | 15.235 | 34.890 | 33.105 | 1.00 | 14.86 |
| ATOM | 3217 | O   | ARG | A | 424 | 0 | 15.354 | 35.771 | 33.959 | 1.00 | 14.64 |
| ATOM | 3218 | CB  | ARG | A | 424 | 0 | 15.158 | 32.367 | 32.994 | 1.00 | 16.11 |
| ATOM | 3219 | CG  | ARG | A | 424 | 0 | 14.036 | 31.864 | 33.849 | 1.00 | 14.06 |
| ATOM | 3220 | CD  | ARG | A | 424 | 0 | 13.447 | 30.506 | 33.427 | 1.00 | 11.65 |
| ATOM | 3221 | NE  | ARG | A | 424 | 0 | 13.422 | 30.395 | 31.961 | 1.00 | 9.03 |
| ATOM | 3222 | CZ  | ARG | A | 424 | 0 | 13.312 | 29.234 | 31.319 | 1.00 | 10.63 |
| ATOM | 3223 | NH1 | ARG | A | 424 | 0 | 13.185 | 28.133 | 32.082 | 1.00 | 11.02 |
| ATOM | 3224 | NH2 | ARG | A | 424 | 0 | 13.403 | 29.213 | 29.988 | 1.00 | 8.52 |
| ATOM | 3225 | N   | ASP | A | 425 | 0 | 14.519 | 34.975 | 31.995 | 1.00 | 13.83 |
| ATOM | 3226 | CA  | ASP | A | 425 | 0 | 13.751 | 36.209 | 31.752 | 1.00 | 15.00 |
| ATOM | 3227 | C   | ASP | A | 425 | 0 | 12.298 | 35.929 | 31.359 | 1.00 | 15.65 |
| ATOM | 3228 | O   | ASP | A | 425 | 0 | 11.474 | 36.850 | 31.271 | 1.00 | 15.11 |
| ATOM | 3229 | CB  | ASP | A | 425 | 0 | 14.499 | 37.130 | 30.797 | 1.00 | 12.96 |
| ATOM | 3230 | CG  | ASP | A | 425 | 0 | 14.609 | 36.652 | 29.371 | 1.00 | 14.32 |
| ATOM | 3231 | OD1 | ASP | A | 425 | 0 | 13.697 | 35.957 | 28.818 | 1.00 | 13.30 |
| ATOM | 3232 | OD2 | ASP | A | 425 | 0 | 15.632 | 37.003 | 28.729 | 1.00 | 13.76 |
| ATOM | 3233 | N   | VAL | A | 426 | 0 | 11.883 | 34.675 | 31.206 | 1.00 | 15.21 |
| ATOM | 3234 | CA  | VAL | A | 426 | 0 | 10.530 | 34.229 | 30.984 | 1.00 | 13.92 |
| ATOM | 3235 | C   | VAL | A | 426 | 0 | 10.247 | 33.000 | 31.865 | 1.00 | 13.98 |
| ATOM | 3236 | O   | VAL | A | 426 | 0 | 10.891 | 31.965 | 31.696 | 1.00 | 15.56 |
| ATOM | 3237 | CB  | VAL | A | 426 | 0 | 10.128 | 33.807 | 29.567 | 1.00 | 12.49 |
| ATOM | 3238 | CG1 | VAL | A | 426 | 0 | 8.629  | 33.473 | 29.531 | 1.00 | 13.99 |
| ATOM | 3239 | CG2 | VAL | A | 426 | 0 | 10.390 | 34.874 | 28.536 | 1.00 | 12.37 |
| ATOM | 3240 | N   | VAL | A | 427 | 0 | 9.274  | 33.090 | 32.766 | 1.00 | 12.82 |
| ATOM | 3241 | CA  | VAL | A | 427 | 0 | 8.979  | 31.969 | 33.639 | 1.00 | 12.27 |
| ATOM | 3242 | C   | VAL | A | 427 | 0 | 7.495  | 31.589 | 33.651 | 1.00 | 14.14 |
| ATOM | 3243 | O   | VAL | A | 427 | 0 | 6.594  | 32.426 | 33.682 | 1.00 | 14.10 |
| ATOM | 3244 | CB  | VAL | A | 427 | 0 | 9.458  | 32.315 | 35.056 | 1.00 | 11.46 |
| ATOM | 3245 | CG1 | VAL | A | 427 | 0 | 8.732  | 33.549 | 35.594 | 1.00 | 9.39 |
| ATOM | 3246 | CG2 | VAL | A | 427 | 0 | 9.353  | 31.116 | 35.982 | 1.00 | 10.53 |
| ATOM | 3247 | N   | SER | A | 428 | 0 | 7.229  | 30.282 | 33.622 | 1.00 | 13.74 |
| ATOM | 3248 | CA  | SER | A | 428 | 0 | 5.889  | 29.766 | 33.721 | 1.00 | 15.16 |
| ATOM | 3249 | C   | SER | A | 428 | 0 | 5.445  | 29.878 | 35.171 | 1.00 | 15.48 |
| ATOM | 3250 | O   | SER | A | 428 | 0 | 6.186  | 29.505 | 36.087 | 1.00 | 15.38 |
| ATOM | 3251 | CB  | SER | A | 428 | 0 | 5.776  | 28.323 | 33.206 | 1.00 | 16.37 |
| ATOM | 3252 | OG  | SER | A | 428 | 0 | 4.464  | 27.821 | 33.484 | 1.00 | 17.00 |
| ATOM | 3253 | N   | LEU | A | 429 | 0 | 4.246  | 30.376 | 35.399 | 1.00 | 15.74 |
| ATOM | 3254 | CA  | LEU | A | 429 | 0 | 3.686  | 30.489 | 36.744 | 1.00 | 15.73 |
| ATOM | 3255 | C   | LEU | A | 429 | 0 | 3.035  | 29.184 | 37.198 | 1.00 | 16.41 |
| ATOM | 3256 | O   | LEU | A | 429 | 0 | 2.741  | 29.041 | 38.390 | 1.00 | 15.74 |
| ATOM | 3257 | CB  | LEU | A | 429 | 0 | 2.669  | 31.627 | 36.886 | 1.00 | 14.99 |
| ATOM | 3258 | CG  | LEU | A | 429 | 0 | 3.155  | 33.027 | 36.540 | 1.00 | 16.60 |
| ATOM | 3259 | CD1 | LEU | A | 429 | 0 | 2.043  | 34.042 | 36.862 | 1.00 | 17.78 |
| ATOM | 3260 | CD2 | LEU | A | 429 | 0 | 4.438  | 33.386 | 37.281 | 1.00 | 16.26 |
| ATOM | 3261 | N   | GLY | A | 430 | 0 | 2.913  | 28.218 | 36.295 | 1.00 | 17.70 |
| ATOM | 3262 | CA  | GLY | A | 430 | 0 | 2.419  | 26.904 | 36.701 | 1.00 | 19.84 |
| ATOM | 3263 | C   | GLY | A | 430 | 0 | 0.894  | 26.836 | 36.778 | 1.00 | 20.72 |
| ATOM | 3264 | O   | GLY | A | 430 | 0 | 0.178  | 27.498 | 36.029 | 1.00 | 20.89 |
| ATOM | 3265 | N   | VAL | A | 431 | 0 | 0.428  | 26.056 | 37.729 | 1.00 | 22.04 |
| ATOM | 3266 | CA  | VAL | A | 431 | 0 | -0.956 | 25.713 | 37.966 | 1.00 | 22.61 |
| ATOM | 3267 | C   | VAL | A | 431 | 0 | -1.337 | 26.028 | 39.409 | 1.00 | 23.06 |
| ATOM | 3268 | O   | VAL | A | 431 | 0 | -0.476 | 26.392 | 40.218 | 1.00 | 22.42 |
| ATOM | 3269 | CB  | VAL | A | 431 | 0 | -1.245 | 24.193 | 37.768 | 1.00 | 23.03 |
| ATOM | 3270 | CG1 | VAL | A | 431 | 0 | -0.795 | 23.672 | 36.416 | 1.00 | 22.74 |
| ATOM | 3271 | CG2 | VAL | A | 431 | 0 | -0.574 | 23.315 | 38.820 | 1.00 | 22.77 |
| ATOM | 3272 | N   | THR | A | 432 | 0 | -2.615 | 25.835 | 39.704 | 1.00 | 23.88 |
| ATOM | 3273 | CA  | THR | A | 432 | 0 | -3.168 | 26.067 | 41.041 | 1.00 | 24.18 |

APPENDIX 1-continued

| ATOM | 3274 | C   | THR | A | 432 | 0 | -2.324  | 25.401 | 42.092 | 1.00 | 23.94 |
|------|------|-----|-----|---|-----|---|---------|--------|--------|------|-------|
| ATOM | 3275 | O   | THR | A | 432 | 0 | -1.915  | 24.249 | 41.909 | 1.00 | 24.69 |
| ATOM | 3276 | CB  | THR | A | 432 | 0 | -4.625  | 25.565 | 41.069 | 1.00 | 25.75 |
| ATOM | 3277 | OG1 | THR | A | 432 | 0 | -5.336  | 26.344 | 40.087 | 1.00 | 25.87 |
| ATOM | 3278 | CG2 | THR | A | 432 | 0 | -5.319  | 25.800 | 42.398 | 1.00 | 26.65 |
| ATOM | 3279 | N   | GLY | A | 433 | 0 | -1.924  | 26.136 | 43.124 | 1.00 | 24.45 |
| ATOM | 3280 | CA  | GLY | A | 433 | 0 | -1.035  | 25.589 | 44.159 | 1.00 | 22.27 |
| ATOM | 3281 | C   | GLY | A | 433 | 0 | 0.394   | 26.120 | 43.983 | 1.00 | 23.26 |
| ATOM | 3282 | O   | GLY | A | 433 | 0 | 1.103   | 26.212 | 45.000 | 1.00 | 23.30 |
| ATOM | 3283 | N   | ASP | A | 434 | 0 | 0.833   | 26.481 | 42.776 | 1.00 | 21.12 |
| ATOM | 3284 | CA  | ASP | A | 434 | 0 | 2.192   | 26.986 | 42.586 | 1.00 | 20.62 |
| ATOM | 3285 | C   | ASP | A | 434 | 0 | 2.360   | 28.408 | 43.126 | 1.00 | 22.36 |
| ATOM | 3286 | O   | ASP | A | 434 | 0 | 1.425   | 29.225 | 43.076 | 1.00 | 21.24 |
| ATOM | 3287 | CB  | ASP | A | 434 | 0 | 2.548   | 27.024 | 41.087 | 1.00 | 18.78 |
| ATOM | 3288 | CG  | ASP | A | 434 | 0 | 2.827   | 25.616 | 40.597 | 1.00 | 19.71 |
| ATOM | 3289 | OD1 | ASP | A | 434 | 0 | 3.304   | 24.828 | 41.409 | 1.00 | 20.43 |
| ATOM | 3290 | OD2 | ASP | A | 434 | 0 | 2.596   | 25.242 | 39.432 | 1.00 | 21.58 |
| ATOM | 3291 | N   | GLU | A | 435 | 0 | 3.585   | 28.721 | 43.562 | 1.00 | 22.08 |
| ATOM | 3292 | CA  | GLU | A | 435 | 0 | 3.853   | 30.077 | 44.068 | 1.00 | 23.24 |
| ATOM | 3293 | C   | GLU | A | 435 | 0 | 5.244   | 30.512 | 43.612 | 1.00 | 20.24 |
| ATOM | 3294 | O   | GLU | A | 435 | 0 | 6.201   | 30.611 | 44.372 | 1.00 | 19.50 |
| ATOM | 3295 | CB  | GLU | A | 435 | 0 | 3.659   | 30.068 | 45.572 | 1.00 | 25.56 |
| ATOM | 3296 | CG  | GLU | A | 435 | 0 | 3.739   | 31.409 | 46.258 | 1.00 | 30.52 |
| ATOM | 3297 | CD  | GLU | A | 435 | 0 | 3.107   | 31.350 | 47.657 | 1.00 | 35.00 |
| ATOM | 3298 | OE1 | GLU | A | 435 | 0 | 2.093   | 30.603 | 47.760 | 1.00 | 35.71 |
| ATOM | 3299 | OE2 | GLU | A | 435 | 0 | 3.658   | 32.020 | 48.579 | 1.00 | 35.91 |
| ATOM | 3300 | N   | VAL | A | 436 | 0 | 5.344   | 30.690 | 42.297 | 1.00 | 17.80 |
| ATOM | 3301 | CA  | VAL | A | 436 | 0 | 6.564   | 31.083 | 41.640 | 1.00 | 15.30 |
| ATOM | 3302 | C   | VAL | A | 436 | 0 | 7.049   | 32.416 | 42.221 | 1.00 | 17.15 |
| ATOM | 3303 | O   | VAL | A | 436 | 0 | 6.326   | 33.402 | 42.275 | 1.00 | 17.48 |
| ATOM | 3304 | CB  | VAL | A | 436 | 0 | 6.360   | 31.219 | 40.129 | 1.00 | 14.63 |
| ATOM | 3305 | CG1 | VAL | A | 436 | 0 | 7.463   | 32.009 | 39.454 | 1.00 | 10.79 |
| ATOM | 3306 | CG2 | VAL | A | 436 | 0 | 6.238   | 29.806 | 39.536 | 1.00 | 14.13 |
| ATOM | 3307 | N   | THR | A | 437 | 0 | 8.290   | 32.391 | 42.691 | 1.00 | 16.51 |
| ATOM | 3308 | CA  | THR | A | 437 | 0 | 8.940   | 33.505 | 43.364 | 1.00 | 16.19 |
| ATOM | 3309 | C   | THR | A | 437 | 0 | 10.254  | 33.817 | 42.668 | 1.00 | 15.24 |
| ATOM | 3310 | O   | THR | A | 437 | 0 | 11.100  | 32.940 | 42.419 | 1.00 | 15.47 |
| ATOM | 3311 | CB  | THR | A | 437 | 0 | 9.190   | 33.067 | 44.827 | 1.00 | 14.95 |
| ATOM | 3312 | OG1 | THR | A | 437 | 0 | 7.969   | 32.499 | 45.308 | 1.00 | 13.50 |
| ATOM | 3313 | CG2 | THR | A | 437 | 0 | 9.599   | 34.232 | 45.697 | 1.00 | 13.41 |
| ATOM | 3314 | N   | ILE | A | 438 | 0 | 10.413  | 35.059 | 42.251 | 1.00 | 13.38 |
| ATOM | 3315 | CA  | ILE | A | 438 | 0 | 11.597  | 35.471 | 41.510 | 1.00 | 15.78 |
| ATOM | 3316 | C   | ILE | A | 438 | 0 | 12.292  | 36.590 | 42.264 | 1.00 | 15.86 |
| ATOM | 3317 | O   | ILE | A | 438 | 0 | 11.617  | 37.270 | 43.048 | 1.00 | 17.32 |
| ATOM | 3318 | CB  | ILE | A | 438 | 0 | 11.249  | 35.848 | 40.053 | 1.00 | 15.40 |
| ATOM | 3319 | CG1 | ILE | A | 438 | 0 | 10.340  | 37.055 | 39.985 | 1.00 | 15.85 |
| ATOM | 3320 | CG2 | ILE | A | 438 | 0 | 10.602  | 34.653 | 39.346 | 1.00 | 17.11 |
| ATOM | 3321 | CD1 | ILE | A | 438 | 0 | 9.971   | 37.607 | 38.632 | 1.00 | 17.49 |
| ATOM | 3322 | N   | ARG | A | 439 | 0 | 13.599  | 36.789 | 42.055 | 1.00 | 16.02 |
| ATOM | 3323 | CA  | ARG | A | 439 | 0 | 14.315  | 37.896 | 42.671 | 1.00 | 13.90 |
| ATOM | 3324 | C   | ARG | A | 439 | 0 | 15.181  | 38.645 | 41.676 | 1.00 | 13.52 |
| ATOM | 3325 | O   | ARG | A | 439 | 0 | 15.748  | 38.056 | 40.762 | 1.00 | 14.74 |
| ATOM | 3326 | CB  | ARG | A | 439 | 0 | 15.193  | 37.501 | 43.850 | 1.00 | 15.15 |
| ATOM | 3327 | CG  | ARG | A | 439 | 0 | 14.457  | 37.235 | 45.147 | 1.00 | 14.83 |
| ATOM | 3328 | CD  | ARG | A | 439 | 0 | 15.367  | 37.337 | 46.355 | 1.00 | 14.08 |
| ATOM | 3329 | NE  | ARG | A | 439 | 0 | 14.613  | 37.000 | 47.566 | 1.00 | 17.06 |
| ATOM | 3330 | CZ  | ARG | A | 439 | 0 | 15.192  | 36.922 | 48.767 | 1.00 | 18.01 |
| ATOM | 3331 | NH1 | ARG | A | 439 | 0 | 16.487  | 37.176 | 48.908 | 1.00 | 17.76 |
| ATOM | 3332 | NH2 | ARG | A | 439 | 0 | 14.459  | 36.604 | 49.818 | 1.00 | 18.55 |
| ATOM | 3333 | N   | PHE | A | 440 | 0 | 15.314  | 39.957 | 41.853 | 1.00 | 14.44 |
| ATOM | 3334 | CA  | PHE | A | 440 | 0 | 16.204  | 40.737 | 40.993 | 1.00 | 15.97 |
| ATOM | 3335 | C   | PHE | A | 440 | 0 | 16.645  | 41.986 | 41.761 | 1.00 | 15.86 |
| ATOM | 3336 | O   | PHE | A | 440 | 0 | 16.113  | 42.313 | 42.801 | 1.00 | 15.79 |
| ATOM | 3337 | CB  | PHE | A | 440 | 0 | 15.638  | 41.081 | 39.620 | 1.00 | 15.17 |
| ATOM | 3338 | CG  | PHE | A | 440 | 0 | 14.416  | 41.948 | 39.647 | 1.00 | 16.95 |
| ATOM | 3339 | CD1 | PHE | A | 440 | 0 | 14.525  | 43.333 | 39.528 | 1.00 | 17.23 |
| ATOM | 3340 | CD2 | PHE | A | 440 | 0 | 13.158  | 41.377 | 39.798 | 1.00 | 16.35 |
| ATOM | 3341 | CE1 | PHE | A | 440 | 0 | 13.397  | 44.152 | 39.566 | 1.00 | 17.07 |
| ATOM | 3342 | CE2 | PHE | A | 440 | 0 | 12.026  | 42.180 | 39.841 | 1.00 | 17.12 |
| ATOM | 3343 | CZ  | PHE | A | 440 | 0 | 12.144  | 43.575 | 39.719 | 1.00 | 18.30 |
| ATOM | 3344 | N   | VAL | A | 441 | 0 | 17.676  | 42.648 | 41.268 | 1.00 | 16.10 |
| ATOM | 3345 | CA  | VAL | A | 441 | 0 | 18.172  | 43.874 | 41.879 | 1.00 | 16.29 |
| ATOM | 3346 | C   | VAL | A | 441 | 0 | 17.776  | 45.035 | 40.972 | 1.00 | 14.00 |
| ATOM | 3347 | O   | VAL | A | 441 | 0 | 17.866  | 44.924 | 39.736 | 1.00 | 12.72 |
| ATOM | 3348 | CB  | VAL | A | 441 | 0 | 19.675  | 43.769 | 42.144 | 1.00 | 18.13 |
| ATOM | 3349 | CG1 | VAL | A | 441 | 0 | 20.195  | 45.040 | 42.794 | 1.00 | 18.53 |
| ATOM | 3350 | CG2 | VAL | A | 441 | 0 | 19.969  | 42.583 | 43.065 | 1.00 | 18.55 |
| ATOM | 3351 | N   | THR | A | 442 | 0 | 17.328  | 46.125 | 41.579 | 1.00 | 11.73 |
| ATOM | 3352 | CA  | THR | A | 442 | 0 | 16.905  | 47.291 | 40.800 | 1.00 | 13.02 |

APPENDIX 1-continued

| ATOM | 3353 | C | THR | A | 442 | 0 | 18.055 | 48.208 | 40.432 | 1.00 | 14.83 |
|---|---|---|---|---|---|---|---|---|---|---|---|
| ATOM | 3354 | O | THR | A | 442 | 0 | 18.218 | 49.323 | 40.947 | 1.00 | 15.17 |
| ATOM | 3355 | CB | THR | A | 442 | 0 | 15.840 | 48.127 | 41.558 | 1.00 | 14.62 |
| ATOM | 3356 | OG1 | THR | A | 442 | 0 | 16.314 | 48.463 | 42.864 | 1.00 | 14.34 |
| ATOM | 3357 | CG2 | THR | A | 442 | 0 | 14.552 | 47.299 | 41.727 | 1.00 | 13.82 |
| ATOM | 3358 | N | ASP | A | 443 | 0 | 18.818 | 47.764 | 39.437 | 1.00 | 15.48 |
| ATOM | 3359 | CA | ASP | A | 443 | 0 | 20.004 | 48.449 | 38.964 | 1.00 | 16.57 |
| ATOM | 3360 | C | ASP | A | 443 | 0 | 19.807 | 49.010 | 37.569 | 1.00 | 15.38 |
| ATOM | 3361 | O | ASP | A | 443 | 0 | 20.788 | 49.208 | 36.858 | 1.00 | 15.57 |
| ATOM | 3362 | CB | ASP | A | 443 | 0 | 21.133 | 47.391 | 38.962 | 1.00 | 19.75 |
| ATOM | 3363 | CG | ASP | A | 443 | 0 | 20.877 | 46.264 | 37.990 | 1.00 | 22.78 |
| ATOM | 3364 | OD1 | ASP | A | 443 | 0 | 21.711 | 45.353 | 37.789 | 1.00 | 25.70 |
| ATOM | 3365 | OD2 | ASP | A | 443 | 0 | 19.836 | 46.161 | 37.313 | 1.00 | 23.88 |
| ATOM | 3366 | N | ASN | A | 444 | 0 | 18.593 | 49.278 | 37.144 | 1.00 | 13.71 |
| ATOM | 3367 | CA | ASN | A | 444 | 0 | 18.388 | 49.721 | 35.752 | 1.00 | 15.87 |
| ATOM | 3368 | C | ASN | A | 444 | 0 | 17.245 | 50.728 | 35.702 | 1.00 | 17.00 |
| ATOM | 3369 | O | ASN | A | 444 | 0 | 16.052 | 50.419 | 35.614 | 1.00 | 16.83 |
| ATOM | 3370 | CB | ASN | A | 444 | 0 | 18.198 | 48.453 | 34.930 | 1.00 | 15.78 |
| ATOM | 3371 | CG | ASN | A | 444 | 0 | 18.225 | 48.675 | 33.442 | 1.00 | 18.49 |
| ATOM | 3372 | OD1 | ASN | A | 444 | 0 | 18.505 | 49.809 | 33.047 | 1.00 | 19.42 |
| ATOM | 3373 | ND2 | ASN | A | 444 | 0 | 17.925 | 47.689 | 32.588 | 1.00 | 15.91 |
| ATOM | 3374 | N | PRO | A | 445 | 0 | 17.598 | 52.003 | 35.890 | 1.00 | 17.59 |
| ATOM | 3375 | CA | PRO | A | 445 | 0 | 16.683 | 53.137 | 35.938 | 1.00 | 16.56 |
| ATOM | 3376 | C | PRO | A | 445 | 0 | 15.788 | 53.217 | 34.721 | 1.00 | 16.99 |
| ATOM | 3377 | O | PRO | A | 445 | 0 | 16.293 | 53.246 | 33.594 | 1.00 | 17.02 |
| ATOM | 3378 | CB | PRO | A | 445 | 0 | 17.552 | 54.418 | 35.951 | 1.00 | 18.28 |
| ATOM | 3379 | CG | PRO | A | 445 | 0 | 18.870 | 53.871 | 36.474 | 1.00 | 18.09 |
| ATOM | 3380 | CD | PRO | A | 445 | 0 | 19.002 | 52.409 | 36.084 | 1.00 | 16.05 |
| ATOM | 3381 | N | GLY | A | 446 | 0 | 14.462 | 53.194 | 34.918 | 1.00 | 17.16 |
| ATOM | 3382 | CA | GLY | A | 446 | 0 | 13.560 | 53.281 | 33.743 | 1.00 | 15.84 |
| ATOM | 3383 | C | GLY | A | 446 | 0 | 12.297 | 52.453 | 33.984 | 1.00 | 14.24 |
| ATOM | 3384 | O | GLY | A | 446 | 0 | 12.192 | 51.797 | 35.005 | 1.00 | 12.22 |
| ATOM | 3385 | N | PRO | A | 447 | 0 | 11.285 | 52.697 | 33.181 | 1.00 | 15.53 |
| ATOM | 3386 | CA | PRO | A | 447 | 0 | 9.999 | 52.048 | 33.195 | 1.00 | 15.24 |
| ATOM | 3387 | C | PRO | A | 447 | 0 | 10.101 | 50.737 | 32.401 | 1.00 | 13.82 |
| ATOM | 3388 | O | PRO | A | 447 | 0 | 10.514 | 50.733 | 31.240 | 1.00 | 13.85 |
| ATOM | 3389 | CB | PRO | A | 447 | 0 | 9.013 | 52.976 | 32.473 | 1.00 | 16.21 |
| ATOM | 3390 | CG | PRO | A | 447 | 0 | 9.933 | 53.729 | 31.554 | 1.00 | 16.19 |
| ATOM | 3391 | CD | PRO | A | 447 | 0 | 11.347 | 53.707 | 32.096 | 1.00 | 17.15 |
| ATOM | 3392 | N | TRP | A | 448 | 0 | 9.787 | 49.623 | 33.021 | 1.00 | 11.83 |
| ATOM | 3393 | CA | TRP | A | 448 | 0 | 9.898 | 48.317 | 32.371 | 1.00 | 14.30 |
| ATOM | 3394 | C | TRP | A | 448 | 0 | 8.610 | 47.493 | 32.427 | 1.00 | 13.12 |
| ATOM | 3395 | O | TRP | A | 448 | 0 | 8.013 | 47.355 | 33.502 | 1.00 | 11.63 |
| ATOM | 3396 | CB | TRP | A | 448 | 0 | 10.985 | 47.483 | 33.095 | 1.00 | 13.17 |
| ATOM | 3397 | CG | TRP | A | 448 | 0 | 12.321 | 48.160 | 33.124 | 1.00 | 14.54 |
| ATOM | 3398 | CD1 | TRP | A | 448 | 0 | 12.897 | 48.728 | 34.239 | 1.00 | 14.19 |
| ATOM | 3399 | CD2 | TRP | A | 448 | 0 | 13.211 | 48.382 | 32.029 | 1.00 | 14.38 |
| ATOM | 3400 | NE1 | TRP | A | 448 | 0 | 14.083 | 49.290 | 33.873 | 1.00 | 15.02 |
| ATOM | 3401 | CE2 | TRP | A | 448 | 0 | 14.308 | 49.095 | 32.527 | 1.00 | 14.41 |
| ATOM | 3402 | CE3 | TRP | A | 448 | 0 | 13.193 | 48.053 | 30.672 | 1.00 | 15.39 |
| ATOM | 3403 | CZ2 | TRP | A | 448 | 0 | 15.388 | 49.467 | 31.729 | 1.00 | 14.57 |
| ATOM | 3404 | CZ3 | TRP | A | 448 | 0 | 14.250 | 48.446 | 29.867 | 1.00 | 14.92 |
| ATOM | 3405 | CH2 | TRP | A | 448 | 0 | 15.355 | 49.135 | 30.399 | 1.00 | 14.93 |
| ATOM | 3406 | N | PHE | A | 449 | 0 | 8.231 | 46.884 | 31.315 | 1.00 | 14.03 |
| ATOM | 3407 | CA | PHE | A | 449 | 0 | 7.023 | 46.039 | 31.297 | 1.00 | 13.60 |
| ATOM | 3408 | C | PHE | A | 449 | 0 | 7.231 | 44.712 | 32.016 | 1.00 | 15.32 |
| ATOM | 3409 | O | PHE | A | 449 | 0 | 8.312 | 44.093 | 31.993 | 1.00 | 13.66 |
| ATOM | 3410 | CB | PHE | A | 449 | 0 | 6.627 | 45.773 | 29.845 | 1.00 | 16.19 |
| ATOM | 3411 | CG | PHE | A | 449 | 0 | 5.221 | 46.033 | 29.380 | 1.00 | 18.26 |
| ATOM | 3412 | CD1 | PHE | A | 449 | 0 | 4.165 | 46.288 | 30.226 | 1.00 | 17.95 |
| ATOM | 3413 | CD2 | PHE | A | 449 | 0 | 4.962 | 46.027 | 28.011 | 1.00 | 20.73 |
| ATOM | 3414 | CE1 | PHE | A | 449 | 0 | 2.899 | 46.565 | 29.745 | 1.00 | 18.55 |
| ATOM | 3415 | CE2 | PHE | A | 449 | 0 | 3.701 | 46.293 | 27.503 | 1.00 | 20.13 |
| ATOM | 3416 | CZ | PHE | A | 449 | 0 | 2.664 | 46.543 | 28.387 | 1.00 | 18.59 |
| ATOM | 3417 | N | PHE | A | 450 | 0 | 6.195 | 44.245 | 32.715 | 1.00 | 12.79 |
| ATOM | 3418 | CA | PHE | A | 450 | 0 | 6.119 | 42.963 | 33.359 | 1.00 | 14.38 |
| ATOM | 3419 | C | PHE | A | 450 | 0 | 4.775 | 42.323 | 32.952 | 1.00 | 15.45 |
| ATOM | 3420 | O | PHE | A | 450 | 0 | 3.743 | 42.812 | 33.423 | 1.00 | 15.30 |
| ATOM | 3421 | CB | PHE | A | 450 | 0 | 6.186 | 43.041 | 34.879 | 1.00 | 15.06 |
| ATOM | 3422 | CG | PHE | A | 450 | 0 | 6.210 | 41.693 | 35.555 | 1.00 | 15.95 |
| ATOM | 3423 | CD1 | PHE | A | 450 | 0 | 7.157 | 40.734 | 35.204 | 1.00 | 16.36 |
| ATOM | 3424 | CD2 | PHE | A | 450 | 0 | 5.325 | 41.398 | 36.570 | 1.00 | 15.45 |
| ATOM | 3425 | CE1 | PHE | A | 450 | 0 | 7.222 | 39.518 | 35.855 | 1.00 | 13.87 |
| ATOM | 3426 | CE2 | PHE | A | 450 | 0 | 5.386 | 40.187 | 37.224 | 1.00 | 16.10 |
| ATOM | 3427 | CZ | PHE | A | 450 | 0 | 6.317 | 39.236 | 36.854 | 1.00 | 15.90 |
| ATOM | 3428 | N | HIS | A | 451 | 0 | 4.737 | 41.301 | 32.122 | 1.00 | 15.54 |
| ATOM | 3429 | CA | HIS | A | 451 | 0 | 3.443 | 40.841 | 31.610 | 1.00 | 16.24 |
| ATOM | 3430 | C | HIS | A | 451 | 0 | 3.461 | 39.426 | 31.073 | 1.00 | 16.95 |
| ATOM | 3431 | O | HIS | A | 451 | 0 | 4.526 | 38.860 | 30.812 | 1.00 | 17.42 |

APPENDIX 1-continued

| ATOM | 3432 | CB  | HIS | A | 451 | 0 | 2.996  | 41.743 | 30.435 | 1.00 | 14.01 |
|------|------|-----|-----|---|-----|---|--------|--------|--------|------|-------|
| ATOM | 3433 | CG  | HIS | A | 451 | 0 | 3.921  | 41.696 | 29.281 | 1.00 | 16.98 |
| ATOM | 3434 | ND1 | HIS | A | 451 | 0 | 3.791  | 40.844 | 28.201 | 1.00 | 18.14 |
| ATOM | 3435 | CD2 | HIS | A | 451 | 0 | 5.058  | 42.435 | 29.046 | 1.00 | 17.88 |
| ATOM | 3436 | CE1 | HIS | A | 451 | 0 | 4.759  | 41.060 | 27.337 | 1.00 | 17.83 |
| ATOM | 3437 | NE2 | HIS | A | 451 | 0 | 5.554  | 42.011 | 27.842 | 1.00 | 18.98 |
| ATOM | 3438 | N   | CYS | A | 452 | 0 | 2.261  | 38.863 | 30.951 | 1.00 | 16.78 |
| ATOM | 3439 | CA  | CYS | A | 452 | 0 | 2.167  | 37.537 | 30.388 | 1.00 | 16.34 |
| ATOM | 3440 | C   | CYS | A | 452 | 0 | 2.604  | 37.623 | 28.924 | 1.00 | 14.77 |
| ATOM | 3441 | O   | CYS | A | 452 | 0 | 2.167  | 38.514 | 28.188 | 1.00 | 13.61 |
| ATOM | 3442 | CB  | CYS | A | 452 | 0 | 0.727  | 36.983 | 30.451 | 1.00 | 18.22 |
| ATOM | 3443 | SG  | CYS | A | 452 | 0 | 0.701  | 35.325 | 29.692 | 1.00 | 19.80 |
| ATOM | 3444 | N   | HIS | A | 453 | 0 | 3.388  | 36.640 | 28.474 | 1.00 | 13.29 |
| ATOM | 3445 | CA  | HIS | A | 453 | 0 | 3.867  | 36.716 | 27.100 | 1.00 | 13.19 |
| ATOM | 3446 | C   | HIS | A | 453 | 0 | 2.983  | 35.987 | 26.099 | 1.00 | 13.47 |
| ATOM | 3447 | O   | HIS | A | 453 | 0 | 3.296  | 35.974 | 24.906 | 1.00 | 11.93 |
| ATOM | 3448 | CB  | HIS | A | 453 | 0 | 5.314  | 36.251 | 27.033 | 1.00 | 13.98 |
| ATOM | 3449 | CG  | HIS | A | 453 | 0 | 6.124  | 36.860 | 25.945 | 1.00 | 11.89 |
| ATOM | 3450 | ND1 | HIS | A | 453 | 0 | 5.835  | 36.763 | 24.612 | 1.00 | 10.68 |
| ATOM | 3451 | CD2 | HIS | A | 453 | 0 | 7.270  | 37.594 | 26.072 | 1.00 | 12.71 |
| ATOM | 3452 | CE1 | HIS | A | 453 | 0 | 6.776  | 37.418 | 23.923 | 1.00 | 12.37 |
| ATOM | 3453 | NE2 | HIS | A | 453 | 0 | 7.663  | 37.930 | 24.793 | 1.00 | 13.20 |
| ATOM | 3454 | N   | ILE | A | 454 | 0 | 1.860  | 35.429 | 26.549 | 1.00 | 15.35 |
| ATOM | 3455 | CA  | ILE | A | 454 | 0 | 0.849  | 34.937 | 25.600 | 1.00 | 15.85 |
| ATOM | 3456 | C   | ILE | A | 454 | 0 | 0.214  | 36.238 | 25.089 | 1.00 | 18.65 |
| ATOM | 3457 | O   | ILE | A | 454 | 0 | -0.452 | 36.997 | 25.824 | 1.00 | 17.92 |
| ATOM | 3458 | CB  | ILE | A | 454 | 0 | -0.156 | 34.001 | 26.280 | 1.00 | 16.46 |
| ATOM | 3459 | CG1 | ILE | A | 454 | 0 | 0.456  | 32.598 | 26.512 | 1.00 | 15.26 |
| ATOM | 3460 | CG2 | ILE | A | 454 | 0 | -1.402 | 33.898 | 25.419 | 1.00 | 14.21 |
| ATOM | 3461 | CD1 | ILE | A | 454 | 0 | -0.249 | 31.804 | 27.592 | 1.00 | 16.26 |
| ATOM | 3462 | N   | GLU | A | 455 | 0 | 0.448  | 36.607 | 23.832 | 1.00 | 21.02 |
| ATOM | 3463 | CA  | GLU | A | 455 | 0 | -0.024 | 37.856 | 23.289 | 1.00 | 23.78 |
| ATOM | 3464 | C   | GLU | A | 455 | 0 | -1.526 | 38.042 | 23.422 | 1.00 | 24.40 |
| ATOM | 3465 | O   | GLU | A | 455 | 0 | -1.953 | 39.161 | 23.700 | 1.00 | 24.30 |
| ATOM | 3466 | CB  | GLU | A | 455 | 0 | 0.399  | 38.090 | 21.830 | 1.00 | 27.20 |
| ATOM | 3467 | CG  | GLU | A | 455 | 0 | 0.602  | 39.599 | 21.595 | 1.00 | 33.86 |
| ATOM | 3468 | CD  | GLU | A | 455 | 0 | 1.783  | 40.205 | 22.309 | 1.00 | 37.49 |
| ATOM | 3469 | OE1 | GLU | A | 455 | 0 | 2.311  | 39.657 | 23.320 | 1.00 | 41.51 |
| ATOM | 3470 | OE2 | GLU | A | 455 | 0 | 2.303  | 41.284 | 21.907 | 1.00 | 41.22 |
| ATOM | 3471 | N   | PHE | A | 456 | 0 | -2.347 | 37.005 | 23.334 | 1.00 | 23.97 |
| ATOM | 3472 | CA  | PHE | A | 456 | 0 | -3.775 | 37.163 | 23.516 | 1.00 | 24.68 |
| ATOM | 3473 | C   | PHE | A | 456 | 0 | -4.084 | 37.533 | 24.959 | 1.00 | 25.11 |
| ATOM | 3474 | O   | PHE | A | 456 | 0 | -5.181 | 38.092 | 25.170 | 1.00 | 27.37 |
| ATOM | 3475 | CB  | PHE | A | 456 | 0 | -4.552 | 35.919 | 23.023 | 1.00 | 24.76 |
| ATOM | 3476 | CG  | PHE | A | 456 | 0 | -4.098 | 35.614 | 21.606 | 1.00 | 24.98 |
| ATOM | 3477 | CD1 | PHE | A | 456 | 0 | -4.392 | 36.500 | 20.590 | 1.00 | 24.98 |
| ATOM | 3478 | CD2 | PHE | A | 456 | 0 | -3.331 | 34.506 | 21.320 | 1.00 | 24.42 |
| ATOM | 3479 | CE1 | PHE | A | 456 | 0 | -3.988 | 36.292 | 19.291 | 1.00 | 25.44 |
| ATOM | 3480 | CE2 | PHE | A | 456 | 0 | -2.913 | 34.293 | 20.015 | 1.00 | 26.40 |
| ATOM | 3481 | CZ  | PHE | A | 456 | 0 | -3.226 | 35.171 | 18.997 | 1.00 | 25.10 |
| ATOM | 3482 | N   | HIS | A | 457 | 0 | -3.205 | 37.294 | 25.922 | 1.00 | 22.35 |
| ATOM | 3483 | CA  | HIS | A | 457 | 0 | -3.508 | 37.682 | 27.291 | 1.00 | 22.55 |
| ATOM | 3484 | C   | HIS | A | 457 | 0 | -3.053 | 39.121 | 27.561 | 1.00 | 23.81 |
| ATOM | 3485 | O   | HIS | A | 457 | 0 | -3.756 | 39.832 | 28.262 | 1.00 | 21.33 |
| ATOM | 3486 | CB  | HIS | A | 457 | 0 | -2.912 | 36.766 | 28.336 | 1.00 | 20.96 |
| ATOM | 3487 | CG  | HIS | A | 457 | 0 | -3.345 | 35.346 | 28.201 | 1.00 | 22.51 |
| ATOM | 3488 | ND1 | HIS | A | 457 | 0 | -2.745 | 34.329 | 28.905 | 1.00 | 21.40 |
| ATOM | 3489 | CD2 | HIS | A | 457 | 0 | -4.291 | 34.771 | 27.404 | 1.00 | 22.50 |
| ATOM | 3490 | CE1 | HIS | A | 457 | 0 | -3.320 | 33.184 | 28.575 | 1.00 | 22.51 |
| ATOM | 3491 | NE2 | HIS | A | 457 | 0 | -4.237 | 33.428 | 27.666 | 1.00 | 23.19 |
| ATOM | 3492 | N   | LEU | A | 458 | 0 | -1.876 | 39.481 | 27.028 | 1.00 | 23.74 |
| ATOM | 3493 | CA  | LEU | A | 458 | 0 | -1.357 | 40.817 | 27.125 | 1.00 | 24.76 |
| ATOM | 3494 | C   | LEU | A | 458 | 0 | -2.411 | 41.828 | 26.616 | 1.00 | 26.52 |
| ATOM | 3495 | O   | LEU | A | 458 | 0 | -2.757 | 42.751 | 27.351 | 1.00 | 25.18 |
| ATOM | 3496 | CB  | LEU | A | 458 | 0 | -0.108 | 40.986 | 26.252 | 1.00 | 23.81 |
| ATOM | 3497 | CG  | LEU | A | 458 | 0 | 0.898  | 42.062 | 26.624 | 1.00 | 24.09 |
| ATOM | 3498 | CD1 | LEU | A | 458 | 0 | 1.619  | 42.606 | 25.390 | 1.00 | 24.28 |
| ATOM | 3499 | CD2 | LEU | A | 458 | 0 | 0.351  | 43.195 | 27.462 | 1.00 | 23.72 |
| ATOM | 3500 | N   | MET | A | 459 | 0 | -2.896 | 41.611 | 25.388 | 1.00 | 28.19 |
| ATOM | 3501 | CA  | MET | A | 459 | 0 | -3.914 | 42.458 | 24.785 | 1.00 | 31.98 |
| ATOM | 3502 | C   | MET | A | 459 | 0 | -5.207 | 42.436 | 25.603 | 1.00 | 29.95 |
| ATOM | 3503 | O   | MET | A | 459 | 0 | -5.886 | 43.439 | 25.520 | 1.00 | 29.10 |
| ATOM | 3504 | CB  | MET | A | 459 | 0 | -4.148 | 42.226 | 23.284 | 1.00 | 35.99 |
| ATOM | 3505 | CG  | MET | A | 459 | 0 | -5.056 | 41.103 | 22.852 | 1.00 | 42.66 |
| ATOM | 3506 | SD  | MET | A | 459 | 0 | -5.296 | 40.817 | 21.069 | 1.00 | 49.28 |
| ATOM | 3507 | CE  | MET | A | 459 | 0 | -6.238 | 39.291 | 21.119 | 1.00 | 47.39 |
| ATOM | 3508 | N   | ASN | A | 460 | 0 | -5.523 | 41.486 | 26.464 | 1.00 | 29.07 |
| ATOM | 3509 | CA  | ASN | A | 460 | 0 | -6.706 | 41.539 | 27.296 | 1.00 | 29.41 |
| ATOM | 3510 | C   | ASN | A | 460 | 0 | -6.407 | 41.908 | 28.746 | 1.00 | 28.46 |

APPENDIX 1-continued

| ATOM | 3511 | O | ASN | A | 460 | 0 | -7.183 | 41.577 | 29.645 | 1.00 | 26.89 |
| ATOM | 3512 | CB | ASN | A | 460 | 0 | -7.537 | 40.253 | 27.210 | 1.00 | 31.34 |
| ATOM | 3513 | CG | ASN | A | 460 | 0 | -8.325 | 40.243 | 25.900 | 1.00 | 33.82 |
| ATOM | 3514 | OD1 | ASN | A | 460 | 0 | -7.909 | 39.609 | 24.926 | 1.00 | 34.29 |
| ATOM | 3515 | ND2 | ASN | A | 460 | 0 | -9.437 | 40.971 | 25.861 | 1.00 | 34.55 |
| ATOM | 3516 | N | GLY | A | 461 | 0 | -5.320 | 42.655 | 28.981 | 1.00 | 26.30 |
| ATOM | 3517 | CA | GLY | A | 461 | 0 | -5.020 | 43.198 | 30.268 | 1.00 | 24.99 |
| ATOM | 3518 | C | GLY | A | 461 | 0 | -4.043 | 42.601 | 31.235 | 1.00 | 24.75 |
| ATOM | 3519 | O | GLY | A | 461 | 0 | -3.879 | 43.228 | 32.304 | 1.00 | 22.69 |
| ATOM | 3520 | N | LEU | A | 462 | 0 | -3.375 | 41.478 | 30.914 | 1.00 | 22.85 |
| ATOM | 3521 | CA | LEU | A | 462 | 0 | -2.478 | 40.872 | 31.913 | 1.00 | 22.10 |
| ATOM | 3522 | C | LEU | A | 462 | 0 | -1.071 | 41.485 | 31.890 | 1.00 | 21.56 |
| ATOM | 3523 | O | LEU | A | 462 | 0 | -0.116 | 40.876 | 31.415 | 1.00 | 20.28 |
| ATOM | 3524 | CB | LEU | A | 462 | 0 | -2.477 | 39.376 | 31.669 | 1.00 | 20.03 |
| ATOM | 3525 | CG | LEU | A | 462 | 0 | -2.010 | 38.393 | 32.720 | 1.00 | 20.40 |
| ATOM | 3526 | CD1 | LEU | A | 462 | 0 | -2.603 | 38.608 | 34.093 | 1.00 | 20.35 |
| ATOM | 3527 | CD2 | LEU | A | 462 | 0 | -2.385 | 36.983 | 32.229 | 1.00 | 21.01 |
| ATOM | 3528 | N | ALA | A | 463 | 0 | -0.908 | 42.695 | 32.408 | 1.00 | 20.00 |
| ATOM | 3529 | CA | ALA | A | 463 | 0 | 0.350 | 43.432 | 32.381 | 1.00 | 20.74 |
| ATOM | 3530 | C | ALA | A | 463 | 0 | 0.398 | 44.511 | 33.481 | 1.00 | 21.85 |
| ATOM | 3531 | O | ALA | A | 463 | 0 | -0.667 | 44.965 | 33.934 | 1.00 | 22.85 |
| ATOM | 3532 | CB | ALA | A | 463 | 0 | 0.559 | 44.179 | 31.060 | 1.00 | 15.13 |
| ATOM | 3533 | N | ILE | A | 464 | 0 | 1.605 | 44.810 | 33.950 | 1.00 | 19.91 |
| ATOM | 3534 | CA | ILE | A | 464 | 0 | 1.852 | 45.905 | 34.850 | 1.00 | 19.81 |
| ATOM | 3535 | C | ILE | A | 464 | 0 | 3.180 | 46.579 | 34.434 | 1.00 | 19.41 |
| ATOM | 3536 | O | ILE | A | 464 | 0 | 3.938 | 46.003 | 33.660 | 1.00 | 18.24 |
| ATOM | 3537 | CB | ILE | A | 464 | 0 | 1.910 | 45.678 | 36.347 | 1.00 | 19.13 |
| ATOM | 3538 | CG1 | ILE | A | 464 | 0 | 2.867 | 44.546 | 36.697 | 1.00 | 19.39 |
| ATOM | 3539 | CG2 | ILE | A | 464 | 0 | 0.520 | 45.455 | 36.924 | 1.00 | 18.48 |
| ATOM | 3540 | CD1 | ILE | A | 464 | 0 | 3.205 | 44.549 | 38.179 | 1.00 | 21.00 |
| ATOM | 3541 | N | VAL | A | 465 | 0 | 3.380 | 47.791 | 34.924 | 1.00 | 18.95 |
| ATOM | 3542 | CA | VAL | A | 465 | 0 | 4.579 | 48.570 | 34.637 | 1.00 | 18.36 |
| ATOM | 3543 | C | VAL | A | 465 | 0 | 5.327 | 48.928 | 35.931 | 1.00 | 18.07 |
| ATOM | 3544 | O | VAL | A | 465 | 0 | 4.787 | 49.424 | 36.931 | 1.00 | 15.19 |
| ATOM | 3545 | CB | VAL | A | 465 | 0 | 4.329 | 49.913 | 33.918 | 1.00 | 19.73 |
| ATOM | 3546 | CG1 | VAL | A | 465 | 0 | 5.659 | 50.605 | 33.602 | 1.00 | 18.34 |
| ATOM | 3547 | CG2 | VAL | A | 465 | 0 | 3.522 | 49.766 | 32.629 | 1.00 | 18.74 |
| ATOM | 3548 | N | PHE | A | 466 | 0 | 6.649 | 48.655 | 35.879 | 1.00 | 17.55 |
| ATOM | 3549 | CA | PHE | A | 466 | 0 | 7.499 | 49.051 | 37.013 | 1.00 | 14.72 |
| ATOM | 3550 | C | PHE | A | 466 | 0 | 8.251 | 50.344 | 36.653 | 1.00 | 12.68 |
| ATOM | 3551 | O | PHE | A | 466 | 0 | 9.007 | 50.420 | 35.679 | 1.00 | 12.23 |
| ATOM | 3552 | CB | PHE | A | 466 | 0 | 8.484 | 47.978 | 37.381 | 1.00 | 15.19 |
| ATOM | 3553 | CG | PHE | A | 466 | 0 | 7.962 | 46.770 | 38.080 | 1.00 | 15.90 |
| ATOM | 3554 | CD1 | PHE | A | 466 | 0 | 7.328 | 46.856 | 39.299 | 1.00 | 16.23 |
| ATOM | 3555 | CD2 | PHE | A | 466 | 0 | 8.153 | 45.533 | 37.492 | 1.00 | 16.23 |
| ATOM | 3556 | CE1 | PHE | A | 466 | 0 | 6.861 | 45.720 | 39.936 | 1.00 | 15.97 |
| ATOM | 3557 | CE2 | PHE | A | 466 | 0 | 7.665 | 44.389 | 38.133 | 1.00 | 18.27 |
| ATOM | 3558 | CZ | PHE | A | 466 | 0 | 7.018 | 44.480 | 39.352 | 1.00 | 16.74 |
| ATOM | 3559 | N | ALA | A | 467 | 0 | 8.045 | 51.361 | 37.443 | 1.00 | 10.60 |
| ATOM | 3560 | CA | ALA | A | 467 | 0 | 8.788 | 52.648 | 37.194 | 1.00 | 12.27 |
| ATOM | 3561 | C | ALA | A | 467 | 0 | 10.007 | 52.526 | 38.111 | 1.00 | 12.02 |
| ATOM | 3562 | O | ALA | A | 467 | 0 | 9.905 | 52.728 | 39.325 | 1.00 | 12.43 |
| ATOM | 3563 | CB | ALA | A | 467 | 0 | 7.845 | 53.790 | 37.501 | 1.00 | 10.50 |
| ATOM | 3564 | N | GLU | A | 468 | 0 | 11.126 | 51.989 | 37.625 | 1.00 | 12.62 |
| ATOM | 3565 | CA | GLU | A | 468 | 0 | 12.263 | 51.683 | 38.515 | 1.00 | 14.63 |
| ATOM | 3566 | C | GLU | A | 468 | 0 | 13.195 | 52.883 | 38.685 | 1.00 | 13.91 |
| ATOM | 3567 | O | GLU | A | 468 | 0 | 13.631 | 53.369 | 37.651 | 1.00 | 13.05 |
| ATOM | 3568 | CB | GLU | A | 468 | 0 | 13.049 | 50.546 | 37.843 | 1.00 | 14.51 |
| ATOM | 3569 | CG | GLU | A | 468 | 0 | 14.256 | 50.035 | 38.629 | 1.00 | 16.84 |
| ATOM | 3570 | CD | GLU | A | 468 | 0 | 14.805 | 48.779 | 37.975 | 1.00 | 17.96 |
| ATOM | 3571 | OE1 | GLU | A | 468 | 0 | 15.985 | 48.479 | 38.124 | 1.00 | 16.98 |
| ATOM | 3572 | OE2 | GLU | A | 468 | 0 | 14.086 | 48.043 | 37.260 | 1.00 | 18.42 |
| ATOM | 3573 | N | ASP | A | 469 | 0 | 13.546 | 53.286 | 39.886 | 1.00 | 15.17 |
| ATOM | 3574 | CA | ASP | A | 469 | 0 | 14.491 | 54.371 | 40.116 | 1.00 | 16.85 |
| ATOM | 3575 | C | ASP | A | 469 | 0 | 14.134 | 55.630 | 39.333 | 1.00 | 16.33 |
| ATOM | 3576 | O | ASP | A | 469 | 0 | 14.851 | 56.046 | 38.437 | 1.00 | 16.59 |
| ATOM | 3577 | CB | ASP | A | 469 | 0 | 15.899 | 53.920 | 39.748 | 1.00 | 19.86 |
| ATOM | 3578 | CG | ASP | A | 469 | 0 | 17.040 | 54.766 | 40.289 | 1.00 | 21.40 |
| ATOM | 3579 | OD1 | ASP | A | 469 | 0 | 16.811 | 55.793 | 40.943 | 1.00 | 22.21 |
| ATOM | 3580 | OD2 | ASP | A | 469 | 0 | 18.216 | 54.403 | 40.069 | 1.00 | 22.21 |
| ATOM | 3581 | N | MET | A | 470 | 0 | 13.007 | 56.246 | 39.635 | 1.00 | 16.12 |
| ATOM | 3582 | CA | MET | A | 470 | 0 | 12.522 | 57.373 | 38.853 | 1.00 | 18.77 |
| ATOM | 3583 | C | MET | A | 470 | 0 | 13.451 | 58.576 | 38.950 | 1.00 | 16.31 |
| ATOM | 3584 | O | MET | A | 470 | 0 | 13.591 | 59.208 | 37.925 | 1.00 | 13.55 |
| ATOM | 3585 | CB | MET | A | 470 | 0 | 11.116 | 57.847 | 39.302 | 1.00 | 20.06 |
| ATOM | 3586 | CG | MET | A | 470 | 0 | 10.041 | 56.941 | 38.684 | 1.00 | 23.99 |
| ATOM | 3587 | SD | MET | A | 470 | 0 | 8.375 | 57.337 | 39.283 | 1.00 | 26.08 |
| ATOM | 3588 | CE | MET | A | 470 | 0 | 8.030 | 58.581 | 38.020 | 1.00 | 24.40 |
| ATOM | 3589 | N | ALA | A | 471 | 0 | 14.046 | 58.793 | 40.117 | 1.00 | 14.69 |

APPENDIX 1-continued

| | | | | | | | | | | | |
|---|---|---|---|---|---|---|---|---|---|---|---|
| ATOM | 3590 | CA | ALA | A | 471 | 0 | 14.953 | 59.906 | 40.287 | 1.00 | 16.97 |
| ATOM | 3591 | C | ALA | A | 471 | 0 | 16.141 | 59.864 | 39.335 | 1.00 | 18.79 |
| ATOM | 3592 | O | ALA | A | 471 | 0 | 16.602 | 60.956 | 38.945 | 1.00 | 21.08 |
| ATOM | 3593 | CB | ALA | A | 471 | 0 | 15.471 | 59.927 | 41.728 | 1.00 | 17.62 |
| ATOM | 3594 | N | ASN | A | 472 | 0 | 16.623 | 58.695 | 38.912 | 1.00 | 17.28 |
| ATOM | 3595 | CA | ASN | A | 472 | 0 | 17.788 | 58.675 | 38.015 | 1.00 | 16.56 |
| ATOM | 3596 | C | ASN | A | 472 | 0 | 17.457 | 58.355 | 36.572 | 1.00 | 16.99 |
| ATOM | 3597 | O | ASN | A | 472 | 0 | 18.407 | 58.143 | 35.795 | 1.00 | 18.74 |
| ATOM | 3598 | CB | ASN | A | 472 | 0 | 18.811 | 57.645 | 38.548 | 1.00 | 14.60 |
| ATOM | 3599 | CG | ASN | A | 472 | 0 | 19.417 | 58.132 | 39.887 | 1.00 | 14.00 |
| ATOM | 3600 | OD1 | ASN | A | 472 | 0 | 18.895 | 57.830 | 40.967 | 1.00 | 12.71 |
| ATOM | 3601 | ND2 | ASN | A | 472 | 0 | 20.468 | 58.916 | 39.775 | 1.00 | 10.80 |
| ATOM | 3602 | N | THR | A | 473 | 0 | 16.174 | 58.284 | 36.239 | 1.00 | 14.26 |
| ATOM | 3603 | CA | THR | A | 473 | 0 | 15.789 | 57.885 | 34.882 | 1.00 | 15.82 |
| ATOM | 3604 | C | THR | A | 473 | 0 | 16.150 | 58.891 | 33.812 | 1.00 | 16.81 |
| ATOM | 3605 | O | THR | A | 473 | 0 | 16.599 | 58.455 | 32.746 | 1.00 | 15.89 |
| ATOM | 3606 | CB | THR | A | 473 | 0 | 14.267 | 57.576 | 34.826 | 1.00 | 16.10 |
| ATOM | 3607 | OG1 | THR | A | 473 | 0 | 14.001 | 56.416 | 35.609 | 1.00 | 15.41 |
| ATOM | 3608 | CG2 | THR | A | 473 | 0 | 13.750 | 57.337 | 33.427 | 1.00 | 15.24 |
| ATOM | 3609 | N | VAL | A | 474 | 0 | 16.000 | 60.195 | 34.081 | 1.00 | 18.57 |
| ATOM | 3610 | CA | VAL | A | 474 | 0 | 16.355 | 61.192 | 33.050 | 1.00 | 21.06 |
| ATOM | 3611 | C | VAL | A | 474 | 0 | 17.859 | 61.209 | 32.817 | 1.00 | 19.12 |
| ATOM | 3612 | O | VAL | A | 474 | 0 | 18.339 | 61.234 | 31.688 | 1.00 | 19.95 |
| ATOM | 3613 | CB | VAL | A | 474 | 0 | 15.860 | 62.616 | 33.424 | 1.00 | 22.91 |
| ATOM | 3614 | CG1 | VAL | A | 474 | 0 | 16.467 | 63.702 | 32.538 | 1.00 | 23.06 |
| ATOM | 3615 | CG2 | VAL | A | 474 | 0 | 14.346 | 62.721 | 33.334 | 1.00 | 23.04 |
| ATOM | 3616 | N | ASP | A | 475 | 0 | 18.647 | 61.175 | 33.886 | 1.00 | 19.20 |
| ATOM | 3617 | CA | ASP | A | 475 | 0 | 20.109 | 61.168 | 33.741 | 1.00 | 18.98 |
| ATOM | 3618 | C | ASP | A | 475 | 0 | 20.578 | 59.899 | 33.047 | 1.00 | 17.52 |
| ATOM | 3619 | O | ASP | A | 475 | 0 | 21.386 | 60.028 | 32.130 | 1.00 | 18.31 |
| ATOM | 3620 | CB | ASP | A | 475 | 0 | 20.780 | 61.273 | 35.119 | 1.00 | 20.27 |
| ATOM | 3621 | CG | ASP | A | 475 | 0 | 22.283 | 61.075 | 35.107 | 1.00 | 20.18 |
| ATOM | 3622 | OD1 | ASP | A | 475 | 0 | 22.950 | 61.889 | 34.431 | 1.00 | 21.73 |
| ATOM | 3623 | OD2 | ASP | A | 475 | 0 | 22.798 | 60.139 | 35.750 | 1.00 | 18.03 |
| ATOM | 3624 | N | ALA | A | 476 | 0 | 20.062 | 58.725 | 33.392 | 1.00 | 18.26 |
| ATOM | 3625 | CA | ALA | A | 476 | 0 | 20.539 | 57.486 | 32.793 | 1.00 | 18.93 |
| ATOM | 3626 | C | ALA | A | 476 | 0 | 20.165 | 57.269 | 31.343 | 1.00 | 20.62 |
| ATOM | 3627 | O | ALA | A | 476 | 0 | 20.845 | 56.502 | 30.661 | 1.00 | 22.64 |
| ATOM | 3628 | CB | ALA | A | 476 | 0 | 19.966 | 56.298 | 33.551 | 1.00 | 18.48 |
| ATOM | 3629 | N | ASN | A | 477 | 0 | 19.047 | 57.787 | 30.858 | 1.00 | 22.66 |
| ATOM | 3630 | CA | ASN | A | 477 | 0 | 18.605 | 57.512 | 29.491 | 1.00 | 25.22 |
| ATOM | 3631 | C | ASN | A | 477 | 0 | 18.578 | 58.782 | 28.683 | 1.00 | 28.55 |
| ATOM | 3632 | O | ASN | A | 477 | 0 | 17.969 | 59.755 | 29.143 | 1.00 | 30.20 |
| ATOM | 3633 | CB | ASN | A | 477 | 0 | 17.172 | 56.948 | 29.560 | 1.00 | 24.22 |
| ATOM | 3634 | CG | ASN | A | 477 | 0 | 17.114 | 55.666 | 30.380 | 1.00 | 23.73 |
| ATOM | 3635 | OD1 | ASN | A | 477 | 0 | 16.747 | 55.672 | 31.570 | 1.00 | 21.33 |
| ATOM | 3636 | ND2 | ASN | A | 477 | 0 | 17.512 | 54.575 | 29.736 | 1.00 | 20.87 |
| ATOM | 3637 | N | ASN | A | 478 | 0 | 19.208 | 58.878 | 27.514 | 1.00 | 31.69 |
| ATOM | 3638 | CA | ASN | A | 478 | 0 | 19.036 | 60.131 | 26.776 | 1.00 | 33.61 |
| ATOM | 3639 | C | ASN | A | 478 | 0 | 18.758 | 59.770 | 25.331 | 1.00 | 32.22 |
| ATOM | 3640 | O | ASN | A | 478 | 0 | 19.602 | 59.478 | 24.508 | 1.00 | 32.16 |
| ATOM | 3641 | CB | ASN | A | 478 | 0 | 20.086 | 61.194 | 27.017 | 1.00 | 38.57 |
| ATOM | 3642 | CG | ASN | A | 478 | 0 | 21.426 | 60.602 | 27.370 | 1.00 | 40.94 |
| ATOM | 3643 | OD1 | ASN | A | 478 | 0 | 21.928 | 59.903 | 26.484 | 1.00 | 44.60 |
| ATOM | 3644 | ND2 | ASN | A | 478 | 0 | 21.866 | 60.861 | 28.578 | 1.00 | 41.32 |
| ATOM | 3645 | N | PRO | A | 479 | 0 | 17.461 | 59.733 | 25.075 | 1.00 | 32.37 |
| ATOM | 3646 | CA | PRO | A | 479 | 0 | 16.890 | 59.381 | 23.790 | 1.00 | 31.84 |
| ATOM | 3647 | C | PRO | A | 479 | 0 | 17.268 | 60.448 | 22.776 | 1.00 | 32.35 |
| ATOM | 3648 | O | PRO | A | 479 | 0 | 17.422 | 61.609 | 23.136 | 1.00 | 32.66 |
| ATOM | 3649 | CB | PRO | A | 479 | 0 | 15.364 | 59.385 | 23.931 | 1.00 | 31.68 |
| ATOM | 3650 | CG | PRO | A | 479 | 0 | 15.126 | 59.724 | 25.373 | 1.00 | 31.69 |
| ATOM | 3651 | CD | PRO | A | 479 | 0 | 16.416 | 60.071 | 26.064 | 1.00 | 32.23 |
| ATOM | 3652 | N | PRO | A | 480 | 0 | 17.399 | 60.036 | 21.537 | 1.00 | 31.62 |
| ATOM | 3653 | CA | PRO | A | 480 | 0 | 17.670 | 60.939 | 20.422 | 1.00 | 30.72 |
| ATOM | 3654 | C | PRO | A | 480 | 0 | 16.452 | 61.827 | 20.225 | 1.00 | 30.37 |
| ATOM | 3655 | O | PRO | A | 480 | 0 | 15.362 | 61.525 | 20.733 | 1.00 | 29.47 |
| ATOM | 3656 | CB | PRO | A | 480 | 0 | 17.935 | 60.035 | 19.203 | 1.00 | 29.87 |
| ATOM | 3657 | CG | PRO | A | 480 | 0 | 17.111 | 58.811 | 19.590 | 1.00 | 30.44 |
| ATOM | 3658 | CD | PRO | A | 480 | 0 | 17.161 | 58.657 | 21.093 | 1.00 | 30.35 |
| ATOM | 3659 | N | VAL | A | 481 | 0 | 16.559 | 62.906 | 19.458 | 1.00 | 31.72 |
| ATOM | 3660 | CA | VAL | A | 481 | 0 | 15.398 | 63.788 | 19.268 | 1.00 | 30.68 |
| ATOM | 3661 | C | VAL | A | 481 | 0 | 14.335 | 63.090 | 18.446 | 1.00 | 29.51 |
| ATOM | 3662 | O | VAL | A | 481 | 0 | 13.134 | 63.284 | 18.648 | 1.00 | 27.97 |
| ATOM | 3663 | CB | VAL | A | 481 | 0 | 15.818 | 65.132 | 18.648 | 1.00 | 33.04 |
| ATOM | 3664 | CG1 | VAL | A | 481 | 0 | 16.126 | 65.010 | 17.161 | 1.00 | 31.91 |
| ATOM | 3665 | CG2 | VAL | A | 481 | 0 | 14.717 | 66.171 | 18.907 | 1.00 | 33.32 |
| ATOM | 3666 | N | GLU | A | 482 | 0 | 14.746 | 62.167 | 17.562 | 1.00 | 28.90 |
| ATOM | 3667 | CA | GLU | A | 482 | 0 | 13.755 | 61.402 | 16.803 | 1.00 | 29.62 |
| ATOM | 3668 | C | GLU | A | 482 | 0 | 12.839 | 60.565 | 17.691 | 1.00 | 28.33 |

APPENDIX 1-continued

| ATOM | 3669 | O | GLU | A | 482 | 0 | 11.704 | 60.287 | 17.280 | 1.00 | 28.36 |
|------|------|-----|-----|---|-----|---|--------|--------|--------|------|-------|
| ATOM | 3670 | CB | GLU | A | 482 | 0 | 14.449 | 60.498 | 15.788 | 1.00 | 30.63 |
| ATOM | 3671 | CG | GLU | A | 482 | 0 | 15.143 | 61.256 | 14.666 | 1.00 | 32.78 |
| ATOM | 3672 | CD | GLU | A | 482 | 0 | 16.522 | 61.784 | 14.990 | 1.00 | 34.96 |
| ATOM | 3673 | OE1 | GLU | A | 482 | 0 | 17.021 | 61.746 | 16.141 | 1.00 | 34.62 |
| ATOM | 3674 | OE2 | GLU | A | 482 | 0 | 17.170 | 62.297 | 14.033 | 1.00 | 37.13 |
| ATOM | 3675 | N | TRP | A | 483 | 0 | 13.311 | 60.124 | 18.857 | 1.00 | 25.91 |
| ATOM | 3676 | CA | TRP | A | 483 | 0 | 12.496 | 59.280 | 19.711 | 1.00 | 25.49 |
| ATOM | 3677 | C | TRP | A | 483 | 0 | 11.224 | 60.011 | 20.125 | 1.00 | 26.47 |
| ATOM | 3678 | O | TRP | A | 483 | 0 | 10.155 | 59.405 | 20.116 | 1.00 | 26.95 |
| ATOM | 3679 | CB | TRP | A | 483 | 0 | 13.216 | 58.807 | 20.974 | 1.00 | 21.98 |
| ATOM | 3680 | CG | TRP | A | 483 | 0 | 12.376 | 58.144 | 22.013 | 1.00 | 21.49 |
| ATOM | 3681 | CD1 | TRP | A | 483 | 0 | 11.960 | 56.827 | 22.003 | 1.00 | 20.81 |
| ATOM | 3682 | CD2 | TRP | A | 483 | 0 | 11.818 | 58.730 | 23.194 | 1.00 | 20.14 |
| ATOM | 3683 | NE1 | TRP | A | 483 | 0 | 11.187 | 56.575 | 23.143 | 1.00 | 20.29 |
| ATOM | 3684 | CE2 | TRP | A | 483 | 0 | 11.097 | 57.736 | 23.868 | 1.00 | 20.29 |
| ATOM | 3685 | CE3 | TRP | A | 483 | 0 | 11.875 | 60.006 | 23.754 | 1.00 | 21.32 |
| ATOM | 3686 | CZ2 | TRP | A | 483 | 0 | 10.422 | 57.973 | 25.062 | 1.00 | 20.89 |
| ATOM | 3687 | CZ3 | TRP | A | 483 | 0 | 11.217 | 60.248 | 24.946 | 1.00 | 20.78 |
| ATOM | 3688 | CH2 | TRP | A | 483 | 0 | 10.495 | 59.227 | 25.596 | 1.00 | 21.44 |
| ATOM | 3689 | N | ALA | A | 484 | 0 | 11.342 | 61.261 | 20.560 | 1.00 | 28.59 |
| ATOM | 3690 | CA | ALA | A | 484 | 0 | 10.165 | 62.003 | 21.029 | 1.00 | 30.73 |
| ATOM | 3691 | C | ALA | A | 484 | 0 | 9.226 | 62.350 | 19.869 | 1.00 | 30.42 |
| ATOM | 3692 | O | ALA | A | 484 | 0 | 8.024 | 62.337 | 20.071 | 1.00 | 31.34 |
| ATOM | 3693 | CB | ALA | A | 484 | 0 | 10.583 | 63.244 | 21.806 | 1.00 | 31.05 |
| ATOM | 3694 | N | GLN | A | 485 | 0 | 9.702 | 62.488 | 18.653 | 1.00 | 30.79 |
| ATOM | 3695 | CA | GLN | A | 485 | 0 | 8.927 | 62.742 | 17.466 | 1.00 | 33.16 |
| ATOM | 3696 | C | GLN | A | 485 | 0 | 8.026 | 61.608 | 17.017 | 1.00 | 32.81 |
| ATOM | 3697 | O | GLN | A | 485 | 0 | 7.044 | 61.847 | 16.302 | 1.00 | 32.74 |
| ATOM | 3698 | CB | GLN | A | 485 | 0 | 9.859 | 63.113 | 16.290 | 1.00 | 34.56 |
| ATOM | 3699 | CG | GLN | A | 485 | 0 | 10.631 | 64.361 | 16.686 | 1.00 | 39.67 |
| ATOM | 3700 | CD | GLN | A | 485 | 0 | 11.559 | 64.919 | 15.640 | 1.00 | 42.86 |
| ATOM | 3701 | OE1 | GLN | A | 485 | 0 | 11.528 | 66.145 | 15.434 | 1.00 | 45.48 |
| ATOM | 3702 | NE2 | GLN | A | 485 | 0 | 12.375 | 64.103 | 14.982 | 1.00 | 44.07 |
| ATOM | 3703 | N | LEU | A | 486 | 0 | 8.328 | 60.380 | 17.443 | 1.00 | 30.46 |
| ATOM | 3704 | CA | LEU | A | 486 | 0 | 7.500 | 59.231 | 17.095 | 1.00 | 27.76 |
| ATOM | 3705 | C | LEU | A | 486 | 0 | 6.051 | 59.510 | 17.509 | 1.00 | 28.23 |
| ATOM | 3706 | O | LEU | A | 486 | 0 | 5.100 | 59.331 | 16.752 | 1.00 | 26.71 |
| ATOM | 3707 | CB | LEU | A | 486 | 0 | 8.043 | 58.034 | 17.838 | 1.00 | 25.03 |
| ATOM | 3708 | CG | LEU | A | 486 | 0 | 8.988 | 57.012 | 17.226 | 1.00 | 24.18 |
| ATOM | 3709 | CD1 | LEU | A | 486 | 0 | 9.780 | 57.416 | 16.011 | 1.00 | 21.41 |
| ATOM | 3710 | CD2 | LEU | A | 486 | 0 | 9.864 | 56.464 | 18.342 | 1.00 | 23.28 |
| ATOM | 3711 | N | CYS | A | 487 | 0 | 5.870 | 59.974 | 18.739 | 1.00 | 28.05 |
| ATOM | 3712 | CA | CYS | A | 487 | 0 | 4.560 | 60.263 | 19.279 | 1.00 | 30.77 |
| ATOM | 3713 | C | CYS | A | 487 | 0 | 3.823 | 61.350 | 18.499 | 1.00 | 33.19 |
| ATOM | 3714 | O | CYS | A | 487 | 0 | 2.627 | 61.170 | 18.263 | 1.00 | 33.69 |
| ATOM | 3715 | CB | CYS | A | 487 | 0 | 4.643 | 60.637 | 20.752 | 1.00 | 27.94 |
| ATOM | 3716 | SG | CYS | A | 487 | 0 | 5.214 | 59.280 | 21.781 | 1.00 | 27.23 |
| ATOM | 3717 | N | GLU | A | 488 | 0 | 4.543 | 62.373 | 18.064 | 1.00 | 35.80 |
| ATOM | 3718 | CA | GLU | A | 488 | 0 | 3.871 | 63.458 | 17.334 | 1.00 | 39.12 |
| ATOM | 3719 | C | GLU | A | 488 | 0 | 3.384 | 62.928 | 15.995 | 1.00 | 37.78 |
| ATOM | 3720 | O | GLU | A | 488 | 0 | 2.186 | 63.025 | 15.711 | 1.00 | 37.61 |
| ATOM | 3721 | CB | GLU | A | 488 | 0 | 4.737 | 64.697 | 17.257 | 1.00 | 42.04 |
| ATOM | 3722 | CG | GLU | A | 488 | 0 | 5.667 | 64.822 | 16.064 | 1.00 | 47.75 |
| ATOM | 3723 | CD | GLU | A | 488 | 0 | 5.634 | 66.239 | 15.500 | 1.00 | 51.36 |
| ATOM | 3724 | OE1 | GLU | A | 488 | 0 | 5.501 | 66.422 | 14.266 | 1.00 | 52.66 |
| ATOM | 3725 | OE2 | GLU | A | 488 | 0 | 5.743 | 67.154 | 16.358 | 1.00 | 53.40 |
| ATOM | 3726 | N | ILE | A | 489 | 0 | 4.263 | 62.253 | 15.267 | 1.00 | 36.63 |
| ATOM | 3727 | CA | ILE | A | 489 | 0 | 3.906 | 61.647 | 14.004 | 1.00 | 36.74 |
| ATOM | 3728 | C | ILE | A | 489 | 0 | 2.754 | 60.662 | 14.113 | 1.00 | 36.98 |
| ATOM | 3729 | O | ILE | A | 489 | 0 | 1.847 | 60.664 | 13.276 | 1.00 | 38.60 |
| ATOM | 3730 | CB | ILE | A | 489 | 0 | 5.089 | 60.903 | 13.361 | 1.00 | 36.57 |
| ATOM | 3731 | CG1 | ILE | A | 489 | 0 | 6.267 | 61.853 | 13.148 | 1.00 | 36.46 |
| ATOM | 3732 | CG2 | ILE | A | 489 | 0 | 4.651 | 60.305 | 12.030 | 1.00 | 36.90 |
| ATOM | 3733 | CD1 | ILE | A | 489 | 0 | 7.535 | 61.194 | 12.654 | 1.00 | 35.62 |
| ATOM | 3734 | N | TYR | A | 490 | 0 | 2.758 | 59.808 | 15.105 | 1.00 | 36.22 |
| ATOM | 3735 | CA | TYR | A | 490 | 0 | 1.771 | 58.765 | 15.298 | 1.00 | 35.95 |
| ATOM | 3736 | C | TYR | A | 490 | 0 | 0.413 | 59.314 | 15.692 | 1.00 | 37.83 |
| ATOM | 3737 | O | TYR | A | 490 | 0 | -0.581 | 58.816 | 15.165 | 1.00 | 39.24 |
| ATOM | 3738 | CB | TYR | A | 490 | 0 | 2.206 | 57.817 | 16.409 | 1.00 | 32.47 |
| ATOM | 3739 | CG | TYR | A | 490 | 0 | 1.314 | 56.641 | 16.663 | 1.00 | 30.55 |
| ATOM | 3740 | CD1 | TYR | A | 490 | 0 | 1.176 | 55.623 | 15.726 | 1.00 | 29.96 |
| ATOM | 3741 | CD2 | TYR | A | 490 | 0 | 0.610 | 56.536 | 17.849 | 1.00 | 29.79 |
| ATOM | 3742 | CE1 | TYR | A | 490 | 0 | 0.378 | 54.528 | 15.975 | 1.00 | 29.51 |
| ATOM | 3743 | CE2 | TYR | A | 490 | 0 | -0.192 | 55.441 | 18.114 | 1.00 | 29.64 |
| ATOM | 3744 | CZ | TYR | A | 490 | 0 | -0.288 | 54.445 | 17.171 | 1.00 | 29.51 |
| ATOM | 3745 | OH | TYR | A | 490 | 0 | -1.101 | 53.363 | 17.437 | 1.00 | 32.06 |
| ATOM | 3746 | N | ASP | A | 491 | 0 | 0.369 | 60.302 | 16.564 | 1.00 | 40.86 |
| ATOM | 3747 | CA | ASP | A | 491 | 0 | -0.909 | 60.887 | 16.963 | 1.00 | 43.97 |

APPENDIX 1-continued

| | | | | | | | | | | |
|---|---|---|---|---|---|---|---|---|---|---|
| ATOM | 3748 | C | ASP | A | 491 | 0 | -1.586 | 61.633 | 15.811 | 1.00 | 45.30 |
| ATOM | 3749 | O | ASP | A | 491 | 0 | -2.809 | 61.752 | 15.820 | 1.00 | 45.60 |
| ATOM | 3750 | CB | ASP | A | 491 | 0 | -0.764 | 61.800 | 18.170 | 1.00 | 44.67 |
| ATOM | 3751 | CG | ASP | A | 491 | 0 | -0.441 | 61.101 | 19.475 | 1.00 | 45.90 |
| ATOM | 3752 | OD1 | ASP | A | 491 | 0 | 0.149 | 61.761 | 20.364 | 1.00 | 46.32 |
| ATOM | 3753 | OD2 | ASP | A | 491 | 0 | -0.763 | 59.911 | 19.669 | 1.00 | 46.04 |
| ATOM | 3754 | N | ASP | A | 492 | 0 | -0.871 | 62.107 | 14.817 | 1.00 | 46.75 |
| ATOM | 3755 | CA | ASP | A | 492 | 0 | -1.323 | 62.804 | 13.653 | 1.00 | 48.98 |
| ATOM | 3756 | C | ASP | A | 492 | 0 | -1.702 | 61.936 | 12.460 | 1.00 | 49.48 |
| ATOM | 3757 | O | ASP | A | 492 | 0 | -2.002 | 62.458 | 11.378 | 1.00 | 50.24 |
| ATOM | 3758 | CB | ASP | A | 492 | 0 | -0.155 | 63.649 | 13.107 | 1.00 | 51.54 |
| ATOM | 3759 | CG | ASP | A | 492 | 0 | -0.168 | 65.081 | 13.587 | 1.00 | 53.57 |
| ATOM | 3760 | OD1 | ASP | A | 492 | 0 | -0.886 | 65.375 | 14.570 | 1.00 | 54.07 |
| ATOM | 3761 | OD2 | ASP | A | 492 | 0 | 0.576 | 65.857 | 12.939 | 1.00 | 55.04 |
| ATOM | 3762 | N | LEU | A | 493 | 0 | -1.554 | 60.630 | 12.584 | 1.00 | 49.01 |
| ATOM | 3763 | CA | LEU | A | 493 | 0 | -1.896 | 59.732 | 11.483 | 1.00 | 47.63 |
| ATOM | 3764 | C | LEU | A | 493 | 0 | -3.377 | 59.872 | 11.137 | 1.00 | 47.61 |
| ATOM | 3765 | O | LEU | A | 493 | 0 | -4.209 | 60.018 | 12.027 | 1.00 | 47.02 |
| ATOM | 3766 | CB | LEU | A | 493 | 0 | -1.661 | 58.296 | 11.940 | 1.00 | 46.08 |
| ATOM | 3767 | CG | LEU | A | 493 | 0 | -0.485 | 57.463 | 11.464 | 1.00 | 45.24 |
| ATOM | 3768 | CD1 | LEU | A | 493 | 0 | 0.616 | 58.224 | 10.756 | 1.00 | 43.57 |
| ATOM | 3769 | CD2 | LEU | A | 493 | 0 | 0.075 | 56.710 | 12.669 | 1.00 | 44.62 |
| ATOM | 3770 | N | PRO | A | 494 | 0 | -3.694 | 59.763 | 9.866 | 1.00 | 48.01 |
| ATOM | 3771 | CA | PRO | A | 494 | 0 | -5.049 | 59.734 | 9*353 | 1.00 | 49.11 |
| ATOM | 3772 | C | PRO | A | 494 | 0 | -5.617 | 58.339 | 9.570 | 1.00 | 51.21 |
| ATOM | 3773 | O | PRO | A | 494 | 0 | -4.919 | 57.325 | 9.495 | 1.00 | 50.61 |
| ATOM | 3774 | CB | PRO | A | 494 | 0 | -4.938 | 59.995 | 7.843 | 1.00 | 48.94 |
| ATOM | 3775 | CG | PRO | A | 494 | 0 | -3.559 | 59.463 | 7.544 | 1.00 | 48.47 |
| ATOM | 3776 | CD | PRO | A | 494 | 0 | -2.714 | 59.538 | 8.797 | 1.00 | 48.22 |
| ATOM | 3777 | N | PRO | A | 495 | 0 | -6.915 | 58.238 | 9.796 | 1.00 | 53.24 |
| ATOM | 3778 | CA | PRO | A | 495 | 0 | -7.630 | 57.006 | 10.055 | 1.00 | 53.93 |
| ATOM | 3779 | C | PRO | A | 495 | 0 | -7.404 | 55.890 | 9.058 | 1.00 | 54.84 |
| ATOM | 3780 | O | PRO | A | 495 | 0 | -7.348 | 54.705 | 9.423 | 1.00 | 55.08 |
| ATOM | 3781 | CB | PRO | A | 495 | 0 | -9.126 | 57.362 | 10.146 | 1.00 | 54.40 |
| ATOM | 3782 | CG | PRO | A | 495 | 0 | -9.090 | 58.848 | 10.391 | 1.00 | 54.17 |
| ATOM | 3783 | CD | PRO | A | 495 | 0 | -7.787 | 59.420 | 9.895 | 1.00 | 53.58 |
| ATOM | 3784 | N | GLU | A | 496 | 0 | -7.190 | 56.198 | 7.784 | 1.00 | 55.36 |
| ATOM | 3785 | CA | GLU | A | 496 | 0 | -6.936 | 55.187 | 6.763 | 1.00 | 55.83 |
| ATOM | 3786 | C | GLU | A | 496 | 0 | -5.582 | 54.521 | 6.971 | 1.00 | 54.09 |
| ATOM | 3787 | O | GLU | A | 496 | 0 | -5.345 | 53.406 | 6.505 | 1.00 | 53.29 |
| ATOM | 3788 | CB | GLU | A | 496 | 0 | -7.091 | 55.805 | 5.378 | 1.00 | 57.96 |
| ATOM | 3789 | CG | GLU | A | 496 | 0 | -6.030 | 55.604 | 4.339 | 1.00 | 61.30 |
| ATOM | 3790 | CD | GLU | A | 496 | 0 | -6.448 | 54.984 | 3.025 | 1.00 | 63.68 |
| ATOM | 3791 | OE1 | GLU | A | 496 | 0 | -7.449 | 55.411 | 2.388 | 1.00 | 65.15 |
| ATOM | 3792 | OE2 | GLU | A | 496 | 0 | -5.747 | 54.034 | 2.586 | 1.00 | 64.91 |
| ATOM | 3793 | N | ALA | A | 497 | 0 | -4.665 | 55.217 | 7.630 | 1.00 | 52.35 |
| ATOM | 3794 | CA | ALA | A | 497 | 0 | -3.326 | 54.738 | 7.886 | 1.00 | 50.83 |
| ATOM | 3795 | C | ALA | A | 497 | 0 | -3.245 | 53.626 | 8.924 | 1.00 | 49.08 |
| ATOM | 3796 | O | ALA | A | 497 | 0 | -2.361 | 52.773 | 8.794 | 1.00 | 47.61 |
| ATOM | 3797 | CB | ALA | A | 497 | 0 | -2.443 | 55.910 | 8.317 | 1.00 | 51.23 |
| ATOM | 3798 | N | THR | A | 498 | 0 | -4.113 | 53.630 | 9.926 | 1.00 | 48.01 |
| ATOM | 3799 | CA | THR | A | 498 | 0 | -4.086 | 52.617 | 10.964 | 1.00 | 48.73 |
| ATOM | 3800 | C | THR | A | 498 | 0 | -5.271 | 51.656 | 10.938 | 1.00 | 48.99 |
| ATOM | 3801 | O | THR | A | 498 | 0 | -5.425 | 50.852 | 11.862 | 1.00 | 47.81 |
| ATOM | 3802 | CB | THR | A | 498 | 0 | -4.055 | 53.223 | 12.388 | 1.00 | 49.04 |
| ATOM | 3803 | OG1 | THR | A | 498 | 0 | -5.315 | 53.816 | 12.752 | 1.00 | 47.95 |
| ATOM | 3804 | CG2 | THR | A | 498 | 0 | -2.919 | 54.223 | 12.514 | 1.00 | 48.94 |
| ATOM | 3805 | N | SER | A | 499 | 0 | -6.101 | 51.756 | 9.911 | 1.00 | 49.78 |
| ATOM | 3806 | CA | SER | A | 499 | 0 | -7.307 | 50.933 | 9.814 | 1.00 | 51.20 |
| ATOM | 3807 | C | SER | A | 499 | 0 | -7.048 | 49.470 | 9.494 | 1.00 | 49.98 |
| ATOM | 3808 | O | SER | A | 499 | 0 | -6.257 | 49.143 | 8.617 | 1.00 | 48.80 |
| ATOM | 3809 | CB | SER | A | 499 | 0 | -8.223 | 51.606 | 8.800 | 1.00 | 52.62 |
| ATOM | 3810 | OG | SER | A | 499 | 0 | -8.428 | 50.827 | 7.596 | 1.00 | 55.22 |
| ATOM | 3811 | N | ILE | A | 500 | 0 | -7.706 | 48.585 | 10.230 | 1.00 | 50.08 |
| ATOM | 3812 | CA | ILE | A | 500 | 0 | -7.563 | 47.151 | 10.077 | 1.00 | 51.25 |
| ATOM | 3813 | C | ILE | A | 500 | 0 | -8.642 | 46.518 | 9.207 | 1.00 | 53.08 |
| ATOM | 3814 | O | ILE | A | 500 | 0 | -9.785 | 46.351 | 9.639 | 1.00 | 54.00 |
| ATOM | 3815 | CB | ILE | A | 500 | 0 | -7.631 | 46.428 | 11.436 | 1.00 | 50.61 |
| ATOM | 3816 | CG1 | ILE | A | 500 | 0 | -6.475 | 46.866 | 12.336 | 1.00 | 50.22 |
| ATOM | 3817 | CG2 | ILE | A | 500 | 0 | -7.619 | 44.907 | 11.302 | 1.00 | 50.34 |
| ATOM | 3818 | CD1 | ILE | A | 500 | 0 | -6.806 | 46.617 | 13.800 | 1.00 | 50.52 |
| ATOM | 3819 | N | GLN | A | 501 | 0 | -8.263 | 46.074 | 8.024 | 1.00 | 54.35 |
| ATOM | 3820 | CA | GLN | A | 501 | 0 | -9.177 | 45.360 | 7.129 | 1.00 | 55.14 |
| ATOM | 3821 | C | GLN | A | 501 | 0 | -9.298 | 43.904 | 7.564 | 1.00 | 55.85 |
| ATOM | 3822 | O | GLN | A | 501 | 0 | -8.335 | 43.130 | 7.556 | 1.00 | 55.59 |
| ATOM | 3823 | CB | GLN | A | 501 | 0 | -8.594 | 45.485 | 5.732 | 1.00 | 55.56 |
| ATOM | 3824 | CG | GLN | A | 501 | 0 | -9.262 | 44.736 | 4.604 | 1.00 | 56.32 |
| ATOM | 3825 | CD | GLN | A | 501 | 0 | -8.874 | 45.369 | 3.271 | 1.00 | 57.46 |
| ATOM | 3826 | OE1 | GLN | A | 501 | 0 | -8.480 | 44.667 | 2.336 | 1.00 | 57.35 |

APPENDIX 1-continued

| ATOM | 3827 | NE2 | GLN | A | 501 | 0 | -8.998 | 46.697 | 3.219 | 1.00 | 57.61 |
|---|---|---|---|---|---|---|---|---|---|---|---|
| ATOM | 3828 | N | THR | A | 502 | 0 | -10.493 | 43.506 | 7.968 | 1.00 | 57.08 |
| ATOM | 3829 | CA | THR | A | 502 | 0 | -10.788 | 42.146 | 8.401 | 1.00 | 58.28 |
| ATOM | 3830 | C | THR | A | 502 | 0 | -10.966 | 41.205 | 7.216 | 1.00 | 58.80 |
| ATOM | 3831 | O | THR | A | 502 | 0 | -11.199 | 41.604 | 6.074 | 1.00 | 58.71 |
| ATOM | 3832 | CB | THR | A | 502 | 0 | -12.046 | 42.108 | 9.293 | 1.00 | 58.99 |
| ATOM | 3833 | OG1 | THR | A | 502 | 0 | -11.794 | 42.909 | 10.464 | 1.00 | 59.62 |
| ATOM | 3834 | CG2 | THR | A | 502 | 0 | -12.421 | 40.707 | 9.749 | 1.00 | 58.74 |
| ATOM | 3835 | N | VAL | A | 503 | 0 | -10.746 | 39.922 | 7.471 | 1.00 | 59.20 |
| ATOM | 3836 | CA | VAL | A | 503 | 0 | -10.904 | 38.877 | 6.468 | 1.00 | 60.27 |
| ATOM | 3837 | C | VAL | A | 503 | 0 | -11.687 | 37.736 | 7.119 | 1.00 | 61.11 |
| ATOM | 3838 | O | VAL | A | 503 | 0 | -11.606 | 37.563 | 8.341 | 1.00 | 61.03 |
| ATOM | 3839 | CB | VAL | A | 503 | 0 | -9.589 | 38.430 | 5.823 | 1.00 | 59.97 |
| ATOM | 3840 | CG1 | VAL | A | 503 | 0 | -8.337 | 38.964 | 6.507 | 1.00 | 59.65 |
| ATOM | 3841 | CG2 | VAL | A | 503 | 0 | -9.467 | 36.914 | 5.722 | 1.00 | 59.97 |
| ATOM | 3842 | N | VAL | A | 504 | 0 | -12.478 | 37.002 | 6.341 | 1.00 | 61.77 |
| ATOM | 3843 | CA | VAL | A | 504 | 0 | -13.203 | 35.863 | 6.911 | 1.00 | 62.40 |
| ATOM | 3844 | C | VAL | A | 504 | 0 | -12.673 | 34.579 | 6.259 | 1.00 | 62.99 |
| ATOM | 3845 | O | VAL | A | 504 | 0 | -11.811 | 33.894 | 6.803 | 1.00 | 63.13 |
| ATOM | 3846 | CB | VAL | A | 504 | 0 | -14.730 | 35.882 | 6.756 | 1.00 | 62.39 |
| ATOM | 3847 | CG1 | VAL | A | 504 | 0 | -15.392 | 36.931 | 7.635 | 1.00 | 61.89 |
| ATOM | 3848 | CG2 | VAL | A | 504 | 0 | -15.127 | 36.068 | 5.297 | 1.00 | 62.17 |
| ATOM | 3849 | C1 | NAG | A | 800 | 0 | -2.401 | 42.835 | 45.802 | 1.00 | 30.44 |
| ATOM | 3850 | C2 | NAG | A | 800 | 0 | -1.327 | 43.232 | 46.780 | 1.00 | 31.80 |
| ATOM | 3851 | N2 | NAG | A | 800 | 0 | -0.119 | 43.561 | 45.983 | 1.00 | 31.37 |
| ATOM | 3852 | C7 | NAG | A | 800 | 0 | 0.179 | 44.844 | 45.683 | 1.00 | 32.37 |
| ATOM | 3853 | O7 | NAG | A | 800 | 0 | -0.549 | 45.688 | 45.982 | 1.00 | 34.61 |
| ATOM | 3854 | C8 | NAG | A | 800 | 0 | 1.457 | 45.094 | 44.983 | 1.00 | 31.67 |
| ATOM | 3855 | C3 | NAG | A | 800 | 0 | -1.015 | 42.187 | 47.801 | 1.00 | 32.94 |
| ATOM | 3856 | O3 | NAG | A | 800 | 0 | -0.264 | 42.838 | 48.796 | 1.00 | 34.46 |
| ATOM | 3857 | C4 | NAG | A | 800 | 0 | -2.351 | 41.662 | 48.377 | 1.00 | 34.05 |
| ATOM | 3858 | O4 | NAG | A | 800 | 0 | -2.097 | 40.644 | 49.344 | 1.00 | 35.62 |
| ATOM | 3859 | C5 | NAG | A | 800 | 0 | -3.128 | 41.025 | 47.202 | 1.00 | 35.11 |
| ATOM | 3860 | O5 | NAG | A | 800 | 0 | -3.466 | 42.046 | 46.295 | 1.00 | 33.06 |
| ATOM | 3861 | C6 | NAG | A | 800 | 0 | -4.444 | 40.420 | 47.673 | 1.00 | 36.66 |
| ATOM | 3862 | O6 | NAG | A | 800 | 0 | -5.199 | 41.411 | 48.288 | 1.00 | 39.73 |
| ATOM | 3863 | C1 | GLC | A | 900 | 0 | -8.957 | 50.280 | 6.333 | 1.00 | 58.53 |
| ATOM | 3864 | C2 | GLC | A | 900 | 0 | -8.500 | 49.605 | 5.037 | 1.00 | 59.25 |
| ATOM | 3865 | C3 | GLC | A | 900 | 0 | -7.806 | 50.686 | 4.219 | 1.00 | 59.71 |
| ATOM | 3866 | C4 | GLC | A | 900 | 0 | -8.691 | 51.905 | 3.987 | 1.00 | 60.13 |
| ATOM | 3867 | CS | GLC | A | 900 | 0 | -9.595 | 52.289 | 5.142 | 1.00 | 59.22 |
| ATOM | 3868 | O5 | GLC | A | 900 | 0 | -10.004 | 51.177 | 5.937 | 1.00 | 59.71 |
| ATOM | 3869 | CU | IUM | B | 1 | 0 | -1.332 | 34.401 | 30.132 | 1.00 | 29.47 |
| ATOM | 3870 | CU | IUM | B | 2 | 0 | 7.297 | 42.245 | 26.618 | 1.00 | 27.01 |
| ATOM | 3871 | CU | IUM | B | 3 | 0 | 9.569 | 38.786 | 23.923 | 1.00 | 21.38 |
| ATOM | 3872 | O | IUM | B | 5 | 0 | 7.445 | 40.703 | 25.162 | 1.00 | 26.99 |
| ATOM | 3873 | OWO | WAT | W | 1 | 0 | 19.509 | 36.893 | 30.054 | 1.00 | 13.07 |
| ATOM | 3874 | OWO | WAT | W | 2 | 0 | 24.726 | 29.672 | 16.651 | 1.00 | 7.67 |
| ATOM | 3875 | OWO | WAT | W | 3 | 0 | 15.295 | 17.988 | 35.061 | 1.00 | 8.65 |
| ATOM | 3876 | OWO | WAT | W | 4 | 0 | 6.481 | 28.311 | 23.427 | 1.00 | 8.00 |
| ATOM | 3877 | OWO | WAT | W | 5 | 0 | 14.921 | 45.178 | 24.306 | 1.00 | 17.04 |
| ATOM | 3878 | OWO | WAT | W | 6 | 0 | 14.413 | 44.401 | 28.162 | 1.00 | 10.12 |
| ATOM | 3879 | OWO | WAT | W | 7 | 0 | 9.967 | 21.576 | 9.620 | 1.00 | 11.43 |
| ATOM | 3880 | OWO | WAT | W | 8 | 0 | 10.088 | 28.675 | 13.038 | 1.00 | 9.27 |
| ATOM | 3881 | OWO | WAT | W | 9 | 0 | 9.808 | 47.902 | 28.959 | 1.00 | 12.71 |
| ATOM | 3882 | OWO | WAT | W | 10 | 0 | 21.976 | 23.052 | 35.604 | 1.00 | 11.72 |
| ATOM | 3883 | OWO | WAT | W | 11 | 0 | 10.862 | 25.744 | 29.928 | 1.00 | 10.21 |
| ATOM | 3884 | OWO | WAT | W | 12 | 0 | 26.087 | 32.996 | 23.097 | 1.00 | 14.21 |
| ATOM | 3885 | OWO | WAT | W | 13 | 0 | 22.256 | 58.745 | 37.931 | 1.00 | 17.85 |
| ATOM | 3886 | OWO | WAT | W | 14 | 0 | -0.104 | 29.831 | 35.249 | 1.00 | 16.36 |
| ATOM | 3887 | OWO | WAT | W | 15 | 0 | 18.153 | 61.857 | 36.641 | 1.00 | 14.38 |
| ATOM | 3888 | OWO | WAT | W | 16 | 0 | 9.426 | 38.431 | 9.161 | 1.00 | 15.35 |
| ATOM | 3889 | OWO | WAT | W | 17 | 0 | 7.639 | 24.371 | 3.713 | 1.00 | 22.18 |
| ATOM | 3890 | OWO | WAT | W | 18 | 0 | 27.977 | 11.643 | 9.481 | 1.00 | 19.22 |
| ATOM | 3891 | OWO | WAT | W | 19 | 0 | 3.140 | 21.028 | 24.695 | 1.00 | 11.12 |
| ATOM | 3892 | OWO | WAT | W | 20 | 0 | 9.847 | 20.701 | 30.902 | 1.00 | 16.16 |
| ATOM | 3893 | OWO | WAT | W | 21 | 0 | -1.517 | 29.009 | 43.180 | 1.00 | 27.18 |
| ATOM | 3894 | OWO | WAT | W | 22 | 0 | 3.497 | 29.138 | 26.088 | 1.00 | 17.2 |
| ATOM | 3895 | OWO | WAT | W | 23 | 0 | 20.614 | 32.765 | 40.433 | 1.00 | 17.63 |
| ATOM | 3896 | OWO | WAT | W | 24 | 0 | 19.098 | 51.778 | 39.452 | 1.00 | 22.33 |
| ATOM | 3897 | OWO | WAT | W | 25 | 0 | 0.977 | 21.396 | 5.064 | 1.00 | 18.54 |
| ATOM | 3898 | OWO | WAT | W | 26 | 0 | 8.546 | 16.150 | 21.761 | 1.00 | 16.40 |
| ATOM | 3899 | OWO | WAT | W | 27 | 0 | 6.102 | 19.858 | 10.350 | 1.00 | 17.79 |
| ATOM | 3900 | OWO | WAT | W | 28 | 0 | 11.702 | 55.189 | 41.955 | 1.00 | 18.92 |
| ATOM | 3901 | OWO | WAT | W | 29 | 0 | 3.360 | 42.251 | 18.209 | 1.00 | 16.26 |
| ATOM | 3902 | OWO | WAT | W | 30 | 0 | 6.232 | 14.672 | 22.473 | 1.00 | 24.49 |
| ATOM | 3903 | OWO | WAT | W | 31 | 0 | 16.729 | 26.542 | 39.731 | 1.00 | 15.28 |
| ATOM | 3904 | OWO | WAT | W | 32 | 0 | 2.834 | 30.640 | 40.601 | 1.00 | 18.11 |
| ATOM | 3905 | OWO | WAT | W | 33 | 0 | 21.893 | 42.837 | 27.884 | 1.00 | 15.08 |

APPENDIX 1-continued

```
ATOM    3906 OWO    WAT    W     34    0     1.581 28.193 27.914  1.00   17.77
ATOM    3907 OWO    WAT    W     35    0    -3.503 21.749 11.578  1.00   15.32
ATOM    3908 OWO    WAT    W     36    0     7.131 33.344 11.786  1.00   18.18
ATOM    3909 OWO    WAT    W     37    0    17.312 38.603 29.961  1.00   14.75
ATOM    3910 OWO    WAT    W     38    0    -6.705 40.723 39.909  1.00   23.49
ATOM    3911 OWO    WAT    W     39    0     9.010 31.121 11.736  1.00   19.99
ATOM    3912 OWO    WAT    W     40    0     9.376 28.353 33.076  1.00   16.22
ATOM    3913 OWO    WAT    W     41    0    30.104 29.895 20.857  1.00   25.77
ATOM    3914 OWO    WAT    W     42    0    -6.950 33.663 21.335  1.00   26.62
ATOM    3915 OWO    WAT    W     43    0     8.541 27.867 36.827  1.00   12.80
ATOM    3916 OWO    WAT    W     44    0     3.590 21.651 11.893  1.00   14.46
ATOM    3917 OWO    WAT    W     45    0    23.290 21.665 37.787  1.00   28.75
ATOM    3918 OWO    WAT    W     46    0    22.724 11.873 22.270  1.00   23.07
ATOM    3919 OWO    WAT    W     47    0    -1.090 42.001 12.877  1.00   19.33
ATOM    3920 OWO    WAT    W     48    0    14.091 27.298 40.583  1.00   18.51
ATOM    3921 OWO    WAT    W     49    0     2.336 52.026 29.983  1.00   25.66
ATOM    3922 OWO    WAT    W     50    0    15.475 14.450 22.853  1.00   20.37
ATOM    3923 OWO    WAT    W     51    0    25.945 26.568 40.287  1.00   24.49
ATOM    3924 OWO    WAT    W     52    0    19.545 41.598 35.087  1.00   20.70
ATOM    3925 OWO    WAT    W     53    0    -3.802 47.942  9.638  1.00   29.98
ATOM    3926 OWO    WAT    W     54    0    -7.478 41.160  9.585  1.00   24.26
ATOM    3927 OWO    WAT    W     55    0    -2.938 29.733 36.048  1.00   22.93
ATOM    3928 OWO    WAT    W     56    0    29.051 32.114 22.680  1.00   22.50
ATOM    3929 OWO    WAT    W     57    0     0.360 29.505  5.595  1.00   17.78
ATOM    3930 OWO    WAT    W     58    0     8.583 57.422 21.440  1.00   21.90
ATOM    3931 OWO    WAT    W     59    0    25.151 31.947 34.812  1.00   22.13
ATOM    3932 OWO    WAT    W     60    0    25.133 62.204 32.968  1.00   25.75
ATOM    3933 OWO    WAT    W     61    0    14.909 40.770 30.294  1.00   17.25
ATOM    3934 OWO    WAT    W     62    0    20.825 30.520 34.676  1.00   16.18
ATOM    3935 OWO    WAT    W     63    0     5.509 26.744 43.167  1.00   30.12
ATOM    3936 OWO    WAT    W     64    0     5.280 57.279 14.627  1.00   22.66
ATOM    3937 OWO    WAT    W     65    0     2.944 53.436 32.359  1.00   22.97
ATOM    3938 OWO    WAT    W     66    0    11.266 43.508  3.407  1.00   20.01
ATOM    3939 OWO    WAT    W     67    0    21.535 45.549 26.563  1.00   24.47
ATOM    3940 OWO    WAT    W     68    0     0.412 33.358 11.837  1.00   19.89
ATOM    3941 OWO    WAT    W     69    0    26.466 32.305 25.785  1.00   20.19
ATOM    3942 OWO    WAT    W     70    0     0.910 45.068  7.829  1.00   22.05
ATOM    3943 OWO    WAT    W     71    0    -2.060 46.506 39.381  1.00   23.49
ATOM    3944 OWO    WAT    W     72    0    20.236 56.718 25.851  1.00   23.74
ATOM    3945 OWO    WAT    W     73    0     3.253 23.017 38.254  1.00   24.83
ATOM    3946 OWO    WAT    W     74    0     9.653 22.835 35.143  1.00   25.79
ATOM    3947 OWO    WAT    W     75    0    16.877 52.904 47.331  1.00   24.42
ATOM    3948 OWO    WAT    W     76    0    14.293 22.021  3.993  1.00   32.28
ATOM    3949 OWO    WAT    W     77    0    -5.287 19.835 18.528  1.00   24.65
ATOM    3950 OWO    WAT    W     78    0     8.414 38.317 49.069  1.00   28.77
ATOM    3951 OWO    WAT    W     79    0     7.070 32.466 47.926  1.00   21.83
ATOM    3952 OWO    WAT    W     80    0    -0.452 28.307 25.779  1.00   16.58
ATOM    3953 OWO    WAT    W     81    0    14.774 15.006 34.455  1.00   25.63
ATOM    3954 OWO    WAT    W     82    0    11.515 54.942 35.962  1.00   14.20
ATOM    3955 OWO    WAT    W     83    0    25.643 33.451 32.105  1.00   30.31
ATOM    3956 OWO    WAT    W     84    0    11.869 12.221 20.394  1.00   31.37
ATOM    3957 OWO    WAT    W     85    0    11.653 51.587 22.411  1.00   16.48
ATOM    3958 OWO    WAT    W     86    0    17.334 40.837 51.079  1.00   30.26
ATOM    3959 OWO    WAT    W     87    0     4.355 25.208 34.030  1.00   32.26
ATOM    3960 OWO    WAT    W     88    0    18.816 52.360 32.512  1.00   21.19
ATOM    3961 OWO    WAT    W     89    0    -2.704 46.518 35.364  1.00   21.99
ATOM    3962 OWO    WAT    W     90    0    18.793 27.893 49.481  1.00   24.52
ATOM    3963 OWO    WAT    W     91    0    22.459 46.584 28.898  1.00   18.99
ATOM    3964 OWO    WAT    W     92    0     7.958 34.422 49.370  1.00   26.14
ATOM    3965 OWO    WAT    W     93    0    23.972 16.246  6.806  1.00   24.35
ATOM    3966 OWO    WAT    W     94    0     1.340 49.185 26.307  1.00   31.64
ATOM    3967 OWO    WAT    W     95    0    -1.830 35.291 12.266  1.00   27.28
ATOM    3968 OWO    WAT    W     96    0    20.460 17.486  3.589  1.00   33.51
ATOM    3969 OWO    WAT    W     97    0    15.177  6.964  9.868  1.00   24.40
ATOM    3970 OWO    WAT    W     98    0    18.616 57.927 43.922  1.00   30.76
ATOM    3971 OWO    WAT    W     99    0    10.562 32.112  9.972  1.00   28.90
ATOM    3972 OWO    WAT    W    100    0     1.630 61.363 10.878  1.00   33.92
ATOM    3973 OWO    WAT    W    101    0    -4.939 49.989 33.211  1.00   29.73
ATOM    3974 OWO    WAT    W    102    0    19.385 44.813 34.546  1.00   23.52
ATOM    3975 OWO    WAT    W    103    0    19.055 43.063 37.581  1.00   30.59
ATOM    3976 OWO    WAT    W    105    0    28.703 33.555 27.406  1.00   32.92
ATOM    3977 OWO    WAT    W    106    0    28.835 19.646 10.759  1.00   40.44
ATOM    3978 OWO    WAT    W    107    0    22.047 22.465  9.758  1.00   29.98
ATOM    3979 OWO    WAT    W    108    0    14.689 61.032 36.346  1.00   30.63
ATOM    3980 OWO    WAT    W    109    0    16.998 24.042  9.318  1.00   23.90
ATOM    3981 OWO    WAT    W    110    0    13.472 30.533 11.848  1.00   34.83
ATOM    3982 OWO    WAT    W    111    0    -2.175 35.601 41.496  1.00   28.55
ATOM    3983 OWO    WAT    W    112    0     1.528 17.373 -1.396  1.00   38.21
ATOM    3984 OWO    WAT    W    113    0    -2.856 29.748 19.681  1.00   30.55
```

APPENDIX 1-continued

| ATOM | 3985 | OWO | WAT | W | 114 | 0 | 2.377 | 42.810 | 47.971 | 1.00 | 26.87 |
|---|---|---|---|---|---|---|---|---|---|---|---|
| ATOM | 3986 | OWO | WAT | W | 115 | 0 | 10.947 | 12.820 | 33.745 | 1.00 | 31.60 |
| ATOM | 3987 | OWO | WAT | W | 116 | 0 | 9.807 | 58.194 | 12.442 | 1.00 | 29.63 |
| ATOM | 3988 | OWO | WAT | W | 117 | 0 | 18.488 | 62.559 | 29.470 | 1.00 | 45.83 |
| ATOM | 3989 | OWO | WAT | W | 118 | 0 | 11.708 | 61.566 | 40.940 | 1.00 | 37.19 |
| ATOM | 3990 | OWO | WAT | W | 119 | 0 | −10.101 | 22.257 | 15.091 | 1.00 | 30.48 |
| ATOM | 3991 | OWO | WAT | W | 120 | 0 | −1.930 | 15.913 | 7.386 | 1.00 | 36.63 |
| ATOM | 3992 | OWO | WAT | W | 121 | 0 | 23.988 | 43.686 | 29.319 | 1.00 | 32.15 |
| ATOM | 3993 | OWO | WAT | W | 122 | 0 | 7.354 | 57.153 | 12.809 | 1.00 | 28.10 |
| ATOM | 3994 | OWO | WAT | W | 123 | 0 | 24.207 | 22.101 | 11.958 | 1.00 | 32.83 |
| ATOM | 3995 | OWO | WAT | W | 124 | 0 | −1.268 | 15.083 | 9.738 | 1.00 | 32.53 |
| ATOM | 3996 | OWO | WAT | W | 125 | 0 | 19.363 | 5.047 | 13.812 | 1.00 | 34.57 |
| ATOM | 3997 | OWO | WAT | W | 126 | 0 | 4.799 | 41.145 | 23.688 | 1.00 | 28.33 |
| ATOM | 3998 | OWO | WAT | W | 127 | 0 | 15.975 | 23.287 | 5.889 | 1.00 | 30.95 |
| ATOM | 3999 | OWO | WAT | W | 128 | 0 | 3.698 | 38.582 | −2.369 | 1.00 | 36.84 |
| ATOM | 4000 | OWO | WAT | W | 129 | 0 | −2.601 | 49.124 | 11.710 | 1.00 | 28.91 |
| ATOM | 4001 | OWO | WAT | W | 130 | 0 | 15.779 | 56.598 | 43.285 | 1.00 | 27.76 |
| ATOM | 4002 | OWO | WAT | W | 131 | 0 | 26.306 | 32.724 | 13.233 | 1.00 | 37.94 |
| ATOM | 4003 | OWO | WAT | W | 132 | 0 | 3.610 | 46.947 | 23.991 | 1.00 | 35.49 |
| ATOM | 4004 | OWO | WAT | W | 133 | 0 | 18.354 | 11.929 | 29.348 | 1.00 | 33.88 |
| ATOM | 4005 | OWO | WAT | W | 134 | 0 | 13.966 | 41.517 | 27.765 | 1.00 | 18.02 |
| ATOM | 4006 | OWO | WAT | W | 135 | 0 | 23.545 | 49.080 | 27.785 | 1.00 | 25.21 |
| ATOM | 4007 | OWO | WAT | W | 136 | 0 | 16.876 | 25.082 | 41.791 | 1.00 | 28.71 |
| ATOM | 4008 | OWO | WAT | W | 137 | 0 | 15.439 | 54.809 | 45.527 | 1.00 | 35.30 |
| ATOM | 4009 | OWO | WAT | W | 138 | 0 | 11.733 | 25.676 | 43.264 | 1.00 | 38.24 |
| ATOM | 4010 | OWO | WAT | W | 139 | 0 | 9.795 | 34.460 | 11.898 | 1.00 | 31.61 |
| ATOM | 4011 | OWO | WAT | W | 140 | 0 | 13.328 | 57.569 | 42.356 | 1.00 | 30.66 |
| ATOM | 4012 | OWO | WAT | W | 141 | 0 | 14.146 | 7.869 | 20.604 | 1.00 | 35.72 |
| ATOM | 4013 | OWO | WAT | W | 142 | 0 | 23.330 | 12.948 | 3.922 | 1.00 | 29.83 |
| ATOM | 4014 | OWO | WAT | W | 143 | 0 | 16.607 | 10.575 | 24.347 | 1.00 | 36.47 |
| ATOM | 4015 | OWO | WAT | W | 144 | 0 | 8.509 | 25.546 | 35.012 | 1.00 | 35.43 |
| ATOM | 4016 | OWO | WAT | W | 145 | 0 | 12.597 | 44.457 | 1.450 | 1.00 | 39.54 |
| ATOM | 4017 | OWO | WAT | W | 146 | 0 | 21.680 | 51.509 | 39.154 | 1.00 | 40.08 |
| ATOM | 4018 | OWO | WAT | W | 147 | 0 | −0.702 | 52.593 | 39.700 | 1.00 | 29.62 |
| ATOM | 4019 | OWO | WAT | W | 148 | 0 | 23.269 | 14.719 | 22.589 | 1.00 | 30.24 |
| ATOM | 4020 | OWO | WAT | W | 149 | 0 | 27.149 | 22.972 | 41.846 | 1.00 | 35.00 |
| ATOM | 4021 | OWO | WAT | W | 150 | 0 | 2.854 | 9.792 | 8.923 | 1.00 | 46.35 |
| ATOM | 4022 | OWO | WAT | W | 151 | 0 | 24.831 | 15.672 | 24.889 | 1.00 | 29.22 |
| ATOM | 4023 | OWO | WAT | W | 152 | 0 | 24.965 | 51.606 | 19.113 | 1.00 | 32.19 |
| ATOM | 4024 | OWO | WAT | W | 153 | 0 | −4.611 | 25.034 | 37.817 | 1.00 | 46.51 |
| ATOM | 4025 | OWO | WAT | W | 154 | 0 | 12.225 | 39.382 | 28.864 | 1.00 | 25.42 |
| ATOM | 4026 | OWO | WAT | W | 155 | 0 | 18.332 | 22.341 | 43.180 | 1.00 | 36.18 |
| ATOM | 4027 | OWO | WAT | W | 156 | 0 | 36.467 | 20.701 | 17.144 | 1.00 | 44.13 |
| ATOM | 4028 | OWO | WAT | W | 157 | 0 | −4.903 | 47.901 | 40.886 | 1.00 | 33.97 |
| ATOM | 4029 | OWO | WAT | W | 158 | 0 | 12.979 | 13.955 | 3.208 | 1.00 | 33.60 |
| ATOM | 4030 | OWO | WAT | W | 159 | 0 | 32.383 | 12.693 | 24.743 | 1.00 | 30.25 |
| ATOM | 4031 | OWO | WAT | W | 160 | 0 | 30.796 | 26.296 | 14.368 | 1.00 | 44.37 |
| ATOM | 4032 | OWO | WAT | W | 161 | 0 | 19.332 | 37.280 | 40.057 | 1.00 | 31.54 |
| ATOM | 4033 | OWO | WAT | W | 162 | 0 | 17.625 | 20.028 | 41.642 | 1.00 | 45.88 |
| ATOM | 4034 | OWO | WAT | W | 163 | 0 | 19.917 | 56.115 | 46.103 | 1.00 | 40.37 |
| ATOM | 4035 | OWO | WAT | W | 164 | 0 | −4.743 | 14.204 | 16.748 | 1.00 | 40.86 |
| ATOM | 4036 | OWO | WAT | W | 165 | 0 | 0.738 | 46.912 | 21.790 | 1.00 | 38.56 |
| ATOM | 4037 | OWO | WAT | W | 166 | 0 | 22.648 | 62.277 | 30.976 | 1.00 | 24.37 |
| ATOM | 4038 | OWO | WAT | W | 167 | 0 | −4.322 | 45.754 | 26.894 | 1.00 | 48.97 |
| ATOM | 4039 | OWO | WAT | W | 168 | 0 | −2.386 | 24.601 | 0.665 | 1.00 | 32.57 |
| ATOM | 4040 | OWO | WAT | W | 169 | 0 | −0.459 | 41.618 | 35.838 | 1.00 | 35.25 |
| ATOM | 4041 | OWO | WAT | W | 170 | 0 | 26.659 | 4.722 | 11.434 | 1.00 | 41.25 |
| ATOM | 4042 | OWO | WAT | W | 171 | 0 | 13.720 | 11.379 | 22.121 | 1.00 | 39.59 |
| ATOM | 4043 | OWO | WAT | W | 172 | 0 | 15.266 | 7.451 | 6.576 | 1.00 | 41.71 |
| ATOM | 4044 | OWO | WAT | W | 173 | 0 | 0.134 | 17.450 | 6.165 | 1.00 | 42.12 |
| ATOM | 4045 | OWO | WAT | W | 174 | 0 | 38.646 | 32.884 | 25.247 | 1.00 | 41.80 |
| ATOM | 4046 | OWO | WAT | W | 175 | 0 | 10.591 | 17.398 | 3.251 | 1.00 | 29.37 |
| ATOM | 4047 | OWO | WAT | W | 176 | 0 | 22.444 | 49.424 | 25.264 | 1.00 | 19.51 |
| ATOM | 4048 | OWO | WAT | W | 177 | 0 | 0.429 | 23.224 | 28.598 | 1.00 | 33.54 |
| ATOM | 4049 | OWO | WAT | W | 178 | 0 | −2.302 | 27.278 | 34.780 | 1.00 | 44.76 |
| ATOM | 4050 | OWO | WAT | W | 179 | 0 | 2.054 | 25.866 | 16.462 | 1.00 | 34.29 |
| ATOM | 4051 | OWO | WAT | W | 180 | 0 | 30.277 | 18.006 | 25.789 | 1.00 | 42.28 |
| ATOM | 4052 | OWO | WAT | W | 181 | 0 | 2.316 | 18.424 | 27.884 | 1.00 | 47.39 |
| ATOM | 4053 | OWO | WAT | W | 182 | 0 | 19.401 | 41.164 | 39.560 | 1.00 | 39.68 |
| ATOM | 4054 | OWO | WAT | W | 183 | 0 | 23.742 | 10.982 | 24.879 | 1.00 | 43.32 |
| ATOM | 4055 | OWO | WAT | W | 184 | 0 | 3.926 | 24.450 | 44.251 | 1.00 | 48.95 |
| ATOM | 4056 | OWO | WAT | W | 185 | 0 | 25.186 | 21.211 | 40.951 | 1.00 | 39.05 |
| ATOM | 4057 | OWO | WAT | W | 186 | 0 | 20.353 | 34.816 | 48.799 | 1.00 | 34.08 |
| ATOM | 4058 | OWO | WAT | W | 187 | 0 | 35.782 | 22.476 | 21.693 | 1.00 | 40.04 |
| ATOM | 4059 | OWO | WAT | W | 188 | 0 | 27.256 | 23.617 | 12.235 | 1.00 | 40.85 |
| ATOM | 4060 | OWO | WAT | W | 189 | 0 | 6.777 | 12.502 | 12.641 | 1.00 | 53.37 |
| ATOM | 4061 | OWO | WAT | W | 190 | 0 | −4.663 | 38.998 | 4.159 | 1.00 | 39.85 |
| ATOM | 4062 | OWO | WAT | W | 191 | 0 | 24.398 | 52.064 | 24.607 | 1.00 | 45.51 |
| ATOM | 4063 | OWO | WAT | W | 192 | 0 | 1.808 | 15.541 | 4.832 | 1.00 | 41.06 |

APPENDIX 1-continued

| | | | | | | | | | | |
|---|---|---|---|---|---|---|---|---|---|---|
| ATOM | 4064 | OWO | WAT | W | 193 | 0 | 5.341 | 36.359 | 7.569 | 1.00 | 39.36 |
| ATOM | 4065 | OWO | WAT | W | 194 | 0 | 32.192 | 38.650 | 21.799 | 1.00 | 37.18 |
| ATOM | 4066 | OWO | WAT | W | 195 | 0 | -10.782 | 36.616 | 38.705 | 1.00 | 50.35 |
| ATOM | 4067 | OWO | WAT | W | 196 | 0 | 4.119 | 64.116 | 32.946 | 1.00 | 34.51 |
| ATOM | 4068 | OWO | WAT | W | 197 | 0 | 19.427 | 22.772 | 5.898 | 1.00 | 37.94 |
| ATOM | 4069 | OWO | WAT | W | 198 | 0 | -4.671 | 33.476 | 1.652 | 1.00 | 43.38 |
| ATOM | 4070 | OWO | WAT | W | 199 | 0 | -8.983 | 23.757 | 17.693 | 1.00 | 57.10 |
| ATOM | 4071 | OWO | WAT | W | 200 | 0 | -6.735 | 22.473 | 20.432 | 1.00 | 38.49 |
| ATOM | 4072 | OWO | WAT | W | 201 | 0 | -6.954 | 26.746 | 37.309 | 1.00 | 55.48 |
| ATOM | 4073 | OWO | WAT | W | 202 | 0 | 23.418 | 38.662 | 33.700 | 1.00 | 42.20 |
| ATOM | 4074 | OWO | WAT | W | 203 | 0 | 9.004 | 24.070 | 36.971 | 1.00 | 40.06 |
| ATOM | 4075 | OWO | WAT | W | 204 | 0 | 18.890 | 42.920 | 51.502 | 1.00 | 46.29 |
| ATOM | 4076 | OWO | WAT | W | 205 | 0 | 13.301 | 18.514 | 3.624 | 1.00 | 42.17 |
| ATOM | 4077 | OWO | WAT | W | 206 | 0 | 31.189 | 12.995 | 19.645 | 1.00 | 51.92 |
| ATOM | 4078 | OWO | WAT | W | 207 | 0 | 15.589 | 57.456 | 13.738 | 1.00 | 38.96 |
| ATOM | 4079 | OWO | WAT | W | 208 | 0 | -3.389 | 12.961 | 12.738 | 1.00 | 46.99 |
| ATOM | 4080 | OWO | WAT | W | 209 | 0 | 9.321 | 30.475 | 6.320 | 1.00 | 49.75 |
| ATOM | 4081 | OWO | WAT | W | 210 | 0 | 1.680 | 61.379 | 33.738 | 1.00 | 37.48 |
| ATOM | 4082 | OWO | WAT | W | 211 | 0 | -3.811 | 36.417 | 3.807 | 1.00 | 46.01 |
| ATOM | 4083 | OWO | WAT | W | 212 | 0 | 17.087 | 46.902 | 3.830 | 1.00 | 45.12 |
| ATOM | 4084 | OWO | WAT | W | 213 | 0 | 23.702 | 22.325 | 43.022 | 1.00 | 36.14 |
| ATOM | 4085 | OWO | WAT | W | 214 | 0 | 10.849 | 60.003 | 14.389 | 1.00 | 32.05 |
| ATOM | 4086 | OWO | WAT | W | 215 | 0 | 34.001 | 25.493 | 20.855 | 1.00 | 40.75 |
| ATOM | 4087 | OWO | WAT | W | 216 | 0 | 27.422 | 37.093 | 28.951 | 1.00 | 42.33 |
| ATOM | 4088 | OWO | WAT | W | 217 | 0 | 2.471 | 63.256 | 35.173 | 1.00 | 48.36 |
| ATOM | 4089 | OWO | WAT | W | 218 | 0 | -0.973 | 59.086 | 28.720 | 1.00 | 53.14 |
| ATOM | 4090 | OWO | WAT | W | 219 | 0 | 28.841 | 9.287 | 6.463 | 1.00 | 39.02 |
| ATOM | 4091 | OWO | WAT | W | 220 | 0 | -5.593 | 21.802 | 9.619 | 1.00 | 44.21 |
| ATOM | 4092 | OWO | WAT | W | 221 | 0 | 22.109 | 15.521 | 1.696 | 1.00 | 38.33 |
| ATOM | 4093 | OWO | WAT | W | 222 | 0 | 13.029 | 32.860 | 12.233 | 1.00 | 37.63 |
| ATOM | 4094 | OWO | WAT | W | 223 | 0 | 11.840 | 33.823 | 3.800 | 1.00 | 42.20 |
| ATOM | 4095 | OWO | WAT | W | 224 | 0 | 8.476 | 42.976 | -0.104 | 1.00 | 40.23 |
| ATOM | 4096 | OWO | WAT | W | 225 | 0 | 6.607 | 9.754 | 13.906 | 1.00 | 41.30 |
| ATOM | 4097 | OWO | WAT | W | 226 | 0 | 22.513 | 32.613 | 49.067 | 1.00 | 47.26 |
| ATOM | 4098 | OWO | WAT | W | 227 | 0 | 13.790 | 4.924 | 16.718 | 1.00 | 38.05 |
| ATOM | 4099 | OWO | WAT | W | 228 | 0 | 4.578 | 46.381 | 2.146 | 1.00 | 38.90 |
| ATOM | 4100 | OWO | WAT | W | 229 | 0 | -0.178 | 18.054 | 23.533 | 1.00 | 43.42 |
| ATOM | 4101 | OWO | WAT | W | 230 | 0 | -5.146 | 34.010 | 4.766 | 1.00 | 38.90 |
| ATOM | 4102 | OWO | WAT | W | 231 | 0 | 20.232 | 28.890 | 51.507 | 1.00 | 44.95 |
| ATOM | 4103 | OWO | WAT | W | 232 | 0 | 16.083 | 32.879 | 10.309 | 1.00 | 45.29 |
| ATOM | 4104 | OWO | WAT | W | 233 | 0 | 22.111 | 51.333 | 10.599 | 1.00 | 34.03 |
| ATOM | 4105 | OWO | WAT | W | 234 | 0 | 3.247 | 15.790 | 28.046 | 1.00 | 50.25 |
| ATOM | 4106 | OWO | WAT | W | 235 | 0 | 5.547 | 11.598 | 9.674 | 1.00 | 56.39 |
| ATOM | 4107 | OWO | WAT | W | 236 | 0 | -1.085 | 18.297 | -2.265 | 1.00 | 45.26 |
| ATOM | 4108 | OWO | WAT | W | 237 | 0 | 30.994 | 12.013 | 22.690 | 1.00 | 50.37 |
| ATOM | 4109 | OWO | WAT | W | 238 | 0 | 24.691 | 33.260 | 27.819 | 1.00 | 37.65 |
| ATOM | 4110 | OWO | WAT | W | 239 | 0 | 18.911 | 40.770 | 5.815 | 1.00 | 44.15 |
| ATOM | 4111 | OWO | WAT | W | 240 | 0 | 21.532 | 53.033 | 33.280 | 1.00 | 31.23 |
| ATOM | 4112 | OWO | WAT | W | 241 | 0 | 19.745 | 46.029 | 4.364 | 1.00 | 46.38 |
| ATOM | 4113 | OWO | WAT | W | 242 | 0 | 27.516 | 16.526 | 25.474 | 1.00 | 51.75 |
| ATOM | 4114 | OWO | WAT | W | 243 | 0 | 34.171 | 19.604 | 8.423 | 1.00 | 55.79 |
| ATOM | 4115 | OWO | WAT | W | 244 | 0 | 23.870 | 53.512 | 11.474 | 1.00 | 42.01 |
| ATOM | 4116 | OWO | WAT | W | 245 | 0 | 14.492 | 23.842 | 44.882 | 1.00 | 52.25 |
| ATOM | 4117 | OWO | WAT | W | 246 | 0 | -3.070 | 63.260 | 33.189 | 1.00 | 40.77 |
| ATOM | 4118 | OWO | WAT | W | 247 | 0 | 22.185 | 55.701 | 37.353 | 1.00 | 39.52 |
| ATOM | 4119 | OWO | WAT | W | 248 | 0 | 14.144 | 26.239 | 42.825 | 1.00 | 42.50 |
| ATOM | 4120 | OWO | WAT | W | 249 | 0 | 25.026 | 36.545 | 35.213 | 1.00 | 58.19 |
| ATOM | 4121 | OWO | WAT | W | 250 | 0 | 27.072 | 34.293 | 43.895 | 1.00 | 46.58 |
| ATOM | 4122 | OWO | WAT | W | 251 | 0 | 11.742 | 7.192 | 4.856 | 1.00 | 42.78 |
| ATOM | 4123 | OWO | WAT | W | 252 | 0 | 0.730 | 46.405 | 24.947 | 1.00 | 39.31 |
| ATOM | 4124 | OWO | WAT | W | 253 | 0 | 28.346 | 34.036 | 30.808 | 1.00 | 43.10 |
| ATOM | 4125 | OWO | WAT | W | 254 | 0 | -3.838 | 40.281 | 1.903 | 1.00 | 38.67 |
| ATOM | 4126 | OWO | WAT | W | 255 | 0 | 6.837 | 35.163 | 51.935 | 1.00 | 58.57 |
| ATOM | 4127 | OWO | WAT | W | 256 | 0 | 19.740 | 62.853 | 17.880 | 1.00 | 52.39 |
| ATOM | 4128 | OWO | WAT | W | 258 | 0 | -0.994 | 41.755 | 22.088 | 0.00 | 69.57 |
| ATOM | 4129 | OWO | WAT | W | 259 | 0 | 1.221 | 10.473 | 15.458 | 1.00 | 54.80 |
| ATOM | 4130 | OWO | WAT | W | 260 | 0 | 23.445 | 55.367 | 31.430 | 1.00 | 48.90 |
| ATOM | 4131 | OWO | WAT | W | 261 | 0 | 23.757 | 57.854 | 34.657 | 1.00 | 37.69 |
| ATOM | 4132 | OWO | WAT | W | 262 | 0 | 8.508 | 19.111 | 34.572 | 1.00 | 55.52 |
| ATOM | 4133 | OWO | WAT | W | 263 | 0 | 22.806 | 22.381 | 3.611 | 1.00 | 64.20 |
| ATOM | 4134 | OWO | WAT | W | 264 | 0 | 0.398 | 22.602 | 42.625 | 1.00 | 58.86 |
| ATOM | 4135 | OWO | WAT | W | 265 | 0 | 4.195 | 52.287 | 43.465 | 1.00 | 36.84 |
| ATOM | 4136 | OWO | WAT | W | 266 | 0 | 20.211 | 6.536 | 4.911 | 1.00 | 39.34 |
| ATOM | 4137 | OWO | WAT | W | 267 | 0 | 14.680 | 16.117 | 2.803 | 1.00 | 45.76 |
| ATOM | 4138 | OWO | WAT | W | 268 | 0 | 14.938 | 25.582 | 6.850 | 1.00 | 41.01 |
| ATOM | 4139 | OWO | WAT | W | 269 | 0 | 7.763 | 7.940 | 31.891 | 0.00 | 71.30 |
| ATOM | 4140 | OWO | WAT | W | 270 | 0 | -3.459 | 33.491 | 39.400 | 1.00 | 40.80 |
| ATOM | 4141 | OWO | WAT | W | 271 | 0 | 23.154 | 22.897 | 6.985 | 1.00 | 48.25 |
| ATOM | 4142 | OWO | WAT | W | 272 | 0 | 34.916 | 25.555 | 28.092 | 1.00 | 52.63 |

APPENDIX 1-continued

| ATOM | 4143 | OW0 | WAT | W | 273 | 0 | 8.332 | 45.481 | 50.776 | 1.00 | 47.23 |
|---|---|---|---|---|---|---|---|---|---|---|---|
| ATOM | 4144 | OW0 | WAT | W | 274 | 0 | -3.441 | 57.643 | 28.775 | 1.00 | 49.70 |
| ATOM | 4145 | OW0 | WAT | W | 275 | 0 | 23.213 | 40.573 | 47.561 | 1.00 | 56.02 |
| ATOM | 4146 | OW0 | WAT | W | 276 | 0 | 5.421 | 55.179 | 45.172 | 1.00 | 52.70 |
| ATOM | 4147 | OW0 | WAT | W | 277 | 0 | -3.012 | 21.908 | 40.933 | 1.00 | 41.69 |
| ATOM | 4148 | OW0 | WAT | W | 278 | 0 | 26.328 | 53.637 | 17.905 | 1.00 | 37.80 |
| ATOM | 4149 | OW0 | WAT | W | 279 | 0 | 9.740 | 58.922 | 43.485 | 1.00 | 52.06 |
| ATOM | 4150 | OW0 | WAT | W | 280 | 0 | 23.545 | 15.660 | 4.258 | 1.00 | 41.55 |
| ATOM | 4151 | OW0 | WAT | W | 281 | 0 | 22.652 | 31.154 | 51.246 | 1.00 | 58.65 |
| ATOM | 4152 | OW0 | WAT | W | 282 | 0 | 22.192 | 51.135 | 8.251 | 1.00 | 44.76 |
| ATOM | 4153 | OW0 | WAT | W | 283 | 0 | -6.046 | 22.886 | 24.288 | 1.00 | 52.40 |
| ATOM | 4154 | OW0 | WAT | W | 284 | 0 | 19.949 | 45.276 | 49.516 | 1.00 | 54.58 |
| ATOM | 4155 | OW0 | WAT | W | 285 | 0 | 7.388 | 22.308 | 32.108 | 1.00 | 43.62 |
| ATOM | 4156 | OW0 | WAT | W | 286 | 0 | 15.080 | 50.452 | 2.795 | 1.00 | 52.20 |
| ATOM | 4157 | OW0 | WAT | W | 287 | 0 | 1.016 | 62.235 | 30.878 | 1.00 | 56.81 |
| ATOM | 4158 | OW0 | WAT | W | 288 | 0 | 23.803 | 52.570 | 27.699 | 1.00 | 56.22 |
| ATOM | 4159 | OW0 | WAT | W | 289 | 0 | -10.525 | 31.623 | 13.870 | 1.00 | 47.21 |
| ATOM | 4160 | OW0 | WAT | W | 290 | 0 | 1.599 | 55.502 | 24.567 | 1.00 | 44.50 |
| ATOM | 4161 | OW0 | WAT | W | 291 | 0 | -15.671 | 37.251 | 14.660 | 1.00 | 83.62 |
| ATOM | 4162 | OW0 | WAT | W | 292 | 0 | 7.231 | 7.950 | 17.754 | 1.00 | 50.61 |
| ATOM | 4163 | OW0 | WAT | W | 293 | 0 | -4.009 | 34.057 | 42.492 | 1.00 | 78.48 |
| ATOM | 4164 | OW0 | WAT | W | 294 | 0 | 21.004 | 58.371 | 18.690 | 1.00 | 61.15 |
| ATOM | 4165 | OW0 | WAT | W | 295 | 0 | 16.405 | 48.869 | 52.211 | 1.00 | 53.17 |
| ATOM | 4166 | OW0 | WAT | W | 296 | 0 | 7.329 | 31.202 | 1.964 | 1.00 | 38.86 |
| ATOM | 4167 | OW0 | WAT | W | 297 | 0 | 9.518 | 53.886 | 5.467 | 1.00 | 41.62 |
| ATOM | 4168 | OW0 | WAT | W | 298 | 0 | 10.398 | 48.995 | 0.335 | 1.00 | 49.64 |
| ATOM | 4169 | OW0 | WAT | W | 299 | 0 | 9.889 | 15.077 | 3.774 | 1.00 | 42.28 |
| ATOM | 4170 | OW0 | WAT | W | 300 | 0 | 15.854 | 56.731 | 10.934 | 1.00 | 44.02 |

We claim:

1. A variant of a parent Coprinus laccase, which variant has increased oxidation potential and comprises a mutation in a position corresponding to at least one of the following positions in SEQ ID No. 1:
G411A,V,P,L, I,F,Y,W;
G412A,V,P,L,I,F,Y,W;
V409P,L,I,F,Y,W;
T257A,V,P,L,I,F,Y,W;
F358Y,W,I;
T359A,V,P,L,I,F,Y,W;
L480I,F,Y,W;
L351 I,F,Y,W;
E473A,V,P,L,I,F,Y,W;
D98A,V,P,L,I,F,Y,W;
G131A,V,P,L,I,F,Y,W;
D443A,V,P,L,I,F,Y,W;
R260 A,V,P,L,I,F,Y,W.

2. A variant of a parent Coprinus laccase, which variant has an altered pH optimum and comprises a mutation in a position corresponding to at least one of the following positions in SEQ ID No. 1:
180–181;
222–224;
257;
281–284;
352–353;
357–358;
409–416;
470–490.

3. A variant of a parent Coprinus laccase, which variant has an altered mediator efficiency and comprises a mutation in a position corresponding to at least one of the following positions in SEQ ID No. 1:
179–182;
223;
281–282;
353–358;
410–412;
472;
474–475;
477–478.

4. A detergent additive comprising a laccase variant according to claim 1 in the form of a non-dusting granulate, a stabilized liquid or a protected enzyme.

5. The detergent additive according to claim 4, which additionally comprises one or more other enzymes including a protease, a lipase, an amylase and/or a cellulase.

6. A detergent composition comprising a laccase variant according to claim 1 and a surfactant.

7. The detergent composition according to claim 6 which additionally comprises one or more other enzymes including a protease, a lipase, an amylase and/or a cellulase.

* * * * *

SEQUENCE LISTING (1) GENERAL INFORMATION:

(iii) NUMBER OF SEQUENCES: 10

(2) INFORMATION FOR SEQ ID NO: 1:

(i) SEQUENCE CHARACTERISTICS:
      (A) LENGTH: 539 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO: 1:

```
Met Phe Lys Asn Leu Leu Ser Phe Ala Leu Leu Ala Ile Ser Val Ala
 1               5                  10                  15

Asn Ala Gln Ile Val Asn Ser Val Asp Thr Met Thr Leu Thr Asn Ala
                20                  25                  30

Asn Val Ser Pro Asp Gly Phe Thr Arg Ala Gly Ile Leu Val Asn Gly
                35                  40                  45

Val His Gly Pro Leu Ile Arg Gly Gly Lys Asn Asp Asn Phe Glu Leu
50                      55                  60

Asn Val Val Asn Asp Leu Asp Asn Pro Thr Met Leu Arg Pro Thr Ser
65                      70                  75                  80

Ile His Trp His Gly Leu Phe Gln Arg Gly Thr Asn Trp Ala Asp Gly
                        85                  90                  95

Ala Asp Gly Val Asn Gln Cys Pro Ile Ser Pro Gly His Ala Phe Leu
                100                 105                 110

Tyr Lys Phe Thr Pro Ala Gly His Ala Gly Thr Phe Trp Tyr His Ser
                115                 120                 125

His Phe Gly Thr Gln Tyr Cys Asp Gly Leu Arg Gly Pro Met Val Ile
130                     135                 140
```

Tyr Asp Asp Asn Asp Pro His Ala Ala Leu Tyr Asp Glu Asp Glu
145                 150                 155                 160

Asn Thr Ile Ile Thr Leu Ala Asp Trp Tyr His Ile Pro Ala Pro Ser
                165                 170                 175

Ile Gln Gly Ala Ala Gln Pro Asp Ala Thr Leu Ile Asn Gly Lys Gly
            180                 185                 190

Arg Tyr Val Gly Gly Pro Ala Ala Glu Leu Ser Ile Val Asn Val Glu
        195                 200                 205

Gln Gly Lys Lys Tyr Arg Met Arg Leu Ile Ser Leu Ser Cys Asp Pro
    210                 215                 220

Asn Trp Gln Phe Ser Ile Asp Gly His Glu Leu Thr Ile Ile Glu Val
225                 230                 235                 240

Asp Gly Gln Leu Thr Glu Pro His Thr Val Asp Arg Leu Gln Ile Phe
                245                 250                 255

Thr Gly Gln Arg Tyr Ser Phe Val Leu Asp Ala Asn Gln Pro Val Asp
            260                 265                 270

Asn Tyr Trp Ile Arg Ala Gln Pro Asn Lys Gly Arg Asn Gly Leu Ala
        275                 280                 285

Gly Thr Phe Ala Asn Gly Val Asn Ser Ala Ile Leu Arg Tyr Ala Gly
    290                 295                 300

Ala Ala Asn Ala Asp Pro Thr Thr Ser Ala Asn Pro Asn Pro Ala Gln
305                 310                 315                 320

Leu Asn Glu Ala Asp Leu His Ala Leu Ile Asp Pro Ala Ala Pro Gly
                325                 330                 335

Ile Pro Thr Pro Gly Ala Ala Asp Val Asn Leu Arg Phe Gln Leu Gly
            340                 345                 350

Phe Ser Gly Gly Arg Phe Thr Ile Asn Gly Thr Ala Tyr Glu Ser Pro
        355                 360                 365

Ser Val Pro Thr Leu Leu Gln Ile Met Ser Gly Ala Gln Ser Ala Asn
    370                 375                 380

Asp Leu Leu Pro Ala Gly Ser Val Tyr Glu Leu Pro Arg Asn Gln Val
385                 390                 395                 400

Val Glu Leu Val Val Pro Ala Gly Val Leu Gly Pro His Pro Phe
                405                 410                 415

His Leu His Gly His Ala Phe Ser Val Val Arg Ser Ala Gly Ser Ser
            420                 425                 430

Thr Tyr Asn Phe Val Asn Pro Val Lys Arg Asp Val Val Ser Leu Gly
        435                 440                 445

Val Thr Gly Asp Glu Val Thr Ile Arg Phe Val Thr Asp Asn Pro Gly
    450                 455                 460

Pro Trp Phe Phe His Cys His Ile Glu Phe His Leu Met Asn Gly Leu
465                 470                 475                 480

Ala Ile Val Phe Ala Glu Asp Met Ala Asn Thr Val Asp Ala Asn Asn
                485                 490                 495

Pro Pro Val Glu Trp Ala Gln Leu Cys Glu Ile Tyr Asp Asp Leu Pro
            500                 505                 510

Pro Glu Ala Thr Ser Ile Gln Thr Val Val Arg Arg Ala Glu Pro Thr
        515                 520                 525

Gly Phe Ser Ala Lys Phe Arg Arg Glu Gly Leu
    530                 535

(2) INFORMATION FOR SEQ ID NO: 2:

(i) SEQUENCE CHARACTERISTICS:

(A) LENGTH: 499 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO: 2:

```
Gly Ile Gly Pro Val Ala Asp Leu Thr Ile Thr Asn Ala Ala Val Ser
1               5                  10                  15

Pro Asp Gly Phe Ser Arg Gln Ala Val Val Asn Gly Gly Thr Pro
            20                  25                  30

Gly Pro Leu Ile Thr Gly Asn Met Gly Asp Arg Phe Gln Leu Asn Val
            35                  40                  45

Ile Asp Asn Leu Thr Asn His Thr Met Leu Lys Ser Thr Ser Ile His
50                  55                  60

Trp His Gly Phe Phe Gln Lys Gly Thr Asn Trp Ala Asp Gly Pro Ala
65                  70                  75                  80

Phe Ile Asn Gln Cys Pro Ile Ser Ser Gly His Ser Phe Leu Tyr Asp
                85                  90                  95

Phe Gln Val Pro Asp Gln Ala Gly Thr Phe Trp Tyr His Ser His Leu
            100                 105                 110

Ser Thr Gln Tyr Cys Asp Gly Leu Arg Gly Pro Phe Val Val Tyr Asp
            115                 120                 125

Pro Asn Asp Pro Ala Ala Asp Leu Tyr Asp Val Asp Asn Asp Asp Thr
130                 135                 140

Val Ile Thr Leu Val Asp Trp Tyr His Val Ala Ala Lys Leu Gly Pro
145                 150                 155                 160

Ala Phe Pro Leu Gly Ala Asp Ala Thr Leu Ile Asn Gly Lys Gly Arg
                165                 170                 175

Ser Pro Ser Thr Thr Thr Ala Asp Leu Ser Val Ile Ser Val Thr Pro
            180                 185                 190

Gly Lys Arg Tyr Arg Phe Arg Leu Val Ser Leu Ser Cys Asp Pro Asn
            195                 200                 205

Tyr Thr Phe Ser Ile Asp Gly His Asn Met Thr Ile Glu Thr Asp
210                 215                 220

Ser Ile Asn Thr Ala Pro Leu Val Val Asp Ser Ile Gln Ile Phe Ala
225                 230                 235                 240

Ala Gln Arg Tyr Ser Phe Val Leu Glu Ala Asn Gln Ala Val Asp Asn
                245                 250                 255

Tyr Trp Ile Arg Ala Asn Pro Asn Phe Gly Asn Val Gly Phe Thr Gly
            260                 265                 270

Gly Ile Asn Ser Ala Ile Leu Arg Tyr Asp Gly Ala Ala Ala Val Glu
            275                 280                 285

Pro Thr Thr Thr Gln Thr Thr Ser Thr Ala Pro Leu Asn Glu Val Asn
290                 295                 300

Leu His Pro Leu Val Thr Thr Ala Val Pro Gly Ser Pro Val Ala Gly
305                 310                 315                 320

Gly Val Asp Leu Ala Ile Asn Met Ala Phe Asn Phe Asn Gly Thr Asn
                325                 330                 335

Phe Phe Ile Asn Gly Ala Ser Phe Thr Pro Pro Thr Val Pro Val Leu
            340                 345                 350

Leu Gln Ile Ile Ser Gly Ala Gln Asn Ala Gln Asp Leu Leu Pro Ser
            355                 360                 365

Gly Ser Val Tyr Ser Leu Pro Ser Asn Ala Asp Ile Glu Ile Ser Phe
            370                 375                 380
```

```
Pro Ala Thr Ala Ala Pro Gly Ala Pro His Pro Phe His Leu His
385                 390                 395                 400

Gly His Ala Phe Ala Val Val Arg Ser Ala Gly Ser Thr Val Tyr Asn
                405                 410                 415

Tyr Asp Asn Pro Ile Phe Arg Asp Val Val Ser Thr Gly Thr Pro Ala
                420                 425                 430

Ala Gly Asp Asn Val Thr Ile Arg Phe Arg Thr Asp Asn Pro Gly Pro
                435                 440                 445

Trp Phe Leu His Cys His Ile Asp Phe His Leu Glu Ala Gly Phe Ala
                450                 455                 460

Val Val Phe Ala Glu Asp Ile Pro Asp Val Ala Ser Ala Asn Pro Val
465                 470                 475                 480

Pro Gln Ala Trp Ser Asp Leu Cys Pro Thr Tyr Asp Ala Leu Asp Pro
                485                 490                 495

Ser Asp Gln
```

(2) INFORMATION FOR SEQ ID NO: 3:

(i) SEQUENCE CHARACTERISTICS:
        (A) LENGTH: 499 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 3:

```
Ala Ile Gly Pro Val Ala Ser Leu Val Val Ala Asn Ala Pro Val Ser
1               5                   10                  15

Pro Asp Gly Phe Leu Arg Asp Ala Ile Val Val Asn Gly Val Val Pro
                20                  25                  30

Ser Pro Leu Ile Thr Gly Lys Lys Gly Asp Arg Phe Gln Leu Asn Val
                35                  40                  45

Val Asp Thr Leu Thr Asn His Ser Met Leu Lys Ser Thr Ser Ile His
50                  55                  60

Trp His Gly Phe Phe Gln Ala Gly Thr Asn Trp Ala Glu Gly Pro Ala
65                  70                  75                  80

Phe Val Asn Gln Cys Pro Ile Ala Ser Gly His Ser Phe Leu Tyr Asp
                85                  90                  95

Phe His Val Pro Asp Gln Ala Gly Thr Phe Trp Tyr His Ser His Leu
                100                 105                 110

Ser Thr Gln Tyr Cys Asp Gly Leu Arg Gly Pro Phe Val Val Tyr Asp
                115                 120                 125

Pro Lys Asp Pro His Ala Ser Arg Tyr Asp Val Asp Asn Glu Ser Thr
                130                 135                 140

Val Ile Thr Leu Thr Asp Trp Tyr His Thr Ala Ala Arg Leu Gly Pro
145                 150                 155                 160

Lys Phe Pro Leu Gly Ala Asp Ala Thr Leu Ile Asn Gly Leu Gly Arg
                165                 170                 175

Ser Ala Ser Thr Pro Thr Ala Ala Leu Ala Val Ile Asn Val Gln His
                180                 185                 190

Gly Lys Arg Tyr Arg Phe Arg Leu Val Ser Ile Ser Cys Asp Pro Asn
                195                 200                 205

Tyr Thr Phe Ser Ile Asp Gly His Asn Leu Thr Val Ile Glu Val Asp
                210                 215                 220

Gly Ile Asn Ser Gln Pro Leu Leu Val Asp Ser Ile Gln Ile Phe Ala
```

-continued

```
            225                 230                 235                 240
Ala Gln Arg Tyr Ser Phe Val Leu Asn Ala Asn Gln Thr Val Gly Asn
                245                 250                 255
Tyr Trp Val Arg Ala Asn Pro Asn Phe Gly Thr Val Gly Phe Ala Gly
            260                 265                 270
Gly Ile Asn Ser Ala Ile Leu Arg Tyr Gln Gly Ala Pro Val Ala Glu
            275                 280                 285
Pro Thr Thr Thr Gln Thr Pro Ser Val Ile Pro Leu Ile Glu Thr Asn
            290                 295                 300
Leu His Pro Leu Ala Arg Met Pro Val Pro Gly Ser Pro Thr Pro Gly
305                 310                 315                 320
Gly Val Asp Lys Ala Leu Asn Leu Ala Phe Asn Phe Asn Gly Thr Asn
                325                 330                 335
Phe Phe Ile Asn Asn Ala Thr Phe Thr Pro Pro Thr Val Pro Val Leu
                340                 345                 350
Leu Gln Ile Leu Ser Gly Ala Gln Thr Ala Gln Asp Leu Leu Pro Ala
                355                 360                 365
Gly Ser Val Tyr Pro Leu Pro Ala His Ser Thr Ile Glu Ile Thr Leu
            370                 375                 380
Pro Ala Thr Ala Leu Ala Pro Gly Ala Pro His Pro Phe His Leu His
385                 390                 395                 400
Gly His Ala Phe Ala Val Val Arg Ser Ala Gly Ser Thr Thr Tyr Asn
                405                 410                 415
Tyr Asn Asp Pro Ile Phe Arg Asp Val Val Ser Thr Gly Thr Pro Ala
                420                 425                 430
Ala Gly Asp Asn Val Thr Ile Arg Phe Gln Thr Asp Asn Pro Gly Pro
                435                 440                 445
Trp Phe Leu His Cys His Ile Asp Phe His Leu Asp Ala Gly Phe Ala
            450                 455                 460
Ile Val Phe Ala Glu Asp Val Ala Asp Val Lys Ala Ala Asn Pro Val
465                 470                 475                 480
Pro Lys Ala Trp Ser Asp Leu Cys Pro Ile Tyr Asp Gly Leu Ser Glu
                485                 490                 495
Ala Asn Gln (2) INFORMATION FOR SEQ ID NO: 4:

(i) SEQUENCE CHARACTERISTICS:
        (A) LENGTH: 548 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 4:

Met His Thr Phe Leu Arg Ser Thr Ala Leu Val Val Ala Gly Leu Ser
1               5                   10                  15
Ala Arg Ala Leu Ala Ser Ile Gly Pro Val Thr Asp Phe His Ile Val
                20                  25                  30
Asn Ala Ala Val Ser Pro Asp Gly Phe Ser Arg Gln Ala Val Leu Ala
            35                  40                  45
Glu Gly Val Phe Pro Gly Pro Leu Ile Ala Gly Asn Lys Gly Asp Asn
        50                  55                  60
Phe Gln Ile Asn Val Ile Asp Glu Leu Thr Asn Ala Thr Met Leu Lys
65                  70                  75                  80
```

| | | | | | | | | | | | |
|---|---|---|---|---|---|---|---|---|---|---|---|
|Thr|Thr|Thr|Ile|His|Trp|His|Gly|Phe|Phe|Gln|His|Gly|Thr|Asn|Trp|
| | | | |85| | | |90| | | |  |  |95|   |

Thr Thr Thr Ile His Trp His Gly Phe Phe Gln His Gly Thr Asn Trp
                85              90              95

Ala Asp Gly Pro Ala Phe Ile Asn Gln Cys Pro Ile Ala Ser Gly Asp
            100             105             110

Ser Phe Leu Tyr Asn Phe Gln Val Pro Asp Gln Ala Gly Thr Phe Trp
        115             120             125

Tyr His Ser His Leu Ser Thr Gln Tyr Cys Asp Gly Leu Arg Gly Pro
    130             135             140

Phe Val Val Tyr Asp Pro Ala Asp Pro Tyr Leu Asp Gln Tyr Asp Val
145             150             155             160

Asp Asp Asp Ser Thr Val Ile Thr Leu Ala Asp Trp Tyr His Thr Ala
            165             170             175

Ala Arg Leu Gly Ser Pro Phe Pro Ala Ala Asp Thr Thr Leu Ile Asn
        180             185             190

Gly Leu Gly Arg Cys Gly Glu Ala Gly Cys Pro Val Ser Asp Leu Ala
    195             200             205

Val Ile Ser Val Thr Lys Gly Lys Arg Tyr Arg Phe Arg Leu Val Ser
210             215             220

Ile Ser Cys Asp Ser Phe Thr Phe Ser Ile Asp Gly His Ser Leu
225             230             235             240

Asn Val Ile Glu Val Asp Ala Thr Asn His Gln Pro Leu Thr Val Asp
            245             250             255

Glu Leu Thr Ile Tyr Ala Gly Gln Arg Tyr Ser Phe Ile Leu Thr Ala
        260             265             270

Asp Gln Asp Val Asp Asn Tyr Trp Ile Arg Ala Asn Pro Gly Ile Gly
    275             280             285

Ile Thr Thr Gly Phe Ala Gly Gly Ile Asn Ser Ala Ile Leu Arg Tyr
    290             295             300

Asp Gly Ala Asp Val Val Glu Pro Thr Thr Thr Gln Ala Thr Ser Pro
305             310             315             320

Val Val Leu Ser Glu Ser Asn Leu Ala Pro Leu Thr Asn Ala Ala Ala
            325             330             335

Pro Gly Leu Pro Glu Val Gly Gly Val Asp Leu Ala Leu Asn Phe Asn
        340             345             350

Leu Thr Phe Asp Gly Pro Ser Leu Lys Phe Gln Ile Asn Gly Val Thr
    355             360             365

Phe Val Pro Pro Thr Val Pro Val Leu Leu Gln Ile Leu Ser Gly Ala
370             375             380

Gln Ser Ala Ala Asp Leu Leu Pro Ser Gly Ser Val Tyr Ala Leu Pro
385             390             395             400

Ser Asn Ala Thr Ile Glu Leu Ser Leu Pro Ala Gly Ala Leu Gly Gly
            405             410             415

Pro His Pro Phe His Leu His Gly His Thr Phe Ser Val Val Arg Pro
        420             425             430

Ala Gly Ser Thr Thr Tyr Asn Tyr Val Asn Pro Val Gln Arg Asp Val
    435             440             445

Val Ser Ile Gly Asn Thr Gly Asp Asn Val Thr Ile Arg Phe Asp Thr
    450             455             460

Asn Asn Pro Gly Pro Trp Phe Leu His Cys His Ile Asp Trp His Leu
465             470             475             480

Glu Ala Ala Leu Pro Leu Ser Ser Leu Arg Thr Ser Leu Thr Leu Arg
            485             490             495

Pro Leu Thr Leu Ser Pro Arg Thr Gly Pro Thr Cys Ala Leu Ser Thr
        500             505             510

Thr Leu Trp Thr His Leu Ile Thr Ser Gly Phe Ala Ser Ile Ile Gln
        515                 520                 525

Trp Met Met Gly Gly Asn Gly Leu Phe Ala Pro His Ala Leu Ser Phe
        530                 535                 540

Leu Gly Ser Gln
545

(2) INFORMATION FOR SEQ ID NO: 5:

(i) SEQUENCE CHARACTERISTICS:
        (A) LENGTH: 529 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 5:

Met Leu Ser Ser Ile Thr Leu Leu Pro Leu Ala Ala Val Ser Thr
1               5                   10                  15

Pro Ala Phe Ala Ala Val Arg Asn Tyr Lys Phe Asp Ile Lys Asn Val
            20                  25                  30

Asn Val Ala Pro Asp Gly Phe Gln Arg Ser Ile Val Ser Val Asn Gly
            35                  40                  45

Leu Val Pro Gly Thr Leu Ile Thr Ala Asn Lys Gly Asp Thr Leu Arg
50                      55                  60

Ile Asn Val Thr Asn Gln Leu Thr Asp Pro Ser Met Arg Arg Ala Thr
65                  70                  75                  80

Thr Ile His Trp His Gly Leu Phe Gln Ala Thr Thr Ala Asp Glu Asp
                85                  90                  95

Gly Pro Ala Phe Val Thr Gln Cys Pro Ile Ala Gln Asn Leu Ser Tyr
                100                 105                 110

Thr Tyr Glu Ile Pro Leu Arg Gly Gln Thr Gly Thr Met Trp Tyr His
            115                 120                 125

Ala His Leu Ala Ser Gln Tyr Val Asp Gly Leu Arg Gly Pro Leu Val
        130                 135                 140

Ile Tyr Asp Pro Asn Asp Pro His Lys Ser Arg Tyr Asp Val Asp Asp
145                 150                 155                 160

Ala Ser Thr Val Val Met Leu Glu Asp Trp Tyr His Thr Pro Ala Pro
                165                 170                 175

Val Leu Glu Lys Gln Met Phe Ser Thr Asn Asn Thr Ala Leu Leu Ser
            180                 185                 190

Pro Val Pro Asp Ser Gly Leu Ile Asn Gly Lys Gly Arg Tyr Val Gly
        195                 200                 205

Gly Pro Ala Val Pro Arg Ser Val Ile Asn Val Lys Arg Gly Lys Arg
210                 215                 220

Tyr Arg Leu Arg Val Ile Asn Ala Ser Ala Ile Gly Ser Phe Thr Phe
225                 230                 235                 240

Ser Ile Glu Gly His Ser Leu Thr Val Ile Glu Ala Asp Gly Ile Leu
            245                 250                 255

His Gln Pro Leu Ala Val Asp Ser Phe Gln Ile Tyr Ala Gly Gln Arg
        260                 265                 270

Tyr Ser Val Ile Val Glu Ala Asn Gln Thr Ala Ala Asn Tyr Trp Ile
    275                 280                 285

Arg Ala Pro Met Thr Val Ala Gly Ala Gly Thr Asn Ala Asn Leu Asp
290                 295                 300

```
Pro Thr Asn Val Phe Ala Val Leu His Tyr Glu Gly Ala Pro Asn Ala
305                 310                 315                 320

Glu Pro Thr Thr Glu Gln Gly Ser Ala Ile Gly Thr Ala Leu Val Glu
            325                 330                 335

Glu Asn Leu His Ala Leu Ile Asn Pro Gly Ala Pro Gly Gly Ser Ala
            340                 345                 350

Pro Ala Asp Val Ser Leu Asn Leu Ala Ile Gly Arg Ser Thr Val Asp
            355                 360                 365

Gly Ile Leu Arg Phe Thr Phe Asn Asn Ile Lys Tyr Glu Ala Pro Ser
370                 375                 380

Leu Pro Thr Leu Leu Lys Ile Leu Ala Asn Asn Ala Ser Asn Asp Ala
385                 390                 395                 400

Asp Phe Thr Pro Asn Glu His Thr Ile Val Leu Pro His Asn Lys Val
            405                 410                 415

Ile Glu Leu Asn Ile Thr Gly Gly Ala Asp His Pro Ile His Leu His
            420                 425                 430

Gly His Val Phe Asp Ile Val Lys Ser Leu Gly Gly Thr Pro Asn Tyr
            435                 440                 445

Val Asn Pro Pro Arg Arg Asp Val Val Arg Val Gly Gly Thr Gly Val
            450                 455                 460

Val Leu Arg Phe Lys Thr Asp Asn Pro Gly Pro Trp Phe Val His Cys
465                 470                 475                 480

His Ile Asp Trp His Leu Glu Ala Gly Leu Ala Leu Val Phe Ala Glu
            485                 490                 495

Ala Pro Ser Gln Ile Arg Gln Gly Val Gln Ser Val Gln Pro Asn Asn
            500                 505                 510

Ala Trp Asn Gln Leu Cys Pro Lys Tyr Ala Ala Leu Pro Pro Asp Leu
            515                 520                 525

Gln (2) INFORMATION FOR SEQ ID NO: 6:

(i) SEQUENCE CHARACTERISTICS:
        (A) LENGTH: 599 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 6:

Met Ala Arg Ser Thr Thr Ser Leu Phe Ala Leu Ser Leu Val Ala Ser
1               5                   10                  15

Ala Phe Ala Arg Val Val Asp Tyr Gly Phe Asp Val Ala Asn Gly Ala
            20                  25                  30

Val Ala Pro Asp Gly Val Thr Arg Asn Ala Val Leu Val Asn Gly Arg
            35                  40                  45

Phe Pro Gly Pro Leu Ile Thr Ala Asn Lys Gly Asp Thr Leu Lys Ile
        50                  55                  60

Thr Val Arg Asn Lys Leu Ser Asp Pro Thr Met Arg Arg Ser Thr Thr
65                  70                  75                  80

Ile His Trp His Gly Leu Leu Gln His Arg Thr Ala Glu Glu Asp Gly
                85                  90                  95

Pro Ala Phe Val Thr Gln Cys Pro Ile Pro Gln Glu Ser Tyr Thr
            100                 105                 110

Tyr Thr Met Pro Leu Gly Glu Gln Thr Gly Thr Tyr Trp Tyr His Ser
            115                 120                 125
```

```
His Leu Ser Ser Gln Tyr Val Asp Gly Leu Arg Gly Pro Ile Val Ile
    130                 135                 140
Tyr Asp Pro His Asp Pro Tyr Arg Asn Tyr Tyr Asp Val Asp Asp Glu
145                 150                 155                 160
Arg Thr Val Phe Thr Leu Ala Asp Trp Tyr His Thr Pro Ser Glu Ala
                165                 170                 175
Ile Ile Ala Thr His Asp Val Leu Lys Thr Ile Pro Asp Ser Gly Thr
                180                 185                 190
Ile Asn Gly Lys Gly Lys Tyr Asp Pro Ala Ser Ala Asn Thr Asn Asn
            195                 200                 205
Thr Thr Leu Glu Asn Leu Tyr Thr Leu Lys Val Lys Arg Gly Lys Arg
210                 215                 220
Tyr Arg Leu Arg Ile Ile Asn Ala Ser Ala Ile Ala Ser Phe Arg Phe
225                 230                 235                 240
Gly Val Gln Gly His Lys Cys Thr Ile Ile Glu Ala Asp Gly Val Leu
                245                 250                 255
Thr Lys Pro Ile Glu Val Asp Ala Phe Asp Ile Leu Ala Gly Gln Arg
            260                 265                 270
Tyr Ser Cys Ile Leu Lys Ala Asp Gln Asp Pro Asp Ser Tyr Trp Ile
        275                 280                 285
Asn Ala Pro Ile Thr Asn Val Leu Asn Thr Asn Val Gln Ala Leu Leu
290                 295                 300
Val Tyr Glu Asp Asp Lys Arg Pro Thr His Tyr Pro Trp Lys Pro Phe
305                 310                 315                 320
Leu Thr Trp Lys Ile Ser Asn Glu Ile Ile Gln Tyr Trp Gln His Lys
                325                 330                 335
His Gly Ser His Gly His Lys Gly Lys Gly His His His Lys Val Arg
                340                 345                 350
Ala Ile Gly Gly Val Ser Gly Leu Ser Ser Arg Val Lys Ser Arg Ala
            355                 360                 365
Ser Asp Leu Ser Lys Lys Ala Val Glu Leu Ala Ala Ala Leu Val Ala
370                 375                 380
Gly Glu Ala Glu Leu Asp Lys Arg Gln Asn Glu Asp Asn Ser Thr Ile
385                 390                 395                 400
Val Leu Asp Glu Thr Lys Leu Ile Pro Leu Val Gln Pro Gly Ala Pro
                405                 410                 415
Gly Gly Ser Arg Pro Ala Asp Val Val Pro Leu Asp Phe Gly Leu
            420                 425                 430
Asn Phe Ala Asn Gly Leu Trp Thr Ile Asn Asn Val Ser Tyr Ser Pro
        435                 440                 445
Pro Asp Val Pro Thr Leu Leu Lys Ile Leu Thr Asp Lys Asp Lys Val
450                 455                 460
Asp Ala Ser Asp Phe Thr Ala Asp Glu His Thr Tyr Ile Leu Pro Lys
465                 470                 475                 480
Asn Gln Val Val Glu Leu His Ile Lys Gly Gln Ala Leu Gly Ile Val
                485                 490                 495
His Pro Leu His Leu His Gly His Ala Phe Asp Val Val Gln Phe Gly
            500                 505                 510
Asp Asn Ala Pro Asn Tyr Val Asn Pro Pro Arg Arg Asp Val Val Gly
        515                 520                 525
Val Thr Asp Ala Gly Val Arg Ile Gln Phe Arg Thr Asp Asn Pro Gly
530                 535                 540
Pro Trp Phe Leu His Cys His Ile Asp Trp His Leu Glu Glu Gly Phe
```

```
                        545                  550                  555                  560
Ala Met Val Phe Ala Glu Ala Pro Glu Asp Ile Lys Lys Gly Ser Gln
                565                  570                  575

Ser Val Lys Pro Asp Gly Gln Trp Lys Lys Leu Cys Glu Lys Tyr Glu
                580                  585                  590

Lys Leu Pro Glu Ala Leu Gln
                595
```

(2) INFORMATION FOR SEQ ID NO: 7:

(i) SEQUENCE CHARACTERISTICS:
        (A) LENGTH: 572 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 7:

```
Met Ala Arg Thr Thr Phe Leu Val Ser Val Ser Leu Phe Val Ser Ala
1                   5                   10                  15

Val Leu Ala Arg Thr Val Glu Tyr Asn Leu Lys Ile Ser Asn Gly Lys
                20                  25                  30

Ile Ala Pro Asp Gly Val Glu Arg Asp Ala Thr Leu Val Asn Gly Gly
            35                  40                  45

Tyr Pro Gly Pro Leu Ile Phe Ala Asn Lys Gly Asp Thr Leu Lys Val
        50                  55                  60

Lys Val Gln Asn Lys Leu Thr Asn Pro Asp Met Tyr Arg Thr Thr Ser
65                  70                  75                  80

Ile His Trp His Gly Leu Leu Gln His Arg Asn Ala Asp Asp Asp Gly
                85                  90                  95

Pro Ala Phe Val Thr Gln Cys Pro Ile Val Pro Gln Ala Ser Tyr Thr
            100                 105                 110

Tyr Thr Met Pro Leu Gly Asp Gln Thr Gly Thr Tyr Trp Tyr His Ser
        115                 120                 125

His Leu Ser Ser Gln Tyr Val Asp Gly Leu Arg Gly Pro Leu Val Ile
    130                 135                 140

Tyr Asp Pro Lys Asp Pro His Arg Arg Leu Tyr Asp Ile Asp Asp Glu
145                 150                 155                 160

Lys Thr Val Leu Ile Ile Gly Asp Trp Tyr His Thr Ser Ser Lys Ala
                165                 170                 175

Ile Leu Ala Thr Gly Asn Ile Thr Leu Gln Gln Pro Asp Ser Ala Thr
            180                 185                 190

Ile Asn Gly Lys Gly Arg Phe Asp Pro Asp Asn Thr Pro Ala Asn Pro
        195                 200                 205

Asn Thr Leu Tyr Thr Leu Lys Val Lys Arg Gly Lys Arg Tyr Arg Leu
    210                 215                 220

Arg Val Ile Asn Ser Ser Ala Ile Ala Ser Phe Arg Met Ser Ile Gln
225                 230                 235                 240

Gly His Lys Met Thr Val Ile Ala Ala Asp Gly Val Ser Thr Lys Pro
                245                 250                 255

Tyr Gln Val Asp Ser Phe Asp Ile Leu Ala Gly Gln Arg Ile Asp Ala
            260                 265                 270

Val Val Glu Ala Asn Gln Glu Pro Asp Thr Tyr Trp Ile Asn Ala Pro
        275                 280                 285

Leu Thr Asn Val Ala Asn Lys Thr Ala Gln Ala Leu Leu Ile Tyr Glu
    290                 295                 300
```

Asp Asp Arg Arg Pro Tyr His Pro Pro Lys Gly Pro Tyr Arg Lys Trp
305             310                 315                 320

Ser Val Ser Glu Ala Ile Ile Lys Tyr Trp Lys His Lys His Gly Arg
            325                 330                 335

Gly Leu Leu Ser Gly His Gly Gly Leu Lys Ala Arg Met Met Glu Gly
                340                 345                 350

Ser Leu His Leu His Gly Arg Arg Asp Ile Val Lys Arg Gln Asn Glu
            355                 360                 365

Thr Thr Thr Val Val Met Asp Glu Thr Lys Leu Val Pro Leu Glu His
370                 375                 380

Pro Gly Ala Ala Cys Gly Ser Lys Pro Ala Asp Leu Val Ile Asp Leu
385                 390                 395                 400

Thr Phe Gly Val Asn Phe Thr Thr Gly His Trp Met Ile Asn Gly Ile
                405                 410                 415

Pro His Lys Ser Pro Asp Met Pro Thr Leu Leu Lys Ile Leu Thr Asp
                420                 425                 430

Thr Asp Gly Val Thr Glu Ser Asp Phe Thr Gln Pro Glu His Thr Ile
            435                 440                 445

Ile Leu Pro Lys Asn Lys Cys Val Glu Phe Asn Ile Lys Gly Asn Ser
450                 455                 460

Gly Leu Gly Ile Val His Pro Ile His Leu His Gly His Thr Phe Asp
465                 470                 475                 480

Val Val Gln Phe Gly Asn Asn Pro Pro Asn Tyr Val Asn Pro Pro Arg
                485                 490                 495

Arg Asp Val Val Gly Ala Thr Asp Glu Gly Val Arg Phe Gln Phe Lys
            500                 505                 510

Thr Asp Asn Pro Gly Pro Trp Phe Leu His Cys His Ile Asp Trp His
            515                 520                 525

Leu Glu Glu Gly Phe Ala Met Val Phe Ala Glu Ala Pro Glu Ala Ile
            530                 535                 540

Lys Gly Gly Pro Lys Ser Val Pro Val Asp Arg Gln Trp Lys Asp Leu
545                 550                 555                 560

Cys Arg Lys Tyr Gly Ser Leu Pro Ala Gly Phe Leu
                565                 570

(2) INFORMATION FOR SEQ ID NO: 8:

(i) SEQUENCE CHARACTERISTICS:
        (A) LENGTH: 575 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 8:

Met Ala Arg Thr Thr Phe Leu Val Ser Val Ser Leu Phe Val Ser Ala
1               5                   10                  15

Val Leu Ala Arg Thr Val Glu Tyr Gly Leu Lys Ile Ser Asp Gly Glu
                20                  25                  30

Ile Ala Pro Asp Gly Val Lys Arg Asn Ala Thr Leu Val Asn Gly Gly
            35                  40                  45

Tyr Pro Gly Pro Leu Ile Phe Ala Asn Lys Gly Asp Thr Leu Lys Val
        50                  55                  60

Lys Val Gln Asn Lys Leu Thr Asn Pro Glu Met Tyr Arg Thr Thr Ser
65                  70                  75                  80

-continued

```
Ile His Trp His Gly Leu Leu Gln His Arg Asn Ala Asp Asp Gly
             85                  90                  95

Pro Ser Phe Val Thr Gln Cys Pro Ile Val Pro Arg Glu Ser Tyr Thr
            100                 105                 110

Tyr Thr Ile Pro Leu Asp Asp Gln Thr Gly Thr Tyr Trp Tyr His Ser
            115                 120                 125

His Leu Ser Ser Gln Tyr Val Asp Gly Leu Arg Gly Pro Leu Val Ile
        130                 135                 140

Tyr Pro Lys Asp Pro His Arg Arg Leu Tyr Asp Val Asp Asp Glu Lys
145                 150                 155                 160

Thr Val Leu Ile Ile Gly Asp Trp Tyr His Glu Ser Ser Lys Ala Ile
                165                 170                 175

Leu Ala Ser Gly Asn Ile Thr Arg Gln Arg Pro Val Ser Ala Thr Ile
            180                 185                 190

Asn Gly Lys Gly Arg Phe Asp Pro Asp Asn Thr Pro Ala Asn Pro Asp
        195                 200                 205

Thr Leu Tyr Thr Leu Lys Val Lys Arg Gly Lys Arg Tyr Arg Leu Arg
210                 215                 220

Val Ile Asn Ser Ser Glu Ile Ala Ser Phe Arg Phe Ser Val Glu Gly
225                 230                 235                 240

His Lys Val Thr Val Ile Ala Ala Asp Gly Val Ser Thr Lys Pro Tyr
                245                 250                 255

Gln Val Asp Ala Phe Asp Ile Leu Ala Gly Gln Arg Ile Asp Cys Val
            260                 265                 270

Val Glu Ala Asn Gln Glu Pro Asp Thr Tyr Trp Ile Asn Ala Pro Leu
        275                 280                 285

Thr Asn Val Pro Asn Lys Thr Ala Gln Ala Leu Leu Val Tyr Glu Glu
290                 295                 300

Asp Arg Arg Pro Tyr His Pro Lys Gly Pro Tyr Arg Lys Trp Ser
305                 310                 315                 320

Val Ser Glu Ala Ile Ile Lys Tyr Trp Asn His Lys His Lys His Gly
                325                 330                 335

Arg Gly Leu Leu Ser Gly His Gly Gly Leu Lys Ala Arg Met Ile Glu
            340                 345                 350

Gly Ser His His Leu His Ser Arg Ser Val Val Lys Arg Gln Asn Glu
        355                 360                 365

Thr Thr Thr Val Val Met Asp Glu Ser Lys Leu Val Pro Leu Glu Tyr
370                 375                 380

Pro Gly Ala Ala Cys Gly Ser Lys Pro Ala Asp Leu Val Leu Asp Leu
385                 390                 395                 400

Thr Phe Gly Leu Asn Phe Ala Thr Gly His Trp Met Ile Asn Gly Ile
                405                 410                 415

Pro Tyr Glu Ser Pro Lys Ile Pro Thr Leu Leu Lys Ile Leu Thr Asp
            420                 425                 430

Glu Asp Gly Val Thr Glu Ser Asp Phe Thr Lys Glu Glu His Thr Val
        435                 440                 445

Ile Leu Pro Lys Asn Lys Cys Ile Glu Phe Asn Ile Lys Gly Asn Ser
450                 455                 460

Gly Ile Pro Ile Thr His Pro Val His Leu His Gly His Thr Trp Asp
465                 470                 475                 480

Val Val Gln Phe Gly Asn Asn Pro Pro Asn Tyr Val Asn Pro Pro Arg
                485                 490                 495

Arg Asp Val Val Gly Ser Thr Asp Ala Gly Val Arg Ile Gln Phe Lys
            500                 505                 510
```

Thr Asp Asn Pro Gly Pro Trp Phe Leu His Cys His Ile Asp Trp His
    515                 520                 525

Leu Glu Glu Gly Phe Ala Met Val Phe Ala Glu Ala Pro Glu Ala Val
    530                 535                 540

Lys Gly Gly Pro Lys Ser Val Ala Val Asp Ser Gln Trp Glu Gly Leu
545                 550                 555                 560

Cys Gly Lys Tyr Asp Asn Trp Leu Lys Ser Asn Pro Gly Gln Leu
                565                 570                 575

(2) INFORMATION FOR SEQ ID NO: 9:

(i) SEQUENCE CHARACTERISTICS:
        (A) LENGTH: 616 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 9:

Met Lys Arg Phe Phe Ile Asn Ser Leu Leu Leu Ala Gly Leu Leu
1               5                   10                  15

Asn Ser Gly Ala Leu Ala Ala Pro Ser Thr His Pro Arg Ser Asn Pro
            20                  25                  30

Asp Ile Leu Leu Glu Arg Asp Asp His Ser Leu Thr Ser Arg Gln Gly
            35                  40                  45

Ser Cys His Ser Pro Ser Asn Arg Ala Cys Trp Cys Ser Gly Phe Asp
50                  55                  60

Ile Asn Thr Asp Tyr Glu Thr Lys Thr Pro Asn Thr Gly Val Val Arg
65                  70                  75                  80

Arg Tyr Thr Phe Asp Ile Thr Glu Val Asp Asn Arg Pro Gly Pro Asp
                85                  90                  95

Gly Val Ile Lys Glu Lys Leu Met Leu Ile Asn Asp Lys Leu Leu Gly
            100                 105                 110

Pro Thr Val Phe Ala Asn Trp Gly Asp Thr Ile Glu Val Thr Val Asn
            115                 120                 125

Asn His Leu Arg Thr Asn Gly Thr Ser Ile His Trp His Gly Leu His
130                 135                 140

Gln Lys Gly Thr Asn Tyr His Asp Gly Ala Asn Gly Val Thr Glu Cys
145                 150                 155                 160

Pro Ile Pro Pro Gly Gly Ser Arg Val Tyr Ser Phe Arg Ala Arg Gln
                165                 170                 175

Tyr Gly Thr Ser Trp Tyr His Ser His Phe Ser Ala Gln Tyr Gly Asn
            180                 185                 190

Gly Val Ser Gly Ala Ile Gln Ile Asn Gly Pro Ala Ser Leu Pro Tyr
            195                 200                 205

Asp Ile Asp Leu Gly Val Leu Pro Leu Xaa Asp Trp Tyr Tyr Lys Ser
210                 215                 220

Ala Asp Gln Leu Val Ile Glu Thr Leu Xaa Lys Gly Asn Ala Pro Phe
225                 230                 235                 240

Ser Asp Asn Val Leu Ile Asn Gly Thr Ala Lys His Pro Thr Thr Gly
                245                 250                 255

Glu Gly Glu Tyr Ala Ile Val Lys Leu Thr Pro Asp Lys Arg His Arg
            260                 265                 270

Leu Arg Leu Ile Asn Met Ser Val Glu Asn His Phe Gln Val Ser Leu
275                 280                 285

```
Ala Lys His Thr Met Thr Val Ile Ala Ala Asp Met Val Pro Val Asn
    290                 295                 300

Ala Met Thr Val Asp Ser Leu Phe Met Ala Val Gly Gln Arg Tyr Asp
305                 310                 315                 320

Val Thr Ile Asp Ala Ser Gln Ala Val Gly Asn Tyr Trp Phe Asn Ile
                325                 330                 335

Thr Phe Gly Gly Gln Gln Lys Cys Gly Phe Ser His Asn Pro Ala Pro
            340                 345                 350

Ala Ala Ile Phe Arg Tyr Glu Gly Ala Pro Asp Ala Leu Pro Thr Asp
        355                 360                 365

Pro Gly Ala Ala Pro Lys Asp His Gln Cys Leu Asp Thr Leu Asp Leu
    370                 375                 380

Ser Pro Val Val Gln Lys Asn Val Pro Val Asp Gly Phe Val Lys Glu
385                 390                 395                 400

Pro Gly Asn Thr Leu Pro Val Thr Leu His Val Asp Gln Ala Ala Ala
                405                 410                 415

Pro His Val Phe Thr Trp Lys Ile Asn Gly Ser Ala Ala Asp Val Asp
            420                 425                 430

Trp Asp Arg Pro Val Leu Glu Tyr Val Met Asn Asn Asp Leu Ser Ser
        435                 440                 445

Ile Pro Val Lys Asn Asn Ile Val Arg Val Asp Gly Val Asn Glu Trp
    450                 455                 460

Thr Tyr Trp Leu Val Glu Asn Asp Pro Glu Gly Arg Leu Ser Leu Pro
465                 470                 475                 480

His Pro Met His Leu His Gly His Asp Phe Phe Val Leu Gly Arg Ser
                485                 490                 495

Pro Asp Val Ser Pro Asp Ser Glu Thr Arg Phe Val Phe Asp Pro Ala
            500                 505                 510

Val Asp Leu Pro Arg Leu Arg Gly His Asn Pro Val Arg Arg Asp Val
        515                 520                 525

Thr Met Leu Pro Ala Arg Gly Trp Leu Leu Leu Ala Phe Arg Thr Asp
    530                 535                 540

Asn Pro Gly Ala Trp Leu Phe His Cys His Ile Ala Xaa His Val Ser
545                 550                 555                 560

Gly Gly Leu Ser Val Asp Phe Leu Glu Arg Pro Asp Glu Leu Arg Gly
                565                 570                 575

Gln Leu Thr Gly Glu Ser Lys Ala Glu Leu Glu Arg Val Cys Arg Glu
            580                 585                 590

Trp Lys Asp Trp Glu Ala Lys Ser Pro His Gly Lys Ile Asp Ser Gly
        595                 600                 605

Leu Lys Gln Arg Arg Trp Asp Ala
    610                 615

(2) INFORMATION FOR SEQ ID NO: 10:

(i) SEQUENCE CHARACTERISTICS:
        (A) LENGTH: 573 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 10:

Gln Gln Ser Cys Asn Thr Pro Ser Asn Arg Ala Cys Trp Thr Asp Gly
1               5                   10                  15

Tyr Asp Ile Asn Thr Asp Tyr Glu Val Asp Ser Pro Asp Thr Gly Val
```

```
                    20                  25                  30
Val Arg Pro Tyr Thr Leu Thr Leu Thr Glu Val Asp Asn Trp Thr Gly
        35                  40                  45

Pro Asp Gly Val Val Lys Glu Lys Val Met Leu Val Asn Asn Ser Ile
 50                  55                  60

Ile Gly Pro Thr Ile Phe Ala Asp Trp Gly Asp Thr Ile Gln Val Thr
 65                  70                  75                  80

Val Ile Asn Asn Leu Glu Thr Asn Gly Thr Ser Ile His Trp His Gly
                 85                  90                  95

Leu His Gln Lys Gly Thr Asn Leu His Asp Gly Ala Asn Gly Ile Thr
            100                 105                 110

Glu Cys Pro Ile Pro Pro Lys Gly Arg Lys Val Tyr Arg Phe Lys
            115                 120                 125

Ala Gln Gln Tyr Gly Thr Ser Trp Tyr His Ser His Phe Ser Ala Gln
        130                 135                 140

Tyr Gly Asn Gly Val Val Gly Ala Ile Gln Ile Asn Gly Pro Ala Ser
145                 150                 155                 160

Leu Pro Tyr Asp Thr Asp Leu Gly Val Phe Pro Ile Ser Asp Tyr Tyr
                165                 170                 175

Tyr Ser Ser Ala Asp Glu Leu Val Glu Leu Thr Lys Asn Ser Gly Ala
            180                 185                 190

Pro Phe Ser Asp Asn Val Leu Phe Asn Gly Thr Ala Lys His Pro Glu
        195                 200                 205

Thr Gly Glu Gly Glu Tyr Ala Asn Val Thr Leu Thr Pro Gly Arg Arg
210                 215                 220

His Arg Leu Arg Leu Ile Asn Thr Ser Val Glu Asn His Phe Gln Val
225                 230                 235                 240

Ser Leu Val Asn His Thr Met Cys Ile Ile Ala Ala Asp Met Val Pro
                245                 250                 255

Val Asn Ala Met Thr Val Asp Ser Leu Phe Leu Gly Val Gly Gln Arg
            260                 265                 270

Tyr Asp Val Val Ile Glu Ala Asn Arg Thr Pro Gly Asn Tyr Trp Phe
        275                 280                 285

Asn Val Thr Phe Gly Gly Gly Leu Leu Cys Gly Gly Ser Arg Asn Pro
        290                 295                 300

Tyr Pro Ala Ala Ile Phe His Tyr Ala Gly Ala Pro Gly Gly Pro Pro
305                 310                 315                 320

Thr Asp Glu Gly Lys Ala Pro Val Asp His Asn Cys Leu Asp Leu Pro
                325                 330                 335

Asn Leu Lys Pro Val Val Ala Arg Asp Val Pro Leu Ser Gly Phe Ala
            340                 345                 350

Lys Arg Ala Asp Asn Thr Leu Asp Val Thr Leu Asp Thr Thr Gly Thr
        355                 360                 365

Pro Leu Phe Val Trp Lys Val Asn Gly Ser Ala Ile Asn Ile Asp Trp
370                 375                 380

Gly Arg Ala Val Val Asp Tyr Val Leu Thr Gln Asn Thr Ser Phe Pro
385                 390                 395                 400

Pro Gly Tyr Asn Ile Val Glu Val Asn Gly Ala Asp Gln Trp Ser Tyr
                405                 410                 415

Trp Leu Ile Glu Asn Asp Pro Gly Ala Pro Phe Thr Leu Pro His Pro
            420                 425                 430

Met His Leu His Gly His Asp Phe Tyr Val Leu Gly Arg Ser Pro Asp
        435                 440                 445
```

-continued

```
Glu Ser Pro Ala Ser Asn Glu Arg His Val Phe Asp Pro Ala Arg Asp
    450             455                 460
Ala Gly Leu Leu Ser Gly Ala Asn Pro Val Arg Arg Asp Val Ser Met
465             470                 475                 480
Leu Pro Ala Phe Gly Trp Val Val Leu Ser Phe Arg Ala Asp Asn Pro
                485                 490                 495
Gly Ala Trp Leu Phe His Cys His Ile Ala Trp His Val Ser Gly Gly
            500             505                 510
Leu Gly Val Val Tyr Leu Glu Arg Ala Asp Asp Leu Arg Gly Ala Val
        515                 520                 525
Ser Asp Ala Asp Ala Asp Asp Leu Asp Arg Leu Cys Ala Asp Trp Arg
    530             535                 540
Arg Tyr Trp Pro Thr Asn Pro Tyr Pro Lys Ser Asp Ser Gly Leu Lys
545             550             555                     560
His Arg Trp Val Glu Glu Gly Glu Trp Leu Val Lys Ala
                565                 570
```